United States Patent
Montasser et al.

(10) Patent No.: US 10,738,284 B2
(45) Date of Patent: Aug. 11, 2020

(54) B4GALT1 CDNA VARIANTS AND COMPOSITIONS COMPRISING THE SAME

(71) Applicants: Regeneron Pharmaceuticals, Inc., Tarrytown, NY (US); University of Maryland, Baltimore, Baltimore, MD (US)

(72) Inventors: May Montasser, Baltimore, MD (US); Cristopher Van Hout, Tarrytown, NY (US); Alan Shuldiner, Tarrytown, NY (US); Giusy Della Gatta, Tarrytown, NY (US); Matthew Healy, Tarrytown, NY (US); Marja Puurunen, Tarrytown, NY (US)

(73) Assignees: Regeneron Pharmaceuticals, Inc., Tarrytown, NY (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 15/996,892

(22) Filed: Jun. 4, 2018

(65) Prior Publication Data

US 2018/0346888 A1 Dec. 6, 2018

Related U.S. Application Data

(60) Provisional application No. 62/515,140, filed on Jun. 5, 2017, provisional application No. 62/550,161, filed on Aug. 25, 2017, provisional application No. 62/659,344, filed on Apr. 18, 2018.

(51) Int. Cl.
*C12N 9/10* (2006.01)
*C12N 15/86* (2006.01)

(52) U.S. Cl.
CPC ........... *C12N 9/1051* (2013.01); *C12N 15/86* (2013.01); *C12Y 204/01133* (2013.01)

(58) Field of Classification Search
None
See application file for complete search history.

(56) References Cited

U.S. PATENT DOCUMENTS

2012/0295815 A1* 11/2012 Lindahl ................ C12Q 1/6886
506/9

FOREIGN PATENT DOCUMENTS

WO 2009025645 2/2009
WO 2009102820 8/2009

OTHER PUBLICATIONS

Database Geneseq, "Human mutant beta-4Gal-T1-M34OH-Y285L DNA Seq ID:1", 2009, GSN: AWI43668.
Machingo et al., "A β1,4-galactosyltransferase is required for convergent extension movements in zebrafish", Developmental Biology, 2006, 297, pp. 471-482.
Shen et al., "Familial Defective Apolopoprotein B-100 and Increased Low-Density Lipoprotein Cholesterol and Coronary Artery Calcification in the Old Order Amish", Arch Intern Med, 2010, 170(20), pp. 1850-1855.
Database Geneseq, "Encodes a HeLa cell galactosyltransferase enzyme", 1993, XP-0027884507.
Database EMBL, "Human DNA sequence from clone RP11-326F20 on chromosome 9", 2000, XP-002784508.
Database Genseq, "LNCap cells/CL1 cells expressed protein, SED ID 1153", 2015, XP-002784509.
Database Geneseq, "Beta-1,4 galactosyltransferase (beta 4Gal-T1) CDS, SEQ ID:1", 2009, XP-002784510.
Humphreys et al., "Isolation and Immunologic Characterization of a Human B-lymphocyte-specific, cell surface antigen", Journal of Experimental Medicine, 1976, pp. 98-112.
Qasba et al., "Structure and function of beta-1,4-galactosyltransferase 1", Curr Drug Targets, 2008, 9(4), pp. 292-309.
Miller et al., "Newly identified loci that influence lipid concentrations and risk of coronary artery disease", Nature Genetics, 2008, 40(2), pp. 1061-4036.

* cited by examiner

*Primary Examiner* — Mindy G Brown
(74) *Attorney, Agent, or Firm* — Stradley Ronon Stevens & Young, LLP

(57) ABSTRACT

Variant B4GALT1 genomic, mRNA, and cDNA nucleic acid molecules, and polypeptides, methods of detecting the presence of these molecules, methods of modulating endogenous B4GALT1 genomic, mRNA, and cDNA nucleic acid molecules, and polypeptides, methods of ascertaining the risk of developing cardiovascular conditions by detecting the presence or absence of the variant B4GALT1 genomic, mRNA, and cDNA nucleic acid molecules, and polypeptides, and methods of treating cardiovascular conditions are provided herein.

13 Claims, 25 Drawing Sheets

Specification includes a Sequence Listing.

| Haplotype | Copies | 9:31523876 | 9:31599161 | 9:31833653 | 9:32231857 | rs551564683 | 9:33892787 | 9:33971380 |
|---|---|---|---|---|---|---|---|---|
| A | 115 | 1 | 1 | 1 | 1 | 1 | 1 | 1 |
| B | 7 | 1 | 1 | 1 | 1 | 1 | 0 | 0 |
| C | 6 | 0 | 0 | 0 | 0 | 1 | 1 | 1 |

| Haplotype | Copies | 9:33991394 | 9:34068523 | 9:34277757 | 9:34520551 | 9:34860904 | 9:35178756 | 9:35570095 |
|---|---|---|---|---|---|---|---|---|
| A | 115 | 1 | 1 | 1 | 1 | 1 | 1 | 1 |
| B | 7 | 0 | 0 | 0 | 0 | 0 | 0 | 0 |
| C | 6 | 1 | 1 | 1 | 1 | 1 | 1 | 1 |

Figure 3

| Population | Population size | # HET carriers | # HOM carriers | AAF |
|---|---|---|---|---|
| BCH | 580 | 0 | 0 | 0.000000 |
| CNCD | 96 | 0 | 0 | 0.000000 |
| COL-CHUNG | 4064 | 0 | 0 | 0.000000 |
| COL-CHUNG_FBC | 1193 | 0 | 0 | 0.000000 |
| CSC | 2084 | 65 | 5 | 0.017994 |
| DHS | 4654 | 0 | 0 | 0.000000 |
| DRIFT-NIMH | 460 | 3 | 0 | 0.002081 |
| DUKE | 8783 | 2 | 0 | 0.000114 |
| ECO | 858 | 0 | 0 | 0.000000 |
| GHS | 66216 | 7 | 0 | 0.000053 |
| IOWA | 58 | 0 | 0 | 0.000000 |
| MADGC | 2393 | 1 | 0 | 0.000209 |
| MARIO | 127 | 0 | 0 | 0.000000 |
| NIAID | 95 | 0 | 0 | 0.000000 |
| SIMONS | 96 | 0 | 0 | 0.000000 |
| SINAI | 96 | 0 | 0 | 0.000000 |
| TAICHI | 13963 | 0 | 0 | 0.000000 |
| TSK | 3407 | 0 | 0 | 0.000000 |
| UCHC | 1039 | 0 | 0 | 0.000000 |
| UMD | 4725 | 548 | 13 | 0.060741 |
| UPENN | 11451 | 1 | 0 | 0.000044 |
| UTAH | 3688 | 0 | 0 | 0.000000 |
| Total | 130126 | 627 | 18 | 0.002548 |

Figure 5B

| Phenotype | Genotypic Means* | Genotypic Means unadjusted | Counts (Ref/Het/Alt) | effect (95% CI) | Pvalue |
|---|---|---|---|---|---|
| Serum lipids | | | | | |
| Cholesterol, mg/dL | 210.6 / 190.9 / 172.7 | 210.4 / 192.3 / 176.2 | 3995/527/12 | -17.18 (-22.4, -11.95) | 1.3E-10 |
| LDL, mg/dL | 134.7 / 117.4 / 103.5 | 134.6 / 118.3 / 103.5 | 3991/526/12 | -14.61 (-19.37, -9.86) | 1.8E-09 |
| HDL, mg/dL | 61.4 / 59.4 / 58.6 | 61.3 / 59.8 / 61.6 | 3995/527/12 | -2.14 (-3.88, -0.41) | 0.0155 |
| Triglycerides (log10), mg/dL | 73.9 / 72.9 / 72.7 | 71.9 / 72.0 / 55.8 | 3995/527/12 | -3.39 (-8.17,1.62) % | 0.1780 |
| Chol/HDL (log10) | 3.39 / 3.15 / 2.94 | 3.39 / 3.16 / 2.87 | 3318/450/11 | -6.67 (-9.80, -2.28) % | 0.0003 |
| NonHDL Cholesterol, mg/dL | 161.5 / 144.5 / 91.1 | 161.0 / 149.0 / 99.0 | 727/87/1 | -14.33 (-23.57, -5.09) | 0.0025 |

0.0774* Genotypic means are on the clinical scale, removing the effects of Age, Age2, Sex, and Study
** Also adjusted for BMI
*** Result generated at UMD in a model with Age Sex, Study as covariates.

| Phenotype | Genotypic Means* | Genotypic Means Unadjusted | Counts (Ref/Het/Alt) | Effect (95% CI) | P-value |
|---|---|---|---|---|---|
| CAD-related traits | | | | | |
| Coronary Calcification (log10) | 0.301 / 0.301 / 35.2 | 0.298 / 0.220 / NA | 202/42/0 | -22.4 (-38.3, -0.92) % | 0.0433 |
| Coronary Calcification (log10)*** | 1.97 / 1.44 / 0 | NA | 546/94/1 | -19 % | 0.1349 |
| Pericardial Fat** | 69.5 / 62.7 / NA | 71.5 / 71.4 / NA | 148/27/0 | 12.76 (1.06, 24.46) | 0.0339 |
| Liver traits | | | | | |
| AST (log10), U/L | 18.0 / 18.6 / 35.2 | 18.0 / 18.7 / 34.3 | 3910/517/12 | 7.15 (4.71, 12.20) % | 6.0E-08 |
| ALT (log10), U/L | 17.2 / 16.9 / 20.3 | 17.2 / 16.9 / 19.7 | 3978/530/13 | -0.23 (-4.50, 4.71) % | 0.8920 |
| AlkPhos (log10), U/L | 53.8 / 52.9 / 62.9 | 53.8 / 53.1 / 61.8 | 3987/531/13 | 0.92 (-3.87, 2.09) % | 0.5391 |
| Liver fat (by EBCT) | 1.27 / 1.33 / NA | 1.27 / 1.32 / NA | 106/38/0 | 0.05 (-0.005, 0.110) | 0.0774 |

\* Genotypic means are on the clinical scale, removing the effects of Age, Age2, Sex, and Study
\*\* Also adjusted for BMI
\*\*\* Result generated at UMD in a model with Age Sex, Study as covariates.

Figure 6 (cont.)

B4GALT1 ASN352SER IS ASSOCIATED WITH DECREASES IN ALL LIPID SUBFRACTIONS
(AMISH HAPI HEART STUDY)

| Phenotype | Genotypic Means* | Genotypic Means Unadjusted | Counts(Ref/Het/Alt) | Effect | Pvalue |
|---|---|---|---|---|---|
| HDL2, mg/dL | 15.9 / 13.5 / 19.6 | 15.9 / 13.7 / 21.0 | 660/74/1 | -2.07 (-3.68, -0.46) | 0.012 |
| HDL2a, mg/dL | 11.2 / 9.7 / 15.3 | 11.2 / 9.8 / 16.4 | 660/74/1 | -1.23 (-2.38, -0.09) | 0.036 |
| HDL2b, mg/dL | 3.2 / 2.9 / 3.6 | 3.2 / 2.9 / 3.9 | 660/74/1 | -0.33 (-0.73, 0.08) | 0.113 |
| HDL2c, mg/dL | 1.5 / 1.1 / 0.1 | 1.5 / 1.1 / 0.2 | 660/74/1 | -0.47 (-0.87, -0.07) | 0.023 |
| HDL3, mg/dL | 39.5 / 36.8 / 39.3 | 39.4 / 37.1 / 41.0 | 660/74/1 | -2.48 (-4.23, -0.72) | 0.006 |
| HDL3a, mg/dL | 14.8 / 12.8 / 17.1 | 14.8 / 12.9 / 18.3 | 660/74/1 | -1.73 (-3, -0.47) | 0.007 |
| HDL3b, mg/dL | 6.2 / 6.4 / 5.8 | 6.2 / 6.4 / 5.9 | 660/74/1 | 0.09 (-0.3, 0.49) | 0.640 |
| HDL3c, mg/dL | 9.5 / 9 / 9.3 | 9.5 / 9.0 / 9.7 | 660/74/1 | -0.49 (-0.96, -0.03) | 0.037 |
| HDL3d, mg/dL | 9 / 8.7 / 7.5 | 8.9 / 8.7 / 7.5 | 660/74/1 | -0.34 (-0.7, 0.03) | 0.070 |
| LDL1, mg/dL | 22.8 / 20.2 / 15.2 | 22.7 / 20.9 / 17.4 | 660/74/1 | -3.17 (-5.89, -0.45) | 0.023 |
| LDL2, mg/dL | 48.3 / 39.4 / 32.1 | 48.2 / 39.7 / 34.4 | 660/74/1 | -8.43 (-14.47, -2.38) | 0.006 |
| LDL3, mg/dL | 45.7 / 43.2 / 18.2 | 45.4 / 44.4 / 18.3 | 660/74/1 | -1.69 (-6.77, 3.38) | 0.513 |
| LipoproteinA, mg/dL | 7.7 / 6.6 / 11.6 | 7.7 / 6.7 / 12.0 | 660/74/1 | -0.66 (-1.56, 0.24) | 0.150 |
| Lpa1 (log10), mg/dL | 3.79 / 3.39 / 5.13 | 3.78 / 3.50 / 5.50 | 220/10/1 | -4.50 (-33.9, 34.9) % | 0.764 |
| Lpa2 (log10), mg/dL | 1.91 / 1.66 / NA | 1.91 / 1.66 / NA | 206/29/0 | -14.9 (-41.1, 23.0) % | 0.395 |
| Lpa3 (log10), mg/dL | 4.58 / 3.72 / NA | 4.58 / 3.72 / NA | 323/47/0 | -18.7 (-30.8, -4.50) % | 0.009 |
| Lpa4 (log10), mg/dL | 3.78 / 3.65 / NA | 3.76 / 3.85 / NA | 204/23/0 | -4.50 (-27.6, 28.8) % | 0.784 |
| Lpa5 (log10), mg/dL | 3.37 / 2.89 / 5.74 | 3.36 / 2.95 / 6.10 | 252/25/1 | -8.80 (-24.1, 9.65) % | 0.339 |

*Statistical models account for Age, Age$^2$, Sex, and Study

Figure 8

*B4GALT1* ASN352SER IS ASSOCIATED WITH DECREASED FIBRINOGEN LEVELS (AMISH PAPI STUDY) + OTHER TRAITS OF POTENTIAL INTEREST

| Phenotype | Genotypic Means* | Genotypic Means Unadjusted | GenoCounts (Ref/Het/Alt) | Effect | Pvalue |
|---|---|---|---|---|---|
| Fibrinogen, drug naïve, mg/dL | 280.8 / 255 / 253.8 | 280.5 / 257.1 / 273.3 | 564/54/3 | -23.97 (-38.35, -9.59) | 1.15E-03 |
| Fibrinogen, post-clopidogrel, mg/dL | 276 / 247.7 / 182 | 275. / 249.7 / 197.0 | 549/54/3 | -32.45 (-47.5, -17.41) | 2.74E-05 |

Of 20+ platelet aggregation measures, pre/post-clopidogrel/post-aspirin, only 2 are nominally significant

| Phenotype | Control Counts (Ref/Het/Alt) | Case Counts (Ref/Het/Alt) | Control Freq | Case Freq | OR (95% CI) | GenoCounts (Ref/Het/Alt) | OR Het (95% CI) | OR Hom | Pvalue |
|---|---|---|---|---|---|---|---|---|---|
| CAD (logistic) | 3535/473/11 | 101/13/0 | 0.061 | 0.057 | 0.78 (0.45, 1.48) | | 0.96 (0.54, 1.72) | - | 0.42 |

| Phenotype | Genotypic Means* | Genotypic Means Unadjusted | Counts (Ref/Het/Alt) | Effect | Pvalue |
|---|---|---|---|---|---|
| Creatinine (log10), mg/dL | 0.747 / 0.767 / 0.789 | 0.748 / 0.763 / 0.756 | 3987/531/13 | 2.23 (0.46, 1.04) % | 0.0095 |
| eGFR, mL/min/1.73m² | 107.2 / 104.1 / 97.0 | 107.2 / 103.5 / 95.5 | 3910/517/12 | -2.86 (-5.10, -0.63) | 0.0121 |
| Basophils (log10), % | 0.402 / 0.376 / 0.369 | 0.402 / 0.378 / 0.370 | 3275/444/11 | -6.67 (-10.87, 0.69) % | 0.0259 |
| Hematocrit, % | 40.5 / 40.8 / 42.8 | 40.5 / 40.7 / 41.4 | 3897/514/12 | 0.34 (0.04, 0.63) | 0.0271 |

*Statistical models account for Age, Age², Sex, and Study

Figure 9

A) B4GALT1 antibody
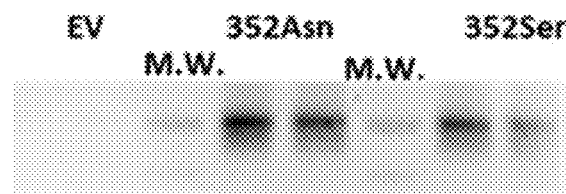
B) Flag Antibody
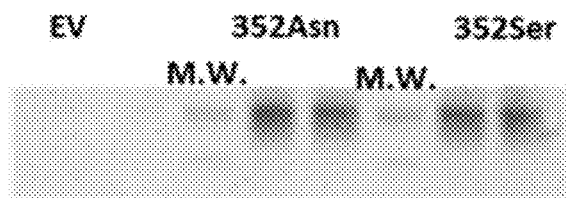
C) activity
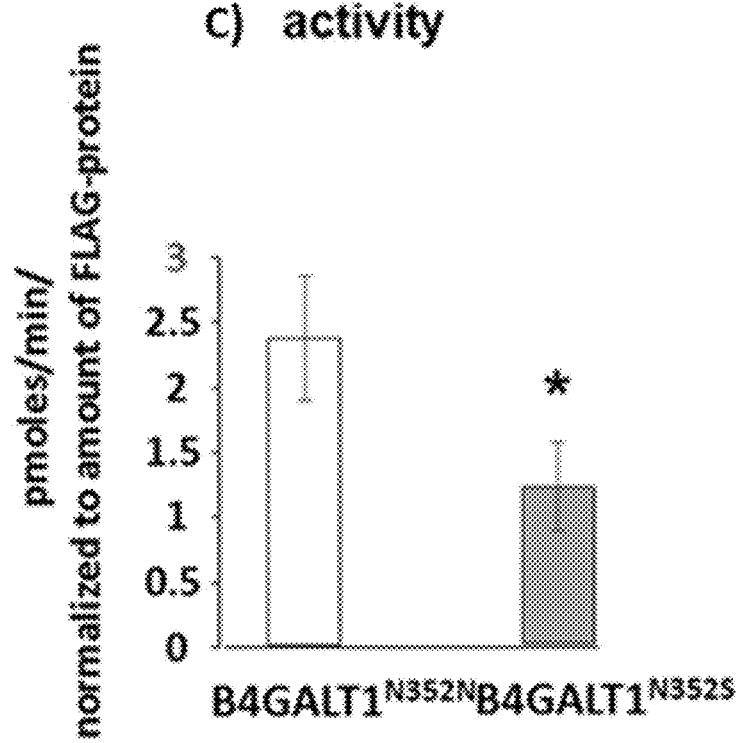
Figure 18

SEQUENCE LISTING

<160> NUMBER OF SEQ ID NOS: 17

<210> SEQ ID NO 1
<211> LENGTH: 56718
<212> TYPE: DNA
<213> ORGANISM: Homo sapien
<220> FEATURE:
<223> OTHER INFORMATION: wild-type B4GALT1 genomic sequence

<400> SEQUENCE: 1

| | | | | | |
|---|---|---|---|---|---|
| gcgcctcggg | cggcttctcg | ccgctcccag | gtctggctgg | ctggaggagt | 50 |
| ctcagctctc | agccgctcgc | ccgccccgc | tccgggccct | ccctagtcg | 100 |
| ccgctgtggg | gcagcgcctg | gcgggcggcc | cgcgggcggg | tcgcctcccc | 150 |
| tcctgtagcc | cacacccttc | ttaaagcggc | ggcgggaaga | tgaggcttcg | 200 |
| ggagccgctc | ctgagcggca | gcgccgcgat | gccaggcgcg | tccctacagc | 250 |
| gggcctgccg | cctgctcgtg | gccgtctgcg | ctctgcacct | tggcgtcacc | 300 |
| ctcgtttact | acctggctgg | ccgcgacctg | agccgcctgc | cccaactggt | 350 |
| cggagtctcc | acaccgctgc | agggcggctc | gaacagtgcc | gccgccatcg | 400 |
| ggcagtcctc | cggggagctc | cggaccggag | gggcccggcc | gccgcctcct | 450 |
| ctaggcgcct | cctcccagcc | gcgcccgggt | ggcgactcca | gcccagtcgt | 500 |
| ggattctggc | cctggccccg | ctagcaactt | gacctcggtc | ccagtgcccc | 550 |
| acaccaccgc | actgtcgctg | cccgcctgcc | ctgaggagtc | cccgctgctt | 600 |
| ggtaaggact | cgggtcggcg | ccagtcggag | gattgggacc | ccccggatt | 650 |
| tccccgacag | ggtcccccag | acattccctc | aggctggctc | ttctacgaca | 700 |
| gccagcctcc | ctcttctgga | tcagagtttt | aaatcccaga | cagaggcttg | 750 |
| ggactggatg | ggagagaagg | tttgcgaggt | gggtccctgg | ggagtcctgt | 800 |
| tggaggcgtg | gggccgggac | cgcacaggga | agtcccgagg | cccctctagc | 850 |
| cccagaacca | gagaaggcct | tggagacttc | cctgctgtgg | cccgaggctc | 900 |
| aggaagtttt | ggagtttggg | tctgcttagg | gcttcgagca | gccttgcact | 950 |
| gagaactctg | gtagggacct | cgagtaatcc | actcccttt | ggggactgac | 1000 |
| gtgaggctcc | cggtggggaa | ggagactgac | ctctcggttc | acgtgtcttg | 1050 |
| ccatagagcc | actctcctga | gtgggttttt | ctcctgatcg | tttgggccaa | 1100 |
| gtgacttctc | tctgaacctc | atatttctct | tctgggataa | taaatggtca | 1150 |
| cccttcaag | ggttgtttt | ggaagatatt | gtgaacaatg | gtaaataagg | 1200 |
| gcttaattaa | tgagggtaag | ccctcagtaa | attgtcactg | tgtgttcatt | 1250 |
| tcttcctctg | tgtggatcgt | gaccgagagc | ccttccccct | agcctcctcc | 1300 |
| tggtatgggt | acccaaaacc | taggtgagca | ggatctctc | ccaggggcag | 1350 |
| agagcttgtg | tactctgggt | gttagagggc | taaaatataa | ccagtcaaca | 1400 |
| ccacgttgcc | catttctggt | acttccggta | gcagcctgag | tctcaattat | 1450 |
| cttgcccaga | tgatctgaac | tctgacctct | agcctgtttc | agcataggca | 1500 |
| gagagcttga | gtaggtgagt | ttgcattcct | catagcagct | ggctgagcct | 1550 |
| agtctggact | tctctttgac | ctgtaaccta | caggcccaca | ggcccaaggc | 1600 |
| aaccacaggt | tgcttccagg | gttaccacac | aggtggtttc | tcatttctaa | 1650 |
| tgctaggttt | tagataattg | ttgtaagtga | ggggccctgg | caggcaggat | 1700 |

```
gacatcctgc caataggagt tttctgtcac tttcccacag agccctggct        1750
actacatact cttgctcaat ttcgccagta attgcgtcaa tgtgttcata        1800
tcaagtttgg gaagaacatc ttggaattgg tcagacgtga actgtggtaa        1850 taatggggggc ttgttttttt aagcagataa ttaaattcct ttgcatttga       1900
tgattattct gggaagcaga ctagtcccat aaaatgaaat ggactctgcc        1950
ttgctgctaa gtgtctgact tgagacatgc tatcgagttt ctcaaaatct        2000
cttccttgtg taaaatgtgg ttgtcgatga ttaccttaca ggggttttttt       2050 taagactaaa tgagatcgtg tacattaaat acaggcactc aggctgggca        2100
tggtggctca cgcctgtaat cctagcactt gggaggctg aggggagtgg         2150 atcacttgag gttaggagtt tgagaccagc ctggccaata tggtgaaaca        2200
ccatcccatc tctacaaaaa tacaaaaaag ttagccaggg gtggtggcat        2250
cgcagctact caggaggccg aggcaggaga attgcttgaa cctgggaggc        2300
agaggttgca gtgagtcaag attgtgccag tacactccag cctgggcgac        2350
gaagcaagac tgtctaaaaa aaaaaaaaaa aaaaaaaata cgggcactca        2400
atacaccgta taataataat atagtaataa tatttgctta ggatctttaa        2450
aaagtttcat tttttcagac tcccacagaa atggctctgc acagcagagt        2500
gaagggggag agagactgag tctccaggcc agaaaaaggc caggtttttt        2550
gcttttgttt ttagttgttg cctggatatt gcacagaaag aaaaaataat        2600
tagcaagtta aacaaaagta ccgcaaagtt gattacattg gtatttgagt        2650
atcacatctt ctctcagaag cgtaagagac aaggtcgtga ccatacctct        2700
gcttagtttt gttttgtaat ggtgttgcta gtgatcggct tgtcaccagt        2750
tactggtgtt tctaaatgga ctataattgg ctacttgaaa ggacttcctg        2800
agaaagaaca ttttggagga cgaggagaga gtgccttctc tattttggct        2850
gctttcatgt gacatgcaag agaccatgac gtttaggctg ctgctgaggc        2900
agccccagaa atgggggccg agaggtcttt tcttcatttt aatagggtct        2950
gtaggttggg gtggttaggt acagttctca gaatggaggt tcctggctat        3000
gaggccttga gaaagctgaa agtctccttg ggagtgtgtg ggtgggggga        3050
gtcgagccca tctgttcatg ggcaggtgtc agccaaagcc cttgcgggtg        3100
gttttgaggt tggtgggaga aagcatccgt ggggtttaga gttgtggcct        3150
tttcactact tgcagttcct ttccccgact tggctttact ttctggtgtc        3200
caggggtctg ggccagatgc tgagattcct ctcagctgac aggtgtgggt        3250
tatgggcaaa cccttccctg gaggacataa ggcaccggat tggactgctg        3300
atgggttgct gttggagttg tcaggccctt ggaatagtct tcagatagac        3350
ttgggttagt gtgacctggg gcaggctgca ggtttggagc catagtaccc        3400
cccgccccca caccgggcac cctgctctgg gctaatgtga ggcttgcagg        3450
agtgagtgat gcagtgggaa gggggggcctt tcctgaggat tctacagctt       3500
tctccaggga atcctcccag gtagtttagg cctgcaggtg ctatgctatc        3550
cttctttcct aaccctgtct caggtcctca gcggggccat gcggcatcca        3600
cttataaccc tgcagcgagg ccctcttttc tggccacctg ggtgtttgcc        3650
```

```
tgctgagatg ggaggaacag tggccttggg cttcttcccc cgtcatgttt       3700
atctctgctc agattgggca gcagctcaat gggacttgac cagctgtggc       3750
actgccagtc tgaagatgag tagggtgatg gggggaggtg ggcagtacct       3800
gaagctgaac tggtgagaga ggcaggctgg cctgggggct cagctgggc        3850 ctgggatggt tggtacagtc ccctcagggg ggtaggggag tgagtgttag       3900
actgcttaag cctcagaggc cgctcttgcc cacctatgct ttgaggagat       3950
cctcttcatt tgttcaaagg gaagactctg atctagagat gggcacttgg       4000
accagcaaac agcagctaca ggtagccagg gcacccgagg agcacttgct       4050
catgagccgg tttccctggt ttttatgggg gctgttgctg agcgtctgcc       4100
agggtttgtg tcctagcact tgctggtctt tgctgggctc tcagctctca       4150
ggtgtttctc taccagcacg tttccccctc cctcatatgc acacatgtgg       4200
acacaagcag gctgcccagg acagagtgta ctttgaggct tgggaaagga       4250
ctctctctcg cccttttggg gatgagcctt ggaacctcat caccttccgg       4300
cttggggtgg agcttcatcc tgggggttga agctttaggc tcagataact       4350
agtcttgtaa gccagttttg tcctgttgtt ttttttcgtgg aaaataatgt      4400 attgacgtat acacagacat tctttgtcta acagtctgag attgagaaat       4450
accctccatg actatttggt ttgctttcat ggtgaaactt ggtcgctttc       4500
ttagacacag cctatggcaa taagagtgat ccctggctgc tgtaattcat       4550
tccagacttt gagcaaacac aaggcaccgc ctccacctgc agtggagcct       4600
ctgatgaacc aaatggaaac tccttgggga atggggagta agagccaaat      4650
gtgggattgg acttaaactg cagcttctta gaactgtagc attccacgat       4700
gggattgtct agtgctcttc ctggaggtta ctattcaata gttggctagt       4750
gcacaggttc aggggtgacc tgatatgccc tagcgtttca gaagatccct       4800
gcaaggtgtg tcttttggtc catctgaagg gtcttgtatg gtgatcttgt       4850
atggatatcc gtgacggcta aggcatctga taacttcatt ccttcagttc       4900
cagcagtgtt cctgtattat gctgggcact agagctacaa agaagaaaac       4950
aaagtgcctc ctcttcagga actcttaatt taggcagggg aggcataatt       5000
gaacagtgct gaggtcatct agggggaacca agtgtgtat ttatccccctt      5050 ccctatcact cccctccctc cttcatttct tcctttcttc tttcagaaac       5100
tccaagttca tatcaaaatt ctccagcccct ggttttattt ggttgtgtga      5150 aaatttttcct ctaatttctg aagctatgca ttagttctgc tgagtaatct     5200
ttaacttgct gctttataat gattataatg agatatcact gggtattatg       5250
gtctttgggt agcagcaggg tagggatttc caggctggga ctaagctaat       5300
ttatgggttg ggaattatgg ggcagttaat agcaaggcag tccaagcttt       5350
ccacagattc caccctaggg accatccaga cttaaggaac agggccggca       5400
ggctcatccc ctttgcactc agctgggcta tgggtgtgtg tttgtgaaag       5450
aggtttattc agtagtcata cctgctgatt tccctgctat ctgtttaccc       5500
agtgcctcct gtaccttgtt tcttactctt tgttctctgc tcttactatg       5550
aagaagcaga gactggaatt ctgcttgaac ccacatctac ctggaaattc       5600 cagttttct tgtccagtgg agcagcaatc cagttgtttt aggacaaatg        5650
```

-continued

| | |
|---|---|
| gtctgccctt gaagcttaaa tcctttgagg gcctggcatg gtgacagttt | 5700 |
| tacatttggc tttggtatag actggtgtgg tccctgggca gtgaggtcac | 5750 |
| tgtaaggcca gccagccaga ccctggctcc tagggaatt aacaaggcat | 5800 |
| gggattagac tcacagggtc cctcctgtcc ctaaacttgg tagggttcc | 5850 |
| tgggagccag actgcgatta agattgtaga gacctgagac ctgagttgta | 5900 |
| ggggcctctg tgttgatctg gccattgcc gggtgagctg aggcggtcac | 5950 |
| tagctcaagg agtgatctca ggatattgtt ctgtaagtca gagacctcca | 6000 |
| ggttggagag tggggcttgg gggtgggga cagggtttag tggggagctg | 6050 |
| gttctgggtg aatgtggcct aaagggattt gtccttagaa gacagagggg | 6100 |
| tgagtcacac actcagtgct tcaggttcca ctttgcggct tggcctcagc | 6150 |
| ccgccccttc cctgcacaaa tgaaggccag ggctatata attggctgtt | 6200 |
| gctgaattct ttggcagtga ttttaaagtc tggtctgggt gtgttatgta | 6250 |
| gctgcttctc tatccactcc ccacacccgc tgcttctcca gaccccctca | 6300 |
| caaagcccag gcagagagag agagagagag agagagaatg acttgcctca | 6350 |
| cagagatgtt ggggataggg atagggtat gggtctttgc ttttgccttt | 6400 |
| tgaggggga taatctcttc cttcatttta aaagtaaaaa gtaatgcagg | 6450 |
| ctcattgaaa ataatttgaa aagttgaaag agatataaaa gcacacccaa | 6500 |
| attcctatca cccaaaagaa acataccggc atatttccta ctagtcttt | 6550 |
| tcatgtttaa gaatatagct gatatatttt tttttctttt tctttttgag | 6600 |
| acagggtttt tgctctgtca cccaggctgg agtgcagtga tcacggctca | 6650 |
| ctgcagcctc gacctctcgg gctaagcgat tctcccactt cagtctcccg | 6700 |
| agttgctggg accacaggtg cacaccgcca tgcctgacta attttgtat | 6750 |
| ttttgtaga gatggggttt tgccatgttg cctaggctgg tctcgaactc | 6800 |
| cagagctcaa gtgattcacc tgccttggcc tcccaaagcg ctgggattat | 6850 |
| aggtgtcagt caccacaccc agtgttatag ctgttgtctt tatagatgaa | 6900 |
| cagatagatt gacatagatt catgtagata gcctggtgtt cagcattttt | 6950 |
| catttaagat tctgtcacag acttgaccct ataccttta aaatcacaaa | 7000 |
| ggcagtatca tagtctgtca gctgaatatg ccataactta aaaaaatcat | 7050 |
| tcaactgttg ctgaacacac acatatacat atatagtttt tgttttttct | 7100 |
| tagtgatgta gtgatgcttg tgcagaaagc tttatgtact ttttggatgg | 7150 |
| tttctgtagg agagctttct aaaaaaggaa aaaagtgtt gaatgttttt | 7200 |
| tgagaagggc tagattttca agccagtctt acaaaaggat agactcattg | 7250 |
| gaaattccag atttgcttag tgctggcaga tgagtatcac ttattgctga | 7300 |
| acaatgtgtc tagaattctg attaaaaaag aaactaggtc caggaagtgc | 7350 |
| ctggggcag gggcaaaggg ccaggctgca ggataggctc ttaggatctg | 7400 |
| gctgagcaga atctgctgt gaacagaatc ggtgggggtg atgctttctc | 7450 |
| agtaacttct ccatttgttt ctttagcagc taagtccctg tgctggactt | 7500 |
| ctgtggacta ctgtggctct ggggctgtgg ttgtgggtga acaacagcta | 7550 |
| gctaaaccag tgctgttgac atcattgaga tgtgacgcac aggaaggtgg | 7600 |

```
gagcaagctt gcaaatcaga ttctgaaaca tatagcacag ctctcccacc      7650
tccaggtggt cctgagatct agggaggagc catagtgaga aactttaggt      7700
ttctaggaat tctcttaggg agaagctctc ttagggagag gcagaacctg      7750
gttctcagtt ggggctgatt caggtgggtt agatcaataa agcctcaggc      7800
cagtgtgcca ggctattccc aaggagtata ctttgaagtt actcccttta      7850
gaatgtcctc agtggagata aattctctct gaggagcagt tttgtctgcc      7900
ggggtcattt ggcacaaagc ctggagtgct agggcgaggt tgcactgagg      7950
gaaggggcag gattatgtca gcagtgtgac ggatacagtg tgaggtcagg      8000
ctccttcctg ccccaccacg ggggcctaga ggtcatgggg agggtccctg      8050
gcagggatt caatcattgc ttggccccat gacagagtat attctaaaaa      8100
tgccttaagt ttttttcttt caaagtttct tcctgttttg cataatggcc      8150
ttttgccttt gacatcctga aaccgcagag ctgtcattgg tgttgcagga      8200
cactgccagc ttgaaaaaaa tcaacaacaa aaaagaaac aggaaggat       8250
gtggagttca gggtgcggcc tagggaagct ggtatttgcg ttatgggatt      8300
gtgggatgt ggtattaagg tgttgggtag cgcctgacat ttagaggagt       8350
actctgggca gagtccctgc ctgcccaaga ataggtagaa ttgagtcttc      8400
acaccaaagt caggagagac cccctccccc caggaagaga atgaacaggg      8450
actcatttcc tcattcagca aacttttatt ggtaactaca ctatatgaag      8500
tgtgagagat agacatgaac aagagaggcc cccactcttg ggcagtccct      8550
tagtagtagt agatagactc tggcaatatg gtgtggtcag agagaggaag      8600
cctgggtgct ttgagggtac tgaggagtg caggagcca aatgggtggt         8650
ctgggccagg gccagagtca gaatgaagga cctctcttcc agacgttgat      8700
tttagcatct ctgtctctca gtatgtttga acagtctccc ttattggaag      8750
ggcaggagtc tactgctaaa agtaacctgc gatttcctct acttgctgtc      8800
atgtggaaag aatactaaag ctgaaattcc aaaagttgca cacctttacc      8850
agcagggcag gagaggaaag gaaatggagg cagagtgagc tgaagatgat      8900
aaaagaaaga gaaggtggtg cagttttggac tgttatggac agaggaagtc     8950
tgagggtagc tggactgagg gatcaaaggg aggcagttga aagggaagag      9000
agctgcagag agggatttct tggtctgcag agggtaggag caagccttga      9050
aggctgctgg agtgaggatt ccgagccctg gtctttattc ttttttctaat     9100
tcattacatc attttaggca agtcctaact cctttggtct ctgttgtctt      9150
tctgaaattt gagtgggctg ggcctgctgg tctttagcct ctgtctttct      9200
ctacctccta gattccagtt tggcgagtgg ggggaaaac ctggttgtat       9250
atgcaacgtg aaaggcctct ggaattcctt ttgaagctca ctacccatga      9300
ggcttctgct aaggatttca tcatgtctgt ctaagcagac ataaaaattt      9350
tagcaggtgg atgacccgta gaaatggcac aaggaatgtt tctttctgtc      9400
acactgtggt atttgattta agaaagttgt tatcctctct gtgcctcagt      9450
gttctcactt gtaaaatggc aataacagta tccaccctcat agatgttatg     9500
aaatacaggt agtagccacg aaagggctta aaacagtgcc taacacagaa      9550
taagttgtga atatatgtta tttattattg gtagtataat gcttatttgt      9600
```

```
gaagattttg gcttttgctt tataggacct tttttttttt tagttgaaaa         9650
tacaatgtta ccatgttaaa tgttaaaaaa aattctactt accattgtaa         9700
cagaacatgc tcccacttct gtaacagagc ttgctattac ttttcaaatg         9750
catacatatt ccaatgcata tattccaatg cagttgtaga gtgaaactgt         9800
ttgcatgcag ccattttat ccaacattat cttataaaat gttatgttgt          9850
ttatgattat cctaattatc ttttgttgct gtctagtatc cttatagata         9900
ttccattagc atacactatt ccaggtttca ctatcgtcga taatctagat         9950
atgaacattt ttgtagtgtg tagctctttg cttcagttga attactttcc         10000
tgggataaat tcctggggaa gaatttctag gccagaggat atggtcatct         10050
tgacaatact gattcacatt gctgcattgc tttccaagag gtttggaatc         10100
attcacaggt tctaaattgg aaaatcctgg cttttgaagt atgtggattc         10150
taagggcgat ttggatctag ctggagcctc acactgacac ttccagccag         10200
tgtgtgtgtg tgtgtgtgtg tgtgtgtgtg tgtgtgtagt tccctatgct         10250
ggacaccgtg tgtgtgtgtg tgtgtgtgtg tgtgtgtgtg tgtgtagttc         10300
cctatgctgg acaccatgtg gcctttctgg acattagggt tttcctgtga         10350
ttgcctcaga gcagttcctg ttgaattcac tctgtgtcca caaaaggagc         10400
cttactgtgg ctcttttcaac acccacctac cttttgccaag ttggtttaca        10450 gaaagtaaga acattctttc cttcttcctt gatatgtggc gctaaaccta         10500
tagcatgggg caggctctgg ctttaaaaac ctgacttaaa aataatggtg         10550
ttgatcaaaa agtttgtgga tcagtttttg gaaacactgc atgtagccat         10600
ccatagaaac ttatattctg ttgggctagc ctgggcgcct gatcatttaa         10650
ctcatgtgga tgaacttcta tgtaatagcc ctggtgtatg ggatccagaa         10700
acagggccct aatgaagaaa ggcttttaaa ttatgttgga taaaaataag         10750
ttgttacaat agcccaaagt ctgcaaatat gaattgccag ttctgtcctt         10800
gtagtcatcc accatgtgcc tgcatctttt gtagactctt gtagattcag         10850
aagcccactg aattgcataa atgatggaat gattttagac ttagtgattt         10900
cagtgactaa aagtttacag atcctggccg ggcacagtgg ctcacacccg         10950
tattcccagc actttgggag gccgaggtgg gtggatcacc tgaggtcagg         11000
agtttgagac cagcctggcc aacatggtga accttgtct ctactaaaaa         11050 tacaaaaatt agccgggtgt ggtggcatgc acctgttgtc ccagctactt         11100
gggaggctga ggtgggagaa tggcttgaac ctgggaggcg gaggttgcag         11150
tgagcccaca tcaggccact gcactccagc ctgggtgaca gagtgagact         11200
ctgtctccac ctcccccgcc cccgaaaaa aaaaaaagtt tacagatcca         11250
gcagatgggg catattcaat ttgtgacagc cactccccttc accttatagc        11300 tatgtcatat gtcttcttct cctttgactg cattctgcag cagtcagttg         11350
tgacttaata tggcactctg ggcccactga attaggtcag agctgctagt         11400
agtatattgt tcctagagac ctagggcaag attttcttac tacataaaat         11450
gagggagata atttcttacc tcaagatgtt ggtaagagga gtgaatgagg         11500
ttagttatat ggtaatatca gtactctgaa tgtcttttga tcaatgccta         11550
```

-continued

| | |
|---|---|
| actcatcttc ttgggcacaa aaggcataca gtcagcaccc ttaggccaca | 11600 |
| tataaaattc ctccaaatgc aggttttcat ctgccttggg gcagagtcaa | 11650 |
| gagaaagaag aggaagaggc gtgaggctct gaccacaact tagggacaga | 11700 |
| atatagccca aagcgagtac cccaggccac aaggagaagg ccgctatctt | 11750 |
| gttgaatcca cagcactgga aacttggagt gtgtgttccc ctgtgtcagt | 11800 |
| tacactggaa ttttatggct gctcacattc ttcccttcag gtggacgttg | 11850 |
| ttcatcagta tcctgggcaa gaggccatca taaaccacag acagctgagt | 11900 |
| gattaggaag aggagctgaa gagggagcat tagatgtttg attgagtctt | 11950 |
| aggtgagaaa gtatatcatt aaaacaaaaa gatagatgta ggcgggctca | 12000 |
| gtcttgtgtg cctggtgtgt tggtagaaaa actaaagcac aagcctgtag | 12050 |
| ataacctgct ttattctacc tcggggctgg tgttggaatc caggatgcca | 12100 |
| gaccctaaag tccagctctc tttccaacct actgaataat ccgagagaaa | 12150 |
| tcatgttctc tctctgggcc tcagtttgcc catgtataaa atgagatgaa | 12200 |
| ggattggctg ggatgctctc cagagtctct tcctgcctgg agttctgacg | 12250 |
| tagccatgta ctcctgctca gcatcgctaa atggcttttgt ggtaggacca | 12300 |
| ttgagtgctg cctccattag ggccagctat gtaatgctgg ggtggctgtc | 12350 |
| actgggccct aagagccagg attggtctta ctggagaaat ccacatccac | 12400 |
| ctaaacttaa gacccagggg tgtccaatct tttggcttcc ccaggccaca | 12450 |
| ctggaagaag aattgtcttg gaccgcatat aaaatacact aattatagcc | 12500 |
| gatgaggtta aaaaaaaaaa actcaatatt ttaagagagt tcatgaattt | 12550 |
| gtgttgagct gcattcaaag ccatcctggc cgcatgtggc ccatgggcca | 12600 |
| tcggttggac atgcttgctt tagacctccc agcaattcta gtctctaaac | 12650 |
| aggaaatcaa aagtcaagat gaatagataa gttggtcagt gtgaaaaagt | 12700 |
| aattggtggg agccactgta gatgcagggt tctaggctcc atcaacaacc | 12750 |
| acctacatca ctgaacgaaa gataatgctt gttcagcact tattacatgc | 12800 |
| caaccatggt aaaaatactt cagatgcatt gttttcatga actctcacag | 12850 |
| cagctctttt tcttgcctaa atgccccgtt agaacctcca gtacaatgtt | 12900 |
| aaatagatat gctaagagac aacatatgtg tcttgttagg gggaaaatat | 12950 |
| ccagtctttg actattaaga atggtgttag cagtgggttt ttcctaggtg | 13000 |
| cccttttatca ggttgaggaa gttcctttct attcctggtt tgttgagtat | 13050 |
| ttttatcatg aaaaggtgat gggttttgtc aaatgctttt ctgtgtctgt | 13100 |
| tgagatgatc atgttttttt gtcatttatt ctattgatat ggtatattat | 13150 |
| acattgattt ttcagatatt aatcttgcat acctgggata aatcccactt | 13200 |
| ggtcatggtg tataattctt tttatttgtt gctggattga gtttgctagt | 13250 |
| attttgttga tttgtattca taacagatag tggtctgtag tctttccctc | 13300 |
| cctccctccc tccctccctc cctccttcc ttccttcctc tctctctctc | 13350 |
| tctctcccct cccctccctt cttttcccct cctctccctc cccttccct | 13400 |
| ttcttctctt tcatagttgt ttaccactgt cagaaaaggt ctgttcgttt | 13450 |
| tctttcgtcg tgagatctttt gtttggtttt ggtatcaggg taatactgcc | 13500 |
| tcaaaaaatg agtagggaag tgttccttcc tcttctgtat tttgagagag | 13550 |

-continued

| | |
|---|---|
| tttgtggtcg gttttttatta attcttctttt aaatatctgg tagcgttcac | 13600 |
| cagtaaagcc atctgggcct gatgttttct ttgtggaaaa cttttttgatt | 13650 |
| cctaattcag tttctggtta taggtctatt cagaccttct attttttctt | 13700 |
| aagtcagttt tgatagtttg tgtcttccaa ggagtttgct tcatctaagt | 13750 |
| catctaattt gttggcatac atttcatagt gattccttat gatccttttt | 13800 |
| atttccgtta aagttggtgt agggatagtc cctctttcat tactgattat | 13850 |
| ataatttga attttctttt tttcttagtc ttgccaaaag cttgtcattt | 13900 |
| ttattgatct tttcagagga ccaactttga gttcattatt tgttctcttt | 13950 |
| gttcttattt ttctgcttca ttaacttctc taatctttat tctttcattc | 14000 |
| tgcttgcttt tggttaagtt tgcttttttct ggtgtcttaa ggtagaaggt | 14050 |
| taggttactg atttgagatt taaagatcat gctctttaaa cgttttgata | 14100 |
| gatactgtca gtttgccctc tggcttttttc tcattaacag tgtataggag | 14150 |
| tgcttattcc tcacactcat accagccctg ggtgttacta acctttatat | 14200 |
| atttgccagt atcatattca gacatagtat cttgttttaa tatgtttctc | 14250 |
| tgattactga tgaagttaag caaattttca cgtgtttatt ggccatctgt | 14300 |
| cttctttttt tcatcctttc tttcaagatg ggagtctttg ccatgttgcc | 14350 |
| caggctggac tcgaactcct gggctcaaat gatcttcctg cctcagcctc | 14400 |
| ctgagtagct gggactatag gcgtgagcca ccatggctgg cttgcccatt | 14450 |
| tgtatttctt atgtgagtat ttttttcttt tttttgaagt ggagtctcac | 14500 |
| tccatcccc agagtggagt gcagttgtcc gatcttggct cactgcaacc | 14550 |
| accgcctccc aggttcaagt gattctcaca ccttagcctc ccaagtatct | 14600 |
| gggactatag gtgtgtgcca ccacacctgg ctaatatttg tattttttagc | 14650 |
| agagatgggg tttcaccatg ttggccaggc tggtttcaaa ctggcctcaa | 14700 |
| gtgattcacc tgcctcggcc tcccaaagtg ctgggattac aggtgtgagc | 14750 |
| cactgtgccc agctgacttt ttttttcttt tttttaaccc tttttttttt | 14800 |
| ttacccttttt tttggcccat tttttttttac ccttttttctt ttaacccatt | 14850 |
| tttctattag ttttaaaaat atgtttgcag gagctttttta tattgtggat | 14900 |
| ttttcttgtt tattacatat catttgtaaa tatggtctct ccatctgtca | 14950 |
| ctcttcttta tctctggttt ctttagctat gtagaagttg ttatgttatg | 15000 |
| ttatgttatg ttatgttatg ttatgttatg ttatgttatg ttatgttatt | 15050 |
| ttttggagag ggagtcttgc tctgtcgccc aggctggagt gcagtggtga | 15100 |
| aatctcggct cactgcaacc tctgcctcct gggttcaagc gattctcctg | 15150 |
| cctcagcttc ccgagaagct gtgattacag gcacccgcca ccacacccag | 15200 |
| ctaattttttg tgttttagta gagacggggt ttcactatgt aggtcaagct | 15250 |
| gatctcaaac tcctgatctc aaatgatcct cccaaagtgc tggggttaca | 15300 |
| ggcgtgagcc actgcactcg gccagaagtt ttgaattttt atgtgtttaa | 15350 |
| atctatgttt tcctttatga cttcaggttg ctttcatact taagcaggtc | 15400 |
| ttcaccatcc caaatgata aaattttttct cctgagtttt cttctaagtt | 15450 |
| ggttctttag aagccaccaa cttggcttcg acagcaaaag atgaacagaa | 15500 |

```
tttctgttca actctcatgc tgcaagaagc tttatgtaat actccaggga      15550 cccttta agg tcccagagtt ttcctccaaa tctatcagtg attctagtgg      15600
ctaagagtag aaatgtgaaa atttagccat gtgtgctgat agagctgtag      15650
taatttgtaa gctctgaagt tctaaggagt caggggagaa gggaaagtaa      15700
catttattga acatctatta gctcaataag aacatgcgat aagtatgtat      15750
atgtattatt tcacttacat ctgaaaggaa ggcataatta tccccactcc      15800
ttagagaagg aaattggagc tggctacatt taaagtagtc ctgacaccag      15850
agagatattg ccaggagtac ttggctggct gagtgcccag atggcccata      15900
ggagtagtgg gccctccaca gtccaaggtc tggttctagg tggagagaga      15950
aggatgtgct cgtagtcagc accgcagctc cagaaaatct gctggggctc      16000
caaaactgat tagaggggca gctgactcag taataaaact cccaggagac      16050
ttacttacat actggaatgc aaagttgcag ctttactggg aagattagaa      16100
ctgttattga gtagcttaga aatctctggc tgaattcact gcaagggaag      16150
ccgcaggata agctaactgc tggtgagtca gcagtcagag cagggaagtg      16200
aatttaacat tagatgggtc agtctctcgt ggctgatgaa ttcatcccca      16250
caatactgta cacctgcctt agggaccttt gtctggacta ggggttgggg      16300 tcccctcct ttgtacagcc ctggaaggac acatccagct ccatccgcca      16350 tctctcccctt acttatttcc ttccttcctt ccttctttcc atccagccat      16400
caagcttcct ttcatggcca ataatcatca ttggggtcta ctcatggact      16450
ctcttgcctc atgtatttgt tttattttgt cctcattccc acttctattt      16500
cccaggtata tcacaggcaa ctattctaac gtatttatag tttgtgtatc      16550 tgttttttgct cttgccaaaa tggaagccac tgctttatac atagatgtat      16600
tcttaacttt aaaaaaaatt ttttagatt aacctacaat aaaattggct      16650
ttttggcata tagtctataa attttaacac atacatattt ttgtgtatct      16700
accaccacaa tcaggataca gaacagttcc atcaccccaa aaaatccct      16750 cttgtagtca cattctcctc ccacccttaa tcccaggcaa ccactgatct      16800
attcttcatt actattgttt tgtctttttg aggatgtcac ataaatggag      16850
tcacacagta tatatacatt tttttaaaca tatgtaaatg gcattttata      16900
gctcattttg attatatgtt tttcatccag ttctgttttt ttttttttatt      16950 tttaaaaagt ttgacataac ttcagactta cagaaaagtt gttagactaa      17000
tacaaagaat tcctggatat cctttggagt ccctaaatgt taacatttta      17050
ctatatttac ttttctccttc tctctctctc tctctctcgc tctgtgtgtg      17100
tgtgtgtgtg tgtgtgtgtg tgtgtatcta cctgtagata gatagatatt      17150
aatataattt tagatagatg tatctagatc tctctctctc atatatatgt      17200
gtgtgtgtat atatctatat ctatatctat atatatctcc ttttaccctt      17250
aaatattcag tgtatatttc ctaacaacaa ggtgatttaa aaatatatat      17300
ataaacatag tataattaac aatcaggaca tcaacattga aacatttctg      17350
ctatgtcatc tacaggcctt aggaagactt tgtcaggtgc cccaataata      17400
gccttgatgg tagaagaaaa ccatgtgttg tattcagttg tcatgtctct      17450
tagtgtcttg taatctgaaa taattcccaa gccctttgga tttcatgaca      17500
```

```
gtgacattgt tgaagagtac aggccagtta ttttgtagaa ggtctctcag      17550
tttaggtctg tctgatgttt cctcctgatc agattcaggt tattcacttt      17600
tgacaggaat accactgaaa tgatgctgag ttcttctcag tgtaacgaga      17650
tctagagaca cacactgtca gtttgttcct tattggcagt gtgaaccttg      17700
aggatttcat tgtagtggca tttggcatta ctccattata gttactattt      17750
taccatttta aattaaaact atctggccgg gcgtagtagc tcatgtctgt      17800
aatcccagca ctttaggagg ctgaggcggg caaattgctt gaggtcagaa      17850
gtttgaaacc atcctagcca acataacatg gtgaaacgcc atctctataa      17900
aaaatacaaa aaattagcct ggcgtggtgg cgcatttgta gttccagcta      17950
ctcaggaggc tgaggcacaa ggcttgcttg agcctgggag gcggaggttg      18000
cagtgagctg aaatcacgcc actgcactct agccagggtg acagagtgag      18050
actctgtctc aaaaaaaaaa agtaaataaa taaaaaaatt ttttaagtat      18100
cttatgggca tatacttgtc ctgttactcc tcaaactttc atccactttt      18150
ttttttttaa attttttttc ttaccttttca tcgttttctt gatatccact      18200
gggttttagc atctacaaat gattcttgcc tgaatcagtt attatggtag      18250
ttgatggttt tctaattcca ttattccttc tatgtttgtt aattttggca      18300
ttcttctata aggaagagct tacccttttt ccctattaat taattcatat      18350
attaatgcag acctatgcat tcttacttca ttaaatcata atcctttact      18400
atcattatgt attctgatgt tcagactatc ccagatttag ccaataagat      18450 cccccttcagg ggaatggtct ttgggattcc tctttagagg ttcctggttc      18500
ctgttttctt ttgacatatc ctattactct ttgagcattt ttttttttt     18550 ttttactttt aggcacagca agaagttcca tggtcctctt gttctttccc      18600
caactcagcc ctagagtcag tcacttctcc aatgagctct agttcctttt      18650
agtagagaat cataattaga aaacaagaat cagtgccaag tgtgcacctt      18700 tgttttttaag gtccatccac gttgccgtgt atatgtccag catgttgatt      18750
ctaactgctg aataatacct catgattgtc atccatccca gtgtttcttt      18800
ttcccttctg taatgaggga ctcctggact gcctccagca ttaccttcac      18850
aaatattgct gtgaggaaaa tccttaaacg tttcctttat gggcaacgtg      18900
tgagcatgtt tatgttgatt caggggtgcc agacacagct ccagaatggc      18950
tgcctcagtt tacatttcca ccagcagagc atgacaggct ctgtgtctcc      19000
gtgaataatc agcattaacc agcttcctat ttttgccaa actaatagat       19050 gtgctaggat aactctttgt tttaacttgt ttttctctga ttaccaatga      19100
gctggagcat ttcttcatat gcctgatggt ctttgggatt cctcttaggt      19150
aaattgctta ttcattataa tcctttgcct gttttttcact ggagttctta     19200 tattttttctt gaagatatgc aggaattcct tatacatcct agatattaat     19250
cccttcctgg tctcagacat tgcagatatc ttctgaatct gttatttact      19300 tatttatttta caattttttt tttaagagtt ggggttttgc tctgtcaccc     19350
agactggagt gcagtggtat gatcatgact cattgtggcc tcgcaatcct      19400
gggcttaagc gatcctccca cctcagcctc ctgagtagtt gggactacag      19450
```

-continued

```
gtatgcacca ccagacttgg ctaattttat tttatttttt agagatggaa        19500
gtcttaatat gttgctcagg ccaatcttga actcctggcc tcaagcaatc        19550
tttccacctc agcctcctgc atctattata tatatgttca ctttgctcat        19600
gctgtatttt gttgcaacat aaaactattt ttcccattgt tttgtgcagt        19650
ctctcaccag cactcttctt tttctgtaac tgtgttaatg ccctttgttc        19700
ttccatatgt taggtatgct ggtatagttg aactctgctg actctcctca        19750
gtaaacagtc tcttttatg acaccttatc ctctactgaa ttctctctat         19800
caagaatgac ttggccgggc atggggctc atgcctgtaa tcccagcatt         19850
ctgggaggcc gaggtgggca gatcacccga ggtcagaagt tcaagaccag        19900
cccggccaac acggtgaaac cctgtctcta tgaaaataca aaaatcagct        19950
gggcgtggtg gcaggtgcct gtaatcccag ctacttggga ggctgaggcg        20000
ggagaatcac ttgaacctga gggggaggtt gcagtaagcc gggatggcac        20050
attgcactcc agactgggtg atggagaaac tccatctcag ggggaaaaaa        20100
aaaaaaaaaa aaagaatgac ttgtcttcct cttagagtgt gaggtctaca        20150
tacaaatatt attcttgtat tcagcaaatg tatgtcatag gcctagtgtg        20200
tgttaggaac tgtgctgtca ccaacaaagt ttagagaggt tataaaactt        20250
gactgtagct ttttagaggt ggaggagtga tttgaaacct aggctgtaat        20300
tccttcctcc tgtgattcct tcctactgtg ttgccttccc ttgaaaattg        20350
catttggggg ccaggtgtgg tggctctcgc ctgtaatccc agcactttgg        20400
gaggctgagg cgggtggatc acctgaggtc aggagttcaa gaccagcctg        20450
gccaacatgg cgaaaccccg tctttactaa aaatacaaaa attagctgga        20500
tgtggtgtgt ggtgacatgc acctatattc ccaggtactc agtaggctga        20550
ggcaagagaa tcacttgaac ccaggaggca gaggctgcag tgagctgaaa        20600
ttgcaccact gcactccagc ctgagtgaca gagtgagact ctgtctcaaa        20650
aaaaaaaaaa agaaaagaaa gaaaattgca tttagttcct gtagactgtg        20700
tgtcaaatgt ctaaatctct tctaacaaat ggcctaagga ggtgcaaagc        20750
gaagcatcct caccagcatc ctgacttggc agtgaggcat gggaccctgg        20800
agggagtagt ggtaagtgtg actctggaat tcttcctggg ctacttgtca        20850
gtgactggct ccagattgag aggagagccc agaggacaca ggtggctgcc        20900
ccagcctgga ggtgaaagtc ttaaaataaa atgccagatg cctagaccat        20950
tctaaacctt tctgagaagc tgaaatcatc ccttctggaa gcgctctagt        21000
tctaaaagga cagatataca gcaagatctt cctggggcta atatggagtt        21050
tataggcaag taggcctcag aacctttccc tggtagtgat atctgtgggc        21100
aggcacagtt tccacacttt ccagaaattc agcggaagg agtgagaagg         21150 aggaatctgc ccttgagtga ggaccaaaga aagcagaaat tcctcttggg        21200 aattttttcct ccagagacca aacactactt gggagcttgt ttactgggct       21250
ttaaaagctt gtgaccccca gtcactcttt cttgacccca aggctttgca        21300
tttctgtggc ttccccactg gacagaagtg gaactgtcat gctgcctgtt        21350
ctggggtctc ccagaggttt ccccatgtcc tctccttgct tctactgccc        21400
cacagaattg gggatctgtg accacatatg gtatagaatt aatgcttgag        21450
```

```
aatggtttag ttcagtgatg tcaaataaga ttcactttta tgccacctcc       21500
atcagttgaa ggcccccctg gcccctaaat tggaaaagat tctgagacag       21550
aatccccgtg ggtacagcgc agggacagta aaggcacgtg tgctgtgatt       21600
tgctatccac tgtgtggatg catccaggaa tatcagaacc ctggaagatt       21650
atttaagggg aagttaggac agcttttttg ccaatccaag ggtgttcttg       21700
aggaagtctg tcttcctgta tggccttcag tttctttcct gtgtaaccat       21750
ggggccaaca cataattccc acagctctat ggcccttgt ctgccaggat        21800 tctctagggt ctgattcgag gtggatcctg gcccttgag gtggcagaat         21850 ctgatcatgg tgctgtttcc ttagatttag gccttgatac ccttggcgag       21900
agcatcctgg gctgagtgac cacctgaggt ttttctggtg attttgtgac       21950
ccatgtaaaa ctttgagctt tgggattatt ctctcaagga aatagtgaca       22000
tttggtgaag agcctgtttg gtgtggctat gtgaggctta gccaagaaaa       22050
tgcaccattt ttattaggag gttaggccat ccgttgccac aaagtgtcag       22100
atgctaggcc tagagcctgg agaaaactta ttttaaaatt gatggggtgc       22150 tggagggggtt gggggggtggt ggctgtagct catgaatcag gtgctaaacc      22200
tagaaacaaa aggcctcatg tggcagactg tttctgagca cagatgaatg       22250
gatgagcaac tggcgcaact ttgcccagtt ggtccagctt cccacttggc       22300
cacctaggct tgctgtgaag acctcgtctg gcagaaatga gagtgttttt       22350
gccccatctt gatcttaact gtaatttaag actaaaatct tagattctaa       22400
aacatcaaag gcaagatggc tcccagctct gtgagctcag cttctcacct       22450
cttagttgaa caagtgcagt gtgggtcaat acatgattgc tgctcttgct       22500
gccaggaact gtcccagcat agaaaggaat gggacacaat ccctgccgtc       22550
aagattctaa gggaggaagc aggcaggtcg actggtgcct catctctgca       22600
gggctccagc caaggtttgt gaaggatttt gcaggcatat ggagtgggga       22650
ctgattgatc ccgagagggg actgggggaaa gctctgaaga ggggatgaca      22700
tttggtttga actccaaaaa atggttgctt tacctgtttc ctgaagtttt       22750
tgaggtggct tataagaaca tataccataa aaaggaccaa tataaattta       22800
aaatcagaaa aagagaaaat gggctgggca tggtggctca tgcctgtaat       22850
cccagcactt tgggaggcca aggtgggtgg atcgtgaggt caggagatcg       22900
agaccatcct gcctggccaa catggtgaaa ccccggctct actaaaaata       22950
caaaaaatta gctgggtgtg gtggcacatg cctgtagtcc cacctacttg       23000
ggaggctgag gcaggagaat cgcttgaaac ctgggaggcg gaggttgcag       23050
tgagctgaga tcgcaccact gcactccagc ctgggcgaca gagtgagact       23100
cctcctcaaa aataaataaa taaagagaaa atggaactta gaaaattaag       23150
aggaagagtg aaaaggtaga tatttagtca ggcacagtgg ctcatgcctg       23200
taatcccaac actttgggag gccaagacag gaaaatctct tgagaccagg       23250
agcttgagac ttgcctggca acatctcagg tgagacctta tctctacaaa       23300
aaatttaaaa attagctgag ctgtgtggct cgtgactgtg atcccagcta       23350
ctcaggaggc cgagaccaca gcccaggagg atcgcttggg cccagcagtt       23400
```

-continued

| | |
|---|---|
| tgaggctgca gtgagctggc accactgcaa ttcagcctgg gctacagagc | 23450 |
| aagacccagt ttaaaaaaaa aaaaaaagat attcaaacca tgggtcccaa | 23500 |
| cgtagttatt atatttgacc atttgcaaaa gctgaaagca aaacatgtta | 23550 |
| cacattttca gagaggaaaa tacacagtag ttcctgagtg taagttgttt | 23600 |
| ttcttgacct cattcttaaa ttgcttcatg agggtgggag ggaagtggta | 23650 |
| gttaataagt gaacctgtaa accagcgttt ctcaaaatgt agtccaggga | 23700 |
| attgcatcaa aattgcagtt acctacagtg cttgttaaaa tgcagattcc | 23750 |
| tgggcccctg ccccaggctt atcaaatcaa tctggtgagt aggactcaag | 23800 |
| aacctgtaaa ttcacatact tctgcagatg attcttcttg cactgcacag | 23850 |
| catgaaagcc tctgcaatag acagaaagct accagcattg cgaaagcaac | 23900 |
| ttgagtgctt ggcctttgaa ggttgagtgg gactttaatg agggagagag | 23950 |
| taaggcatga gaaatggcag ttccactgag gtcagtcagt ggttcattgc | 24000 |
| tgacgaagtc acttttaagt catgttttag aagaactacc aagtgtggca | 24050 |
| ggtcaggcat gtggcaggac tgtttctgag cacagatgaa tggatgagca | 24100 |
| cctggcccca ctgtgcccag ttggtctagc ttcccacttg gccacctacg | 24150 |
| gtctgctgtg tggaccttgt ctggcagtct cctttaattt attttttatt | 24200 |
| atttttttct ttttgagatg gagtcttgct ttgttgccca ggctagagtg | 24250 |
| cagtggcatg atctcggctc actgcagcct ccacttccca ggttccagcg | 24300 |
| attctcctgc ctcagcctcc caggtagctg ggatcacagg caagtgccac | 24350 |
| cacgcccagc taattttgt atttttaata gagacatggt tttaccatgt | 24400 |
| tggccaggct ggtctcgaac tcctgacctc aggtgatcca cccatctcag | 24450 |
| cctcccaaaa tgctggaatt acaggtgtga gccaccgcac ctggcctatt | 24500 |
| ttttttcagc aaattctttg ttttttctctc tgttcccaaa tgcagggtac | 24550 |
| tgagaccaca gatgtattct gtttcctgtt gaaaaaatgt ttctcactta | 24600 |
| gctgggtgtg gtagcatgca ctgcagtccc acgggaggct gaggcgagag | 24650 |
| gattgcttga gcccaggagt tcgataatca tgccattgca ctctggtctg | 24700 |
| ggtaacagag cgagaaactg tctcttaaaa aaagaaaaa gaaaagagg | 24750 |
| tcctagggaa agaaacaaat agtggcttgg atggtgagtt ggtggaaaga | 24800 |
| acagtggggt ttgggggtgt tgaacttgtg tttgtgtgtg gtgtacccaa | 24850 |
| gacatatcat gtcagcatta agaatagact attcctgttt tctggtcact | 24900 |
| gagttgtatg ttttgacatc cttatttgg aagatacttc cttactagga | 24950 |
| atgggatagg gaggggtca cctttcccat ctgtgggtca tattttaaaa | 25000 |
| tatttattgt tcaagtttaa agatataacc aaaggtataa agaaaaatac | 25050 |
| cacaaacatc tgatttaaga aacaaaccag ccgagcgcgg tggctcgtgc | 25100 |
| ctgtaatccc agcactgtgg gaggccgagg caggcagatc atgaggtcaa | 25150 |
| gagatcgaga ccatcctggc caacatggtg aaacccgtc tctactgaaa | 25200 |
| atacaaaaat taactggtca tggtggtgtg tgcctgtagt cccagctact | 25250 |
| cgggaggctg tggcaggaga atcgcttgaa cccaggaggc ggaggttgta | 25300 |
| gtgagccaag attgtgccac tgcattctag cctggcgaca gagtgagact | 25350 |
| ccgtctcaaa aagaaaaaaa aagaaagaa atcatttcct acaccttcga | 25400 |

-continued

| | |
|---|---|
| agccttcatg agttagattt tgaaacagtg caaaatgctt cacgtgagaa | 25450 |
| tcgagagtcc cttctggtgg ctctccatcc cctgctcttc tgtcaggttt | 25500 |
| tcttgtaggt ttatggaaac ctttgttact tgtgcaggtg gcagagaagc | 25550 |
| agagaggata gctgcgcgcc acccacacag ctaggattta ttggcgtact | 25600 |
| cccacgtgca tggcagccaa gtggacacaa ctctgtgatg aatcctccca | 25650 |
| agagaactga ggggccctga tggaggagct gcttcttttgc aaagctttcc | 25700 |
| ttgactctct tcctgtcccc tagttgattc cccttctgtg ctagttttag | 25750 |
| cttattgttt gttacctgtc acacttagca gtactgttgg ctttgctggt | 25800 |
| ctccttgact actgggggta aagaccttt gttgttgttg ttgagacaga | 25850 |
| gtcttgctct gtcgcccagg ctggagtgca atggcgtgat ttcggctcac | 25900 |
| tgcaaccttc acctcccagg ttcaagagat tctcctgcct cagcctccta | 25950 |
| agtagctggg attacagcta caccacaccc ggttaatttt tgtattttta | 26000 |
| atagagatgg ggtttagtag agatggggtt tcaccatgtt ggccaggctg | 26050 |
| gtctcaagcc cctgacctca aggtgacctg cctgtctcag cctcccaaag | 26100 |
| tgctgggatt acagacatga gccaccatgc ccagcctcaa agacctcttc | 26150 |
| tttacttgct caccctgccg cccactcccc taccaacccc tgcatgccct | 26200 |
| ataccacctg gcacatgata catactaact gggtacatgt ttgaatatga | 26250 |
| atggatgtgg tgctgtgaat gcttaggga agtgggtgaa atgcttaaga | 26300 |
| accaaccttg agtggtctgg gaaggcttcc tgggagggtg gtgtttgagc | 26350 |
| taaggccagg cagctgttag atttgttaga ctgaagccct tgcagactta | 26400 |
| gagagcttgt gctcttccca gaatgacggg tgagccacgt acagtaaatg | 26450 |
| gtgcttctca tttctagccc aaggggcctc aaggggcacc gtgatttcac | 26500 |
| gagaatgctg caagcaaatc ttttctcaag ctggggaatt tggtggtaat | 26550 |
| gcctggctca gcttgcggtg cgcacctggc cttttggaaga ttggtacaga | 26600 |
| gagaagcggc ccatccacat gagcctgtgg aacagcactg gtggggagc | 26650 |
| tgatttgtga agaggggctg tgcagtgtac tgtcaggtct gagacccagg | 26700 |
| aagaaattcc agtatcccag ctctcagaat cacagagttc taggcactgc | 26750 |
| ctagttccac gtgttcccaa atgtttcctg aatacttgga tttcctgtcc | 26800 |
| agagaatttt caaaacaaac ttagaggcct gacccatggc tgccaaggaa | 26850 |
| ggatttttt tttaaattaa attttaaaaa tcagtccagc atgaaaatct | 26900 |
| atgatgattt cataagagaa aggacatttt aatattcaaa gagtaagaag | 26950 |
| cacttaatct tggaagaaag ggcattccta tactttgatt acctttagtt | 27000 |
| taattaaaaa acacctacat ggtctttact tctgtgattt cattcctggg | 27050 |
| ctagtgaaac attgtcacaa taaagcatca ggccaacgct tctttcgacc | 27100 |
| cactggccaa tcagttgaca aacagtgact agatgtttca gcctattttg | 27150 |
| ctgaggctaa aggattgaac tagtgcttca gccagcatga aaaccagtca | 27200 |
| ggagtccgtg ctggtgttgg cttagattag cagggccttt gatggagggg | 27250 |
| catgtatgtg tttgggtttg ctgtgccagg caggggagca gtggaatttg | 27300 |
| tctgaattga gctcacacat tgaagttatt gagcgactta catgcaaggc | 27350 |

```
catgacctgg actcccagcc gagaggccca cgtggcgggg cttgagctgg      27400
gggagccgag gacagcttac atctgctcat ctgcttacgt aaccctgcct      27450
cccagcttcc agagccaaga aaacacacaa gccagcccag cggggccgag      27500
agcctgtggt agcacacgcc atgcgccgca cagcaagggc gccttggctc      27550
ggcttgaggc ctgtcatgaa gccctcagcc ctctgcctcc tcccagagct      27600
tctccccacc accccaggca gtggctctga aacctggtcg caggtctgca      27650
tgattctgaa cagaggtagt cgttgccttc ctggagtctg agctctctgg      27700
agtttctcac tgggacagag ccaggtgtgt agcagagcat ggtccctgca      27750
gtatggcagg aggtgtgcag ggcattcagg aggcctcctg gctggcactc      27800
gacccaatta gtcattcaac gccaggtctg ggctgctgt ctgttgtctc       27850
aaaggtgtga gctgcaagat ccttagagtt gtggagaaaa aattgccaga      27900
ttggcaagaa gggcaggatt gggggtcaag gtgtctcagt gtgttggaag      27950
catgatgggg gttgtgcaag gggcacagcg agttcagaaa ggagcaggag      28000
agtgagaaga ggctgttcag tgataaagct ctgcacagag ccattggagg      28050
agcaagctcc ttgaccatcc ttaaaccagg gtaattttca tttaggttct      28100
gccacacgct cagcagggaa ctcctggaag gcaggatttg tcttgtccat      28150
cctccctccc tacctcaacc cactcctcct tgggctggca cacagtaggt      28200
acccagaaag tatcaattga aacaaattga aagtggtctt gatacatatc      28250
acagggcaag tttgcagtta acagacattt cagagtaaag actctctggc      28300
ttggtgctcg atcggcttct gtgggttgtc agcatgctgt ggacagcccc      28350
ggcatggagg cgagtgggcg tgtgtgtgtg tgtatgtgag ggtgagagag      28400
cgttagtgtg tgtgttgggg ttggggagag aggaggggga atagaagatg      28450
gaccacccgg gtatcagctt ctgccctggg gagatggtgg tgtcagttgc      28500
tgagggaatc ctgagaagca ggtctggctg taggtggtga tggtggtggg      28550
gttgcatgag aatccatttg gggcaggttg aatttgaggt gcccatgaca      28600
tatggctagc catgttctgt tggctgtgag gtcaggagag agacatgaga      28650
tggaaacaga ggtttgggaa ctgtcatgtg cttaaaccaa agacctgggt      28700
atagggagag tgagaagaga aggggcaaa gatggacatc caagaaagaa        28750
gctgagaaag cctaggaatt tgaggtaaga ggagacgtag gtaaatgtga      28800
cgcttggtga tcaaggcttc tttccacctc tcctatgctg gacactcacg      28850
tctcctgtct gcttggaaat tcatgctgag ggcagggaag gtgggagcaa      28900
ggatttgtct aaagatcttg ctttggatcc ctgcactcct cctggtttac      28950
caagtgtcac tggacacgtc agggcgttct gagaccttag agagcatcca      29000
gtcctgtccc tgcagtttac aaatgaggaa accagtaccc tgagagtggc      29050
tgtactatcc actctcagga taccaaagat catctggaaa gtcactggtg      29100
gagctggacc ggggcccagg catctcttct cctgtccggg gctcttgact      29150
tcaggaccac ctttctgaaa cccatgatgg ggcaacacca ggacactttc      29200
cagcctgcag gtgtctgtcc cgcggaagcg agccaggcca catgtgaatt      29250
cctgtttttct gggtgggttt cagaaggtac gagcaagtcg gcagggtgac    29300
agcccaggtg cttcttgggt tccccaaaac gcggttatgt ttagcagcat      29350
```

-continued

| | |
|---|---|
| cctcagaacc aaaggtgggg tgggggctgc agatgttgtg ggggccctct | 29400 |
| gaagtgaaaa gagccctgtg acagatcttt tcttcatgtt tttcacaagt | 29450 |
| tcactgtgca gcagggcccc cccagtagcc tttgcccagg gttgggtgtt | 29500 |
| gggcagccca ggcctggctg accttgtggg aagggtgtg aatggtggga | 29550 |
| atccccgagg gccctctttg cccgaaagcc ctaagccttg acatcagatg | 29600 |
| cccatcagat ggtccatcgg agccctacta cccagcttgc ccagtgagaa | 29650 |
| tcatctgggc tccttgttag gtagccattt aggtccttcc caaaatccac | 29700 |
| agactctcta agggaagggc ccgagatgct gtacttgtac taacttcctc | 29750 |
| aagcaattct tgtgataggt ttgggaaaaa cttgtccagg gtgaccactg | 29800 |
| actgagtcct ggtcttctct gaagagcaca gtgcctgctc actttagggc | 29850 |
| accctgggag gtgggagctg gctcagcagg cagtcttata agggactgag | 29900 |
| cttcaaggcc tctgtccctc caggagggag gtgcatgacc agagagggag | 29950 |
| gcctgaggat cttcttccct gccccagagg gtctgctgcc tgagctctgt | 30000 |
| gatagcgcag agagtaaaag gatcaagctt gattgaggcc tatctctcaa | 30050 |
| tgcgaaagtt tgctagttaa gaggagagtg ggaagggcat ttctggcaaa | 30100 |
| gagaaaagtg tggacaggca tggcttaagg gatgggagg gagacagaca | 30150 |
| gagctgaggg tgaagggcct tttgctcagc tgtgggcctt ggccttccct | 30200 |
| tgtgcaggga cacacagcct tagagccact ggaggtttta gtgggaaagt | 30250 |
| aatatggtcg gggctgtatc tcagaagaaa acaaactaat gggaacaggt | 30300 |
| cctgtgatgg tggacctggg tcagctacgg agggagggaa gatgtgagat | 30350 |
| gtgtactggg aaggggggtg gaagtggcag ctatctggtg agaggaagca | 30400 |
| ggcccacagc ttttttttctc aagctgttga attcagaagg gcgagtgatt | 30450 |
| ccgggagtag ggggtgcttg gagagccacg cgttattgat aaacagggca | 30500 |
| ggctgaagcc tgctcactgg ccctgggcgg ttctcacca gcatgtttca | 30550 |
| ggttttgatc tgtgcttgtg gttggtgttc ctacctgttc tctaggttcc | 30600 |
| ttcctttgtt cttgtggctc atttgcttca caggtgaagc tggttacact | 30650 |
| agagtaacag ttcccaaagt gtgttccctg gaaaatggt tctgtagcca | 30700 |
| aataagcttg ggaaatggtg ggttaaatat aacgaagggg gttttcgac | 30750 |
| tgcacaactt ctcagagcct ttggtgtgtg tcgtgacttt gcagaagcag | 30800 |
| gatttaatac gcagcattcc cgttcttatt tgaccacgag acatgttttt | 30850 |
| ccattaagca tcttgctggg tctgatgttt tctggaaccc attttgaggc | 30900 |
| ggtctggtct gcagagagta tggggagcct gggttcaagc cttggctctt | 30950 |
| gactctcagc agagccttga ttccctgtgt tgcctggact gcaccacgtg | 31000 |
| taccacatac ccggtatgtg acgttttcct catccctctt cccacctgcc | 31050 |
| gttacctcac aatccacaat ctgcacctca tccattttc ttctgaggca | 31100 |
| agcactctct tactaactta cttatctcat ctgcatccat gttcttctag | 31150 |
| gccagaaact tgggagtcat ccctccctct tgttacttc ttcttcctct | 31200 |
| ttgttacttt atccctctg ttactaaaca ttccttctgtg tttccagcta | 31250 |
| tttcttttat tttccctcgg tctcctttgg ggtttctttg cctccatctc | 31300 |

-continued

| | |
|---|---|
| tcccagacct tggttcacct tccatcgagt cccttcctgg gacatgggca | 31350 |
| ctcatgccac tcctgctacc ttccacttcg aagctaactc cctccacact | 31400 |
| gacgtcccca acatgcatgc atacacacac acacacacac acacacatac | 31450 |
| acacacacac acacacactt ccccagttag gctagaatca gagagatgat | 31500 |
| gtcagccatt tgtccaaggc cacgcagctg ggaggtcaca gagctaagtc | 31550 |
| tcaacctcag gggttttgag aaattgcctt ctcatccgtg atcactgatt | 31600 |
| tctacaacag cctgtcagga agtctgggta gaaattactt ccattttaca | 31650 |
| gtggagtcag agcggggagg gtcctgggca ggcgagtgct tcacagagtg | 31700 |
| accaaccatc taggtttgcc ccacactgaa gggggtttct ggggatggtt | 31750 |
| ggtcacccta atgctggatg tggtgcctga tgctgggcag gagggccctc | 31800 |
| tccgtggcca cgttgcctcc caggaggaga catttcctct gcagctgcag | 31850 |
| ctgcagcctg gccatctgat gcagcctgtg gagcggtggc gagtcctgtg | 31900 |
| gcctgctaac ttctccctcc ctccacctct ctagtgggcc ccatgctgat | 31950 |
| tgagtttaac atgcctgtgg acctggagct cgtggcaaag cagaacccaa | 32000 |
| atgtgaagat gggcggccgc tatgccccca gggactgcgt ctctcctcac | 32050 |
| aaggtggcca tcatcattcc attccgcaac cggcaggagc acctcaagta | 32100 |
| ctggctatat tatttgcacc cagtcctgca gcgccagcag ctggactatg | 32150 |
| gcatctatgt tatcaaccag gtgaggcctg ggaaggtgga atgagagagg | 32200 |
| gtgtgtgtgc atgcagatgt gtatcagatg tgtgtgtaat gagggcaggg | 32250 |
| gaaggggagt gatttcacag acacctggca cttacagcga ggaaccagcc | 32300 |
| ccccagccac caccagtgca gatgaggtaa acgccaaaca gtgtgcttgc | 32350 |
| ctattgctgt caactctata gccaagggaa atgctggagt gttttcgttg | 32400 |
| ttctgttttt gttttctgga agtagccttc cagcaagatt gggaaaaaag | 32450 |
| acaaccctaa ttattccaaa gtacacactg attattccct ggctttgtgt | 32500 |
| agctgtgtat tttccttta aaaataaaac caccatttag atgtcagact | 32550 |
| tttaggtaac ttcaaagttt atccagtcag tcagagcgtg tctcctgggg | 32600 |
| cacctggaga cagtgccctt agttcaggtc acatgcctac atgccagccc | 32650 |
| ctggtgaaat atctggagaa gtctgattcg tgggccatct gagagttatg | 32700 |
| tggactgggc cgagtctgag aaaaagtttc tcactgctcg tctgatccat | 32750 |
| atgtgttggg ctttagccct gcttaggaaa gtaatgctaa ggataggtca | 32800 |
| actttcatca ccatggcatg gagaatcaga ttgatctaag aggcatcttt | 32850 |
| attgaaataa attttcagt ttatttgagg agcattattt tcccaagagt | 32900 |
| ataactttga tatttcaaga ttaccctaa cacttaaatt catgttttta | 32950 |
| gactataacc tcctaggtgc aatgacacat ctaacttatc taagcaccca | 33000 |
| gtttcattga aattcatttg aagagtctga gtacgcccat ttctacaagg | 33050 |
| cccaatgtcc atttcatttc gagataaact ctgctttagg taggaggatt | 33100 |
| gttggcagtt tacggcttcc atcaaggtca aggaactctg tgcaccttcc | 33150 |
| ctatgacccc aggggaagca ctcgaggact gctgtggcat tgtgctgcat | 33200 |
| cacttgctgc agggagattc tgaagaagtg taaggtctca gtcctgccct | 33250 |
| gtcccgaagc ctccaaccca cttctggcaa gtgggacctt cccagggaac | 33300 |

```
aatttgttaa cagacccaaa tatcctgtga ttggatggtg gctgccaaat       33350
gctttggaag ctcagaggaa ggagagagag caatggcttg gaagaaccag       33400
gatataaact aggttctaaa gtctgcaggg agatgggctt ctcagctggg       33450
gccagtgagc agggacctta aggcagaaag gagccttgca tgttcctgga       33500
aattgagatg cccactgggg taggaaagca ccagaagctc tgggaccagg       33550
tgtcagagtt aagcctgtga ggcaggagag agcagaacaa gccctgttac       33600
aaggaaactg aagcaggaga gcaggtggtg ggcaaacccc ttgaggctgt       33650
ttgaattctt cggccaagtg aggtacagac cagggcccta tgaacacctg       33700
caagcaagac agccacgcag ttgtgggtca ccttggaaga atattggaga       33750
atgcaagaga gaacaggtaa atgtcctgca aaatgcgggt cactttaacc       33800
caacacatat tcatttaaga aaagctctgt gattgagaaa catttgtctg       33850
atgccagtta gcacatacca atgacggcaa gattcaggag cctgttatta       33900
aagcagtggc agcgagcacc tggaagaggc ggccaccatc accaggagcc       33950
agcagggatg actaataagc cgtgccagct gcatctcgtt tctctcttga       34000
cagttgctat gccagtagat gagggatgta ctgtggatac aatgctgtca       34050
tatcttattc agcagggcat ctgatagcat cccacaaatc tgcctgagta       34100
gaagacagac agctgtggtc tgggtgccat ataggtaggt taaaatatat       34150
atttgggcct aggcgcagtg gctcatgcct gtaatcccag cactttggga       34200
ggccaaggca ggcggatcac ttgaagtcag gagttcaaga ccagcctggc       34250
caacatggcg aaaccccgtc tctactaaaa atacaaaaat tagctggaca       34300
tagtggtggg cggctgtaat cccagctact cgggaggctg aggcaggaga       34350
atctcttgaa cccaggaggc agaggttgca gtgagccgag atcatgccac       34400
tgcactccag cctgggcaac agagtgagac tctgtctcaa aaaaataaaa       34450
taaataaata aataaataaa atatatactt gggtaaagag gataaaagag       34500
ttagcgatga tgctgaattt ttgaactgag gtggctgttt tcaaggaaga       34550
ctggagggtg ggatgctacg tctagatatg ttgcagttta ggtgaatgtg       34600
agacttccct gttttgaagt caaatattgg accagtaaaa tctagccatc       34650
agcttaaatt cctatgatac aatttacata ctccccaggc tcaacacagt       34700
agatttctga atgtcctctg ccagctacat gctcctgccc acctcaatcc       34750
gagtagatgg aacaactaac caagccagct cagaccggtg gcacagctgt       34800
gctggctaac actgggcacc acctaagaga gtgcttctcc aaaagtgtgc       34850
ttccccaaat ggagcgaaat acgcttgagg aatgttgggt tgaaccatgt       34900
aaagcaggtc tcattcccgc agagcctttg gtacccggt gtacactgta       34950 accccagaag tgtttcctga gcttgcctga cgagacaact tttccaagaa       35000
ccgtctcaag tgatgagtgt tttgtgagtc acactttggg gaaagcgggc       35050
ctaagttagc atctcctccc agctgcctcc ctgctttccc tggaacacta       35100
ggaactgccc gtcctccctc cctccctcct cttcccactt cacaacttag       35150
catcaggaat attttagttt tggttttcca aacatatata cctccttttt       35200
tcttatcttg tcaatatcat cttttttttt tctttgcttt tcctcatact       35250
```

```
tttttttctc ttcatccttt ccttctccaa gggttaactt tccaccttag      35300
gagaatcttt tctgctttt ctcccacttc cccagctact ctcttatcat      35350
ctgctccaat ctcaccctaa ttgatcattt tgggaaaata tggtcagagt      35400
ccagataact aagttgagaa atgcttaaac tctgccatac ctttccagta      35450
aagaatatta cctaataaat aataaaatgg taatgggaaa cctgaaccct      35500
gaaaaaaaag aggtggaagg agaaacattt ggagcacatc ctgtctacaa      35550
attaggaact gcctgtgtta tctgttttat ggttatattc tagaagaaga      35600
aagggatttt gtagcacctg gttttgacct ttctgcactg tttgttgagc      35650
aaataaacct tatgggctgt tagccctctt tatagcctct cagcttatcc      35700
ctggcccaga caccctgctg tcattttgac ttttcattcc cacacacaca      35750
tacacatgca cacacatgta cacacacaca cataccattt aagattagac      35800
agaagtaatg ctcaaaatgg agtggcttct gagacattta gtccaagggt      35850
tcccaaacag gcttttcagt atcagatttc tttctgcccc attgaaatgc      35900
tacacaacct tccgcttaca gcaggtcaca agggtttcat tctacttgaa      35950
gtaggggcca tgtcccattt ccacttcctt ggcttcccat tcagtcactg      36000
ctaggatttg cctagacccc tgaggccaga caatgtagaa acttctgctc      36050
catgtcacag gtgaggaaac aggctcagag agggacaggc tccgaaagtc      36100
acatagacaa cagtagggct gcggctcaaa ccccagcgtc tgactccagg      36150
tttagtgcct tctcagggca tcagtgacac tcctcatggc cagggtgccc      36200
ccagtgttgc tcacagtctg gtatccaggg ctgagagtgt gctgtgtgct      36250
cagactgcct gggttcagtc ctggcactgc cactttacag tcagtgacct      36300
caggcaggtt acttaagctc tgcaggcctc agtttcctcc ttggtgggga      36350
gggttatgag gcatccttct catggtaaac cttcagtaaa taccagccgt      36400
tactaggagg gtccactcct gcctctccac tctccattca tcctgcctgt      36450
ttcctctgcc tgcttcctct gcctgcttct gtggtggtga attcttcatg      36500
gctcccaccg cctcctgctg cacccccact cagggcccgc atcaggaccc      36550
ttcctcctat tggtttgaac tccttggagt cagagggtaa tggatagtgg      36600
agtgagccag gtggcagaat ctcagaggcc atcccgggcc tataagcctc      36650
ttcaaaatag ggccacgtat caagctttac acacaggagt gaactttcac      36700
aagttgttat gactcatact ctgtctatag taagctgtta accactccca      36750
tttggcttat gcctctgtaa ttattgtact aacttatatc ttaaaataag      36800
gatattgaag gaatgagccg ggagaggctt tcctggttga gatatagaag      36850
aacaagagtt gctctttttc cttaaggtct ctcctcccac ccctgacctt      36900
agctcaccag catgggagaa tactatttga ctccttgtac tctgagacgt      36950
ggatttcaag atatagcatt ccaacttcaa cggcagcaag aaaagaagca      37000
acagaaggag aagacatcat agcaaacagg gatgcatgct gcatttccta      37050
atactcaaac ccggaaacga gacttcactc aaggtgaagg gagggcaggt      37100
caccacctgg tagcactagc cctaaattaa ggaatgcaga atgtttgtgg      37150
gattgcccat cataaaaatt acaaaatgag taaggaatgc aggcacagct      37200
ggccaggtgg gtttgtcaca accatggcag cccttttgccc cacagccagt     37250
```

```
acacagaact ggtctctcca attccgattg catatcttct ggcacctctg      37300
ttcctctccc tcagctgccc aggatttttc tggttctgac catgttactt      37350
cctcttttaa acctgttagc atttcacgac tgcctacagg caacggtcta      37400
aatggtcgga aggcccaagc ttagcatccg agaccctgac ctacctccag      37450
ccacttcctc ctcctctcca cttcactgga ctccccatct ccacccagac      37500
acctctgttc tcccctctgt gtgcctttgc ttatgctgtc ccctgtgttc      37550
ctagtgtgtc tctggctatc ttttaagctt ccctccccaa cctcattagt      37600
tctgtggagc ccctggaata gagctgactt ctccttccct gctgctccca      37650
ggctgctcag aactttctgg aaagggatga ttatctgagt tccagcctca      37700
ccccagcccc cggactctga gtccctcatg tctgcctccc ttctttctct      37750
ctgaccacac agctggtaca tagtcagtac agacgcagtc agtgagtgga      37800
gcacggggct tctctccagg attcctgccc ctttgtttat ccctagtctc      37850
aggactccct actcctggtc ttctgcctaa atctgtgcct cttggaagtg      37900
aagcctccgt tcccagtggg gccaggtcct gaccctgggg aacttgcagg      37950
atccctccct tgggcctctc cccgaagctt ccagctcaat gctgaccaga      38000
gcacaggctg cctgtgacag tccttgggt gacctccctt atcaggaaaa       38050
atgcagaaaa cctattaata ccttagcctt gtgattgtta atggtcacaa      38100
aactcccttta gggtcctttg gactcagcac ctttatggtc tcactttgaa     38150
ttttgaacct cccacctccc cccatccccc agagtaaggc aaatggtctt      38200
ctgattgttc ctgcagaggg aaggctccac aggtaagcac acgatggcca      38250
ggaagcagag ctggagcctg cctgaaaggc tgtggagaaa tggagggagg      38300
gctgccctga ggactctgtc tggctttgaa gttttctact gtttcctttt      38350
cttctgtgca ctgtttagg atgatggggt gatagttcca ggctggttga      38400
ggatggattt ggagacagtc ctttgtaccc tcagtgagca agagtatctg      38450
tcaccctacc tcagcagttg tctctgtcac tggtccaagc agctggttcc      38500
tacacaaggt caagatcaac tggggagaag cagactcctg ggtctatccc     38550
attagtgagg acagctgcct gggcttatgg cctcattggt ttggtttcta      38600
tcttgatcat ctctaccatc cccccatccc ggccttccat tttctacctc      38650
agctgtcagt gcacagattg atgtgtgtgg aacggagctc tgggaggagt      38700
ggggtagggc tggtcctgtc ctgtagcctc cccttccttc gggcacttgg      38750
acccttggga gcttgccggg gtggggaatg ggagtgggaa ggccagggag      38800
tgtctctgca ccatcactgt ttgagtgttg ccccttttgct gtgtgcccca     38850
cctagtctat gtgtgtctct gttctctggg gactcaattt gctggtgaat      38900
tgcttccatg gacattgttc tgggaaatgc catttttttct gctcacccat     38950
gactctgtga caaggaatga cagcttatta ggaatttgtt tttgcattgg      39000
aacagtggtc atcagaatgg gccccttttc ccttgcagct ttgacatttg      39050
cctctctttt cctcacctct ctcccttgca tccacccttt tctctttttc      39100
ttcttttttg ttttccttct agcagggcc ttttaccttt acttgttaat       39150
cctgtttgta gcaaagcaag tggaaggagg agttcctctc tgatctgctt      39200
```

| | |
|---|---|
| cttattctcc acctaccttc tcttctgtac tttccgcctc ctagagagag | 39250 |
| agagagagag aggaatgccg acctaactac cgctgccact gctgctgcca | 39300 |
| ccaccgctgc caccaccacc ctggtaatgt tcacatgtcc tcaaatcaac | 39350 |
| ccagagccag ggccctgctg gtcaggggga ggctatgtaa ataatcccat | 39400 |
| gagtgtgcca tcctcaggcc ctgggtctc ctaggcaaga ccagggcctc | 39450 |
| tgtgggctct ctcggaaatg ctgaggttgc tggaagccag cccgtcatac | 39500 |
| agggtctgag agtttaactt cttttaaatt aaaccacagt tgagctcatg | 39550 |
| ctgtgtgtgt ataaactttt gtatcctgct ttttccttaa attctttatc | 39600 |
| atcagcatct tcccatgtta tttcatagtc ttcatcatca tcactttcca | 39650 |
| taccttcata gtagttgatc gtagaattcc atcataatta acttgtcttt | 39700 |
| tctctcttag aagtccctta ggtaatgtcc aattttccgt gagtgtaagt | 39750 |
| aataccataa tgaacatctt ggagtctgaa gtttattctg tgttggtttg | 39800 |
| ttccacattt aggatcattt tcccaggcta gattttcaga tgtgggatta | 39850 |
| tgggttcaga tatggtttac acatttttat agttcttaat acagatggcc | 39900 |
| aaattgcttt ctgaaagaga agcttttctt aagtattttt ctccaacttg | 39950 |
| tatcttaaac atcctgaaca tgcttagcac cactgtcttg atatatctgc | 40000 |
| ggaaagccac gtctccactt ttcagtgtgt cgggccctgg gagaggcagg | 40050 |
| catcctgcgc tggctccttg gagctgggtt taaaattgtc tcctctggct | 40100 |
| gggcgtggtg gctcacacct gtaatcccag tactttggga ggccgaggtg | 40150 |
| ggcggatcac taggtcagga gatcgagacc atcctggcta acatggtgaa | 40200 |
| accccgtctc tactaaaaat acaaaaaatt agccgggcgt ggtggcgggc | 40250 |
| acttgaaaag tcccagctac tcgggaggct gaggcaggag aatgatatga | 40300 |
| acccgggagg cggagcttgc agtgagccga gatcgcgcca ctgcactcca | 40350 |
| gcctgggcga cagagtgaga ctccatttta aaaaacaaa caaacaaaac | 40400 |
| aaaaaaacaa acaaacaaaa actgtctctt ctgtgctcac ttcacccaga | 40450 |
| atccctgttg ggctcttcaa ggagctcagt tctctctgaa agcaacttta | 40500 |
| tagcctcagt ccagtctgtg ttcctgtgtg gcagggtca agggtatgct | 40550 |
| cactcttgag agtggtgtct ttggttgacc aagaaccact cccatagcct | 40600 |
| ggtccctaac ccttgaaggc ccatctctct cactcactgg ggtgaagagt | 40650 |
| ttaaatctca gatccaagtt ttgttgagag ctctgagcta ccatattgct | 40700 |
| atggttaaca atagttaaca atgttaacaa tggttaacta tggttaacaa | 40750 |
| tagttaacaa tgtttaacaa ctagagccca gctgggtgtg gtggcatgtg | 40800 |
| ctaacagtcc cagcttctca agaggctgag gtgagaagat tgctggagtc | 40850 |
| caggagctca aggccagcct gggcaacatg gcgagaccct gtctccctg | 40900 |
| caaaaaaaca acaacaacaa aagcaaaact agagcccaac tgctgtgaac | 40950 |
| tcatggctga gtagatatta ttagccctcc acaaactcag catttgtata | 41000 |
| atcccaggct gttccagta attctctggg gatcatctcc cagcctgtcc | 41050 |
| actgttccag gatccacact taggcctata ggaatgcccc gtcagagctt | 41100 |
| ctgctgccgc tgatctgtta ctgtttcatg caacccactc ggcctagttc | 41150 |
| cttcctctta ctgtctcagt gggcacagaa aagcatacag agggtgtttc | 41200 |

```
agcaaacatt gccactggct gcagacctgc ccccggatct gtcctgttga      41250
gagcttagtg ctgcgttctt gcatggtggg gagggtgtg gctctgtgat       41300
gagccagggc atgtgtatag gagcaacagt gtctctctta tcacgtagaa      41350
gttctgactc attgcgagtc ttggctttgg gttaatggtt ccagccatgt      41400
tgctgctgtg tcttttggtg caggagaggc tgggcacagt tggtccctaa      41450
gccattatgg ataagggatg tgtctgctga tatacacaca tggacctgac      41500
atccagggaa ggcagggtga ttggacagaa cagttcttcc agaagctgtt      41550
ggaacttgga caagagtggc ccttggcttt ctgtagttgg tcatctgtcc      41600
cctgttgcaa tcagggaag gccacacttg ccttccttaa ccacagttag       41650
gatttcttg gggattagac cagattctag cacctgtcct gaacctctcg       41700
ccccgcccct acaaaggctg cttgcaagtg tagtgcacat acacagggag      41750
caggtggggc atggaagtgg aagtggagcc cctgcctttg gcccttgggg      41800
gaggcactgt ctgcttaccc acggttgttg cctcatagga atcatacaac      41850
agcttcctaa ctggtctcct tgccttcagt tggattgggg cacaaatccc      41900
tccttgacat ataaaccatg gtttaaggct ccctgtggcc taaataaaga      41950
taaagcttaa gtatcttaac aagcacctaa cccttctccc cagcctcggt      42000
gatttggctc atcgctgcct tcatgtttca ttctggcttc actcattcgg      42050
aatttcttgt agttccttgg ctgttctctt ttccttaccg cctttacaaa      42100
tgctctcacc atgcatgctt ttctctgctc ctacagatgc cttctctccc      42150
agcaccgcct ccagagtcta tgtctggtcg attctgtctg ctgtctccag      42200
tccccatctt gtggcagtct ctgctcaatc atttgggat tttatatgtt       42250
ttctggcctt tcttttgggg gcctgtcttc tccttctaaa agcagccagt      42300
tgacctagaa ggaagggata actgtaactc ttgtctacca acataagatt      42350
aggcccaccc tttaaaagct gcgtctttga aagggacacc tgcacccagc      42400
atgctggctt ctcttcacca agcgtgactt cctacgcatt tcacaggcct      42450
ccagaggtcc ccctgactct cttctgctgt gagaaactct aatcatgtaa      42500
gccacaggct aattcccttg agccttaaat gttttagta atttcccatt       42550
catcagagaa gcaggatttg ggaggaattt tgaagcaaac actacagaag      42600
gcagagtctc caggtaggat atctaagaga catttggaat ggtctgactg      42650
ttcaagatgg atgggaaagc ctcttcctgt aatgatagta gccaacattt      42700
gttgtcaggc agtggggccc catttttgag atggggtctc tgtcacccag      42750
gttggagtgc ggtggtgctg tcatggctca ctgcaacctc agcctccccg      42800
ggctgggtct tcttaattct gaaaaaccca gcttttaaag ggtggaccta      42850
atcttatgtt ggtagacaat gttgtctcat ttaatacaat gcacatgctc      42900
tcccctaac acaaaagagg gaactgaggc ctggaggtgt gatgtacccc       42950
aagtcacata gctaataaat aaagaagcca gcattcctgg gattaaaaat      43000
gcatgtgtct gtcactgtgg tgtatttggt gcttgatcaa tgtttacttg      43050
agcaaatgga ggggcagagg taccgatgag tgtgctcagt gaggagggca      43100
ggagtgaagc tgggcgtctt cccgcctctt gtgagtggtg gggcttggtg      43150
```

| | |
|---|---|
| agcttgccag ggcctgtctt tcttatcaaa gaaggtgtgt gccccagtgt | 43200 |
| tacagcattt cacccaaagc agcctagaaa atgcttgact tttctgtcat | 43250 |
| tccggggagg acactttcct cctccactgt tctgctggcc tggtgtaccc | 43300 |
| acggccctg atagatgata gcacctgcta aagtgcacca tgcccttccg | 43350 |
| tctcactgca tcccacagat gaggccaggc tgggatgagg gagaaaggga | 43400 |
| gggatatata gttcaggtta ttttggaaaa ctgcctgacc aattttaagt | 43450 |
| ctgggccgga cactggggca tctccaccacg ttgaaagggc cgtggcaccc | 43500 |
| cgggcggtga aaggggctgg aaccaggtct gcttcttggg cttctcctcc | 43550 |
| agggtgccat tgctcatggg ccttggctgc agaggtgctc attcgtggtt | 43600 |
| ccaaaattcc aattcctggg agaggaaaaa tgcttagttc agtctcagtt | 43650 |
| aggcctctgc ttagatcaaa cagccaaggc cagtaggccc agtcctatgg | 43700 |
| tagagacatg gcctcaaaga gccctctgct gcagttgttg gggagtgtac | 43750 |
| caagagaagg gagcattgtc ctgggctggg cagccctggg ggtctagtgc | 43800 |
| atagatgtag aaaggctctg ttggtatacc tcccttgct tgttggaaag | 43850 |
| tgctcaacgg ggctgaattg tgtttgacag tgtaagtctg ggctggggtg | 43900 |
| agggttgtta caagattgtc aagatgatta aatgaaatgc catttgaaac | 43950 |
| acttatccat gccttgtgta tggtatcccc accagtgaat attcacagta | 44000 |
| tattataata attccaacaa cttcataatt ttcatatgca atttctaaac | 44050 |
| tttgaacttt ttttttttt tttttttttt tgagacagtg tctcgctctg | 44100 |
| ttgcccaggc tggagtgcag tggcgcaatc ttggctcact gcaacctcca | 44150 |
| cctcccggct tcaagtgatt ctcctgcctc agcctcctga gtagctagga | 44200 |
| atccaggcgc ccgccaccac acccagctaa ttttttgtatt tttagtagag | 44250 |
| acgggctttc gccatgttgg ccaggctggt ctcaaactcc tgacctgagg | 44300 |
| tgatccaccg ccttggcctt ccaaagtgct aggattacat acgtgagcca | 44350 |
| ctgtgcccgg caattttttg tgtttttagt agagatgggg tttcaccatg | 44400 |
| ttggccaggc tggtctcgaa ctcctgacct caagtgatct gcccgcctca | 44450 |
| gcctccctaa tgctgggatt acaggtgtga gccaccacgc ccagcctaaa | 44500 |
| ctttgaattt ctttgaaccc atgacttaca cagaattagc tgaacgcaga | 44550 |
| attccaaatc aactcagcct gtgggacagc caaaaacac agtgtgcctt | 44600 |
| tgggctcctt cactcaccac gcggggttag aaaactttgt cagaggcttt | 44650 |
| aaaaaaggag ctcttgtgtg taaaatgttt ccttgattct ctttctggtg | 44700 |
| cctctctttc tctaagtggt ttgcttcccc aagttcccca cctgagtctg | 44750 |
| ggtggctgtg gcacatctgt gcattctgta cgcacacagg cagccttttg | 44800 |
| gagtgccagt ttccaggtct tggttttatt tatttattta tttattttt | 44850 |
| tgagatgggg gtctcactct gccgcccagg ctggagtgca gtggtgccgt | 44900 |
| catggctcac tgcaacctca acctcctgg gatcagttga gcctcctacc | 44950 |
| tcagcctcca gagtactagg gaccaccatg cctggcaaat ttttgtaatt | 45000 |
| ttttgtagag gcagagtctc accatgttgc tcaggctggt ctcgagctcc | 45050 |
| tagactcaag tgatctgccc accttggcct cccaagtgtt aggattacaa | 45100 |
| gtgtgagcca ccatgcccag cccaggtcat cttttgaggg catggagaga | 45150 |

-continued

| | |
|---|---|
| agactttgag catcccactt ttgagattgt gtaccagtcg caagcccta | 45200 |
| tgacacactt ttttccccaaa gtagagggct ctgactatgt tgatcccaag | 45250 |
| agagatggga aagagcattg aatgaggatt ccaaagtatt gggccttagt | 45300 |
| tcgtttcctc atgttggtgt tgtgaagatt ctggttagga taacagcatg | 45350 |
| tgtgcaggag gctttgtgaa ctgctgagag tgaggcgtgg caatgtcagt | 45400 |
| gctaggtttg tccttactaa cctggggcca tgggaattga taagaccaga | 45450 |
| ttcccaactc taccccacaa tgtgatccct gtggtgaccc ctcacagggc | 45500 |
| tctttggtcg agcttcccag aagggatcac catctgccat tgtatgttga | 45550 |
| accccattca ttcattcatt cattcagcca accagcaact atttgttgag | 45600 |
| ctcttattgt gtgagaagca gtcttcaagg aactgggtga taaaaaaaaa | 45650 |
| caaaacatcc taaccttcat tgagcttaca ttcttactga aagaaaacaa | 45700 |
| ataaaacata catgtaatcc tagcactttg ggaggccaag gcaggcggat | 45750 |
| cacttgaggt caggaatttg aaaccagcct ggccaacgtg aaacccatct | 45800 |
| ctactgaaaa ttaaaaaaaa aaaaaaaaaa aagccgggca tggtggcaca | 45850 |
| tgcctgtaat cccagctact cgcgaggcta aggcaggaga atcgcttgaa | 45900 |
| tcctggaggc agaggttgca gtgagccaag atcataccat tatactccag | 45950 |
| cctcagtgat gaagcaagac tccatctcaa aaataaaaaa taaaaataaa | 46000 |
| aatatgcatt ccctttgcac cagcacactt ggtgcctggg gacctcgtgg | 46050 |
| ttggcaccct gaagcaggtg tccctcttct gtcttgcaca ccttgcttct | 46100 |
| gtcctggtgt gtatggcatg gccttctgcc ctccatggtg agcactgtga | 46150 |
| gggcagaggt tgagttgggt ttgctgtatt tctcaggtgc ctaggtttgt | 46200 |
| gcttgacagg tagatggaag gcacacaatg tggtcatcaa acctcagtca | 46250 |
| accatataag gaaggtagaa gtgaaaagtc ccataggtac ccaactaatg | 46300 |
| tcaccagttt cctggatacc tttcctggag tttatttata gtgtgtataa | 46350 |
| ataaatgatg tatgtgttta aatgccttt tcacctttcc ttttagagct | 46400 |
| gcctcttttt aacagttcca ttccattgta tggatgtact atgatttatt | 46450 |
| gaaccagttc cctactgatt attctgtttt ttgcagtctt ttgttatgat | 46500 |
| gaacattcca cagtgacaat gttgttcata gtcattcaca cacatgcaag | 46550 |
| tccttctgca ggatatattt ctagagggga attgctgact cagaggtttt | 46600 |
| ggtactctgt gttgattgta gagtgacggc agaaaagtga ggcccaagag | 46650 |
| tttcctagtg accatgtgta gtggacaagt caccagtccc tgtgagtgtt | 46700 |
| tggcccaaag gctttaaggc atttgatatc actgtttttg tttctgcacc | 46750 |
| aggcgggaga cactatattc aatcgtgcta agctcctcaa tgttggcttt | 46800 |
| caagaagcct tgaaggacta tgactacacc tgctttgtgt ttagtgacgt | 46850 |
| ggacctcatt ccaatgaatg accataatgc gtacaggtgt ttttcacagc | 46900 |
| cacggcacat ttccgttgca atggataagt ttggattcag gtaagagata | 46950 |
| ctcagtcaga atctgtggta aacatgtctc tctcatgtgt tgactaggaa | 47000 |
| atgcagtcct ggcagctcaa gagtgcctct ttaagtctg gagcagaatg | 47050 |
| cctcctctga gaaatgggtg ctttgtatta gttgagatgg aaagaagaga | 47100 |

| | |
|---|---|
| ccagaaatgc ctgtagtctc tgcacatcca gacaaaaaca aattttcccc | 47150 |
| cctttttttt ttttgtttgt tttttgagac agggtctggc tctgtcaccc | 47200 |
| aggctggagt gcagtgccgt gatcttggct caccgcaacc tctgcctccc | 47250 |
| gggttcatgc catcctgtca cctcagcctc ctgagtagct gggactacaa | 47300 |
| acacttgcca ccatgcgcag ctaattttttg tatatttttgt agagatgggg | 47350 |
| ttttgctgta ttgcccagtc tggtctcgaa ctcctgagct caagcaatcc | 47400 |
| atctgccttg gcctctcgaa gtgctggatt ataggcatgt ggcaccatgc | 47450 |
| ctggcctaag aacagttttt agcatttggg aggggctctc atctttaagc | 47500 |
| tccaaatgat actgtatttt cttgcttttt tctttctctt gccccacaag | 47550 |
| ttttggaaag taaattggaa tagtttttccc ccactgaatt atttagcttg | 47600 |
| tatacctcag cagatgttcc ttggcctgtt ttgttttgtt tttgagacag | 47650 |
| ggtcttgctc tgtcacccag gctggagtgc agtgacacaa tcatggctca | 47700 |
| ctgcagcctt gactgcctgg gctcaatcca tcctgcagcc tcagcctcct | 47750 |
| gagtagttgg gactacaggc atgagccagc atgtccagct aatttttttat | 47800 |
| ttttagtgga gatgaggtct ggctatgttg cccaagctgg gcttgaactc | 47850 |
| ttgggctcaa gtgatcctct cacctcagcc ttccaaagca ttgggattac | 47900 |
| aggtgtgaac cactgctccc gcccttggcc ctataagaag gaatgtgatt | 47950 |
| ctgttttcca gcagggcaca aacttctgct taaatacaaa gcccaaattt | 48000 |
| ttccaccaaa atgcccctag tgaagtggcc agcccagatg cccgactagc | 48050 |
| gtattatcca aagcatattg tcattggtgg aaaatggcct tatagtccat | 48100 |
| tgttttgtct taaaagtaaa tatataaata aacttgtata ttgtttccta | 48150 |
| attccgtgtt tatattaaca taaaagtgtt ttaaattacc tgtcagtggc | 48200 |
| caggtgcagt ggctcgtgcc tgtaatcgca gcactttggg aggccgaggc | 48250 |
| gggcagatca cctgaggtca ggagttcgag accagcctga ccagcatggt | 48300 |
| gaaaccctgt ctctactaaa aatacaaaaa ttagccaggt gtggtggcag | 48350 |
| gtgcctgtaa tcccagctac tcgggaagct gaggcaggag aattgcttga | 48400 |
| acccgggagg cagaggttgc agtgagttga gatcgcgcca ttgaacttca | 48450 |
| acttgggcaa cagagcaaga ctctgtctca gagaaagaaa aaaaaaaacc | 48500 |
| tatcagttga ataacaaaac ccttttccttc cttgctttaa gtgaatctga | 48550 |
| agatccagga gctgtgctgc aggtaccctc tatgttgggt acccctggtt | 48600 |
| taggctgact agtacagtgt ggttggctca tgtagacagc agacccttta | 48650 |
| ttttagatac aactttttttt cttttttcttt tatttttttt gagacagagt | 48700 |
| cttgcttgtc acccagcctg gagtgcagtg gcgtgatcat ggctcactat | 48750 |
| agccttaaac tccctggctc aagtgatcct ctcacctcgg ctttcctagt | 48800 |
| agctgggacc acaggtgtgg gccagcaccc ctggctgatt taaaaaaaaa | 48850 |
| aaaatttttt tttttagaga tgtctcacta tgttacccag gctggtcttg | 48900 |
| aactcctggg ggctcaagca atcctcctgc tttgacctcc caaagtgctg | 48950 |
| ggatgacagg catgaactac tgcacctgct gagatgcaac agctttctgt | 49000 |
| cagactcatt ttattctcat catttcttcc tgtcctccct tgctgggagc | 49050 |
| atgagagctg tgatgggaat ataggaatgt atgaagtcct tctcccagat | 49100 |

| | |
|---|---|
| caaaaatcct aacttcttgt cttaaaggga ggaaaatttg aatgtaacct | 49150 |
| tactttaga ctcttcagaa atccttctat acccttccgt ccccgctttc | 49200 |
| acccttcctc cctctccgtg tgtgtatctt cttctcttga aacacacagg | 49250 |
| tttataccct gacccctctt gattcatccc ttgaagcaca gtggtgaaca | 49300 |
| aggaaggggc ccgtgatgcc ctaattcttt gccacagcac catgtttgtt | 49350 |
| tcacaaggag cctggcaggt ttgggcttgg ggcagatagg ggagagaaag | 49400 |
| cagcagagac agcaaaacca aatcatgtca gcttggcatg tacttccctc | 49450 |
| tgaaatagct aagaatccat ttctgtaaaa gcactgatta tcagaaaacc | 49500 |
| ttattggcct ggccacctt ggttcaaacc ctcacattaa taatgtggac | 49550 |
| agtagtatga ggtgtgccaa aggtggatga ctcagcacct aagtgatgac | 49600 |
| acctaattac gaataggttc attaaagcag accccctggg gacctttgct | 49650 |
| tgaggatcct tacagtcaga attcctgaat atatttgaaa ataataattg | 49700 |
| catctttatt ttcatatgtt ctgtatggtt tggctgactt cccctcaaa | 49750 |
| gtctgagtta gagttttcct taatttatgt gatgggtttg gtcttttgg | 49800 |
| attccagaaa gagctgggtg tggtttggag ctgcactcag agtcacacaa | 49850 |
| aaccacagcc tttagagaac ccacaggaag gctttggggc acgtcctgat | 49900 |
| tcttgacatt tctcatcagt gctgactttg tatcccttag gagttcacaa | 49950 |
| ttcataacca ctgaaatatt aaaatacaaa aagttttgga aggatgagag | 50000 |
| cccagatgct ctactacttg aaaatatgtt aaaacataag ttcatcatta | 50050 |
| tacattttgc taaatcagga taaagtctga gtttcaaag aagttttatt | 50100 |
| ttagcaaatt ttcagaaaca ctgcctcaac tgttagggcc agtgttctag | 50150 |
| tcagtatgcc tttggaagca tgaaagctgg attggtcgat aggatgggtg | 50200 |
| tggaagggg gctgtgactg ggtgggtaca gagaggctct gaaacaatct | 50250 |
| cagattccag gagttcctgg ataaggactt catgtgcggg aacagagcac | 50300 |
| aggagaagca gattcctgag ccactcagga agaactgggc ctaggcctgc | 50350 |
| tcttgtcact gactggcttt ctacataacc acagaaacag cactgtgttg | 50400 |
| tagaaagagg aagatcatac ttttgatat ctgtgtctaa tttaaggtca | 50450 |
| tctgagccct gatagaaaag caaaacagac aaaaccttg taactgctcc | 50500 |
| ctcccacccc acccaccatc aaaaaagctt tagagaggct ggacatggtg | 50550 |
| gctcttgcct gtgatcccag cactttggga ggctaaggtg ggtggatcac | 50600 |
| ctgaggtcag gagttcgaga ccagcctgac caatatggtg aaaccccatc | 50650 |
| tgtactaaaa atacaaaaat tagccaggtg tggtggcaca cgcctgtagt | 50700 |
| cccagctact gggaggctg agacaggaga attacttgaa aacctgggag | 50750 |
| gcggaggttg cagtgagccg agatcacgcc attgtactcc agcctgggct | 50800 |
| acagagcgag actccttcaa aaaaaaaaaa aaaaaagat ccggtttggt | 50850 |
| gtcttacaac tgtaatccca gcactttggg aggccgaggc ggtggatca | 50900 |
| cgaggttaag agatcaagac catcctgacc aacatggtga acccctgtct | 50950 |
| ctactaaaaa ttagctgggc gtggtggcag gcgcctgtag tcccagctcc | 51000 |
| tcaggaggct gaggcagaag aatcgcttga acccgggagg cggaagttgc | 51050 |

-continued

| | |
|---|---|
| agtgagccta gatcgcgccc ctgcactcca gcctggcaac agagcaagac | 51100 |
| tacgtctcaa aaaaaaaata aataaaaact ctagagaagc aaaaagaata | 51150 |
| actttaaaag tgtttatgtt ctcagcaagc tttattttgg ggatgtcaga | 51200 |
| acttaactaa ccactgctcc ttctgtgtgt atgttttttcc tccagcctac | 51250 |
| cttatgttca gtattttgga ggtgtctctg ctctaagtaa acaacagttt | 51300 |
| ctaaccatca atggatttcc taataattat tggggctggg gaggagaaga | 51350 |
| tgatgacatt tttaacaggt aatggtcata acttagatat ctttctcctc | 51400 |
| tgtcaacctt cacttccagt ttttaacca atgcttggtt gttccccaag | 51450 |
| gactgaccct cagatgggat gcaccctag tcagcccaca ttcttaggtg | 51500 |
| tggcttccta caggtcctgc aggtgctaaa agggatctgt aggaaaatga | 51550 |
| gtttctgaga tttttgtatt ggcctggaaa aatgtcaaat gggaaccaag | 51600 |
| tgacggggca agtttacttt gacttgctgc atgccgtttt gtactcaagg | 51650 |
| agtaaaccaa tgtcctttgt aaaatccct cctttcatta tggtcccctt | 51700 |
| tcactgtgaa acaagtttcc ttgagcagaa tcctaactgt cttcacagaa | 51750 |
| gctttgtgtt atattttat tttggagtat tttcacatat acaaaagaga | 51800 |
| tactgtagta aataaacct ttgaggacct atccagcccc agcaaccatt | 51850 |
| atggcctggt cagttctgtc ccatccacat cctggggctc ttttaagct | 51900 |
| ggtaaatcat tatgatgtgg gttgtcattt acagtggtaa aaaacatcta | 51950 |
| tcagtagcat ttgaaagaac attctgctca gtcctctggc tgtagaggct | 52000 |
| tcaaccccac cagccaccga tgagcacctt ctccctccag gagccagtct | 52050 |
| gagctcatta ctgagtttaa tatcagaata caccctggtg cagcctttct | 52100 |
| aaattgcagt accagttaac agaaggtgtc tgtcagagca cacccaagt | 52150 |
| cattcaagtt accattgtgt gcaaacttaa cagagaccca cgtcttcaat | 52200 |
| ataagccttg aaggaaactc cagttttagt atgtagatgg ggtatcaagt | 52250 |
| gtgtgcacat tgaacatctg ctgcatacag agcactgtgc caggcaggcc | 52300 |
| caggacactg aaaacctgga catagggtcc agacagaagc aagcctgctt | 52350 |
| ccacagaggc actcctgggc agacactctg gactgatatg acagtgtgca | 52400 |
| gggccgacag gataccacag gtctgaatgg tcagaacagc tggggaggga | 52450 |
| gggagcatcc gcaggcatct agtcccatgc taacgcagtg gcactagaag | 52500 |
| gatgggtggt gtgtggagca actttcttga aagataaagg acctaacact | 52550 |
| ttctatgcac cacttactgt gtgccaggca aggccaggaa tgtttaagtg | 52600 |
| gtctgggatc agccagttct gcctcttaac taactttgct gtcctgctct | 52650 |
| ccaggctttc attttggtcc tcattccttt tccttggacc aacacagaat | 52700 |
| cctccaccct gttctggctg cctctagtct tgttctcagc cctccatttg | 52750 |
| ttttttttctg cctttttccca catgttctga agccctccat tcgtatacta | 52800 |
| cttccagag acttccccat ggctaaaagc attttggaaa tactgtatat | 52850 |
| taggcccctt tcagatactg gcaaccgttt gtgggatgct ctgagaaggc | 52900 |
| ctctgtgact tagcctggcc cttttcagcc catcacctgc cacgtcctac | 52950 |
| cccagaccct tgtcaccagt ccccaggagc ttacgttgct ccctgagggc | 53000 |
| actaggcttg ctctcacttc catgcctttg cctgtgccat cctggctgcc | 53050 |

```
caaaatgcta tggcagatac ctgttcatcc tcaactgggc tctgcctagg      53100
cttgctccag cagaggttac aaactctatg cttcttcctc tgtgtctcca      53150
acctcatctt cctcttctca cctccatcct ggccctaaag gccctatgtt      53200
tgaagcattc acactgtata ttctgtgggg cacacggccc cagtgtctgg      53250
cacatggtag tcaacaccac aaaccgcaga accagttgta aaaggacatg      53300
gagtcggaat gtgagtttta accagggtca tgctgggctg ggttctggca      53350
tgatgctggg ttgtgggctg agtgagaaca gcaagggtga tggtggatgg      53400
agcaacagtc ttgcagccgg ggctctcagg ccaagtgtat ggcagctctg      53450
tgataatgac tttccctttta ctctttgcag attagttttt agaggcatgt     53500
ctatatctcg cccaaatgct gtggtcggga ggtgtcgcat gatccgccac      53550
tcaagagaca agaaaaatga acccaatcct cagaggtgca ttctttgttt      53600
attcatactc cttcccccctt taggatgagg taggctgcag gtccgaggct    53650
ctgggcctag agggaaattg aggtggtcag gttacagtgg agagggagga      53700
ggaagtacgt gtgatgattt cttcttaaga ttttttgtttt aagacaatct    53750 ccttgtgctc ttttccttgt aggtttgacc gaattgcaca cacaaaggag      53800
acaatgctct ctgatggttt gaactcactc acctaccagg tgctggatgt      53850
acagagatac ccattgtata cccaaatcac agtggacatc gggacaccga      53900
gctagcgttt tggtacacgg ataagagacc tgaaattagc cagggacctc      53950
tgctgtgtgt ctctgccaat ctgctgggct ggtccctctc attttttacca    54000 gtctgagtga caggtcccct tcgctcatca ttcagatggc tttccagatg      54050
accaggacga gtgggatatt tgcccccaa cttggctcgg catgtgaatt       54100
cttagctctg caaggtgttt atgccttttgc gggtttcttg atgtgttcgc    54150
agtgtcaccc cagagtcaga actgtacaca tcccaaaatt tggtggccgt      54200
ggaacacatt cccggtgata gaattgctaa attgtcgtga aataggttag      54250
aatttttctt taaattatgg ttttcttatt cgtgaaaatt cggagagtgc     54300
tgctaaaatt ggattggtgt gatctttttg gtagttgtaa tttaacagaa     54350
aaacacaaaa tttcaaccat tcttaatgtt acgtcctccc cccaccccct     54400
tctttcagtg gtatgcaacc actgcaatca ctgtgcatat gtcttttctt     54450
agcaaaagga ttttaaaact tgagccctgg acctttttgtc ctatgtgtgt   54500 ggattccagg gcaactctag catcagagca aaagccttgg gtttctcgca      54550
ttcagtggcc tatctccaga ttgtctgatt tctgaatgta aagttgttgt     54600
gttttttttt aaatagtagt ttgtagtatt ttaaagaaag aacagatcga     54650
gttctaatta tgatctagct tgattttgtg ttgatccaaa tttgcatagc     54700
tgtttaatgt taagtcatga caatttattt ttcttggcat gctatgtaaa     54750
cttgaatttc ctatgtatt ttattgtggt gttttaaata tggggagggg      54800
tattgagcat ttttaggga gaaaataaa tatatgctgt agtggccaca        54850
aataggccta tgatttagct ggcaggccag gttttctcaa gagcaaaatc     54900
accctctggc cccttggcag gtaaggcctc ccggtcagca ttatcctgcc     54950
agacctcggg gaggatacct gggagacaga agcctctgca cctactgtgc     55000
```

| | |
|---|---:|
| agaactctcc acttccccaa ccctccccag gtgggcaggg cggagggagc | 55050 |
| ctcagcctcc ttagactgac ccctcaggcc cctaggctgg ggggttgtaa | 55100 |
| ataacagcag tcaggttgtt taccagccct ttgcacctcc ccaggcagag | 55150 |
| ggagcctctg ttctggtggg ggccacctcc ctcagaggct ctgctagcca | 55200 |
| cactccgtgg cccacccttt gttaccagtt cttcctcctt cctcttttcc | 55250 |
| cctgcctttc tcattccttc cttcgtctcc ctttttgttc ctttgcctct | 55300 |
| tgcctgtccc ctaaaacttg actgtggcac tcagggtcaa acagactatc | 55350 |
| cattccccag catgaatgtg cctttaattt agtgatctag aaagaagttc | 55400 |
| agccgaaccc acaccccaac tccctcccaa gaacttcggt gcctaaagcc | 55450 |
| tcctgttcca cctcaggttt tcacaggtgc tcccacccca gttgaggctc | 55500 |
| ccacccacag ggctgtctgt cacaaaccca cctctgttgg gagctattga | 55550 |
| gccacctggg atgagatgac acaaggcact cctaccactg agcgcctttg | 55600 |
| ccaggtccag cctgggctca ggttccaaga ctcagctgcc taatcccagg | 55650 |
| gttgagcctt gtgctcgtgg cggacccaa accactgccc tcctgggtac | 55700 |
| cagccctcag tgtggaggct gagctggtgc ctggccccag tcttatctgt | 55750 |
| gcctttactg ctttgcgcat ctcagatgct aacttggttc tttttccaga | 55800 |
| agcctttgta ttggttaaaa attattttcc attgcagaag cagctggact | 55850 |
| atgcaaaaag tatttctctg tcagttcccc actctatacc aaggatatta | 55900 |
| ttaaaactag aaatgactgc attgagaggg agttgtggga aataagaaga | 55950 |
| atgaaagcct ctctttctgt ccgcagatcc tgacttttcc aaagtgcctt | 56000 |
| aaaagaaatc agacaaatgc cctgagtggt aacttctgtg ttattttact | 56050 |
| cttaaaacca aactctacct tttcttgttg tttttttttt tttttttttt | 56100 |
| ttttttttgg ttaccttctc attcatgtca agtatgtggt tcattcttag | 56150 |
| aaccaaggga aatactgctc cccccatttg ctgacgtagt gctctcatgg | 56200 |
| gctcacctgg gccaaggca cagccagggc acagttaggc ctggatgttt | 56250 |
| gcctggtccg tgagatgccg cgggtcctgt ttccttactg gggatttcag | 56300 |
| ggctgggggt tcaggagca tttccttttc ctgggagtta tgaccgcgaa | 56350 |
| gttgtcatgt gccgtgccct tttctgtttc tgtgtatcct attgctggtg | 56400 |
| actctgtgtg aactggcctt tgggaaagat cagagagggc agaggtggca | 56450 |
| caggacagta aaggagatgc tgtgctggcc ttcagcctgg acagggtctc | 56500 |
| tgctgactgc caggggcggg ggctctgcat agccaggatg acggctttca | 56550 |
| tgtcccagag acctgttgtg ctgtgtattt tgatttcctg tgtatgcaaa | 56600 |
| tgtgtgtatt taccattgtg tagggggctg tgtctgatct tggtgttcaa | 56650 |
| aacagaactg tattttgcc tttaaaatta aataatataa cgtgaataaa | 56700 |
| tgaccctatc tttgtaac | 56718 |

<210> SEQ ID NO 2
<211> LENGTH: 56718
<212> TYPE: DNA
<213> ORGANISM: Homo sapien
<220> FEATURE:
<223> OTHER INFORMATION: variant B4GALT1 genomic sequence

<400> SEQUENCE: 2

-continued

| | |
|---|---|
| gcgcctcggg cggcttctcg ccgctcccag gtctggctgg ctggaggagt | 50 |
| ctcagctctc agccgctcgc ccgccccgc tccgggccct ccctagtcg | 100 |
| ccgctgtggg gcagcgcctg gcgggcggcc cgcgggcggg tcgcctcccc | 150 |
| tcctgtagcc cacaccettc ttaaagcggc ggcgggaaga tgaggcttcg | 200 |
| ggagccgctc ctgagcggca gcgccgcgat gccaggcgcg tccctacagc | 250 |
| gggcctgccg cctgctcgtg gccgtctgcg ctctgcacct tggcgtcacc | 300 |
| ctcgtttact acctggctgg ccgcgacctg agccgcctgc cccaactggt | 350 |
| cggagtctcc acaccgctgc agggcggctc gaacagtgcc gccgccatcg | 400 |
| ggcagtcctc cggggagctc cggaccggag gggcccggcc gccgcctcct | 450 |
| ctaggcgcct cctcccagcc gcgcccgggt ggcgactcca gcccagtcgt | 500 |
| ggattctggc cctggccccg ctagcaactt gacctcggtc ccagtgcccc | 550 |
| acaccaccgc actgtcgctg cccgcctgcc ctgaggagtc cccgctgctt | 600 |
| ggtaaggact cgggtcggcg ccagtcggag gattgggacc cccccggatt | 650 |
| tccccgacag ggtcccccag acattccctc aggctggctc ttctacgaca | 700 |
| gccagcctcc ctcttctgga tcagagttt aaatcccaga cagaggcttg | 750 |
| ggactggatg ggagagaagg tttgcgaggt gggtccctgg ggagtcctgt | 800 |
| tggaggcgtg gggccgggac cgcacaggga agtcccgagg cccctctagc | 850 |
| cccagaacca gagaaggcct tggagacttc cctgctgtgg cccgaggctc | 900 |
| aggaagtttt ggagtttggg tctgcttagg gcttcgagca gccttgcact | 950 |
| gagaactctg gtagggacct cgagtaatcc actccctttt ggggactgac | 1000 |
| gtgaggctcc cggtggggaa ggagactgac ctctcggttc acgtgtcttg | 1050 |
| ccatagagcc actctcctga gtgggttttt ctcctgatcg tttgggccaa | 1100 |
| gtgacttctc tctgaacctc atatttctct tctgggataa taaatggtca | 1150 |
| cccctttcaag gggttgtttt ggaagatatt gtgaacaatg gtaaataagg | 1200 |
| gcttaattaa tgagggtaag ccctcagtaa attgtcactg tgtgttcatt | 1250 |
| tcttcctctg tgtggatcgt gaccgagagc ccttccccct agcctcctcc | 1300 |
| tggtatgggt acccaaaacc taggtgagca gggatctctc ccaggggcag | 1350 |
| agagcttgtg tactctgggt gttagagggc taaaatataa ccagtcaaca | 1400 |
| ccacgttgcc catttctggt acttccggta gcagcctgag tctcaattat | 1450 |
| cttgcccaga tgatctgaac tctgacctct agcctgtttc agcataggca | 1500 |
| gagagcttga gtaggtgagt ttgcattcct catagcagct ggctgagcct | 1550 |
| agtctggact tctctttgac ctgtaaccta caggcccaca ggcccaaggc | 1600 |
| aaccacaggt tgcttccagg gttaccacac aggtggtttc tcatttctaa | 1650 |
| tgctaggttt tagataattg ttgtaagtga ggggccctgg caggcaggat | 1700 |
| gacatcctgc caataggagt tttctgtcac tttcccacag agccctggct | 1750 |
| actacatact cttgctcaat ttcgccagta attgcgtcaa tgtgttcata | 1800 |
| tcaagtttgg gaagaacatc ttggaattgg tcagacgtga actgtggtaa | 1850 |
| taatgggggc ttgttttttt aagcagataa ttaaattcct ttgcatttga | 1900 |
| tgattattct gggaagcaga ctagtcccat aaaatgaaat ggactctgcc | 1950 |

```
ttgctgctaa gtgtctgact tgagacatgc tatcgagttt ctcaaaatct       2000
cttccttgtg taaaatgtgg ttgtcgatga ttaccttaca gggtttttt        2050 taagactaaa tgagatcgtg tacattaaat acaggcactc aggctgggca       2100
tggtggctca cgcctgtaat cctagcactt gggaggctg aggggagtgg        2150 atcacttgag gttaggagtt tgagaccagc ctggccaata tggtgaaaca       2200
ccatcccatc tctacaaaaa tacaaaaaag ttagccaggg gtggtggcat       2250
cgcagctact caggaggccg aggcaggaga attgcttgaa cctgggaggc       2300
agaggttgca gtgagtcaag attgtgccag tacactccag cctgggcgac       2350
gaagcaagac tgtctaaaaa aaaaaaaaaa aaaaaaata cgggcactca        2400 atacaccgta taataataat atagtaataa tatttgctta ggatctttaa       2450
aaagtttcat ttttcagac tcccacagaa atggctctgc acagcagagt         2500 gaaggggag agagactgag tctccaggcc agaaaaaggc caggttttt          2550 gcttttgttt ttagttgttg cctggatatt gcacagaaag aaaaaataat       2600
tagcaagtta aacaaaagta ccgcaaagtt gattacattg gtatttgagt       2650
atcacatctt ctctcagaag cgtaagagac aaggtcgtga ccatacctct       2700
gcttagtttt gttttgtaat ggtgttgcta gtgatcggct tgtcaccagt       2750
tactggtgtt tctaaatgga ctataattgg ctacttgaaa ggacttcctg       2800
agaaagaaca ttttggagga cgaggagaga gtgccttctc tattttggct       2850
gctttcatgt gacatgcaag agaccatgac gtttaggctg ctgctgaggc       2900
agccccagaa atgggggccg agaggtcttt tcttcatttt aatagggtct       2950
gtaggtttgg gtggttaggt acagttctca gaatggaggt tcctggctat       3000
gaggccttga gaaagctgaa agtctccttg ggagtgtgtg ggtggggga        3050 gtcgagccca tctgttcatg ggcaggtgtc agccaaagcc cttgcgggtg       3100
gttttgaggt tggtgggaga aagcatccgt ggggtttaga gttgtggcct       3150
tttcactact tgcagttcct ttccccgact tggctttact ttctggtgtc       3200
caggggtctg ggccagatgc tgagattcct ctcagctgac aggtgtgggt       3250
tatgggcaaa cccttccctg gaggacataa ggcaccggat tggactgctg       3300
atgggttgct gttggagttg tcagggcctt ggaatagtct tcagatagac       3350
ttgggttagt gtgacctggg gcaggctgca ggtttggagc catagtaccc       3400
cccgccccca caccgggcac cctgctctgg gctaatgtga ggcttgcagg       3450
agtgagtgat gcagtgggaa gggggccctt tcctgaggat tctacagctt       3500
tctccaggga atcctcccag gtagtttagg cctgcaggtg ctatgctatc       3550
cttctttcct aaccctgtct caggtcctca gcggggccat gcggcatcca       3600
cttataaccc tgcagcgagg ccctcttttc tggccacctg ggtgtttgcc       3650
tgctgagatg ggaggaacag tggccttggg cttcttcccc cgtcatgttt       3700
atctctgctc agattgggca gcagctcaat gggacttgac cagctgtggc       3750
actgccagtc tgaagatgag taggggtgatg gggggaggtg ggcagtacct      3800
gaagctgaac tggtgagaga ggcaggctgg cctgggggct cagctggggc       3850
ctgggatggt tggtacagtc ccctcagggg ggtaggggga tgagtgttag       3900
actgcttaag cctcagaggc cgctcttgcc cacctatgct ttgaggagat       3950
```

-continued

| | |
|---|---|
| cctcttcatt tgttcaaagg gaagactctg atctagagat gggcacttgg | 4000 |
| accagcaaac agcagctaca ggtagccagg gcacccgagg agcacttgct | 4050 |
| catgagccgg tttccctggt ttttatgggg gctgttgctg agcgtctgcc | 4100 |
| agggtttgtg tcctagcact tgctggtctt tgctgggctc tcagctctca | 4150 |
| ggtgtttctc taccagcacg tttcccctc cctcatatgc acacatgtgg | 4200 |
| acacaagcag gctgcccagg acagagtgta ctttgaggct tgggaaagga | 4250 |
| ctctctctcg ccctttttggg gatgagcctt ggaacctcat caccttccgg | 4300 |
| cttggggtgg agcttcatcc tgggggttga agctttaggc tcagataact | 4350 |
| agtcttgtaa gccagttttg tcctgttgtt ttttttcgtgg aaaataatgt | 4400 |
| attgacgtat acacagacat tctttgtcta acagtctgag attgagaaat | 4450 |
| accctccatg actatttggt ttgctttcat ggtgaaactt ggtcgctttc | 4500 |
| ttagacacag cctatggcaa taagagtgat ccctggctgc tgtaattcat | 4550 |
| tccagacttt gagcaaacac aaggcaccgc ctccacctgc agtggagcct | 4600 |
| ctgatgaacc aaatggaaac tccttgggga atggggagta agagccaaat | 4650 |
| gtgggattgg acttaaactg cagcttctta gaactgtagc attccacgat | 4700 |
| gggattgtct agtgctcttc ctggaggtta ctattcaata gttggctagt | 4750 |
| gcacaggttc aggggtgacc tgatatgccc tagcgtttca gaagatccct | 4800 |
| gcaaggtgtg tcttttggtc catctgaagg gtccttgtatg gtgatcttgt | 4850 |
| atggatatcc gtgacggcta aggcatctga taacttcatt ccttcagttc | 4900 |
| cagcagtgtt cctgtattat gctgggcact agagctacaa agaagaaaac | 4950 |
| aaagtgcctc ctcttcagga actcttaatt taggcagggg aggcataatt | 5000 |
| gaacagtgct gaggtcatct aggggaacca aagtgtgtat ttatccccct | 5050 |
| ccctatcact cccctccctc cttcatttct tcctttcttc tttcagaaac | 5100 |
| tccaagttca tatcaaaatt ctccagccct ggttttattt ggttgtgtga | 5150 |
| aaattttcct ctaatttctg aagctatgca ttagttctgc tgagtaatct | 5200 |
| ttaacttgct gctttataat gattataatg agatatcact gggtattatg | 5250 |
| gtctttgggt agcagcaggg tagggatttc caggctggga ctaagctaat | 5300 |
| ttatgggttg ggaattatgg ggcagttaat agcaaggcag tccaagcttt | 5350 |
| ccacagattc caccctaggg accatccaga cttaaggaac agggccggca | 5400 |
| ggctcatccc ctttgcactc agctgggcta tgggtgtgtg tttgtgaaag | 5450 |
| aggtttattc agtagtcata cctgctgatt tccctgctat ctgtttaccc | 5500 |
| agtgcctcct gtaccttgtt tcttactctt tgttctctgc tcttactatg | 5550 |
| aagaagcaga gactggaatt ctgcttgaac ccacatctac ctggaaattc | 5600 |
| cagttttttct tgtccagtgg agcagcaatc cagttgtttt aggacaaatg | 5650 |
| gtctgccctt gaagcttaaa tccttttgagg gcctggcatg gtgacagttt | 5700 |
| tacatttggc tttggtatag actggtgtgg tccctgggca gtgaggtcac | 5750 |
| tgtaaggcca gccagccaga ccctggctcc tagggggaatt aacaaggcat | 5800 |
| gggattagac tcacagggtc cctcctgtcc ctaaacttgg taggggttcc | 5850 |
| tgggagccag actgcgatta agattgtaga gacctgagac ctgagttgta | 5900 |

| | |
|---|---|
| ggggcctctg tgttgatctg ggccattgcc gggtgagctg aggcggtcac | 5950 |
| tagctcaagg agtgatctca ggatattgtt ctgtaagtca gagacctcca | 6000 |
| ggttggagag tggggcttgg gggtggggga cagggtttag tggggagctg | 6050 |
| gttctggggtg aatgtggcct aaagggattt gtccttagaa dacagagggg | 6100 |
| tgagtcacac actcagtgct tcaggttcca ctttgcggct tggcctcagc | 6150 |
| ccgcccttc cctgcacaaa tgaaggccag gggctatata attggctgtt | 6200 |
| gctgaattct ttggcagtga ttttaaagtc tggtctgggt gtgttatgta | 6250 |
| gctgcttctc tatccactcc ccacacccgc tgcttctcca gagcccctca | 6300 |
| caaagcccag gcagagagag agagagagag agagagaatg acttgcctca | 6350 |
| cagagatgtt ggggatagggg ataggggtat gggtctttgc ttttgccttt | 6400 |
| tgagggggga taatctcttc cttcatttta aagtaaaaaa gtaatgcagg | 6450 |
| ctcattgaaa ataatttgaa aagttgaaag agatataaaa gcacacccaa | 6500 |
| attcctatca cccaaaagaa atataccggc atatttccta ctagtctttt | 6550 |
| tcatgtttaa gaatatagct gatatatttt tttttctttt tcttttttgag | 6600 |
| acagggtttt tgctctgtca cccaggctgg agtgcagtga tcacggctca | 6650 |
| ctgcagcctc gacctctcgg gctaagcgat tctcccactt cagtctcccg | 6700 |
| agttgctggg accacaggtg cacaccgcca tgcctgacta attttgtat | 6750 |
| ttttgtaga gatggggttt tgccatgttg cctaggctgg tctcgaactc | 6800 |
| cagagctcaa gtgattcacc tgccttggcc tcccaaagcg ctgggattat | 6850 |
| aggtgtcagt caccacaccc agtgttatag ctgttgtctt tatagatgaa | 6900 |
| cagatagatt gacatagatt catgtagata gcctggtgtt cagcattttt | 6950 |
| catttaagat tctgtcacag acttgacccct ataccttttaa aaatcacaaa | 7000 |
| ggcagtatca tagtctgtca gctgaatatg ccataactta aaaaaatcat | 7050 |
| tcaactgttg ctgaacacac acatatacat atatagttt tgttttttct | 7100 |
| tagtgatgta gtgatgcttg tgcagaaagc tttatgtact ttttggatgg | 7150 |
| tttctgtagg agagctttct aaaaaaggaa aaaagtgtt gaatgttttt | 7200 |
| tgagaagggc tagattttca agccagtctt acaaaaggat agactcattg | 7250 |
| gaaattccag atttgcttag tgctggcaga tgagtatcac ttattgctga | 7300 |
| acaatgtgtc tagaattctg attaaaaaag aaactaggtc caggaagtgc | 7350 |
| ctgggggcag gggcaaaggg ccaggctgca ggataggctc ttaggatctg | 7400 |
| gctgagcaga aatctgctgt gaacagaatc ggtgggggtg atgctttctc | 7450 |
| agtaacttct ccatttgttt ctttagcagc taagtccctg tgctggactt | 7500 |
| ctgtggacta ctgtggctct ggggctgtgg ttgtgggtga acaacagcta | 7550 |
| gctaaaccag tgctgttgac atcattgaga tgtgacgcac aggaaggtgg | 7600 |
| gagcaagctt gcaaatcaga ttctgaaaca tatagcacag ctctcccacc | 7650 |
| tccaggtggt cctgagatct agggaggagc catagtgaga aactttaggt | 7700 |
| ttctaggaat tctcttaggg agaagctctc ttagggagag gcagaacctg | 7750 |
| gttctcagtt ggggctgatt caggtgggtt agatcaataa agcctcaggc | 7800 |
| cagtgtgcca ggctattccc aaggagtata ctttgaagtt actccctta | 7850 |
| gaatgtcctc agtggagata aattctctct gaggagcagt tttgtctgcc | 7900 |

-continued

| | |
|---|---|
| ggggtcattt ggcacaaagc ctggagtgct agggcgaggt tgcactgagg | 7950 |
| gaagggcag gattatgtca gcagtgtgac ggatacagtg tgaggtcagg | 8000 |
| ctccttcctg ccccaccacg ggggcctaga ggtcatgggg agggtccctg | 8050 |
| gcaggggatt caatcattgc ttggccccat gacagagtat attctaaaaa | 8100 |
| tgccttaagt ttttttcttt caaagtttct tcctgttttg cataatggcc | 8150 |
| ttttgccttt gacatcctga aaccgcagag ctgtcattgg tgttgcagga | 8200 |
| cactgccagc ttgaaaaaaa tcaacaacaa aaaagaaac aggaaaggat | 8250 |
| gtggagttca gggtgcggcc tagggaagct ggtatttgcg ttatgggatt | 8300 |
| gtgggatgt ggtattaagg tgttgggtag cgcctgacat ttagaggagt | 8350 |
| actctgggca gagtccctgc ctgcccaaga ataggtagaa ttgagtcttc | 8400 |
| acaccaaagt caggagagac cccctccccc caggaagaga atgaacaggg | 8450 |
| actcatttcc tcattcagca aacttttatt ggtaactaca ctatatgaag | 8500 |
| tgtgagagat agacatgaac aagagaggcc cccactcttg ggcagtccct | 8550 |
| tagtagtagt agatagactc tggcaatatg gtgtggtcag agagaggaag | 8600 |
| cctgggtgct ttgagggtac tgaggaggtg cagggagcca aatgggtggt | 8650 |
| ctgggccagg gccagagtca gaatgaagga cctctcttcc agacgttgat | 8700 |
| tttagcatct ctgtctctca gtatgtttga acagtctccc ttattggaag | 8750 |
| ggcaggagtc tactgctaaa agtaacctgc gatttcctct acttgctgtc | 8800 |
| atgtggaaag aatactaaag ctgaaattcc aaaagttgca cacctttacc | 8850 |
| agcagggcag gagaggaaag gaaatggagg cagagtgagc tgaagatgat | 8900 |
| aaaagaaaga gaaggtggtg cagtttggac tgttatggac agaggaagtc | 8950 |
| tgagggtagc tggactgagg gatcaaaggg aggcagttga aagggaagag | 9000 |
| agctgcagag agggatttct tggtctgcag agggtaggag caagccttga | 9050 |
| aggctgctgg agtgaggatt ccgagccctg gtctttattc ttttttctaat | 9100 |
| tcattacatc atttttaggca agtcctaact cctttggtct ctgttgtctt | 9150 |
| tctgaaattt gagtgggctg ggcctgctgg tcttttagcct ctgtcttttct | 9200 |
| ctacctccta gattccagtt tggcgagtgg ggggaaaac ctggttgtat | 9250 |
| atgcaacgtg aaaggcctct ggaattcctt ttgaagctca ctacccatga | 9300 |
| ggcttctgct aaggatttca tcatgtctgt ctaagcagac ataaaaattt | 9350 |
| tagcaggtgg atgacccgta gaaatggcac aaggaatgtt tctttctgtc | 9400 |
| acactgtggt atttgattta agaaagttgt tatcctctct gtgcctcagt | 9450 |
| gttctcactt gtaaaatggc aataacagta tccacctcat agatgttatg | 9500 |
| aaatacaggt agtagccacg aaagggctta aacagtgcc taacacagaa | 9550 |
| taagttgtga atatatgtta tttattattg gtagtataat gcttatttgt | 9600 |
| gaagattttg gcttttgctt tataggacct tttttttttt tagttgaaaa | 9650 |
| tacaatgtta ccatgttaaa tgttaaaaaa aattctactt accattgtaa | 9700 |
| cagaacatgc tcccacttct gtaacagagc ttgctattac ttttcaaatg | 9750 |
| catacatatt ccaatgcata tattccaatg cagttgtaga gtgaaactgt | 9800 |
| ttgcatgcag ccatttttat ccaacattat cttataaaat gttatgttgt | 9850 |

-continued

| | |
|---|---|
| ttatgattat cctaattatc ttttgttgct gtctagtatc cttatagata | 9900 |
| ttccattagc atacactatt ccaggtttca ctatcgtcga taatctagat | 9950 |
| atgaacattt ttgtagtgtg tagctctttg cttcagttga attactttcc | 10000 |
| tgggataaat tcctggggaa gaatttctag gccagaggat atggtcatct | 10050 |
| tgacaatact gattcacatt gctgcattgc ttttccaagag gtttggaatc | 10100 |
| attcacaggt tctaaattgg aaaatcctgg cttttgaagt atgtggattc | 10150 |
| taagggcgat ttggatctag ctggagcctc acactgacac ttccagccag | 10200 |
| tgtgtgtgtg tgtgtgtgtg tgtgtgtgtg tgtgtgtagt tccctatgct | 10250 |
| ggacaccgtg tgtgtgtgtg tgtgtgtgtg tgtgtgtgtg tgtgtagttc | 10300 |
| cctatgctgg acaccatgtg gcctttctgg acattagggt tttcctgtga | 10350 |
| ttgcctcaga gcagttcctg ttgaattcac tctgtgtcca caaaaggagc | 10400 |
| cttactgtgg ctcttttcaac acccacctac cttttgccaag ttggtttaca | 10450 |
| gaaagtaaga acattctttc cttcttcctt gatatgtggc gctaaaccta | 10500 |
| tagcatgggg caggctctgg ctttaaaaac ctgacttaaa aataatggtg | 10550 |
| ttgatcaaaa agtttgtgga tcagttttttg gaaacactgc atgtagccat | 10600 |
| ccatagaaac ttatattctg ttgggctagc ctgggcgcct gatcatttaa | 10650 |
| ctcatgtgga tgaacttcta tgtaatagcc ctggtgtatg ggatccagaa | 10700 |
| acagggccct aatgaagaaa ggcttttaaa ttatgttgga taaaaataag | 10750 |
| ttgttacaat agcccaaagt ctgcaaatat gaattgccag ttctgtcctt | 10800 |
| gtagtcatcc accatgtgcc tgcatctttt gtagactctt gtagattcag | 10850 |
| aagcccactg aattgcataa atgatggaat gattttagac ttagtgattt | 10900 |
| cagtgactaa aagtttacag atcctggccg ggcacagtgg ctcacacccg | 10950 |
| tattcccagc actttgggag gccgaggtgg gtggatcacc tgaggtcagg | 11000 |
| agtttgagac cagcctggcc aacatggtga aaccttgtct ctactaaaaa | 11050 |
| tacaaaaatt agccgggtgt ggtggcatgc acctgttgtc ccagctactt | 11100 |
| gggaggctga ggtgggagaa tggcttgaac ctgggaggcg gaggttgcag | 11150 |
| tgagcccaca tcaggccact gcactccagc ctgggtgaca gagtgagact | 11200 |
| ctgtctccac ctccccgcc ccgaaaaa aaaaaagtt tacagatcca | 11250 |
| gcagatgggg catattcaat ttgtgacagc cactcccttc acttatagc | 11300 |
| tatgtcatat gtcttcttct cctttgactg cattctgcag cagtcagttg | 11350 |
| tgacttaata tggcactctg ggcccactga attaggtcag agctgctagt | 11400 |
| agtatattgt tcctagagac ctagggcaag attttcttac tacataaaat | 11450 |
| gagggagata atttcttacc tcaagatgtt ggtaagagga gtgaatgagg | 11500 |
| ttagttatat ggtaatatca gtactctgaa tgtcttttga tcaatgccta | 11550 |
| actcatcttc ttgggcacaa aaggcataca gtcagcaccc ttaggccaca | 11600 |
| tataaaattc ctccaaatgc aggttttcat ctgccttggg gcagagtcaa | 11650 |
| gagaaagaag aggaagaggc gtgaggctct gaccacaact tagggacaga | 11700 |
| atatagccca aagcgagtac cccaggccac aaggagaagg ccgctatctt | 11750 |
| gttgaatcca cagcactgga aacttggagt gtgtgttccc ctgtgtcagt | 11800 |
| tacactggaa ttttatggct gctcacattc ttcccttcag gtggacgttg | 11850 |

```
ttcatcagta tcctgggcaa gaggccatca taaaccacag acagctgagt         11900
gattaggaag aggagctgaa gagggagcat tagatgtttg attgagtctt         11950
aggtgagaaa gtatatcatt aaaacaaaaa gatagatgta ggcgggctca         12000
gtcttgtgtg cctggtgtgt tggtagaaaa actaaagcac aagcctgtag         12050
ataacctgct ttattctacc tcggggctgg tgttggaatc caggatgcca         12100
gaccctaaag tccagctctc tttccaacct actgaataat ccgagagaaa         12150
tcatgttctc tctctgggcc tcagtttgcc catgtataaa atgagatgaa         12200
ggattggctg ggatgctctc cagagtctct tcctgcctgg agttctgacg         12250
tagccatgta ctcctgctca gcatcgctaa atggctttgt ggtaggacca         12300
ttgagtgctg cctccattag ggccagctat gtaatgctgg ggtggctgtc         12350
actgggccct aagagccagg attggtctta ctggagaaat ccacatccac         12400
ctaaacttaa gacccagggg tgtccaatct tttggcttcc ccaggccaca         12450
ctggaagaag aattgtcttg gaccgcatat aaaatacact aattatagcc         12500
gatgaggtta aaaaaaaaaa actcaatatt ttaagagagt tcatgaattt         12550
gtgttgagct gcattcaaag ccatcctggc cgcatgtggc ccatgggcca         12600
tcggttggac atgcttgctt tagacctccc agcaattcta gtctctaaac         12650
aggaaatcaa aagtcaagat gaatagataa gttggtcagt gtgaaaaagt         12700
aattggtggg agccactgta gatgcagggt tctaggctcc atcaacaacc         12750
acctacatca ctgaacgaaa gataatgctt gttcagcact tattacatgc         12800
caaccatggt aaaaatactt cagatgcatt gttttcatga actctcacag         12850
cagctctttt tcttgcctaa atgccccgtt agaacctcca gtacaatgtt         12900
aaatagatat gctaagagac aacatatgtg tcttgttagg gggaaaatat         12950
ccagtctttg actattaaga atggtgttag cagtgggttt ttcctaggtg         13000 cccttt atca ggttgaggaa gttccttt ct attcctggtt tgttgagtat         13050
ttttatcatg aaaaggtgat gggttttgtc aaatgctttt ctgtgtctgt         13100
tgagatgatc atgttttttt gtcatttatt ctattgatat ggtatattat         13150
acattgattt ttcagatatt aatcttgcat acctgggata aatcccactt         13200
ggtcatggtg tataattctt tttatttgtt gctggattga gtttgctagt         13250
attttgttga tttgtattca taacagatag tggtctgtag tctttccctc         13300
cctccctccc tccctccctc cctcccttcc ttccttcctc tctctctctc         13350
tctctcccct ccccctccctt cttttcccct cctctcccct cccctttccct        13400 ttcttctctt tcatagttgt ttaccactgt cagaaaaggt ctgttcgttt         13450
tctttcgtcg tgagatcttt gtttggtttt ggtatcaggg taatactgcc         13500
tcaaaaaatg agtagggaag tgttccttcc tcttctgtat tttgagagag         13550
tttgtggtcg gtttttatta attcttcttt aaatatctgg tagcgttcac         13600
cagtaaagcc atctgggcct gatgtttt ct tgtggaaaa cttttt gatt         13650 cctaattcag tttctggtta taggtctatt cagaccttct attttt tctt         13700 aagtcagttt tgatagtttg tgtcttccaa ggagtttgct tcatctaagt         13750
catctaattt gttggcatac atttcatagt gattccttat gatccttttt         13800
```

| | |
|---|---|
| atttccgtta aagttggtgt agggatagtc cctctttcat tactgattat | 13850 |
| aataatttga atttctttt tttcttagtc ttgccaaaag cttgtcattt | 13900 |
| ttattgatct tttcagagga ccaactttga gttcattatt tgttctcttt | 13950 |
| gttcttattt ttctgcttca ttaacttctc taatctttat tctttcattc | 14000 |
| tgcttgcttt tggttaagtt tgcttttct ggtgtcttaa ggtagaaggt | 14050 |
| taggttactg atttgagatt taaagatcat gctctttaaa cgttttgata | 14100 |
| gatactgtca gtttgccctc tggcttttc tcattaacag tgtataggag | 14150 |
| tgcttattcc tcacactcat accagccctg ggtgttacta acctttatat | 14200 |
| atttgccagt atcatattca gacatagtat cttgttttaa tatgtttctc | 14250 |
| tgattactga tgaagttaag caaattttca cgtgtttatt ggccatctgt | 14300 |
| cttttctttt tcatcctttc tttcaagatg ggagtctttg ccatgttgcc | 14350 |
| caggctggac tcgaactcct gggctcaaat gatcttcctg cctcagcctc | 14400 |
| ctgagtagct gggactatag gcgtgagcca ccatggctgg cttgcccatt | 14450 |
| tgtatttctt atgtgagtat ttttttcttt ttttgaagt ggagtctcac | 14500 |
| tccatccccc agagtggagt gcagttgtcc gatcttggct cactgcaacc | 14550 |
| accgcctccc aggttcaagt gattctcaca ccttagcctc ccaagtatct | 14600 |
| gggactatag gtgtgtgcca ccacacctgg ctaatatttg tattttagc | 14650 |
| agagatgggg tttcaccatg ttggccaggc tggtttcaaa ctggcctcaa | 14700 |
| gtgattcacc tgcctcggcc tcccaaagtg ctgggattac aggtgtgagc | 14750 |
| cactgtgccc agctgacttt tttttcttt ttttaaccc tttttttt | 14800 |
| ttacccttt tttggcccat tttttttac ccttttctt ttaacccatt | 14850 |
| tttctattag ttttaaaaat atgtttgcag gagcttttta tattgtggat | 14900 |
| ttttcttgtt tattacatat catttgtaaa tatggtctct ccatctgtca | 14950 |
| ctcttcttta tctctggttt ctttagctat gtagaagttg ttatgttatg | 15000 |
| ttatgttatg ttatgttatg ttatgttatg ttatgttatg ttatgttatt | 15050 |
| ttttggagag ggagtcttgc tctgtcgccc aggctggagt gcagtggtga | 15100 |
| aatctcggct cactgcaacc tctgcctcct gggttcaagc gattctcctg | 15150 |
| cctcagcttc ccgagaagct gtgattacag gcacccgcca ccacacccag | 15200 |
| ctaattttg tgttttagta gagacggggt ttcactatgt aggtcaagct | 15250 |
| gatctcaaac tcctgatctc aaatgatcct cccaaagtgc tggggttaca | 15300 |
| ggcgtgagcc actgcactcg gccagaagtt ttgaatttt atgtgtttaa | 15350 |
| atctatgttt tcctttatga cttcaggttg ctttcatact taagcaggtc | 15400 |
| ttcaccatcc caaatgata aaattttct cctgagtttt cttctaagtt | 15450 |
| ggttctttag aagccaccaa cttggcttcg acagcaaaag atgaacagaa | 15500 |
| tttctgttca actctcatgc tgcaagaagc tttatgtaat actccaggga | 15550 |
| cccttaagg tccagagtt ttcctccaaa tctatcagtg attctagtgg | 15600 |
| ctaagagtag aaatgtgaaa atttagccat gtgtgctgat agagctgtag | 15650 |
| taatttgtaa gctctgaagt tctaaggagt caggggagaa gggaaagtaa | 15700 |
| catttattga acatctatta gctcaataag aacatgcgat aagtatgtat | 15750 |
| atgtattatt tcacttacat ctgaaaggaa ggcataatta tccccactcc | 15800 |

```
ttagagaagg aaattggagc tggctacatt taaagtagtc ctgacaccag         15850
agagatattg ccaggagtac ttggctggct gagtgcccag atggcccata         15900
ggagtagtgg gccctccaca gtccaaggtc tggttctagg tggagagaga         15950
aggatgtgct cgtagtcagc accgcagctc cagaaaatct gctggggctc         16000
caaaactgat tagaggggca gctgactcag taataaaact cccaggagac         16050
ttacttacat actggaatgc aaagttgcag ctttactggg aagattagaa         16100
ctgttattga gtagcttaga aatctctggc tgaattcact gcaagggaag         16150
ccgcaggata agctaactgc tggtgagtca gcagtcagag cagggaagtg         16200
aatttaacat tagatgggtc agtctctcgt ggctgatgaa ttcatcccca         16250
caatactgta cacctgcctt agggaccttt gtctggacta ggggttgggg         16300 tcccctcct ttgtacagcc ctggaaggac acatccagct ccatccgcca         16350
tctctccctt acttatttcc ttccttcctt ccttctttcc atccagccat         16400
caagcttcct ttcatggcca ataatcatca ttggggtcta ctcatggact         16450
ctcttgcctc atgtatttgt tttattttgt cctcattccc acttctattt         16500
cccaggtata tcacaggcaa ctattctaac gtatttatag tttgtgtatc         16550 tgttttgct cttgccaaaa tggaagccac tgctttatac atagatgtat         16600
tcttaacttt aaaaaaaatt ttttagatt aacctacaat aaaattggct         16650
ttttggcata tagtctataa attttaacac atacatattt ttgtgtatct         16700
accaccacaa tcaggataca gaacagttcc atcaccccaa aaaaatccct         16750
cttgtagtca cattctcctc ccaccttaa tcccaggcaa ccactgatct         16800
attcttcatt actattgttt tgtctttttg aggatgtcac ataaatggag         16850
tcacacagta tatatacatt tttttaaaca tatgtaaatg gcattttata         16900
gctcattttg attatatgtt tttcatccag ttctgttttt tttttttatt         16950 tttaaaagt ttgacataac ttcagactta cagaaaagtt gttagactaa         17000
tacaaagaat tcctggatat cctttggagt ccctaaatgt taacattta         17050 ctatatttac tttttccttc tctctctctc tctctctcgc tctgtgtgtg         17100
tgtgtgtgtg tgtgtgtgtg tgtgtatcta cctgtagata gatagatatt         17150
aatataattt tagatagatg tatctagatc tctctctctc atatatatgt         17200
gtgtgtgtat atatctatat ctatatctat atatatctcc tttacccctt         17250
aaatattcag tgtatatttc ctaacaacaa ggtgatttaa aaatatatat         17300
ataaacatag tataattaac aatcaggaca tcaacattga acatttctg         17350 ctatgtcatc tacaggcctt aggaagactt tgtcaggtgc cccaataata         17400
gccttgatgg tagaagaaaa ccatgtgttg tattcagttg tcatgtctct         17450
tagtgtcttg taatctgaaa taattcccaa gcccttgga tttcatgaca         17500 gtgacattgt tgaagagtac aggccagtta ttttgtagaa ggtctctcag         17550
tttaggtctg tctgatgttt cctcctgatc agattcaggt tattcacttt         17600
tgacaggaat accactgaaa tgatgctgag ttcttctcag tgtaacgaga         17650
tctagagaca cacactgtca gtttgttcct tattggcagt gtgaaccttg         17700
aggatttcat tgtagtggca tttggcatta ctccattata gttactattt         17750
```

```
taccatttta aattaaaact atctggccgg gcgtagtagc tcatgtctgt      17800
aatcccagca ctttaggagg ctgaggcggg caaattgctt gaggtcagaa      17850
gtttgaaacc atcctagcca acataacatg gtgaaacgcc atctctataa      17900
aaaatacaaa aaattagcct ggcgtggtgg cgcatttgta gttccagcta      17950
ctcaggaggc tgaggcacaa ggcttgcttg agcctgggag gcggaggttg      18000
cagtgagctg aaatcacgcc actgcactct agccagggtg acagagtgag      18050
actctgtctc aaaaaaaaaa agtaaataaa taaaaaaatt ttttaagtat      18100
cttatgggca tatacttgtc ctgttactcc tcaaactttc atccactttt      18150
ttttttttaa atttttttc ttaccttcca tcgttttctt gatatccact       18200
gggttttagc atctacaaat gattcttgcc tgaatcagtt attatggtag      18250
ttgatggttt tctaattcca ttattccttc tatgtttgtt aattttggca      18300
ttcttctata aggaagagct taccctttt ccctattaat taattcatat       18350
attaatgcag acctatgcat tcttacttca ttaaatcata atcctttact      18400
atcattatgt attctgatgt tcagactatc ccagatttag ccaataagat      18450 cccccttcagg ggaatggtct ttgggattcc tctttagagg ttcctggttc     18500
ctgttttctt ttgacatatc ctattactct ttgagcattt ttttttttt       18550 ttttacttt aggcacagca agaagttcca tggtcctctt gttctttccc        18600
caactcagcc ctagagtcag tcacttctcc aatgagctct agttcctttt      18650
agtagagaat cataattaga aaacaagaat cagtgccaag tgtgcacctt      18700
tgtttttaag gtccatccac gttgccgtgt atatgtccag catgttgatt      18750
ctaactgctg aataatacct catgattgtc atccatccca gtgtttcttt      18800
ttcccttctg taatgaggga ctcctggact gcctccagca ttaccttcac      18850
aaatattgct gtgaggaaaa tccttaaacg tttccttat gggcaacgtg        18900 tgagcatgtt tatgttgatt caggggtgcc agacacagct ccagaatggc      18950
tgcctcagtt tacatttcca ccagcagagc atgacaggct ctgtgtctcc      19000
gtgaataatc agcattaacc agcttcctat ttttgccaa actaatagat        19050 gtgctaggat aactctttgt tttaacttgt ttttctctga ttaccaatga      19100
gctggagcat ttcttcatat gcctgatggt ctttgggatt cctcttaggt      19150
aaattgctta ttcattataa tccttgcct gtttttcact ggagttctta       19200
tatttttctt gaagatatgc aggaattcct tatacatcct agatattaat      19250
cccttcctgg tctcagacat tgcagatatc ttctgaatct gttatttact      19300
tatttattta caatttttt tttaagagtt ggggttttgc tctgtcaccc       19350
agactggagt gcagtggtat gatcatgact cattgtggcc tcgcaatcct      19400
gggcttaagc gatcctccca cctcagcctc ctgagtagtt gggactacag      19450
gtatgcacca ccagacttgg ctaatttat ttatttttt agagatggaa         19500 gtcttaatat gttgctcagg ccaatcttga actcctggcc tcaagcaatc      19550
tttccacctc agcctcctgc atctattata tatatgttca ctttgctcat      19600
gctgtatttt gttgcaacat aaaactattt ttcccattgt tttgtgcagt      19650
ctctcaccag cactcttctt tttctgtaac tgtgttaatg ccctttgttc      19700
ttccatatgt taggtatgct ggtatagttg aactctgctg actctcctca      19750
```

-continued

```
gtaaacagtc tcttttatg acaccttatc ctctactgaa ttctctctat      19800
caagaatgac ttggccgggc atgggggctc atgcctgtaa tcccagcatt      19850
ctgggaggcc gaggtgggca gatcacccga ggtcagaagt tcaagaccag      19900
cccggccaac acggtgaaac cctgtctcta tgaaaataca aaaatcagct      19950
gggcgtggtg gcaggtgcct gtaatcccag ctacttggga ggctgaggcg      20000
ggagaatcac ttgaacctga gggggaggtt gcagtaagcc gggatggcac      20050
attgcactcc agactgggtg atggagaaac tccatctcag ggggaaaaaa      20100
aaaaaaaaaa aaagaatgac ttgtcttcct cttagagtgt gaggtctaca      20150
tacaaatatt attcttgtat tcagcaaatg tatgtcatag gcctagtgtg      20200
tgttaggaac tgtgctgtca ccaacaaagt ttagagaggt tataaaactt      20250
gactgtagct tttagaggt ggaggagtga tttgaaacct aggctgtaat        20300
tccttcctcc tgtgattcct tcctactgtg ttgccttccc ttgaaaattg      20350
catttggggg ccaggtgtgg tggctctcgc ctgtaatccc agcactttgg      20400
gaggctgagg cgggtggatc acctgaggtc aggagttcaa gaccagcctg      20450
gccaacatgg cgaaaccccg tctttactaa aaatacaaaa attagctgga      20500
tgtggtgtgt ggtgacatgc acctatattc ccaggtactc agtaggctga      20550
ggcaagagaa tcacttgaac ccaggaggca gaggctgcag tgagctgaaa      20600
ttgcaccact gcactccagc ctgagtgaca gagtgagact ctgtctcaaa      20650
aaaaaaaaa agaaaagaaa gaaaattgca tttagttcct gtagactgtg       20700
tgtcaaatgt ctaaatctct tctaacaaat ggcctaagga ggtgcaaagc      20750
gaagcatcct caccagcatc ctgacttggc agtgaggcat gggaccctgg      20800
agggagtagt ggtaagtgtg actctggaat tcttcctggg ctacttgtca      20850
gtgactggct ccagattgag aggagagccc agaggacaca ggtggctgcc      20900
ccagcctgga ggtgaaagtc ttaaaataaa atgccagatg cctagaccat      20950
tctaaacctt tctgagaagc tgaaatcatc ccttctggaa gcgctctagt      21000
tctaaaagga cagatataca gcaagatctt cctggggcta atatggagtt      21050
tataggcaag taggcctcag aacctttccc tggtagtgat atctgtgggc      21100
aggcacagtt tccacacttt ccagaaattc cagcggaagg agtgagaagg      21150
aggaatctgc ccttgagtga ggaccaaaga aagcagaaat tcctcttggg      21200
aattttccct ccagagacca aacactactt gggagcttgt ttactgggct      21250
ttaaaagctt gtgaccccca gtcactcttt cttgacccca aggctttgca      21300
tttctgtggc ttccccactg gacagaagtg gaactgtcat gctgcctgtt      21350
ctggggtctc ccagaggttt ccccatgtcc tctccttgct tctactgccc      21400
cacagaattg gggatctgtg accacatatg gtatagaatt aatgcttgag      21450
aatggtttag ttcagtgatg tcaaataaga ttcacttta tgccacctcc        21500
atcagttgaa ggccccctg gccctaaat tggaaagat tctgagacag          21550
aatccccgtg ggtacagcgc agggacagta aaggcacgtg tgctgtgatt      21600
tgctatccac tgtgtggatg catccaggaa tatcagaacc ctggaagatt      21650
atttaagggg aagttaggac agcttttttg ccaatccaag ggtgttcttg      21700
```

```
aggaagtctg tcttcctgta tggccttcag tttctttcct gtgtaaccat      21750
ggggccaaca cataattccc acagctctat tggcccttgt ctgccaggat      21800
tctctagggt ctgattcgag gtggatcctg gcccttcgag gtggcagaat      21850
ctgatcatgg tgctgtttcc ttagatttag gccttgatac ccttggcgag      21900
agcatcctgg gctgagtgac cacctgaggt ttttctggtg attttgtgac      21950
ccatgtaaaa ctttgagctt tgggattatt ctctcaagga aatagtgaca      22000
tttggtgaag agcctgtttg gtgtggctat gtgaggctta gccaagaaaa      22050
tgcaccattt ttattaggag gttaggccat ccgttgccac aaagtgtcag      22100
atgctaggcc tagagcctgg agaaaactta ttttaaaatt gatggggtgc      22150
tggaggggtt gggggtggt ggctgtagct catgaatcag gtgctaaacc      22200
tagaaacaaa aggcctcatg tggcagactg tttctgagca cagatgaatg      22250
gatgagcaac tggcgcaact ttgcccagtt ggtccagctt cccacttggc      22300
cacctaggct tgctgtgaag acctcgtctg gcagaaatga gagtgttttt      22350
gccccatctt gatcttaact gtaatttaag actaaaatct tagattctaa      22400
aacatcaaag gcaagatggc tcccagctct gtgagctcag cttctcacct      22450
cttagttgaa caagtgcagt gtgggtcaat acatgattgc tgctcttgct      22500
gccaggaact gtcccagcat agaaaggaat gggacacaat ccctgccgtc      22550
aagattctaa gggaggaagc aggcaggtcg actggtgcct catctctgca      22600
gggctccagc caaggtttgt gaaggatttt gcaggcatat ggagtgggga      22650
ctgattgatc ccgagagggg actggggaaa gctctgaaga ggggatgaca      22700
tttggtttga actccaaaaa atggttgctt tacctgtttc ctgaagtttt      22750
tgaggtggct tataagaaca tataccataa aaaggaccaa tataaattta      22800
aaatcagaaa aagagaaaat gggctgggca tggtggctca tgcctgtaat      22850
cccagcactt tgggaggcca aggtgggtgg atcgtgaggt caggagatcg      22900
agaccatcct gcctggccaa catggtgaaa ccccggctct actaaaaata      22950
caaaaaatta gctgggtgtg gtggcacatg cctgtagtcc cacctacttg      23000
ggaggctgag gcaggagaat cgcttgaaac ctggggaggcg gaggttgcag      23050
tgagctgaga tcgcaccact gcactccagc ctgggcgaca gagtgagact      23100
cctcctcaaa aataaataaa taagagaaa atggaactta gaaaattaag      23150
aggaagagtg aaaaggtaga tatttagtca ggcacagtgg ctcatgcctg      23200
taatcccaac actttgggag gccaagacag gaaaatctct tgagaccagg      23250
agcttgagac ttgcctggca acatctcagg tgagacctta tctctacaaa      23300
aaatttaaaa attagctgag ctgtgtggct cgtgactgtg atcccagcta      23350
ctcaggaggc cgagaccaca gcccaggagg atcgcttggg cccagcagtt      23400
tgaggctgca gtgagctggc accactgcaa ttcagcctgg gctacagagc      23450
aagacccagt ttaaaaaaaa aaaaaagat attcaaacca tgggtcccaa      23500
cgtagttatt atatttgacc atttgcaaaa gctgaaagca aaacatgtta      23550
cacattttca gagaggaaaa tacacagtag ttcctgagtg taagttgttt      23600
ttcttgacct cattcttaaa ttgcttcatg agggtgggag ggaagtggta      23650
gttaataagt gaacctgtaa accagcgttt ctcaaaatgt agtccaggga      23700
```

-continued

| | |
|---|---|
| attgcatcaa aattgcagtt acctacagtg cttgttaaaa tgcagattcc | 23750 |
| tgggcccctg ccccaggctt atcaaatcaa tctggtgagt aggactcaag | 23800 |
| aacctgtaaa ttcacatact tctgcagatg attcttcttg cactgcacag | 23850 |
| catgaaagcc tctgcaatag acagaaagct accagcattg cgaaagcaac | 23900 |
| ttgagtgctt ggcctttgaa ggttgagtgg gactttaatg agggagagag | 23950 |
| taaggcatga gaaatggcag ttccactgag gtcagtcagt ggttcattgc | 24000 |
| tgacgaagtc acttttaagt catgttttag aagaactacc aagtgtggca | 24050 |
| ggtcaggcat gtggcaggac tgtttctgag cacagatgaa tggatgagca | 24100 |
| cctggcccca ctgtgcccag ttggtctagc ttcccacttg gccacctacg | 24150 |
| gtctgctgtg tggaccttgt ctggcagtct cctttaattt attttttatt | 24200 |
| atttttttct ttttgagatg gagtcttgct ttgttgccca ggctagagtg | 24250 |
| cagtggcatg atctcggctc actgcagcct ccacttccca ggttccagcg | 24300 |
| attctcctgc ctcagcctcc caggtagctg ggatcacagg caagtgccac | 24350 |
| cacgcccagc taattttgt atttttaata gagacatggt tttaccatgt | 24400 |
| tggccaggct ggtctcgaac tcctgacctc aggtgatcca cccatctcag | 24450 |
| cctcccaaaa tgctggaatt acaggtgtga gccaccgcac ctggcctatt | 24500 |
| tttttcagc aaattctttg tttttctctc tgttcccaaa tgcagggtac | 24550 |
| tgagaccaca gatgtattct gtttcctgtt gaaaaatgt ttctcactta | 24600 |
| gctgggtgtg gtagcatgca ctgcagtccc acgggaggct gaggcgagag | 24650 |
| gattgcttga gcccaggagt tcgataatca tgccattgca ctctggtctg | 24700 |
| ggtaacagag cgagaaactg tctcttaaaa aaaagaaaaa gaaaagagg | 24750 |
| tcctagggaa agaaacaaat agtggcttgg atggtgagtt ggtggaaaga | 24800 |
| acagtgggtg ttgggggtgt tgaacttgtg tttgtgtgtg gtgtacccaa | 24850 |
| gacatatcat gtcagcatta agaatagact attcctgttt tctggtcact | 24900 |
| gagttgtatg ttttgacatc cttatttgg aagatacttc cttactagga | 24950 |
| atgggatagg gagggggtca cctttcccat ctgtgggtca tattttaaaa | 25000 |
| tatttattgt tcaagtttaa agatataacc aaaggtataa agaaaaatac | 25050 |
| cacaaacatc tgatttaaga aacaaaccag ccgagcgcgg tggctcgtgc | 25100 |
| ctgtaatccc agcactgtgg gaggccgagg caggcagatc atgaggtcaa | 25150 |
| gagatcgaga ccatcctggc caacatggtg aaaccccgtc tctactgaaa | 25200 |
| atacaaaaat taactggtca tggtggtgtg tgcctgtagt cccagctact | 25250 |
| cgggaggctg tggcaggaga atcgcttgaa cccaggaggc ggaggttgta | 25300 |
| gtgagccaag attgtgccac tgcattctag cctggcgaca gagtgagact | 25350 |
| ccgtctcaaa aagaaaaaaa aagaaagaa atcatttcct acaccttcga | 25400 |
| agccttcatg agttagattt tgaaacagtg caaaatgctt cacgtgagaa | 25450 |
| tcgagagtcc cttctggtgg ctctccatcc cctgctcttc tgtcaggttt | 25500 |
| tcttgtaggt ttatggaaac ctttgttact tgtgcaggtg cagagaagc | 25550 |
| agagaggata gctgcgcgcc acccacacag ctaggattta ttggcgtact | 25600 |
| cccacgtgca tggcagccaa gtggacacaa ctctgtgatg aatcctccca | 25650 |

```
agagaactga gggccctga tggaggagct gcttctttgc aaagctttcc       25700
ttgactctct tcctgtcccc tagttgattc cccttctgtg ctagttttag      25750
cttattgttt gttacctgtc acacttagca gtactgttgg ctttgctggt      25800
ctccttgact actgggggta aagacctttt gttgttgttg ttgagacaga      25850
gtcttgctct gtcgcccagg ctggagtgca atggcgtgat tcggctcac       25900 tgcaaccttc acctcccagg ttcaagagat tctcctgcct cagcctccta      25950
agtagctggg attacagcta caccacaccc ggttaatttt tgtatttta       26000 atagagatgg ggtttagtag agatggggtt tcaccatgtt ggccaggctg      26050
gtctcaagcc cctgacctca aggtgacctg cctgtctcag cctcccaaag      26100
tgctgggatt acagacatga gccaccatgc ccagcctcaa agacctcttc      26150
tttacttgct caccctgccg cccactcccc taccaacccc tgcatgccct      26200
ataccacctg gcacatgata catactaact gggtacatgt ttgaatatga      26250
atggatgtgg tgctgtgaat gcttagggga agtgggtgaa atgcttaaga      26300
accaaccttg agtggtctgg gaaggcttcc tgggagggtg gtgtttgagc      26350
taaggccagg cagctgttag atttgttaga ctgaagccct tgcagactta      26400
gagagcttgt gctcttccca gaatgacggg tgagccacgt acagtaaatg      26450
gtgcttctca tttctagccc aaggggcctc aaggggcacc gtgatttcac      26500
gagaatgctg caagcaaatc tttctcaag ctggggaatt tggtggtaat       26550
gcctggctca gcttgcggtg cgcacctggc ctttggaaga ttggtacaga      26600
gagaagcggc ccatccacat gagcctgtgg aacagcactg gtgggggagc      26650
tgatttgtga agagggggctg tgcagtgtac tgtcaggtct gagacccagg     26700
aagaaattcc agtatcccag ctctcagaat cacagagttc taggcactgc      26750
ctagttccac gtgttcccaa atgtttcctg aatacttgga tttcctgtcc      26800
agagaatttt caaaacaaac ttagaggcct gacccatggc tgccaaggaa      26850
ggattttttt tttaaattaa attttaaaaa tcagtccagc atgaaaatct      26900
atgatgattt cataagagaa aggacatttt aatattcaaa gagtaagaag      26950
cacttaatct tggaagaaag ggcattccta tactttgatt acctttagtt      27000
taattaaaaa acacctacat ggtctttact tctgtgattt cattcctggg      27050
ctagtgaaac attgtcacaa taaagcatca ggccaacgct tctttcgacc      27100
cactggccaa tcagttgaca aacagtgact agatgtttca gcctattttg      27150
ctgaggctaa aggattgaac tagtgcttca gccagcatga aaaccagtca      27200
ggagtccgtg ctggtgttgg cttagattag cagggccttt gatggagggg      27250
catgtatgtg tttgggtttg ctgtgccagg caggggagca gtggaatttg      27300
tctgaattga gctcacacat tgaagttatt gagcgactta catgcaaggc      27350
catgacctgg actccagcc gagaggccca cgtggcgggg cttgagctgg       27400
gggagccgag acagcttac atctgctcat ctgcttacgt aaccctgcct       27450
cccagcttcc agagccaaga aaacacacaa gccagcccag cggggccgag      27500
agcctgtggt agcacacgcc atgcgccgca cagcaagggc gccttggctc      27550
ggcttgaggc ctgtcatgaa gccctcagcc ctctgcctcc tcccagagct      27600
tctccccacc accccaggca gtggctctga aacctggtcg caggtctgca      27650
```

```
tgattctgaa cagaggtagt cgttgccttc ctggagtctg agctctctgg      27700
agtttctcac tgggacagag ccaggtgtgt agcagagcat ggtccctgca      27750
gtatggcagg aggtgtgcag ggcattcagg aggcctcctg gctggcactc      27800
gacccaatta gtcattcaac gccaggtctg gggctgctgt ctgttgtctc      27850
aaaggtgtga gctgcaagat ccttagagtt gtggagaaaa aattgccaga      27900
ttggcaagaa gggcaggatt gggggtcaag gtgtctcagt gtgttggaag      27950
catgatgggg gttgtgcaag gggcacagcg agttcagaag ggagcaggag      28000
agtgagaaga ggctgttcag tgataaagct ctgcacagag ccattggagg      28050
agcaagctcc ttgaccatcc ttaaaccagg gtaattttca tttaggttct      28100
gccacacgct cagcagggaa ctcctggaag gcaggatttg tcttgtccat      28150
cctccctccc tacctcaacc cactcctcct gggctggca cacagtaggt       28200 acccagaaag tatcaattga aacaaattga aagtggtctt gatacatatc      28250
acagggcaag tttgcagtta acagacattt cagagtaaag actctctggc      28300
ttggtgctcg atcggcttct gtgggttgtc agcatgctgt ggacagcccc      28350
ggcatgggag cgagtgggcg tgtgtgtgtg tgtatgtgag ggtgagagag      28400
cgttagtgtg tgtgttgggg ttggggagag aggaggggga atagaagatg      28450
gaccacccgg gtatcagctt ctgccctggg gagatggtgg tgtcagttgc      28500
tgagggaatc ctgagaagca ggtctggctg taggtggtga tggtggtggg      28550
gttgcatgag aatccatttg gggcaggttg aatttgaggt gcccatgaca      28600
tatggctagc catgttctgt tggctgtgag gtcaggagag agacatgaga      28650
tggaaacaga ggtttgggaa ctgtcatgtg cttaaaccaa agacctgggt      28700
atagggagag tgagaagaga aggggcaaa gatggacatc caagaaagaa       28750
gctgagaaag cctaggaatt tgaggtaaga ggagacgtag gtaaatgtga      28800
cgcttggtga tcaaggcttc tttccacctc tcctatgctg gacactcacg      28850
tctcctgtct gcttggaaat tcatgctgag ggcagggaag gtgggagcaa      28900
ggatttgtct aaagatcttg cttttggatcc ctgcactcct cctggtttac     28950
caagtgtcac tggacacgtc agggcgttct gagaccttag agagcatcca     29000
gtcctgtccc tgcagtttac aaatgaggaa accagtaccc tgagagtggc     29050
tgtactatcc actctcagga taccaaagat catctggaaa gtcactggtg     29100
gagctggacc ggggcccagg catctcttct cctgtccggg gctcttgact     29150
tcaggaccac ctttctgaaa cccatgatgg ggcaacacca ggacactttc     29200
cagcctgcag gtgtctgtcc cgcggaagcg agccaggcca catgtgaatt     29250
cctgttttct gggtgggttt cagaaggtac gagcaagtcg gcagggtgac     29300
agcccaggtg cttcttgggt tccccaaaac gcggttatgt ttagcagcat     29350
cctcagaacc aaaggtgggg tggggctgc agatgttgtg ggggccctct      29400
gaagtgaaaa gagccctgtg acagatcttt tcttcatgtt tttcacaagt     29450
tcactgtgca gcagggcccc cccagtagcc tttgcccagg gttgggtgtt     29500
gggcagccca ggcctggctg accttgtggg gaagggtgtg aatggtggga     29550
atccccgagg gccctctttg cccgaaagcc ctaagccttg acatcagatg     29600
```

```
cccatcagat ggtccatcgg agccctacta cccagcttgc ccagtgagaa         29650
tcatctgggc tccttgttag gtagccattt aggtccttcc caaaatccac         29700
agactctcta agggaagggc ccgagatgct gtacttgtac taacttcctc         29750
aagcaattct tgtgataggt ttgggaaaaa cttgtccagg gtgaccactg         29800
actgagtcct ggtcttctct gaagagcaca gtgcctgctc actttagggc         29850
accctgggag gtgggagctg gctcagcagg cagtcttata agggactgag         29900
cttcaaggcc tctgtccctc caggagggag gtgcatgacc agagagggag         29950
gcctgaggat cttcttccct gccccagagg gtctgctgcc tgagctctgt         30000
gatagcgcag agagtaaaag gatcaagctt gattgaggcc tatctctcaa         30050
tgcgaaagtt tgctagttaa gaggagagtg ggaagggcat ttctggcaaa         30100
gagaaaagtg tggacaggca tggcttaagg gatggggagg gagacagaca         30150
gagctgaggg tgaagggcct tttgctcagc tgtgggcctt ggccttccct         30200
tgtgcaggga cacacagcct tagagccact ggaggtttta gtgggaaagt         30250
aatatggtcg gggctgtatc tcagaagaaa acaaactaat gggaacaggt         30300
cctgtgatgg tggacctggg tcagctacgg agggagggaa gatgtgagat         30350
gtgtactggg gaaggggtg gaagtggcag ctatctggtg agaggaagca          30400
ggcccacagc ttttttctc aagctgttga attcagaagg gcgagtgatt           30450
ccgggagtag ggggtgcttg gagagccacg cgttattgat aaacagggca         30500
ggctgaagcc tgctcactgg ccctgggcgg gttctcacca gcatgtttca         30550
ggttttgatc tgtgcttgtg gttggtgttc ctacctgttc tctaggttcc         30600
ttcctttgtt cttgtggctc atttgcttca caggtgaagc tggttacact         30650
agagtaacag ttcccaaagt gtgttccctg gaaaaatggt tctgtagcca         30700
aataagcttg ggaaatggtg ggttaaatat aacgaagggg ttttttcgac         30750
tgcacaactt ctcagagcct ttggtgtgtg tcgtgacttt gcagaagcag         30800
gatttaatac gcagcattcc cgttcttatt tgaccacgag acatgttttt         30850
ccattaagca tcttgctggg tctgatgttt tctggaaccc attttgaggc         30900
ggtctggtct gcagagagta tggggagcct gggttcaagc cttggctctt         30950
gactctcagc agagccttga ttccctgtgt tgcctggact gcaccacgtg         31000
taccacatac ccggtatgtg acgttttcct catccctctt cccacctgcc         31050
gttacctcac aatccacaat ctgcacctca tccattttc ttctgaggca          31100
agcactctct tactaactta cttatctcat ctgcatccat gttcttctag         31150
gccagaaact tgggagtcat ccctccctct ttgttacttc ttcttcctct         31200
ttgttacttt atcccctctg ttactaaaca ttcttctgtg tttccagcta         31250
tttcttttat tttccctcgg tctcctttgg ggtttctttg cctccatctc         31300
tcccagacct tggttcacct tccatcgagt cccttcctgg gacatgggca         31350
ctcatgccac tcctgctacc ttccacttcg aagctaactc cctccacact         31400
gacgtcccca acatgcatgc atacacacac acacacacac acacacatac         31450
acacacacac acacacactt ccccagttag gctagaatca gagagatgat         31500
gtcagccatt tgtccaaggc cacgcagctg ggaggtcaca gagctaagtc         31550
tcaacctcag gggttttgag aaattgcctt ctcatccgtg atcactgatt         31600
```

```
tctacaacag cctgtcagga agtctgggta gaaattactt ccattttaca      31650
gtggagtcag agcggggagg gtcctgggca ggcgagtgct tcacagagtg      31700
accaaccatc taggtttgcc ccacactgaa gggggtttct ggggatggtt      31750
ggtcacccta atgctggatg tggtgcctga tgctgggcag gagggccctc      31800
tccgtggcca cgttgcctcc caggaggaga catttcctct gcagctgcag      31850
ctgcagcctg gccatctgat gcagcctgtg gagcggtggc gagtcctgtg      31900
gcctgctaac ttctccctcc ctccacctct ctagtgggcc ccatgctgat      31950
tgagtttaac atgcctgtgg acctggagct cgtggcaaag cagaacccaa      32000
atgtgaagat gggcggccgc tatgccccca gggactgcgt ctctcctcac      32050
aaggtggcca tcatcattcc attccgcaac cggcaggagc acctcaagta      32100
ctggctatat tatttgcacc cagtcctgca gcgccagcag ctggactatg      32150
gcatctatgt tatcaaccag gtgaggcctg gaaggtggga atgagagagg      32200
gtgtgtgtgc atgcagatgt gtatcagatg tgtgtgtaat gagggcaggg      32250
gaaggggagt gatttcacag acacctggca cttacagcga ggaaccagcc      32300
ccccagccac caccagtgca gatgaggtaa acgccaaaca gtgtgcttgc      32350
ctattgctgt caactctata gccaagggaa atgctgagt gttttcgttg       32400 ttctgttttt gttttctgga agtagccttc cagcaagatt gggaaaaaag      32450
acaaccctaa ttattccaaa gtacacactg attattccct ggctttgtgt      32500
agctgtgtat tttcctttta aaataaaac caccatttag atgtcagact        32550
tttaggtaac ttcaaagttt atccagtcag tcagagcgtg tctcctgggg      32600
cacctggaga cagtgcccctt agttcaggtc acatgcctac atgccagccc     32650
ctggtgaaat atctggagaa gtctgattcg tgggccatct gagagttatg      32700
tggactgggc cgagtctgag aaaaagtttc tcactgctcg tctgatccat      32750
atgtgttggg ctttagcccct gcttaggaaa gtaatgctaa ggataggtca     32800
actttcatca ccatggcatg gagaatcaga ttgatctaag aggcatcttt      32850
attgaaataa attttttcagt ttatttgagg agcattattt tcccaagagt     32900
ataactttga tatttcaaga ttaccccctaa cacttaaatt catgttttta     32950
gactataacc tcctaggtgc aatgacacat ctaacttatc taagcaccca      33000
gtttcattga aattcatttg aagagtctga gtacgcccat ttctacaagg      33050
cccaatgtcc atttcatttc gagataaact ctgctttagg taggaggatt      33100
gttggcagtt tacggcttcc atcaaggtca aggaactctg tgcaccttcc      33150
ctatgacccc aggggaagca ctcgaggact gctgtggcat tgtgctgcat      33200
cacttgctgc agggagattc tgaagaagtg taaggtctca gtcctgccct      33250
gtcccgaagc ctccaaccca cttctggcaa gtgggacctt cccagggaac      33300
aatttgttaa cagacccaaa tatcctgtga ttggatggtg gctgccaaat      33350
gctttggaag ctcagaggaa ggagagagag caatggcttg gaagaaccag      33400
gatataaact aggttctaaa gtctgcaggg agatgggctt tcagctgggg      33450
gccagtgagc agggacctta aggcagaaag gagccttgca tgttcctgga     33500
aattgagatg cccactgggg taggaaagca ccagaagctc tgggaccagg      33550
```

-continued

```
tgtcagagtt aagcctgtga ggcaggagag agcagaacaa gccctgttac      33600
aaggaaactg aagcaggaga gcaggtggtg ggcaaacccc ttgaggctgt      33650
ttgaattctt cggccaagtg aggtacagac cagggcccta tgaacacctg      33700
caagcaagac agccacgcag ttgtgggtca ccttggaaga atattggaga      33750
atgcaagaga gaacaggtaa atgtcctgca aaatgcgggt cactttaacc      33800
caacacatat tcatttaaga aaagctctgt gattgagaaa catttgtctg      33850
atgccagtta gcacatacca atgacggcaa gattcaggag cctgttatta      33900
aagcagtggc agcgagcacc tggaagaggc ggccaccatc accaggagcc      33950
agcagggatg actaataagc cgtgccagct gcatctcgtt tctctcttga      34000
cagttgctat gccagtagat gagggatgta ctgtggatac aatgctgtca      34050
tatcttattc agcagggcat ctgatagcat cccacaaatc tgcctgagta      34100
gaagacagac agctgtggtc tgggtgccat ataggtaggt taaaatatat      34150
atttgggcct aggcgcagtg gctcatgcct gtaatcccag cactttggga      34200
ggccaaggca ggcggatcac ttgaagtcag gagttcaaga ccagcctggc      34250
caacatggcg aaaccccgtc tctactaaaa atacaaaaat tagctggaca      34300
tagtggtggg cggctgtaat cccagctact cgggaggctg aggcaggaga      34350
atctcttgaa cccaggaggc agaggttgca gtgagccgag atcatgccac      34400
tgcactccag cctgggcaac agagtgagac tctgtctcaa aaaaataaaa      34450
taaataaata aataaataaa atatatactt gggtaaagag gataaaagag      34500
ttagcgatga tgctgaattt ttgaactgag gtggctgttt tcaaggaaga      34550 ctggaggggtg ggatgctacg tctagatatg ttgcagttta ggtgaatgtg    34600
agacttccct gttttgaagt caaatattgg accagtaaaa tctagccatc      34650
agcttaaatt cctatgatac aatttacata ctccccaggc tcaacacagt      34700
agatttctga atgtcctctg ccagctacat gctcctgccc acctcaatcc      34750
gagtagatgg aacaactaac caagccagct cagaccggtg gcacagctgt      34800
gctggctaac actgggcacc acctaagaga gtgcttctcc aaaagtgtgc      34850
ttccccaaat ggagcgaaat acgcttgagg aatgttgggt tgaaccatgt      34900
aaagcaggtc tcattcccgc agagcctttg gtaccccggt gtacactgta      34950
accccagaag tgtttcctga gcttgcctga cgagacaact tttccaagaa      35000
ccgtctcaag tgatgagtgt tttgtgagtc acactttggg gaaagcgggc      35050
ctaagttagc atctcctccc agctgcctcc ctgctttccc tggaacacta      35100
ggaactgccc gtcctccctc cctccctcct cttcccactt cacaacttag      35150
catcaggaat attttagttt tggtttttca aacatatata cctccttttt      35200
tcttatcttg tcaatatcat ctttttttt tctttgcttt tcctcatact      35250 ttttttttctc ttcatccttt ccttctccaa gggttaactt tccaccttag      35300
gagaatcttt tctgcttttt ctcccacttc cccagctact ctcttatcat      35350
ctgctccaat ctcaccctaa ttgatcattt tgggaaaata tggtcagagt      35400
ccagataact aagttgagaa atgcttaaac tctgccatac cttttccagta     35450 aagaatatta cctaataaat aataaaatgg taatgggaaa cctgaaccct      35500
gaaaaaaaag aggtggaagg agaaacattt ggagcacatc ctgtctacaa      35550
```

```
attaggaact gcctgtgtta tctgttttat ggttatattc tagaagaaga       35600
aagggatttt gtagcacctg gttttgacct ttctgcactg tttgttgagc       35650
aaataaacct tatgggctgt tagccctctt tatagcctct cagcttatcc       35700
ctggcccaga caccctgctg tcattttgac ttttcattcc cacacacaca       35750
tacacatgca cacacatgta cacacacaca cataccattt aagattagac       35800
agaagtaatg ctcaaaatgg agtggcttct gagacattta gtccaagggt       35850
tcccaaacag gcttttcagt atcagatttc tttctgcccc attgaaatgc       35900
tacacaacct tccgcttaca gcaggtcaca agggtttcat tctacttgaa       35950
gtagggccca tgtcccattt ccacttcctt ggcttcccat tcagtcactg       36000
ctaggatttg cctagacccc tgaggccaga caatgtagaa acttctgctc       36050
catgtcacag gtgaggaaac aggctcagag agggacaggc tccgaaagtc       36100
acatagacaa cagtagggct gcggctcaaa ccccagcgtc tgactccagg       36150
tttagtgcct tctcagggca tcagtgacac tcctcatggc cagggtgccc       36200
ccagtgttgc tcacagtctg gtatccaggg ctgagagtgt gctgtgtgct       36250
cagactgcct gggttcagtc ctggcactgc cactttacag tcagtgacct       36300
caggcaggtt acttaagctc tgcaggcctc agtttcctcc ttggtgggga       36350
gggttatgag gcatccttct catggtaaac cttcagtaaa taccagccgt       36400
tactaggagg gtccactcct gcctctccac tctccattca tcctgcctgt       36450
ttcctctgcc tgcttcctct gcctgcttct gtggtggtga attcttcatg       36500
gctcccaccg cctcctgctg caccccccact cagggcccgc atcaggaccc       36550
ttcctcctat tggtttgaac tccttggagt cagagggtaa tggatagtgg       36600
agtgagccag gtggcagaat ctcagaggcc atcccgggcc tataagcctc       36650
ttcaaaatag ggccacgtat caagctttac acacaggagt gaactttcac       36700
aagttgttat gactcatact ctgtctatag taagctgtta accactccca       36750
tttggcttat gcctctgtaa ttattgtact aacttatatc ttaaaataag       36800
gatattgaag gaatgagccg ggagaggctt tcctggttga gatatagaag       36850
aacaagagtt gctcttttc cttaaggtct ctcctcccac ccctgacctt       36900
agctcaccag catgggagaa tactatttga ctccttgtac tctgagacgt       36950
ggatttcaag atatagcatt ccaacttcaa cggcagcaag aaaagaagca       37000
acagaaggag aagacatcat agcaaacagg gatgcatgct gcatttccta       37050
atactcaaac ccggaaacga gacttcactc aaggtgaagg gagggcaggt       37100
caccacctgg tagcactagc cctaaattaa ggaatgcaga atgtttgtgg       37150
gattgcccat cataaaaatt acaaaatgag taaggaatgc aggcacagct       37200
ggccaggtgg gtttgtcaca accatggcag ccctttgccc cacagccagt       37250
acacagaact ggtctctcca attccgattg catatcttct ggcacctctg       37300
ttcctctccc tcagctgccc aggatttttc tggttctgac catgttactt       37350 cctctttaa acctgttagc atttcacgac tgcctacagg caacggtcta       37400
aatggtcgga aggcccaagc ttagcatccg agaccctgac ctacctccag       37450
ccacttcctc ctcctctcca cttcactgga ctccccatct ccacccagac       37500
```

```
acctctgttc tccctctgt gtgcctttgc ttatgctgtc ccctgtgttc      37550
ctagtgtgtc tctggctatc ttttaagctt ccctccccaa cctcattagt      37600
tctgtggagc ccctggaata gagctgactt ctccttccct gctgctccca      37650
ggctgctcag aactttctgg aaagggatga ttatctgagt tccagcctca      37700
ccccagcccc cggactctga gtccctcatg tctgcctccc ttctttctct      37750
ctgaccacac agctggtaca tagtcagtac agacgcagtc agtgagtgga      37800
gcacggggct tctctccagg attcctgccc ctttgtttat ccctagtctc      37850
aggactccct actcctggtc ttctgcctaa atctgtgcct cttggaagtg      37900
aagcctccgt tcccagtggg gccaggtcct gacccttggg aacttgcagg      37950
atccctccct tgggcctctc cccgaagctt ccagctcaat gctgaccaga      38000
gcacaggctg cctgtgacag tccttggggt gacctccctt atcaggaaaa      38050
atgcagaaaa cctattaata ccttagcctt gtgattgtta atggtcacaa      38100
aactccttta gggtcctttg gactcagcac ctttatggtc tcactttgaa      38150
ttttgaacct cccacctccc ccatccccc agagtaaggc aaatggtctt      38200
ctgattgttc ctgcagaggg aaggctccac aggtaagcac acgatggcca      38250
ggaagcagag ctggagcctg cctgaaaggc tgtggagaaa tggagggagg      38300
gctgccctga ggactctgtc tggctttgaa gttttctact gtttcctttt      38350
cttctgtgca ctgttttagg atgatggggt gatagttcca ggctggttga      38400
ggatggattt ggagacagtc ctttgtaccc tcagtgagca agagtatctg      38450
tcaccctacc tcagcagttg tctctgtcac tggtccaagc agctggttcc      38500
tacacaaggt caagatcaac tggggagaag cagactcctg ggtctatccc      38550
attagtgagg acagctgcct gggcttatgg cctcattggt ttggtttcta      38600
tcttgatcat ctctaccatc cccccatccc ggccttccat tttctacctc      38650
agctgtcagt gcacagattg atgtgtgtgg gaacggagct tgggaggagt      38700
ggggtagggc tggtcctgtc ctgtagcctc cccttccttc gggcacttgg      38750
acccttttgga gcttgccggg gtggggaatg ggagtgggaa ggccagggag      38800
tgtctctgca ccatcactgt ttgagtgttg ccccttttgct gtgtgcccca      38850
cctagtctat gtgtgtctct gttctctggg gactcaattt gctggtgaat      38900
tgcttccatg gacattgttc tgggaaatgc catttttttct gctcacccat      38950
gactctgtga caaggaatga cagcttatta ggaatttgtt tttgcattgg      39000
aacagtggtc atcagaatgg gcccctttttc ccttgcagct ttgacatttg      39050
cctctctttt cctcacctct ctcccttgca tccacccttt tctcttttttc      39100
ttcttttttg ttttccttct agcaggggcc ttttacctttt acttgttaat      39150
cctgtttgta gcaaagcaag tggaaggagg agttcctctc tgatctgctt      39200
cttattctcc acctaccttc tcttctgtac tttccgcctc ctagagagag      39250
agagagagag aggaatgccg acctaactac cgctgccact gctgctgcca      39300
ccaccgctgc caccaccacc ctggtaatgt tcacatgtcc tcaaatcaac      39350
ccagagccag ggccctgctg gtcaggggga ggctatgtaa ataatcccat      39400
gagtgtgcca tcctcaggcc ctgggtctc ctaggcaaga ccagggcctc      39450
tgtgggctct ctcggaaatg ctgaggttgc tggaagccag cccgtcatac      39500
```

```
agggtctgag agtttaactt cttttaaatt aaaccacagt tgagctcatg      39550
ctgtgtgtgt ataaactttt gtatcctgct ttttccttaa attctttatc      39600
atcagcatct tcccatgtta tttcatagtc ttcatcatca tcactttcca      39650
taccttcata gtagttgatc gtagaattcc atcataatta acttgtcttt      39700
tctctcttag aagtccctta ggtaatgtcc aattttccgt gagtgtaagt      39750
aataccataa tgaacatctt ggagtctgaa gtttattctg tgttggtttg      39800
ttccacattt aggatcattt tcccaggcta gattttcaga tgtgggatta      39850
tgggttcaga tatggtttac acatttttat agttcttaat acagatggcc      39900
aaattgcttt ctgaaagaga agcttttctt aagtatttt ctccaacttg       39950
tatcttaaac atcctgaaca tgcttagcac cactgtcttg atatatctgc      40000
ggaaagccac gtctccactt ttcagtgtgt cgggccctgg gagaggcagg      40050
catcctgcgc tggctccttg gagctgggtt taaaattgtc tcctctggct      40100
gggcgtggtg gctcacacct gtaatcccag tactttggga ggccgaggtg      40150
ggcggatcac taggtcagga gatcgagacc atcctggcta acatggtgaa      40200
accccgtctc tactaaaaat acaaaaaatt agccgggcgt ggtggcgggc      40250
acttgaaaag tcccagctac tcgggaggct gaggcaggag aatgatatga      40300
acccgggagg cggagcttgc agtgagccga gatcgcgcca ctgcactcca      40350
gcctgggcga cagagtgaga ctccatttta aaaaacaaa caaacaaaac        40400
aaaaaaacaa acaaacaaaa actgtctctt ctgtgctcac ttcacccaga      40450
atccctgttg ggctcttcaa ggagctcagt tctctctgaa agcaactta        40500
tagcctcagt ccagtctgtg ttcctgtgtg gcaggggtca agggtatgct      40550
cactcttgag agtggtgtct ttggttgacc aagaaccact cccatagcct      40600
ggtccctaac ccttgaaggc ccatctctct cactcactgg ggtgaagagt      40650
ttaaatctca gatccaagtt tgttgagag ctctgagcta ccatattgct        40700
atggttaaca atagttaaca atgttaacaa tggttaacta tggttaacaa      40750
tagttaacaa tgtttaacaa ctagagccca gctgggtgtg gtggcatgtg      40800
ctaacagtcc cagcttctca agaggctgag gtgagaagat tgctggagtc      40850
caggagctca aggccagcct gggcaacatg gcgagaccct gtctcccctg      40900
caaaaaaaca acaacaacaa aagcaaaact agagcccaac tgctgtgaac      40950
tcatggctga gtagatatta ttagccctcc acaaactcag catttgtata      41000
atcccaggct gtttccagta attctctggg gatcatctcc cagcctgtcc      41050
actgttccag gatccacact taggcctata ggaatgcccc gtcagagctt      41100
ctgctgccgc tgatctgtta ctgtttcatg caacccactc ggcctagttc      41150
cttcctctta ctgtctcagt gggcacagaa aagcatacag agggtgtttc      41200
agcaaacatt gccactggct gcagacctgc ccccggatct gtcctgttga      41250
gagcttagtg ctgcgttctt gcatggtggg gaggggtgtg gctctgtgat      41300
gagccagggc atgtgtatag gagcaacagt gtctctctta tcacgtagaa      41350
gttctgactc attgcgagtc ttggcttggg gttaatggtt ccagccatgt      41400
tgctgctgtg tcttttggtg caggagaggc tgggcacagt tggtccctaa      41450
```

```
gccattatgg ataagggatg tgtctgctga tatacacaca tggacctgac    41500
atccagggaa ggcagggtga ttggacagaa cagttcttcc agaagctgtt    41550
ggaacttgga caagagtggc ccttggcttt ctgtagttgg tcatctgtcc    41600
cctgttgcaa tcaggggaag gccacacttg ccttccttaa ccacagttag    41650
gattttcttg gggattagac cagattctag cacctgtcct gaacctctcg    41700
ccccgcccct acaaaggctg cttgcaagtg tagtgcacat acacagggag    41750
caggtggggc atggaagtgg aagtggagcc cctgcctttg gcccttgggg    41800
gaggcactgt ctgcttaccc acggttgttg cctcatagga atcatacaac    41850
agcttcctaa ctggtctcct tgccttcagt tggattgggg cacaaatccc    41900
tccttgacat ataaccatg gtttaaggct ccctgtggcc taaataaaga     41950
taaagcttaa gtatcttaac aagcacctaa cccttctccc cagcctcggt    42000
gatttggctc atcgctgcct tcatgtttca ttctggcttc actcattcgg    42050
aatttcttgt agttccttgg ctgttctctt ttccttaccg cctttacaaa    42100
tgctctcacc atgcatgctt ttctctgctc ctacagatgc cttctctccc    42150
agcaccgcct ccagagtcta tgtctggtcg attctgtctg ctgtctccag    42200
tccccatctt gtggcagtct ctgctcaatc atttggggat tttatatgtt    42250
ttctggcctt tcttttgggg gcctgtcttc tccttctaaa agcagccagt    42300
tgacctagaa ggaagggata actgtaactc ttgtctacca acataagatt    42350
aggcccaccc tttaaaagct gcgtctttga aagggacacc tgcacccagc    42400
atgctggctt ctcttcacca agcgtgactt cctacgcatt tcacaggcct    42450
ccagaggtcc ccctgactct cttctgctgt gagaaactct aatcatgtaa    42500
gccacaggct aattcccttg agccttaaat gtttttagta atttcccatt    42550
catcagagaa gcaggatttg ggaggaattt tgaagcaaac actacagaag    42600
gcagagtctc caggtaggat atctaagaga catttggaat ggtctgactg    42650
ttcaagatgg atgggaaagc ctcttcctgt aatgatagta gccaacattt    42700
gttgtcaggc agtggggccc cattttgag atggggtctc tgtcacccag     42750
gttggagtgc ggtggtgctg tcatggctca ctgcaacctc agcctccccg    42800
ggctgggtct tcttaattct gaaaaaccca gcttttaaag ggtggaccta    42850
atcttatgtt ggtagacaat gttgtctcat ttaatacaat gcacatgctc    42900
tccccataac acaaaagagg gaactgaggc ctggaggtgt gatgtacccc    42950
aagtcacata gctaataaat aaagaagcca gcattcctgg gattaaaaat    43000
gcatgtgtct gtcactgtgg tgtatttggt gcttgatcaa tgtttacttg    43050
agcaaatgga ggggcagagg taccgatgag tgtgctcagt gaggagggca    43100
ggagtgaagc tgggcgtctt cccgcctctt gtgagtggtg gggcttggtg    43150
agcttgccag ggcctgtctt tcttatcaaa gaaggtgtgt gccccagtgt    43200
tacagcattt cacccaaagc agcctagaaa atgcttgact tttctgtcat    43250
tccggggagg acactttcct cctccactgt tctgctggcc tggtgtaccc    43300
acggcccctg atagatgata gcacctgcta aagtgcacca tgcccttccg    43350
tctcactgca tccacagat gaggccaggc tgggatgagg gagaaaggga     43400
gggatatata gttcaggtta ttttggaaaa ctgcctgacc aattttaagt    43450
```

| | |
|---|---|
| ctgggccgga cactggggca tctcaccacg ttgaaagggc cgtggcaccc | 43500 |
| cgggcggtga aagggctgg aaccaggtct gcttcttggg cttctcctcc | 43550 |
| agggtgccat tgctcatggg ccttggctgc agaggtgctc attcgtggtt | 43600 |
| ccaaaattcc aattcctggg agaggaaaaa tgcttagttc agtctcagtt | 43650 |
| aggcctctgc ttagatcaaa cagccaaggc cagtaggccc agtcctatgg | 43700 |
| tagagacatg gcctcaaaga gccctctgct gcagttgttg gggagtgtac | 43750 |
| caagagaagg gagcattgtc ctgggctggg cagccctggg ggtctagtgc | 43800 |
| atagatgtag aaaggctctg ttggtatacc tcccttcgt tgttggaaag | 43850 |
| tgctcaacgg ggctgaattg tgtttgacag tgtaagtctg ggctggggtg | 43900 |
| agggttgtta caagattgtc aagatgatta aatgaaatgc catttgaaac | 43950 |
| acttatccat gccttgtgta tggtatcccc accagtgaat attcacagta | 44000 |
| tattataata attccaacaa cttcataatt ttcatatgca atttctaaac | 44050 |
| tttgaacttt tttttttttt tttttttttt tgagacagtg tctcgctctg | 44100 |
| ttgcccaggc tggagtgcag tggcgcaatc ttggctcact gcaacctcca | 44150 |
| cctcccggct tcaagtgatt ctcctgcctc agcctcctga gtagctagga | 44200 |
| atccaggcgc ccgccaccac acccagctaa tttttgtatt tttagtagag | 44250 |
| acgggctttc gccatgttgg ccaggctggt ctcaaactcc tgacctgagg | 44300 |
| tgatccaccg ccttggcctt ccaaagtgct aggattacat acgtgagcca | 44350 |
| ctgtgcccgg caatttttg tgttttagt agagatgggg tttcaccatg | 44400 |
| ttggccaggc tggtctcgaa ctcctgacct caagtgatct gcccgcctca | 44450 |
| gcctccctaa tgctgggatt acaggtgtga gccaccacgc ccagcctaaa | 44500 |
| ctttgaattt ctttgaaccc atgacttaca cagaattagc tgaacgcaga | 44550 |
| attccaaatc aactcagcct gtgggacagc caaaaaacac agtgtgcctt | 44600 |
| tgggctcctt cactcaccac gcggggttag aaaactttgt cagaggcttt | 44650 |
| aaaaaaggag ctcttgtgtg taaaatgttt ccttgattct ctttctggtg | 44700 |
| cctctctttc tctaagtggt ttgcttcccc aagttcccca cctgagtctg | 44750 |
| ggtggctgtg gcacatctgt gcattctgta cgcacacagg cagccttttg | 44800 |
| gagtgccagt ttccaggtct tggttttatt tatttattta tttatttttt | 44850 |
| tgagatgggg gtctcactct gccgcccagg ctggagtgca gtggtgccgt | 44900 |
| catggctcac tgcaacctca acctccctgg gatcagttga gcctcctacc | 44950 |
| tcagcctcca gagtactagg gaccaccatg cctggcaaat ttttgtaatt | 45000 |
| ttttgtagag gcagagtctc accatgttgc tcaggctggt ctcgagctcc | 45050 |
| tagactcaag tgatctgccc accttggcct cccaagtgtt aggattacaa | 45100 |
| gtgtgagcca ccatgcccag cccaggtcat ctttgaggg catggagaga | 45150 |
| agactttgag catcccactt ttgagattgt gtaccagtcg caagcccta | 45200 |
| tgacacactt ttttccccaaa gtagggggct ctgactatgt tgatcccaag | 45250 |
| agagatggga aagagcattg aatgaggatt ccaaagtatt gggccttagt | 45300 |
| tcgtttcctc atgttggtgt tgtgaagatt ctggttagga taacagcatg | 45350 |
| tgtgcaggag gctttgtgaa ctgctgagag tgaggcgtgg caatgtcagt | 45400 |

```
gctaggtttg tccttactaa cctggggcca tgggaattga taagaccaga    45450
ttcccaactc tacccacaa tgtgatccct gtggtgaccc ctcacagggc     45500
tctttggtcg agcttccag aagggatcac catctgccat tgtatgttga     45550
accccattca ttcattcatt cattcagcca accagcaact atttgttgag    45600
ctcttattgt gtgagaagca gtcttcaagg aactgggtga ataaaaaaaa    45650
caaaacatcc taaccttcat tgagcttaca ttcttactga agaaaacaa     45700
ataaaacata catgtaatcc tagcactttg ggaggccaag gcaggcggat    45750
cacttgaggt caggaatttg aaaccagcct ggccaacgtg aaacccatct    45800
ctactgaaaa ttaaaaaaaa aaaaaaaaaa aagccgggca tggtggcaca    45850
tgcctgtaat cccagctact cgcgaggcta aggcaggaga atcgcttgaa    45900
tcctggaggc agaggttgca gtgagccaag atcataccat tatactccag    45950
cctcagtgat gaagcaagac tccatctcaa aataaaaaa taaaaataaa     46000
aatatgcatt ccctttgcac cagcacactt ggtgcctggg gacctcgtgg    46050
ttggcaccct gaagcaggtg tccctcttct gtcttgcaca ccttgcttct    46100
gtcctggtgt gtatggcatg gccttctgcc ctccatggtg agcactgtga    46150
gggcagaggt tgagttgggt ttgctgtatt tctcaggtgc ctaggtttgt    46200
gcttgacagg tagatggaag gcacacaatg tggtcatcaa acctcagtca    46250
accatataag gaaggtagaa gtgaaaagtc ccataggtac ccaactaatg    46300
tcaccagttt cctggatacc tttcctggag tttatttata gtgtgtataa    46350
ataaatgatg tatgtgttta aatgcctttt tcacctttcc ttttagagct    46400
gcctcttttt aacagttcca ttccattgta tggatgtact atgatttatt    46450
gaaccagttc cctactgatt attctgtttt ttgcagtctt ttgttatgat    46500
gaacattcca cagtgacaat gttgttcata gtcattcaca cacatgcaag    46550
tccttctgca ggatatattt ctagagggga attgctgact cagaggtttt    46600
ggtactctgt gttgattgta gagtgacggc agaaaagtga ggcccaagag    46650
tttcctagtg accatgtgta gtggacaagt caccagtccc tgtgagtgtt    46700
tggcccaaag gctttaaggc atttgatatc actgtttttg tttctgcacc    46750
aggcgggaga cactatattc aatcgtgcta agctcctcaa tgttggcttt    46800
caagaagcct tgaaggacta tgactacacc tgctttgtgt ttagtgacgt    46850
ggacctcatt ccaatgaatg accataatgc gtacaggtgt ttttcacagc    46900
cacggcacat ttccgttgca atggataagt ttggattcag gtaagagata    46950
ctcagtcaga atctgtggta aacatgtctc tctcatgtgt tgactaggaa    47000
atgcagtcct ggcagctcaa gagtgcctct ttaagctctg gagcagaatg    47050
cctcctctga gaaatgggtg ctttgtatta gttgagatgg aaagaagaga    47100
ccagaaatgc ctgtagtctc tgcacatcca gacaaaaaca aattttcccc    47150
ccttttttt ttttgtttgt ttttgagac agggtctggc tctgtcaccc     47200
aggctggagt gcagtgccgt gatcttggct caccgcaacc tctgcctccc    47250
gggttcatgc catcctgtca cctcagcctc ctgagtagct gggactacaa    47300
acacttgcca ccatgcgcag ctaattttg tatattttgt agagatgggg    47350
ttttgctgta ttgcccagtc tggtctcgaa ctcctgagct caagcaatcc    47400
```

-continued

| | |
|---|---|
| atctgccttg gcctctcgaa gtgctggatt ataggcatgt ggcaccatgc | 47450 |
| ctggcctaag aacagttttt agcatttggg aggggctctc atctttaagc | 47500 |
| tccaaatgat actgtatttt cttgctttt tctttctctt gccccacaag | 47550 |
| ttttggaaag taaattggaa tagttttccc ccactgaatt atttagcttg | 47600 |
| tatacctcag cagatgttcc ttggcctgtt ttgttttgtt tttgagacag | 47650 |
| ggtcttgctc tgtcacccag gctggagtgc agtgacacaa tcatggctca | 47700 |
| ctgcagcctt gactgcctgg gctcaatcca tcctgcagcc tcagcctcct | 47750 |
| gagtagttgg gactacaggc atgagccagc atgtccagct aatttttat | 47800 |
| ttttagtgga gatgaggtct ggctatgttg cccaagctgg gcttgaactc | 47850 |
| tgggctcaa gtgatcctct cacctcagcc ttccaaagca ttgggattac | 47900 |
| aggtgtgaac cactgctccc gcccttggcc ctataagaag gaatgtgatt | 47950 |
| ctgttttcca gcagggcaca aacttctgct taaatacaaa gcccaaattt | 48000 |
| ttccaccaaa atgcccctag tgaagtggcc agcccagatg cccgactagc | 48050 |
| gtattatcca aagcatattg tcattggtgg aaaatggcct tatagtccat | 48100 |
| tgttttgtct taaaagtaaa tatataaata aacttgtata ttgtttccta | 48150 |
| attccgtgtt tatattaaca taaaagtgtt ttaaattacc tgtcagtggc | 48200 |
| caggtgcagt ggctcgtgcc tgtaatcgca gcactttggg aggccgaggc | 48250 |
| gggcagatca cctgaggtca ggagttcgag accagcctga ccagcatggt | 48300 |
| gaaaccctgt ctctactaaa aatacaaaaa ttagccaggt gtggtggcag | 48350 |
| gtgcctgtaa tcccagctac tcgggaagct gaggcaggag aattgcttga | 48400 |
| acccgggagg cagaggttgc agtgagttga gatcgcgcca ttgaacttca | 48450 |
| acttgggcaa cagagcaaga ctctgtctca gagaaagaaa aaaaaaaacc | 48500 |
| tatcagttga ataacaaaac cctttccttc cttgctttaa gtgaatctga | 48550 |
| agatccagga gctgtgctgc aggtaccctc tatgttgggt accctggtt | 48600 |
| taggctgact agtacagtgt ggttggctca tgtagacagc agacccttta | 48650 |
| ttttagatac aactttttt cttttctctt tatttttttt gagacagagt | 48700 |
| cttgcttgtc acccagcctg gagtgcagtg gcgtgatcat ggctcactat | 48750 |
| agccttaaac tccctggctc aagtgatcct ctcacctcgg ctttcctagt | 48800 |
| agctgggacc acaggtgtgg gccagcaccc ctggctgatt taaaaaaaaa | 48850 |
| aaaattttt ttttagaga tgtctcacta tgttacccag gctggtcttg | 48900 |
| aactcctggg ggctcaagca atcctcctgc tttgacctcc caaagtgctg | 48950 |
| ggatgacagg catgaactac tgcacctgct gagatgcaac agctttctgt | 49000 |
| cagactcatt ttattctcat catttcttcc tgtcctccct tgctgggagc | 49050 |
| atgagagctg tgatgggaat ataggaatgt atgaagtcct tctcccagat | 49100 |
| caaaaatcct aacttcttgt cttaaaggga ggaaaatttg aatgtaacct | 49150 |
| tacttttaga ctccttcagaa atccttctat acccttccgt ccccgctttc | 49200 |
| acccttcctc cctctccgtg tgtgtatctt cttctcttga aacacacagg | 49250 |
| tttatacccct gaccctctt gattcatccc ttgaagcaca gtggtgaaca | 49300 |
| aggaaggggc ccgtgatgcc ctaattcttt gccacagcac catgtttgtt | 49350 |

```
tcacaaggag cctggcaggt ttgggcttgg ggcagatagg ggagagaaag      49400
cagcagagac agcaaaacca aatcatgtca gcttggcatg tacttccctc      49450
tgaaatagct aagaatccat ttctgtaaaa gcactgatta tcagaaaacc      49500
ttattggcct ggccaccttt ggttcaaacc ctcacattaa taatgtggac      49550
agtagtatga ggtgtgccaa aggtggatga ctcagcacct aagtgatgac      49600
acctaattac gaataggttc attaaagcag accccctggg gacctttgct      49650
tgaggatcct tacagtcaga attcctgaat atatttgaaa ataataattg      49700
catctttatt ttcatatgtt ctgtatggtt tggctgactt cccctcaaa       49750 gtctgagtta gagttttcct taatttatgt gatgggtttg gtcttttttgg    49800 attccagaaa gagctgggtg tggttttggag ctgcactcag agtcacacaa     49850
aaccacagcc tttagagaac ccacaggaag gctttggggc acgtcctgat      49900
tcttgacatt tctcatcagt gctgactttg tatcccttag gagttcacaa      49950
ttcataacca ctgaaatatt aaatacaaa agttttggga aggatgagag       50000
cccagatgct ctactacttg aaaatatgtt aaaacataag ttcatcatta     50050
tacattttgc taaatcagga taaagtctga agtttcaaag aagttttatt     50100
ttagcaaatt ttcagaaaca ctgcctcaac tgttagggcc agtgttctag      50150
tcagtatgcc tttggaagca tgaaagctgg attggtcgat aggatgggtg      50200 tggaagggggg gctgtgactg ggtgggtaca gagaggctct gaaacaatct    50250
cagattccag gagttcctgg ataaggactt catgtgcggg aacagagcac     50300
aggagaagca gattcctgag ccactcagga agaactgggc ctaggcctgc     50350
tcttgtcact gactggcttt ctacataacc acagaaacag cactgtgttg     50400
tagaaagagg aagatcatac tttttgatat ctgtgtctaa tttaaggtca     50450
tctgagccct gatagaaaag caaaacagac aaaacccttg taactgctcc     50500
ctcccacccc acccaccatc aaaaaagctt tagagaggct ggacatggtg     50550
gctcttgcct gtgatcccag cactttggga ggctaaggtg ggtggatcac     50600
ctgaggtcag gagttcgaga ccagcctgac caatatggtg aaacccccatc    50650 tgtactaaaa atacaaaaat tagccaggtg tggtggcaca cgcctgtagt     50700
cccagctact tgggaggctg agacaggaga attacttgaa aacctgggag     50750
gcggaggttg cagtgagccg agatcacgcc attgtactcc agcctgggct     50800
acagagcgag actccttcaa aaaaaaaaa aaaaaagat ccggtttggt       50850 gtcttacaac tgtaatccca gcactttggg aggccgaggc cggtggatca     50900
cgaggttaag agatcaagac catcctgacc aacatggtga aaccctgtct     50950
ctactaaaaa ttagctgggc gtggtggcag gcgcctgtag tcccagctcc     51000
tcaggaggct gaggcagaag aatcgcttga acccgggagg cggaagttgc     51050
agtgagccta gatcgcgccc ctgcactcca gcctggcaac agagcaagac     51100
tacgtctcaa aaaaaaaata aataaaaact ctagagaagc aaaagaata      51150 actttaaaag tgtttatgtt ctcagcaagc tttattttgg ggatgtcaga     51200
acttaactaa ccactgctcc ttctgtgtgt atgttttttcc tccagcctac    51250 cttatgttca gtattttgga ggtgtctctg ctctaagtaa acaacagttt     51300
ctaaccatca atggatttcc taataattat tggggctggg gaggagaaga     51350
```

```
tgatgacatt tttaacaggt aatggtcata acttagatat ctttctcctc        51400
tgtcaacctt cacttccagt tttttaacca atgcttggtt gttccccaag        51450
gactgaccct cagatgggat gcaccsctag tcagcccaca ttcttaggtg        51500
tggcttccta caggtcctgc aggtgctaaa agggatctgt aggaaaatga        51550
gtttctgaga tttttgtatt ggcctggaaa aatgtcaaat gggaaccaag        51600
tgacggggca agtttacttt gacttgctgc atgccgtttt gtactcaagg        51650
agtaaaccaa tgtcctttgt aaaaatccct cctttcatta tggtcccctt        51700
tcactgtgaa acaagtttcc ttgagcagaa tcctaactgt cttcacagaa        51750
gctttgtgtt atattttat tttggagtat tttcacatat acaaaagaga        51800
tactgtagta aataaacct ttgaggacct atccagcccc agcaaccatt        51850
atggcctggt cagttctgtc ccatccacat cctgggctc ttttaagct          51900 ggtaaatcat tatgatgtgg ttgtcattt acagtggtaa aaacatcta          51950 tcagtagcat ttgaaagaac attctgctca gtcctctggc tgtagaggct         52000
tcaaccccac cagccaccga tgagcacctt ctccctccag gagccagtct         52050
gagctcatta ctgagtttaa tatcagaata caccctggtg cagcctttct         52100
aaattgcagt accagttaac agaaggtgtc tgtcagagca cacccaagt          52150 cattcaagtt accattgtgt gcaaacttaa cagagaccca cgtcttcaat         52200
ataagccttg aaggaaactc cagttttagt atgtagatgg ggtatcaagt         52250
gtgtgcacat tgaacatctg ctgcatacag agcactgtgc caggcaggcc         52300
caggacactg aaaacctgga catagggtcc agacagaagc aagcctgctt         52350
ccacagaggc actcctgggc agacactctg gactgatatg acagtgtgca         52400
gggccgacag gataccacag gtctgaatgg tcagaacagc tggggaggga         52450
gggagcatcc gcaggcatct agtcccatgc taacgcagtg gcactagaag         52500
gatgggtggt gtgtggagca actttcttga aagataaagg acctaacact         52550
ttctatgcac cacttactgt gtgccaggca aggccaggaa tgtttaagtg         52600
gtctgggatc agccagttct gcctcttaac taactttgct gtcctgctct         52650
ccaggctttc attttggtcc tcattccttt tccttggacc aacacagaat         52700
cctccaccct gttctggctg cctctagtct tgttctcagc cctccatttg         52750
tttttttctg ccttttccca catgttctga agccctccat tcgtatacta         52800
ctttccagag acttccccat ggctaaaagc attttggaaa tactgtatat         52850
taggcccctt tcagatactg gcaaccgttt gtgggatgct ctgagaaggc         52900
ctctgtgact tagcctggcc cttttcagcc catcacctgc cacgtcctac         52950
cccagaccct tgtcaccagt ccccaggagc ttacgttgct ccctgagggc         53000
actaggcttg ctctcacttc catgcctttg cctgtgccat cctggctgcc         53050
caaaatgcta tggcagatac ctgttcatcc tcaactgggc tctgcctagg         53100
cttgctccag cagaggttac aaactctatg cttcttcctc tgtgtctcca         53150
acctcatctt cctcttctca cctccatcct ggccctaaag gccctatgtt         53200
tgaagcattc acactgtata ttctgtgggg cacacggccc cagtgtctgg         53250
cacatggtag tcaacaccac aaaccgcaga accagttgta aaaggacatg         53300
```

```
gagtcggaat gtgagtttta accagggtca tgctgggctg ggttctggca         53350
tgatgctggg ttgtgggctg agtgagaaca gcaagggtga tggtggatgg         53400
agcaacagtc ttgcagccgg ggctctcagg ccaagtgtat ggcagctctg         53450
tgataatgac tttcccttta ctcttttgcag attagttttt agaggcatgt        53500
ctatatctcg cccaaatgct gtggtcggga ggtgtcgcat gatccgccac         53550
tcaagagaca agaaaaatga acccagtcct cagaggtgca ttctttgttt         53600
attcatactc cttcccccttt aggatgagg taggctgcag gtccgaggct         53650
ctgggcctag agggaaattg aggtggtcag gttacagtgg agaggagga          53700 ggaagtacgt gtgatgattt cttcttaaga tttttgtttt aagacaatct         53750
ccttgtgctc ttttccttgt aggtttgacc gaattgcaca cacaaaggag         53800
acaatgctct ctgatggttt gaactcactc acctaccagg tgctggatgt         53850
acagagatac ccattgtata cccaaatcac agtggacatc gggacaccga         53900
gctagcgttt tggtacacgg ataagagacc tgaaattagc cagggacctc         53950
tgctgtgtgt ctctgccaat ctgctgggct ggtccctctc atttttacca         54000
gtctgagtga caggtcccct tcgctcatca ttcagatggc tttccagatg         54050
accaggacga gtgggatatt ttgcccccaa cttggctcgg catgtgaatt         54100
cttagctctg caaggtgttt atgccttttgc gggtttcttg atgtgttcgc        54150
agtgtcaccc cagagtcaga actgtacaca tcccaaaatt tggtggccgt         54200
ggaacacatt cccggtgata gaattgctaa attgtcgtga aataggttag         54250 aattttctt taaattatgg ttttcttatt cgtgaaaatt cggagagtgc          54300
tgctaaaatt ggattggtgt gatctttttg gtagttgtaa tttaacagaa         54350
aaacacaaaa tttcaaccat tcttaatgtt acgtcctccc cccacccct          54400 tctttcagtg gtatgcaacc actgcaatca ctgtgcatat gtcttttctt         54450
agcaaaagga ttttaaaact tgagccctgg acctttttgtc ctatgtgtgt        54500 ggattccagg gcaactctag catcagagca aaagccttgg gtttctcgca         54550
ttcagtggcc tatctccaga ttgtctgatt tctgaatgta aagttgttgt         54600
gttttttttt aaatagtagt ttgtagtatt ttaaagaaag aacagatcga         54650
gttctaatta tgatctagct tgattttgtg ttgatccaaa tttgcatagc         54700
tgtttaatgt taagtcatga caatttattt ttccttggcat gctatgtaaa        54750 cttgaatttc ctatgtatt ttattgtggt gttttaaata tggggagggg          54800
tattgagcat ttttaaggga gaaaataaa tatatgctgt agtggccaca          54850
aataggccta tgatttagct ggcaggccag gttttctcaa gagcaaaatc         54900
accctctggc cccttggcag gtaaggcctc ccggtcagca ttatcctgcc         54950
agacctcggg gaggatacct gggagacaga agcctctgca cctactgtgc         55000
agaactctcc acttccccaa ccctccccag gtgggcaggg cggagggagc         55050
ctcagcctcc ttagactgac ccctcaggcc cctaggctgg ggggttgtaa         55100
ataacagcag tcaggttgtt taccagccct ttgcacctcc ccaggcagag         55150
ggagcctctg ttctggtggg ggccacctcc ctcagaggct ctgctagcca         55200
cactccgtgg cccaccctttt gttaccagtt cttcctcctt cctctttttcc       55250 cctgcctttc tcattccttc cttcgtctcc cttttttgttc ctttgcctct        55300
```

```
tgcctgtccc ctaaaacttg actgtggcac tcagggtcaa acagactatc        55350
cattccccag catgaatgtg cctttaatt agtgatctag aaagaagttc         55400
```
(continuing as shown)

```
tgcctgtccc ctaaaacttg actgtggcac tcagggtcaa acagactatc        55350
cattccccag catgaatgtg ccttttaatt agtgatctag aaagaagttc        55400
agccgaaccc acaccccaac tccctcccaa gaacttcggt gcctaaagcc        55450
tcctgttcca cctcaggttt tcacaggtgc tcccacccca gttgaggctc        55500
ccacccacag ggctgtctgt cacaaaccca cctctgttgg gagctattga        55550
gccacctggg atgagatgac acaaggcact cctaccactg agcgcctttg        55600
ccaggtccag cctgggctca ggttccaaga ctcagctgcc taatcccagg        55650
gttgagcctt tgctcgtgg cggaccccaa accactgccc tcctgggtac         55700
cagccctcag tgtggaggct gagctggtgc ctggccccag tcttatctgt        55750
gcctttactg ctttgcgcat ctcagatgct aacttggttc tttttccaga        55800
agcctttgta ttggttaaaa attattttcc attgcagaag cagctggact        55850
atgcaaaaag tatttctctg tcagttcccc actctatacc aaggatatta       55900
ttaaaactag aaatgactgc attgagaggg agttgtggga aataagaaga        55950
atgaaagcct ctctttctgt ccgcagatcc tgacttttcc aaagtgcctt       56000
aaaagaaatc agacaaatgc cctgagtggt aacttctgtg ttattttact       56050
cttaaaacca aactctacct tttcttgttg tttttttttt tttttttttt       56100
ttttttttgg ttaccttctc attcatgtca agtatgtggt tcattcttag       56150
aaccaaggga aatactgctc cccccatttg ctgacgtagt gctctcatgg       56200
gctcacctgg gcccaaggca cagccagggc acagttaggc ctggatgttt       56250
gcctggtccg tgagatgccg cgggtcctgt ttccttactg gggatttcag       56300
ggctgggggt tcagggagca tttcctttc ctggagttta tgaccgcgaa         56350
gttgtcatgt gccgtgccct tttctgtttc tgtgtatcct attgctggtg       56400
actctgtgtg aactggcctt tgggaaagat cagagagggc agaggtggca       56450
caggacagta aaggagatgc tgtgctggcc ttcagcctgg acagggtctc       56500
tgctgactgc caggggcggg ggctctgcat agccaggatg acggctttca       56550
tgtcccagag acctgttgtg ctgtgtattt tgatttcctg tgtatgcaaa       56600
tgtgtgtatt taccattgtg tagggggctg tgtctgatct tggtgttcaa       56650
aacagaactg tattttgcc tttaaaatta aataatataa cgtgaataaa         56700
tgaccctatc tttgtaac                                           56718
```

<210> SEQ ID NO 3
<211> LENGTH: 4214
<212> TYPE: DNA
<213> ORGANISM: Homo sapien
<220> FEATURE:
<223> OTHER INFORMATION: wild-type B4GALT1 mRNA sequence

<400> SEQUENCE: 3

```
gcgccucggg cggcuucucg ccgcucccag gucuggcugg cuggaggagu          50
cucagcucuc agccgcucgc ccgccccgc uccgggcccu ccccuagucg          100
ccgcugugg gcagcgccug gcgggcggcc cgcgggcggg ucgccucccc          150
uccuguagcc cacaccccuuc uuaaagcggc ggcgggaaga ugaggcuucg        200
ggagccgcuc cugagcggca gcgccgcgau gccaggcgcg uccccuacagc        250
```

```
gggccugccg ccugcucgug gccgucugcg cucugcaccu uggcgucacc    300
cucguuuacu accuggcugg ccgcgaccug agccgccugc cccaacuggu    350
cggagucucc acaccgcugc agggcggcuc gaacagugcc gccgccaucg    400
ggcagcccuc cggggagcuc cggaccgag  gggcccggcc gccgccuccu    450
cuaggcgccu ccucccagcc gcgcccgggu ggcgacucca gcccagucgu    500
ggauucuggc ccuggccccg cuagcaacuu gaccucgguc ccagugcccc    550
acaccaccgc acugucgcug cccgccugcc cugaggaguc cccgcugcuu    600
gugggcccca ugcugauuga guuuaacaug ccuguggacc uggagcucgu    650
ggcaaagcag aacccaaaug ugaagauggg cggccgcuau gccccagggg    700
acugcgucuc uccucacaag guggccauca ucauuccauu ccgcaaccgg    750
caggagcacc ucaaguacug gcuauauuau uugcacccag ccugcagcg    800 ccagcagcug gacuauggca ucuauguauu caaccaggcg ggagacacua    850
uauucaaucg ugcuaagcuc cucaauguug gcuuucaaga agccuugaag    900
gacuaugacu acaccugcuu uguguuuagu gacguggacc ucauuccaau    950
gaaugaccau aaugcguaca ggugguuuuc acagccacgg cacauuuccg   1000
uugcaaugga uaaguuugga uucagccuac cuuauguuca guauuuugga   1050
ggugucucug cucuaaguaa acaacaguuu cuaaccauca auggauuucc   1100
uaauaauuau uggggcuggg gaggagaaga ugaugacauu uuuaacagau   1150
uaguuuuuag aggcaugucu auaucucgcc caaaugcugu ggucgggagg   1200
ugucgcauga uccgccacuc aagagacaag aaaaaugaac ccaauccuca   1250
gagguuugac cgaauugcac acacaaagga gacaaugcuc ucugaugguu   1300
ugaacucacu caccuaccag gugcuggaug uacagagaua cccauuguau   1350
acccaaauca caguggacau cgggacaccg agcuagcguu uugguacacg   1400
gauaagagac cugaaauuag ccagggaccu cugcugugug ucucugccaa   1450
ucugcugggc uggucccucu cauuuuuacc agcugagug  acaggucccc   1500 uucgcucauc auucagaugg cuuccagau  gaccaggacg agugggauau   1550
uuugccccca acuggcucg  gcaugugaau ucuuagcucu gcaaggyguu   1600
uaugccuuug cgggpuucuu gauguguucg cagugucacc ccagagucag   1650
aacuguacac aucccaaaau uggugccg   uggaacacau cccggugau    1700 agaauugcua aauugucgug aaauagguua gaauuuucu  uuaaauuaug   1750 guuucuuau  ucgugaaaau ucggagagug cugcuaaaau uggauuggug   1800 ugaucuuuu  gguaguugua auuuaacaga aaaacacaaa auucaaccaa   1850
uucuuaaugu uacguccucc cccaccccc  ucuuucagu  gguaugcaac   1900 cacugcaauc acugugcaua ugucuuuucu uagcaaaagg auuuuaaaac   1950
uugagcccug gaccuuuugu ccuaugugug uggauuccag ggcaacucua   2000
gcaucagagc aaaagccuug gguuucgc   auucagguggc cuaucuccag   2050 auugucugau uucugaaugu aaaguuguug uguuuuuuu  uaaauaguag   2100 uuuguaguau uuuaaagaaa gaacagaucg aguucuaauu augaucuagc   2150
uugauuuugu guugauccaa auuugcauag cuguuuaaug uuaagucaug   2200
acaauuuauu uuucuuggca ugcuauguaa acuugaauuu ccuaugucau   2250
```

```
uuuauugugg uguuuuaaau auggggaggg guauugagca uuuuuuaggg        2300
agaaaaauaa auauaugcug uaguggccac aaauaggccu augauuuagc        2350
uggcaggcca gguuuucuca agagcaaaau cacccucugg ccccuuggca        2400
gguaaggccu cccggucagc auuauccugc cagaccucgg ggaggauacc        2450
ugggagacag aagccucugc accuacugug cagaacucuc cacuucccca        2500
acccucccca gguggggcagg gcggagggag ccucagccuc cuuagacuga       2550
ccccucaggc cccuaggcug ggggguugua aauaacagca gucagguugu        2600
uuaccagccc uuugcaccuc cccaggcaga gggagccucu guucuggugg        2650
gggccaccuc ccucagaggc ucugcuagcc acacuccgug gcccacccuu        2700
uguuaccagu ucuuccuccu uccucuuuuc cccugccuuu ucauuccuu         2750 ccuucgucuc ccuuuuuguu ccuuugccuc ugccugucc ccuaaaacuu         2800 gacuguggca cucaggguca aacagacuau ccauucccca gcaugaaugu        2850
gccuuuuaau uagugaucua gaaagaaguu cagccgaacc cacaccccaa        2900
cucccuccca agaacuucgg ugccuaaagc cuccuguucc accucagguu        2950
uucacaggug cucccaccc aguugaggcu cccacccaca gggcugucug         3000
ucacaaaccc accucuguug ggagcuauug agccaccugg gaugagauga        3050
cacaaggcac uccuaccacu gagcgccuuu gccaggucca gccugggcuc        3100
agguuccaag acucagcugc cuaaucccag gguugagccu ugugcucgug        3150
gcggacccca aaccacugcc cuccugggua ccagcccuca gugguggaggc       3200 ugagcugguug ccuggcccca gucuuaucug ugccuuuacu gcuugcgca        3250 ucucagaugc uaacuugguu cuuuuuccag aagccuuugu auugguuaaa        3300
aauuauuuuc cauugcagaa gcagcuggac uaugcaaaaa guauuucucu        3350
gucaguuccc cacucuauac caaggauauu auuaaaacua gaaaugacug        3400
cauugagagg gaguugugg aaauaagaag aaugaaagcc ucucuuucug         3450
uccgcagauc cugacuuuuc caaagugccu uaaaagaaau cagacaaaug        3500
cccugagugg uaacuucugu guuauuuuac ucuuaaaacc aaacucuacc        3550
uuuucuuguu guuuuuuuu uuuuuuuuu uuuuuuuug guuaccuucu           3600 cauucauguc aaguaugugg uucauucuua gaaccaaggg aaauacugcu        3650 cccccauuu gcugacguag ugcucucaug ggcucaccug ggcccaaggc         3700
acagccaggg cacaguuagg ccuggauguu ugccuggucc gugagaugcc        3750 gcgguccug uuuccuuacu ggggauuuca gggcuggggg uucagggagc         3800
auuuccuuuu ccugggaguu augaccgcga aguugucaug ugccgugccc        3850
uuuucuguuu cuguguaucc uauugcuggu gacucugugu gaacuggccu        3900
uugggaaaga ucagagaggg cagagguggc acaggacagu aaaggagaug        3950
cugugcuggc cuucagccug gacagggucu cugcugacug ccaggggcgg        4000
gggcucugca uagccaggau gacggcuuuc augcccagaa gaccguugu         4050 gcugguguau uugauuuccu guguaugcaa augugucuau uuaccauugu        4100 guaggggcu gugucugauc uuggguguuca aaacagaacu guauuuugc         4150 cuuuaaaauu aaauaauaua acgugaauaa augacccuau cuuuguaaca        4200
```
aaaaaaaaaa aaaa                                                    4214

<210> SEQ ID NO 4
<211> LENGTH: 4214
<212> TYPE: DNA
<213> ORGANISM: Homo sapien
<220> FEATURE:
<223> OTHER INFORMATION: variant B4GALT1 mRNA sequence

<400> SEQUENCE: 4

| | |
|---|---:|
| gcgccucggg cggcuucucg ccgcucccag gucuggcugg cuggaggagu | 50 |
| cucagcucuc agccgcucgc ccgccccgc uccgggcccu ccccuagucg | 100 |
| ccgcugugg gcagcgccug gcgggcggcc cgcgggcggg ucgccucccc | 150 |
| uccuguagcc cacacccuuc uuaaagcggc ggcgggaaga ugaggcuucg | 200 |
| ggagccgcuc cugagcggca gcgccgcgau gccaggcgcg ucccuacagc | 250 |
| gggccugccg ccugcucgug gccgucgcgc ucugcaccu uggcgucacc | 300 |
| cucguuuacu accuggcugg ccgcgaccug agccgccugc ccaacuggu | 350 |
| cggagucucc acaccgcugc agggcggcuc gaacagugcc gccgccaucg | 400 |
| gcagcccuc cggggagcuc cggaccgag gggcccggcc gccgccuccu | 450 |
| cuaggcgccu ccucccagcc gcgcccgggu ggcgacucca gcccagucgu | 500 |
| ggauucuggc ccuggccccg cuagcaacuu gaccucgguc ccagugcccc | 550 |
| acaccaccgc acugucgcug cccgccugcc cugaggaguc cccgcugcuu | 600 |
| gugggcccca gcugauuga guuuaacaug ccuguggacc uggagcucgu | 650 |
| ggcaaagcag aacccaaaug ugaagauggg cggccgcuau gcccccaggg | 700 |
| acugcgcucu ccucacaag guggccauca ucauuccauu ccgcaaccgg | 750 |
| caggagcacc ucaaguacug gcuauauau uugcacccag ccugcagcg | 800 |
| ccagcagcug gacuauggca ucuauguau caaccaggcg ggagacacua | 850 |
| uauucaaucg ugcuaagcuc cucaauguug gcuucaaga agccuugaag | 900 |
| gacuaugacu acaccugcuu uguguuuagu gacguggacc ucauuccaau | 950 |
| gaaugaccau aaugcguaca ggguguuuuc acagccacgg cacauuuccg | 1000 |
| uugcaaugga uaaguuugga uucagccuac cuuauguuca guauuuugga | 1050 |
| ggugucucug cucuaaguaa acaacaguuu cuaaccauca auggauuucc | 1100 |
| uaauaauuau uggggcuggg gaggagaaga ugaugacauu uuuaacagau | 1150 |
| uaguuuuuag aggcaugucu auaucucgcc caaaugcugu ggucgggagg | 1200 |
| ugucgcauga uccgccacuc aagagacaag aaaaaugaac ccaguccuca | 1250 |
| gagguuugac cgaauugcac acacaaagga gacaaugcuc ucugauggu | 1300 |
| ugaacucacu caccuaccag gugcuggaug uacagagaua cccauuguau | 1350 |
| acccaaauca caguggacau cgggacaccg agcuagcguu uggguacacg | 1400 |
| gauaagagac cugaaauuag ccagggaccu cugcugugug ucucugccaa | 1450 |
| ucugcugggc uggucccucu cauuuuuacc agcugagag acaggucccc | 1500 |
| uucgcucauc auucagaugg cuuuccagau gaccaggacg aguggggauau | 1550 |
| uuugccccca acuuggcucg gcaugugaau ucuuagcucu gcaaggguu | 1600 |
| uaugccuuug cgguuucuu gaugugucg cagucacc ccagagucag | 1650 |
| aacuguacac aucccaaaau uggugggccg uggaacacau ucccggugau | 1700 |

```
agaauugcua aauugucgug aaauagguua gaauuuuucu uuaaauuaug        1750
guuuucuuau ucgugaaaau ucggagagug cugcuaaaau uggauuggug        1800
ugaucuuuuu gguaguugua auuuaacaga aaaacacaaa auuucaacca        1850
uucuuaaugu uacguccucc ccccaccccc uucuuucagu gguaugcaac        1900
cacugcaauc acugugcaua ugucuuuucu uagcaaaagg auuuuaaaac        1950
uugagcccug gaccuuuugu ccuaugugug uggauuccag ggcaacucua        2000
gcaucagagc aaaagccuug gguuucucgc auucagugge cuaucuccag        2050 auugucugau uucugaaugu aaaguuguug uguuuuuuu uaaauaguag         2100 uuuguaguau uuuaaagaaa gaacagaucg aguucuaauu augaucuagc        2150
uugauuuugu guugauccaa auuugcauag cuguuuaaug uuaagucaug        2200
acaauuuauu uuucuuggca ugcuauguaa acuugaauuu ccuauguauu        2250
uuuauugugg uguuuuaaau auggggaggg guauugagca uuuuuuaggg       2300 agaaaauaa auauaugcug uaguggccac aaauaggccu augauuuagc         2350
uggcaggcca gguuuucuca agagcaaaau cacccucugg ccccuuggca        2400
gguaaggccu cccggucagc auuauccugc cagaccucgg ggaggauacc        2450
ugggagacag aagccucugc accuacugug cagaacucuc cacuucccca        2500 acccuccccca gguggcagg gcggagggag ccucagccuc cuuagacuga        2550 cccccucaggc cccuaggcug gggguugua aauaacagca gucagguugu       2600
uuaccagccc uuugcaccuc cccaggcaga gggagccucu guucuggugg       2650
gggccaccuc ccucagaggc ucugcuagcc acacuccgug gcccacccuu       2700
uguuaccagu ucuccuccu uccucuuuuc cccugccuuu ucauuccuu         2750 ccuucgucuc ccuuuuuguu ccuugcccuc uugccuagucc cuaaaacuu       2800 gacugulggca cucagggugca aacagacuau ccauuccca gcaugaaugu     2850 gccuuuuaau uagugaucua gaaagaaguu cagccgaacc cacaccccaa       2900
cucccuccca agaacuucgg ugccuaaagc cuccuguucc accucagguu       2950 uucacagguug cucccacccc aguugaggcu cccacccaca gggcugucug     3000
ucacaaaccc accucuguug ggagcuauug agccaccugg gaugaguaga       3050
cacaaggcac uccuaccacu gagcgccuuu gccaggucca gccgggcuc        3100 agguccaag acucagcugc cuaaucccag gguugagccu ugcucgug         3150 gcggacccca aaccacugcc cuccugggua ccagcccuca gugugaggc        3200 ugagcugGgug ccuggcccca gucuuaucug ugccuuuacu gcuuugcgca      3250
ucucagaugc uaacuugguu cuuuuuccag aagccuuugu auuggulaaa       3300 aauuauuuuc cauugcagaa gcagcuggac uaugcaaaaa guauuucucu       3350
gucaguuccc cacucuauac caaggauauu auuaaaacua gaaaugacug       3400
cauugagagg gaguugugggg aaauaagaag aaugaaagcc ucucuuucug     3450
uccgcagauc cugacuuuuc caaagugccu uaaaagaaau cagacaaaug       3500
cccugagugg uaacuucugu guuauuuuac ucuuaaaacc aaacucuacc       3550 uuucuuguu guuuuuuuu uuuuuuuuu uuuuuuuug guuaccuucu          3600 cauucaugluc aaguaugugg uucauucuua gaaccaaggg aaauacugcu     3650
```

| | | |
|---|---|---|
| cccccccauuu gcugacguag ugcucucaug ggcucaccug ggcccaaggc | 3700 | |
| acagccaggg cacaguuagg ccuggauguu ugccuggucc gugagaugcc | 3750 | |
| gcggguccug uuccuuacu ggggauuuca gggcugggg uucagggagc | 3800 | |
| auuuccuuuu ccugggaguu augaccgcga aguugucaug ugccgugccc | 3850 | |
| uuuucuguuu cuguguaucc uauugcuggu gacucugugu gaacuggccu | 3900 | |
| uugggaaaga ucagagaggg cagagguggc acaggacagu aaaggagaug | 3950 | |
| cugugcuggc cuucagccug gacaggguca cugcugacug ccaggggcgg | 4000 | |
| gggcucugca uagccaggau gacggcuuuc augucccaga gaccuguugu | 4050 | |
| gcuguguauu uugauuuccu guguaugcaa augugguauu uuaccauugu | 4100 | |
| guaggggcu cugucugauc uugguguuca aaacagaacu guauuuuugc | 4150 | |
| cuuuaaaauu aaauaauaua acgugaauaa augacccuau cuuuguaaca | 4200 | |
| aaaaaaaaaa aaaa | 4214 | |

<210> SEQ ID NO 5
<211> LENGTH: 1197
<212> TYPE: DNA
<213> ORGANISM: Homo sapien
<220> FEATURE:
<223> OTHER INFORMATION: wild-type B4GALT1 cDNA sequence

<400> SEQUENCE: 5

| | | |
|---|---|---|
| atgaggcttc gggagccgct cctgagcggc agcgccgcga tgccaggcgc | 50 | |
| gtccctacag cgggcctgcc gcctgctcgt ggccgtctgc gctctgcacc | 100 | |
| ttggcgtcac cctcgtttac tacctggctg ccgcgacct gagccgcctg | 150 | |
| ccccaactgg tcgagtctc cacccgctg cagggcggc cgaacagtgc | 200 | |
| cgccgccatc gggcagtcct ccggggagct ccggaccgga ggggcccggc | 250 | |
| cgccgcctcc tctaggcgcc tcctcccagc cgcgcccggg tggcgactcc | 300 | |
| agcccagtcg tggattctgg ccctggcccc gctagcaact tgacctcggt | 350 | |
| cccagtgccc cacaccaccg cactgtcgct gcccgcctgc cctgaggagt | 400 | |
| ccccgctgct tgtgggcccc atgctgattg agtttaacat gcctgtggac | 450 | |
| ctggagctcg tggcaaagca gaacccaaat gtgaagatgg gcggccgcta | 500 | |
| tgcccccagg gactgcgtct ctcctcacaa ggtggccatc atcattccat | 550 | |
| tccgcaaccg gcaggagcac ctcaagtact ggctatatta tttgcaccca | 600 | |
| gtcctgcagc gccagcagct ggactatggc atctatgtta tcaaccaggc | 650 | |
| gggagacact atattcaatc gtgctaagct cctcaatgtt ggctttcaag | 700 | |
| aagccttgaa ggactatgac tacacctgct tgtgtttag tgacgtggac | 750 | |
| ctcattccaa tgaatgacca taatgcgtac aggtgttttt cacagccacg | 800 | |
| gcacatttcc gttgcaatgg ataagttgg attcagccta ccttatgttc | 850 | |
| agtattttgg aggtgtctct gctctaagta acaacagtt tctaaccatc | 900 | |
| aatgatttc ctaataatta ttggggctgg ggaggagaag atgatgacat | 950 | |
| ttttaacaga ttagttttta gaggcatgtc tatatctcgc ccaaatgctg | 1000 | |
| tggtcgggag gtgtcgcatg atccgccact caagagacaa gaaaaatgaa | 1050 | |
| cccaatcctc agaggtttga ccgaattgca cacacaaagg agacaatgct | 1100 | |
| ctctgatggt ttgaactcac tcacctacca ggtgctggat gtacagagat | 1150 | | acccattgta tacccaaatc acagtggaca tcgggacacc gagctag        1197

<210> SEQ ID NO 6
<211> LENGTH: 1197
<212> TYPE: DNA
<213> ORGANISM: Homo sapien
<220> FEATURE:
<223> OTHER INFORMATION: variant B4GALT1 cDNA sequence

<400> SEQUENCE: 6

| | |
|---|---|
| atgaggcttc gggagccgct cctgagcggc agcgccgcga tgccaggcgc | 50 |
| gtccctacag cgggcctgcc gcctgctcgt ggccgtctgc gctctgcacc | 100 |
| ttggcgtcac cctcgtttac tacctggctg gccgcgacct gagccgcctg | 150 |
| ccccaactgg tcggagtctc acaccgctg cagggcggct cgaacagtgc | 200 |
| cgccgccatc gggcagtcct ccggggagct ccggaccgga ggggcccggc | 250 |
| cgccgcctcc tctaggcgcc tcctcccagc cgcgcccggg tggcgactcc | 300 |
| agcccagtcg tggattctgg ccctggcccc gctagcaact tgacctcggt | 350 |
| cccagtgccc cacaccaccg cactgtcgct gcccgcctgc cctgaggagt | 400 |
| ccccgctgct tgtgggcccc atgctgattg agtttaacat gcctgtggac | 450 |
| ctggagctcg tggcaaagca gaacccaaat gtgaagatgg gcggccgcta | 500 |
| tgcccccagg gactgcgtct ctcctcacaa ggtggccatc atcattccat | 550 |
| tccgcaaccg gcaggagcac ctcaagtact ggctatatta tttgcaccca | 600 |
| gtcctgcagc gccagcagct ggactatggc atctatgtta tcaaccaggc | 650 |
| gggagacact atattcaatc gtgctaagct cctcaatgtt ggctttcaag | 700 |
| aagccttgaa ggactatgac tacacctgct tgtgtttag tgacgtggac | 750 |
| ctcattccaa tgaatgacca taatgcgtac aggtgttttt cacagccacg | 800 |
| gcacatttcc gttgcaatgg ataagtttgg attcagccta ccttatgttc | 850 |
| agtattttgg aggtgtctct gctctaagta acaacagtt tctaaccatc | 900 |
| aatggatttc ctaataatta ttggggctgg ggaggagaag atgatgacat | 950 |
| ttttaacaga ttagtttta gaggcatgtc tatatctcgc ccaaatgctg | 1000 |
| tggtcgggag gtgtcgcatg atccgccact caagagacaa gaaaaatgaa | 1050 |
| cccagtcctc agaggtttga ccgaattgca cacacaaagg agacaatgct | 1100 |
| ctctgatggt ttgaactcac tcacctacca ggtgctggat gtacagagat | 1150 |
| acccattgta tacccaaatc acagtggaca tcgggacacc gagctag | 1197 |

<210> SEQ ID NO 7
<211> LENGTH: 398
<212> TYPE: PRT
<213> ORGANISM: Homo sapien
<220> FEATURE:
<223> OTHER INFORMATION: wild-type B4GALT1 sequence

<400> SEQUENCE: 7

Met Arg Leu Arg Glu Pro Leu Leu Ser Gly Ser Ala Ala Met Pro Gly
1               5                   10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

```
Arg Leu Pro Gln Leu Val Gly Val Ser Thr Pro Leu Gln Gly Gly Ser
     50                  55                  60

Asn Ser Ala Ala Ala Ile Gly Gln Ser Ser Gly Glu Leu Arg Thr Gly
 65                  70                  75                  80

Gly Ala Arg Pro Pro Pro Leu Gly Ala Ser Ser Gln Pro Arg Pro
                 85                  90                  95

Gly Gly Asp Ser Ser Pro Val Val Asp Ser Gly Pro Gly Pro Ala Ser
                100                 105                 110

Asn Leu Thr Ser Val Pro Val Pro His Thr Thr Ala Leu Ser Leu Pro
            115                 120                 125

Ala Cys Pro Glu Glu Ser Pro Leu Leu Val Gly Pro Met Leu Ile Glu
130                 135                 140

Phe Asn Met Pro Val Asp Leu Glu Leu Val Ala Lys Gln Asn Pro Asn
145                 150                 155                 160

Val Lys Met Gly Gly Arg Tyr Ala Pro Arg Asp Cys Val Ser Pro His
                165                 170                 175

Lys Val Ala Ile Ile Ile Pro Phe Arg Asn Arg Gln Glu His Leu Lys
            180                 185                 190

Tyr Trp Leu Tyr Tyr Leu His Pro Val Leu Gln Arg Gln Gln Leu Asp
    195                 200                 205

Tyr Gly Ile Tyr Val Ile Asn Gln Ala Gly Asp Thr Ile Phe Asn Arg
210                 215                 220

Ala Lys Leu Leu Asn Val Gly Phe Gln Glu Ala Leu Lys Asp Tyr Asp
225                 230                 235                 240

Tyr Thr Cys Phe Val Phe Ser Asp Val Asp Leu Ile Pro Met Asn Asp
                245                 250                 255

His Asn Ala Tyr Arg Cys Phe Ser Gln Pro Arg His Ile Ser Val Ala
            260                 265                 270

Met Asp Lys Phe Gly Phe Ser Leu Pro Tyr Val Gln Tyr Phe Gly Gly
        275                 280                 285

Val Ser Ala Leu Ser Lys Gln Gln Phe Leu Thr Ile Asn Gly Phe Pro
290                 295                 300

Asn Asn Tyr Trp Gly Trp Gly Gly Glu Asp Asp Asp Ile Phe Asn Arg
305                 310                 315                 320

Leu Val Phe Arg Gly Met Ser Ile Ser Arg Pro Asn Ala Val Val Gly
                325                 330                 335

Arg Cys Arg Met Ile Arg His Ser Arg Asp Lys Lys Asn Glu Pro Asn
            340                 345                 350

Pro Gln Arg Phe Asp Arg Ile Ala His Thr Lys Glu Thr Met Leu Ser
        355                 360                 365

Asp Gly Leu Asn Ser Leu Thr Tyr Gln Val Leu Asp Val Gln Arg Tyr
370                 375                 380

Pro Leu Tyr Thr Gln Ile Thr Val Asp Ile Gly Thr Pro Ser
385                 390                 395

<210> SEQ ID NO 8
<211> LENGTH: 398
<212> TYPE: PRT
<213> ORGANISM: Homo sapien
<220> FEATURE:
<223> OTHER INFORMATION: variant B4GALT1 sequence

<400> SEQUENCE: 8

Met Arg Leu Arg Glu Pro Leu Leu Ser Gly Ser Ala Ala Met Pro Gly
 1               5                  10                  15
```

```
Ala Ser Leu Gln Arg Ala Cys Arg Leu Leu Val Ala Val Cys Ala Leu
         20                  25                  30
His Leu Gly Val Thr Leu Val Tyr Leu Ala Gly Arg Asp Leu Ser
     35                  40                  45
Arg Leu Pro Gln Leu Val Gly Val Ser Thr Pro Leu Gln Gly Gly Ser
 50                  55                  60
Asn Ser Ala Ala Ile Gly Gln Ser Ser Gly Glu Leu Arg Thr Gly
 65                  70                  75                  80
Gly Ala Arg Pro Pro Pro Leu Gly Ala Ser Ser Gln Pro Arg Pro
                 85                  90                  95
Gly Gly Asp Ser Ser Pro Val Val Asp Ser Gly Pro Gly Pro Ala Ser
             100                 105                 110
Asn Leu Thr Ser Val Pro Val Pro His Thr Thr Ala Leu Ser Leu Pro
             115                 120                 125
Ala Cys Pro Glu Glu Ser Pro Leu Leu Val Gly Pro Met Leu Ile Glu
 130                 135                 140
Phe Asn Met Pro Val Asp Leu Glu Leu Val Ala Lys Gln Asn Pro Asn
145                 150                 155                 160
Val Lys Met Gly Gly Arg Tyr Ala Pro Arg Asp Cys Val Ser Pro His
                 165                 170                 175
Lys Val Ala Ile Ile Ile Pro Phe Arg Asn Arg Gln Glu His Leu Lys
             180                 185                 190
Tyr Trp Leu Tyr Tyr Leu His Pro Val Leu Gln Arg Gln Leu Asp
             195                 200                 205
Tyr Gly Ile Tyr Val Ile Asn Gln Ala Gly Asp Thr Ile Phe Asn Arg
 210                 215                 220
Ala Lys Leu Leu Asn Val Gly Phe Gln Glu Ala Leu Lys Asp Tyr Asp
225                 230                 235                 240
Tyr Thr Cys Phe Val Phe Ser Asp Val Asp Leu Ile Pro Met Asn Asp
                 245                 250                 255
His Asn Ala Tyr Arg Cys Phe Ser Gln Pro Arg His Ile Ser Val Ala
             260                 265                 270
Met Asp Lys Phe Gly Phe Ser Leu Pro Tyr Val Gln Tyr Phe Gly Gly
             275                 280                 285
Val Ser Ala Leu Ser Lys Gln Gln Phe Leu Thr Ile Asn Gly Phe Pro
 290                 295                 300
Asn Asn Tyr Trp Gly Trp Gly Gly Glu Asp Asp Asp Ile Phe Asn Arg
305                 310                 315                 320
Leu Val Phe Arg Gly Met Ser Ile Ser Arg Pro Asn Ala Val Val Gly
                 325                 330                 335
Arg Cys Arg Met Ile Arg His Ser Arg Asp Lys Lys Asn Glu Pro Ser
             340                 345                 350
Pro Gln Arg Phe Asp Arg Ile Ala His Thr Lys Glu Thr Met Leu Ser
             355                 360                 365
Asp Gly Leu Asn Ser Leu Thr Tyr Gln Val Leu Asp Val Gln Arg Tyr
 370                 375                 380
Pro Leu Tyr Thr Gln Ile Thr Val Asp Ile Gly Thr Pro Ser
385                 390                 395

<210> SEQ ID NO 9
<211> LENGTH: 20
<212> TYPE: DNA
<213> ORGANISM: Artificial Sequence
<220> FEATURE:
```

```
<223> OTHER INFORMATION: guide RNA recognition sequences

<400> SEQUENCE: 9
attagttttt agaggcatgt                                                    20

<210> SEQ ID NO 10
<211> LENGTH: 20
<212> TYPE: DNA
<213> ORGANISM: Artificial Sequence
<220> FEATURE:
<223> OTHER INFORMATION: guide RNA recognition sequences

<400> SEQUENCE: 10
ggctctcagg ccaagtgtat                                                    20

<210> SEQ ID NO 11
<211> LENGTH: 20
<212> TYPE: DNA
<213> ORGANISM: Artificial Sequence
<220> FEATURE:
<223> OTHER INFORMATION: guide RNA recognition sequences

<400> SEQUENCE: 11
tactccttcc ccctttagga                                                    20

<210> SEQ ID NO 12
<211> LENGTH: 20
<212> TYPE: DNA
<213> ORGANISM: Artificial Sequence
<220> FEATURE:
<223> OTHER INFORMATION: guide RNA recognition sequences

<400> SEQUENCE: 12
gtccgaggct ctgggcctag                                                    20

<210> SEQ ID NO 13
<211> LENGTH: 6
<212> TYPE: DNA
<213> ORGANISM: Artificial Sequence
<220> FEATURE:
<223> OTHER INFORMATION: PAM for Cas9 from S. aureus
<220> FEATURE:
<221> NAME/KEY: n is A, G, C, or T
<222> LOCATION: (1)..(2)
<220> FEATURE:
<221> NAME/KEY: r is A or G
<222> LOCATION: (4)..(5)

<400> SEQUENCE: 13 nngrrt                                                                    6

<210> SEQ ID NO 14
<211> LENGTH: 5
<212> TYPE: DNA
<213> ORGANISM: Artificial Sequence
<220> FEATURE:
<223> OTHER INFORMATION: PAM for Cas9 from S. aureus
<220> FEATURE:
<221> NAME/KEY: n is A, G, C, or T
<222> LOCATION: (1)..(2)
<220> FEATURE:
<221> NAME/KEY: r is A or G
<222> LOCATION: (4)..(5)

<400> SEQUENCE: 14 nngrr                                                                     5
```

```
<210> SEQ ID NO 15
<211> LENGTH: 23
<212> TYPE: DNA
<213> ORGANISM: Artificial Sequence
<220> FEATURE:
<223> OTHER INFORMATION: target motif preceding NGG recognized by Cas9
      protein
<220> FEATURE:
<221> NAME/KEY: n is A, G, C, or T
<222> LOCATION: (2) .. (21)

<400> SEQUENCE: 15
gnnnnnnnnn nnnnnnnnnn ngg                                               23

<210> SEQ ID NO 16
<211> LENGTH: 23
<212> TYPE: DNA
<213> ORGANISM: Artificial Sequence
<220> FEATURE:
<223> OTHER INFORMATION: target motif preceding NGG recognized by Cas9
      protein
<220> FEATURE:
<221> NAME/KEY: n is A, G, C, or T
<222> LOCATION: (1) .. (21)

<400> SEQUENCE: 16
nnnnnnnnnn nnnnnnnnnn ngg                                               23

<210> SEQ ID NO 17
<211> LENGTH: 25
<212> TYPE: DNA
<213> ORGANISM: Artificial Sequence
<220> FEATURE:
<223> OTHER INFORMATION: RNA recognition sequence
<220> FEATURE:
<221> NAME/KEY: n is A, G, C, or T
<222> LOCATION: (3) .. (23)

<400> SEQUENCE: 17
ggnnnnnnnn nnnnnnnnnn nnngg                                             25
```

B4GALT1 CDNA VARIANTS AND COMPOSITIONS COMPRISING THE SAME

CROSS-REFERENCE TO RELATED APPLICATIONS

This application claims priority to U.S. Application No. 62/659,344, filed Apr. 18, 2018, to U.S. Application No. 62/550,161, filed Aug. 25, 2017, and to U.S. Application No. 62/515,140, filed Jun. 5, 2017, each of which is incorporated herein by reference in its entirety.

REFERENCE TO GOVERNMENT GRANTS

This invention was made with government support under HL121007 awarded by the National Institutes of Health. The government has certain rights in the invention.

REFERENCE TO A SEQUENCE LISTING

This application includes a Sequence Listing submitted electronically as a text file named 18923800201SEQ, created on Jun. 4, 2018, with a size of 161 KB. The Sequence Listing is incorporated by reference herein.

FIELD

The present disclosure provides variant B4GALT1 genomic, mRNA, and cDNA nucleic acid molecules, and polypeptides, methods of detecting the presence of these molecules, methods of modulating endogenous B4GALT1 genomic, mRNA, and cDNA nucleic acid molecules, and polypeptides, methods of ascertaining the risk of developing cardiovascular conditions by detecting the presence or absence of the variant B4GALT1 genomic, mRNA, and cDNA nucleic acid molecules, and polypeptides, and methods of treating cardiovascular conditions.

BACKGROUND

Various publications, including patents, published applications, accession numbers, technical articles and scholarly articles are cited throughout the specification. Each cited publication is incorporated by reference herein, in its entirety and for all purposes.

Beta-1,4-galactosyltransferase 1 (B4GALT1) is a member of the beta-1,4-galactosyltransferase gene family which encode type II membrane-bound glycoproteins that play a role in the biosynthesis of different glycoconjugates and saccharide structures. The enzyme encoded by B4GALT1 plays a critical role in the processing of N-linked oligosaccharide moieties in glycoproteins, and protein-linked sugar chains often modulate the biological functions of the glycoprotein. Thus, an impaired B4GALT1 activity has potential to alter the structure of all glycoproteins containing N-linked oligosaccharides. The long form of the B4GALT1 enzyme is localized in the trans-Golgi, where it transfers galactosyl residues to N-acetylglucosamine residues during the course of biosynthetic processing of high-mannose to complex-type N-linked oligosaccharides. Because addition of galactosyl residues is a pre-requisite for addition of sialic acids, a defect in B4GALT1 exerts an indirect effect to block addition of sialic acid residues and, therefore, may alter the half-life of plasma glycoproteins. Defects in glycosylation have been reported to impair intracellular trafficking of various glycoproteins—including the LDL receptor. Further, structural abnormalities in N-linked oligosaccharides have the potential to alter protein folding, which in turn could alter the function of glycoproteins and their secretion. A large percentage of proteins contain N-linked glycosylation, including cell surface receptors (e.g., LDL receptors and insulin receptors) as well as various circulating plasma proteins (e.g., apolipoprotein B and fibrinogen). There have been reports of patients with genetic disease due to homozygosity for protein-truncating mutations in the B4GALT1 gene. One such patient had a severe phenotype characterized by a) severe neurodevelopmental abnormalities (including hydrocephalus), b) myopathy, and c) blood clotting abnormalities. As predicted, oligosaccharides derived from circulating transferrin lacked galactose and sialic acid residues. Two additional patients with the same genetic defect presented with a milder phenotype, characterized by coagulation disturbances, hepatopathy, and dysmorphic features.

Cardiovascular disease is the leading cause of death in the United States and other westernized countries. Major risk factors for atherothrombotic cardiovascular diseases such as stroke and myocardial infarction include increased blood cholesterol and thrombotic tendency. Many proteins that are involved in lipid metabolism and coagulation are glycosylated and, thus, subject to modulation by B4GALT1. Knowledge of genetic factors underlying the development and progression of cardiovascular conditions could improve risk stratification and provide the foundation for novel therapeutic strategies.

SUMMARY

The present disclosure provides nucleic acid molecules comprising a nucleic acid sequence at least about 90% identical to the B4GALT1 variant genomic sequence (that comprises the SNP designated rs551564683), provided that the nucleic acid sequence also comprises nucleotides that encode a serine at the position corresponding to position 352 of the full length/mature B4GALT1 polypeptide.

The present disclosure also provides nucleic acid molecules comprising a nucleic acid sequence at least about 90% identical to the B4GALT1 variant mRNA sequence (that comprises the SNP designated rs551564683), provided that the nucleic acid sequence also encodes a serine at the position corresponding to position 352 of the full length/mature B4GALT1 polypeptide.

The present disclosure also provides cDNA molecules encoding a B4GALT1 polypeptide that comprise a nucleic acid sequence at least about 90% identical to the B4GALT1 variant cDNA sequence (that comprises the SNP designated rs551564683), provided that the nucleic acid sequence also encodes a serine at the position corresponding to position 352 in the full length/mature B4GALT1 polypeptide.

The present disclosure also provides vectors or exogenous donor sequences comprising any one or more of these nucleic acid molecules.

The present disclosure also provides isolated polypeptides comprising an amino acid sequence at least about 90% identical to a B4GALT1 polypeptide having a serine at the position corresponding to position 352 in the full length/mature B4GALT1 polypeptide.

The present disclosure also provides host cells comprising any one of more of these nucleic acid molecules operably linked to a heterologous promoter active in the host cell.

The present disclosure also provides methods of producing the B4GALT1 polypeptide by culturing a host cell containing a nucleic acid molecule encoding the B4GALT1 polypeptide, wherein the nucleic acid molecule is operably linked to a heterologous promoter active in the host cell, whereby the nucleic acid molecule is expressed, and recovering the isolated polypeptide.

The present disclosure also provides compositions comprising these nucleic acid molecules, or polypeptides, and a carrier for increasing their stability.

The present disclosure also provides methods of detecting the presence or absence of a B4GALT1 variant nucleic acid molecule (that comprises the SNP designated rs551564683) in a human subject, comprising performing an assay on a biological sample from the human subject that determines whether a nucleic acid molecule in the biological sample comprises a nucleic acid sequence that encodes a variant B4GALT1 polypeptide having a serine at the position corresponding to position 352 in the full length/mature B4GALT1 polypeptide.

The present disclosure also provides methods of detecting the presence of a variant B4GALT1 polypeptide having a serine at the position corresponding to position 352 in the full length/mature B4GALT1 polypeptide in a human subject, comprising performing an assay on a biological sample from the human subject that determines the presence of the variant B4GALT1 polypeptide.

The present disclosure also provides methods of determining a human subject's susceptibility to developing a cardiovascular condition, comprising: a) performing an assay on a biological sample from the human subject that determines whether a nucleic acid molecule in the biological sample comprises a nucleic acid sequence that encodes a variant B4GALT1 polypeptide having a serine at the position corresponding to position 352 in the full length/mature B4GALT1 polypeptide; and b) classifying the human subject as being at decreased risk for developing the cardiovascular condition if a nucleic acid molecule comprising a nucleic acid sequence that encodes a variant B4GALT1 polypeptide having a serine at the position corresponding to position 352 in the full length/mature B4GALT1 polypeptide is detected in the biological sample, or classifying the human subject as being at increased risk for developing the cardiovascular condition if a nucleic acid molecule comprising a nucleic acid sequence that encodes a variant B4GALT1 polypeptide having a serine at the position corresponding to position 352 in the full length/mature B4GALT1 polypeptide is not detected in the biological sample.

The present disclosure also provides methods of determining a human subject's susceptibility to developing a cardiovascular condition, comprising: a) performing an assay on a biological sample from the human subject that determines whether a B4GALT1 polypeptide in the biological sample comprises a serine at a position corresponding to position 352; and b) classifying the human subject as being at decreased risk for developing the cardiovascular condition if a B4GALT1 polypeptide having a serine at the position corresponding to position 352 in the full length/mature B4GALT1 polypeptide is detected in the biological sample, or classifying the human subject as being at increased risk for developing the cardiovascular condition if a B4GALT1 polypeptide having a serine at the position corresponding to position 352 in the full length/mature B4GALT1 polypeptide is not detected in the biological sample.

The present disclosure also provides guide RNA molecules effective to direct a Cas enzyme to bind to or cleave an endogenous B4GALT1 gene, wherein the guide RNA comprises a DNA-targeting segment that hybridizes to a guide RNA recognition sequence within the endogenous B4GALT1 gene that includes or is proximate (for instance, within a certain number of nucleotides, such as discussed below) to a position corresponding to positions 53575 to 53577 of the wild-type B4GALT1 gene.

The present disclosure also provides methods of modifying an endogenous B4GALT1 gene in a cell, comprising contacting the genome of the cell with: a) a Cas protein; and b) a guide RNA that forms a complex with the Cas protein and hybridizes to a guide RNA recognition sequence within the endogenous B4GALT1 gene, wherein the guide RNA recognition sequence includes or is proximate (for instance, within a certain number of nucleotides, such as discussed below) to a position corresponding to positions 53575 to 53577 of the wild-type B4GALT1 gene, wherein the Cas protein cleaves the endogenous B4GALT1 gene.

The present disclosure also provides methods of modifying an endogenous B4GALT1 gene in a cell, comprising contacting the genome of the cell with: a) a Cas protein; and b) a first guide RNA that forms a complex with the Cas protein and hybridizes to a first guide RNA recognition sequence within the endogenous B4GALT1 gene, wherein the first guide RNA recognition sequence comprises the start codon for the B4GALT1 gene or is within about 1,000 nucleotides of the start codon, wherein the Cas protein cleaves or alters expression of the endogenous B4GALT1 gene.

The present disclosure also provides methods for modifying a cell, comprising introducing an expression vector into the cell, wherein the expression vector comprises a recombinant B4GALT1 gene comprising a nucleotide sequence encoding a B4GALT1 polypeptide having a serine at the position corresponding to position 352 in the full length/mature B4GALT1 polypeptide.

The present disclosure also provides methods for modifying a cell, comprising introducing an expression vector into the cell, wherein the expression vector comprises a nucleic acid molecule encoding a polypeptide that is at least about 90% identical to a B4GALT1 polypeptide having a serine at the position corresponding to position 352 in the full length/mature B4GALT1 polypeptide, wherein the polypeptide also comprises a serine at the position corresponding to position 352 in the full length/mature B4GALT1 polypeptide.

The present disclosure also provides methods for modifying a cell, comprising introducing a polypeptide, or fragment thereof, into the cell, wherein the polypeptide is at least 90% identical to a B4GALT1 polypeptide having a serine at the position corresponding to position 352 in the full length/ mature B4GALT1 polypeptide, and wherein the polypeptide also comprises a serine at the position corresponding to position 352 in the full length/mature B4GALT1 polypeptide.

The present disclosure also provides methods of treating a subject who is not a carrier of the B4GALT1 variant nucleic acid molecule or polypeptide (that comprises the SNP designated rs551564683) and has or is susceptible to developing a cardiovascular condition, comprising introducing into the subject: a) a Cas protein or a nucleic acid encoding the Cas protein; b) a guide RNA or a nucleic acid encoding the guide RNA, wherein the guide RNA forms a complex with the Cas protein and hybridizes to a guide RNA recognition sequence within an endogenous B4GALT1 gene, wherein the guide RNA recognition sequence includes or is proximate to a position corresponding to positions 53575 to 53577 of the wild-type B4GALT1 gene; and c) an exogenous donor sequence comprising a 5' homology arm that hybridizes to a target sequence 5' of the positions corresponding to positions 53575 to 53577 of the wild-type B4GALT1 gene, a 3' homology arm that hybridizes to a target sequence 3' of the positions corresponding to positions 53575 to 53577 of the wild-type B4GALT1 gene, and a nucleic acid insert comprising a nucleotide sequence encoding a B4GALT1 polypeptide having a serine at the position corresponding to position 352 in the full length/mature B4GALT1 polypeptide flanked by the 5' homology arm and the 3' homology arm, wherein the Cas protein cleaves the endogenous B4GALT1 gene in a cell in the subject and the exogenous donor sequence recombines with the endogenous B4GALT1 gene in the cell, wherein upon recombination of the exogenous donor sequence with the endogenous B4GALT1 gene, the serine is inserted at nucleotides corresponding to positions 53575 to 53577 of the wild-type B4GALT1 gene.

The present disclosure also provides methods of treating a subject who is not a carrier of the B4GALT1 variant nucleic acid molecule or polypeptide (that comprises the SNP designated rs551564683) and has or is susceptible to developing a cardiovascular condition, comprising introducing into the subject: a) a Cas protein or a nucleic acid encoding the Cas protein; b) a first guide RNA or a nucleic acid encoding the first guide RNA, wherein the first guide RNA forms a complex with the Cas protein and hybridizes to a first guide RNA recognition sequence within the endogenous B4GALT1 gene, wherein the first guide RNA recognition sequence comprises the start codon for the endogenous B4GALT1 gene or is within about 1,000 nucleotides of the start codon; and c) an expression vector comprising a recombinant B4GALT1 gene comprising a nucleotide sequence encoding a B4GALT1 polypeptide having a serine at the position corresponding to position 352 in the full length/mature B4GALT1 polypeptide, wherein the Cas protein cleaves or alters expression of the endogenous B4GALT1 gene in a cell in the subject and the expression vector expresses the recombinant B4GALT1 gene in the cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing into the subject an antisense DNA, RNA, an siRNA, or an shRNA that hybridizes to a sequence within the endogenous B4GALT1 gene and decreases expression of B4GALT1 polypeptide in a cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing an expression vector into the subject, wherein the expression vector comprises a recombinant B4GALT1 gene comprising a nucleotide sequence encoding a B4GALT1 polypeptide having a serine at the position corresponding to position 352 in the full length/mature B4GALT1 polypeptide, wherein the expression vector expresses the recombinant B4GALT1 gene in a cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing an expression vector into the subject, wherein the expression vector comprises a nucleic acid molecule encoding a B4GALT1 polypeptide having a serine at the position corresponding to position 352 in the full length/mature B4GALT1 polypeptide, wherein the expression vector expresses the nucleic acid encoding the B4GALT1 polypeptide in a cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing an mRNA into the subject, wherein the mRNA encodes a B4GALT1 polypeptide having a serine at the position corresponding to position 352 in the full length/mature B4GALT1 polypeptide, wherein the mRNA expresses the B4GALT1 polypeptide in a cell in the subject.

The present disclosure also provides methods of treating a subject who is not a carrier of the B4GALT1 variant nucleic acid molecule or polypeptide (that comprises the SNP designated rs551564683) and has or is susceptible to developing a cardiovascular condition comprising introducing a B4GALT1 polypeptide having a serine at the position corresponding to position 352 in the full length/mature B4GALT1 polypeptide or fragment thereof into the subject.

In any of the methods described or exemplified herein, a cardiovascular condition may comprise levels of one or more serum lipids that increase atherosclerotic risk. The serum lipids comprise one or more of cholesterol, LDL, HDL, triglycerides, HDL-cholesterol, and non-HDL cholesterol, or any subfraction thereof (e.g., HDL2, HDL2a, HDL2b, HDL2c, HDL3, HDL3a, HDL3b, HDL3c, HDL3d, LDL1, LDL2, LDL3, lipoprotein A, Lpa1, Lpa1, Lpa3, Lpa4, or Lpa5). A cardiovascular condition may comprise elevated levels of coronary artery calcification. A cardiovascular condition may comprise elevated levels of pericardial fat. A cardiovascular condition may comprise an atherothrombotic condition. The atherothrombotic condition may comprise elevated levels of fibrinogen. The atherothrombotic condition may comprise a fibrinogen-mediated blood clot. A cardiovascular condition may comprise elevated levels of fibrinogen. A cardiovascular condition may comprise a fibrinogen-mediated blood clot. A cardiovascular condition may comprise a blood clot formed from the involvement of fibrinogen activity. A fibrinogen-mediated blood clot or blood clot formed from the involvement of fibrinogen activity may be in any vein or artery in the body.

BRIEF DESCRIPTION OF THE FIGURES

FIG. 3 shows the results of a representative haplotype structure of the top B4GALT1-associated SNPs.

FIGS. 5A and 5B show that the frequency of the variant B4GALT1 gene is greater than 1000-fold enriched in the Amish.

FIG. 6 shows the association of B4GALT1 Asn352Ser with decreased serum lipids.

FIG. 8 shows the association of B4GALT1 Asn352Ser with all lipid subfractions.

FIG. 9 shows the association of B4GALT1 Asn352Ser with decreased fibrinogen levels.

FIG. 18 (Panels A, B, and C) shows the effect of 352Ser mutation on activity; (Panels A and B) COS7 cells expressing either 352Asn or 352Ser Flag tag proteins fusion expressed in COS7 cells and analyzed by Western blot for B4GALT1 or Flag; (Panel C) B4GALT1 activity in the immunoprecipitates.

DETAILED DESCRIPTION

Figure 1:
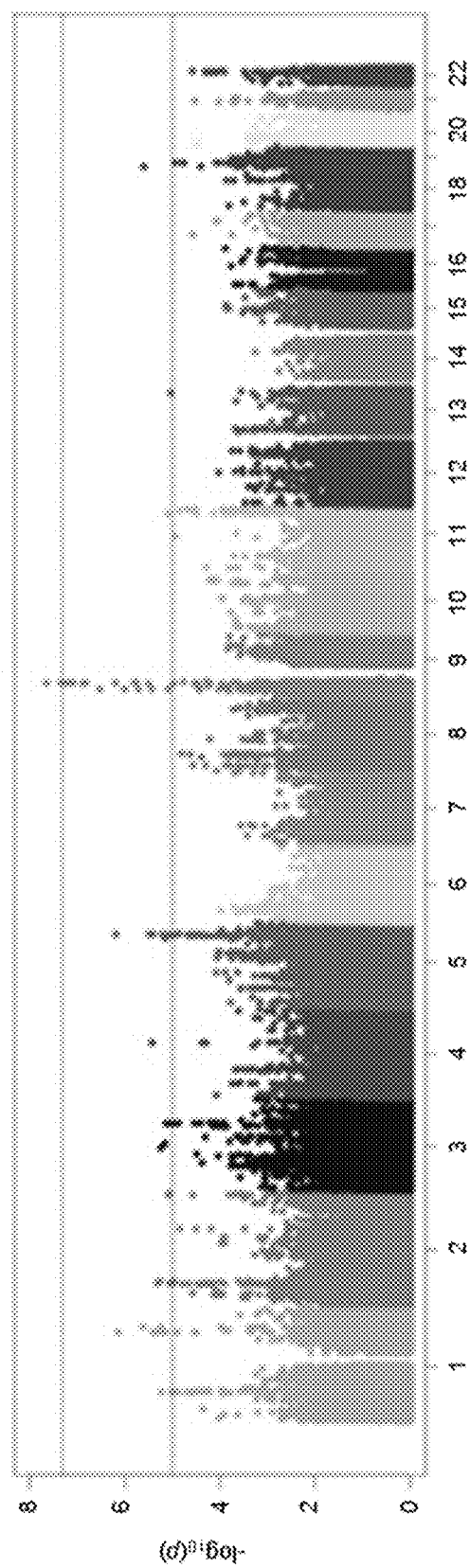
FIG. 1 shows the results of a representative genome-wide association of variant B4GALT1 with LDL.

As set forth herein, sequencing studies have identified a variant of B4GALT1 having a serine at the position corresponding to position 352 in the full length/mature B4GALT1 polypeptide instead of an asparagine present in about 11%-12% of individuals of the Old Order Amish (OOA) (alternate allele frequency=6%), and is extremely rare in the general population. This mutation changes the asparagine to serine in position 352 (N352S) of the 398 amino acid long human protein, or in position 311 of the short isoform. The variant B4GALT1 has been observed to be associated with lower levels of low density lipoprotein cholesterol (LDL), total cholesterol, and fibrinogen and eGFR, increased levels of aspartate transaminase (AST) (but not alanine transaminase (ALT)) and serum levels of creatine kinase and creatinine, expression in muscle tissue (but not liver or red blood cells), and a decrease in basophils. It is believed that the N352S variant is protective against one or more cardiovascular conditions. It is further believed that B4GALT1, including its variant status, may be used to diagnose a patient's risk of developing cardiovascular conditions.

The phrase "corresponding to" when used in the context of the numbering of a given amino acid or polynucleotide sequence refers to the numbering of the residues of a specified reference sequence when the given amino acid or polynucleotide sequence is compared to the reference sequence (with the reference sequence herein being the polynucleotide (gDNA sequence, mRNA sequence, cDNA sequence) or polypeptide of (wild-type/full length) B4GALT1). In other words, the residue number or residue position of a given polymer is designated with respect to the reference sequence rather than by the actual numerical position of the residue within the given amino acid or polynucleotide sequence. For example, a given amino acid sequence can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

As used herein, the singular forms of the articles "a," "an," and "the" include plural references unless the context clearly dictates otherwise.

As used herein, and unless otherwise apparent from the context, "about" encompasses values within a standard margin of error of measurement (e.g., SEM) of a stated value.

As used herein, "and/or" refers to and encompasses any and all possible combinations of one or more of the associated listed items, as well as the lack of combinations when interpreted in the alternative ("or").

As used herein, the terms "comprising" or "including" means that one or more of the recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed subject matter. Thus, the term "consisting essentially of" when used in a claim of the present disclosure is not intended to be interpreted to be equivalent to "comprising."

As used herein, "optional" or "optionally" means that the subsequently described event or circumstance may or may not occur and that the description includes instances in which the event or circumstance occurs and instances in which it does not.

As used herein, "or" refers to any one member of a particular list and also includes any combination of members of that list.

Designation of a range of values includes all integers within or defining the range (including the two endpoint values), and all subranges defined by integers within the range.

It should be appreciated that particular features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

The present disclosure provides isolated B4GALT1 genomic and mRNA variants, B4GALT1 cDNA variants, or any complement thereof, and isolated B4GALT1 polypeptide variants. These variants are believed to be associated with a diminished risk of developing various cardiovascular conditions including, but not limited to, elevated levels of serum lipids, and elevated levels fibrinogen, coronary artery calcification, coronary artery disease (CAD), and increased levels of aspartate aminotransferase (AST), but not alanine transaminase (ALT). Without wishing to be bound by any theory, it is believed that these B4GALT1 variants associate with expression in muscle tissue, and not liver or red blood cells, as evidenced by the experimentally-observed increased levels of AST, but not ALT. Compositions comprising B4GALT1 genomic and mRNA variants, B4GALT1 cDNA variants, and isolated B4GALT1 polypeptide variants are also provided herein. Nucleic acid molecules that hybridize to the B4GALT1 genomic and mRNA variants and B4GALT1 cDNA variants are also provided herein. The present disclosure also provides vectors and cells comprising B4GALT1 genomic and mRNA variants, B4GALT1 cDNA variants, and B4GALT1 polypeptide variants.

The present disclosure also provides methods of detecting the presence of and/or levels of genomic and/or mRNA variants, B4GALT1 cDNA variants, or complement thereof, and/or B4GALT1 polypeptide variants in a biological sample. Also provided are methods for determining a subject's susceptibility to developing a cardiovascular condition, and methods of diagnosing a subject with a cardiovascular condition or at risk for a cardiovascular condition. Also provided are methods for modifying a cell through the use of any combination of nuclease agents, exogenous donor sequences, transcriptional activators, transcriptional repressors, and expression vectors for expressing a recombinant B4GALT1 gene or a nucleic acid encoding an B4GALT1 polypeptide. Also provided are therapeutic and prophylactic methods for treating a subject having or at risk of developing a cardiovascular condition.

The wild-type human genomic B4GALT1 nucleic acid is approximately 56.7 kb in length, includes 6 exons, and is located at chromosome 9 in the human genome. An exemplary wild-type human genomic B4GALT1 sequence is assigned NCBI Accession No. NG_008919.1 (SEQ ID NO:1). A variant of human genomic B4GALT1 is shown in SEQ ID NO:2, and comprises a single nucleotide polymorphism (SNP) (A to G at position 53576; referred to herein as a variant B4GALT1). The variant SNP results in a serine at the position corresponding to position 352 in the full length/mature B4GALT1 polypeptide of the encoded B4GALT1 variant polypeptide, rather than the asparagine encoded by the wild-type B4GALT1 polypeptide. The variant human genomic B4GALT1 nucleic acid comprises, for example, three bases (e.g., "agt") encoding a serine at the positions corresponding to positions 53575 to 53577 of the wild-type human genomic B4GALT1, as opposed to the three bases "aat" at positions 53575 to 53577 of the wild-type human genomic B4GALT1 (comparing SEQ ID NO:2 to SEQ ID NO:1, respectively). In some embodiments, the isolated nucleic acid molecule comprises SEQ ID NO:2. In some embodiments, the isolated nucleic acid molecule consists of SEQ ID NO:2. In some embodiments, the isolated nucleic acid molecule is a complement of any genomic B4GALT1 nucleic acid molecule disclosed herein.

In some embodiments, the isolated nucleic acid molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to SEQ ID NO:2. In some embodiments, such nucleic acid sequence also comprises nucleotides corresponding to positions 53575 to 53577 of SEQ ID NO:2. In some embodiments, the isolated nucleic acid molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:2 that comprises exons 1 to 6 of the B4GALT1 gene. In some embodiments, such nucleic acid sequence also comprises nucleotides corresponding to positions 53575 to 53577 of SEQ ID NO:2. In some embodiments, the isolated nucleic acid molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:2 comprising exon 5. In some embodiments, such nucleic acid sequence also comprises nucleotides corresponding to positions 53575 to 53577 of SEQ ID NO:2. In some embodiments, the isolated nucleic acid molecule comprises a nucleic acid sequence at least about 90% identical to SEQ ID NO:2, provided that the nucleic acid sequence comprises nucleotides corresponding to positions 53575 to 53577 of SEQ ID NO:2.

Percent complementarity between particular stretches of nucleic acid sequences within nucleic acids can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

In some embodiments, the isolated nucleic acid molecules comprise less than the entire genomic sequence. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, at least about 18000, at least about 19000, or at least about 20000 contiguous nucleotides of SEQ ID NO:2. In some embodiments, such isolated nucleic acid molecules also comprise nucleotides corresponding to positions 53575 to 53577 of SEQ ID NO:2. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 contiguous nucleotides of SEQ ID NO:2. In some embodiments, such isolated nucleic acid molecules also comprise nucleotides corresponding to positions 53575 to 53577 of SEQ ID NO:2. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 contiguous nucleotides of exon 5 of SEQ ID NO:2. In some embodiments, such isolated nucleic acid molecules also comprise nucleotides corresponding to positions 53575 to 53577 of SEQ ID NO:2.

For example, in some embodiments, the isolated nucleic acid molecule comprises at least 15 contiguous nucleotides of SEQ ID NO:2, wherein the contiguous nucleotides include nucleotides 53575 to 53577 of SEQ ID NO:2. In some such embodiments, the isolated nucleic acid molecule comprises at least 20, at least 25 or at least 30 contiguous nucleotides of SEQ ID NO:2. In some embodiments, the isolated nucleic acid molecule comprises between 15 and 50 contiguous nucleotides of SEQ ID NO:2, wherein the contiguous nucleotides include nucleotides 53575 to 53577 of SEQ ID NO:2. In some such embodiments, the isolated nucleic acid molecule comprises at least 20, at least 25 or at least 30 contiguous nucleotides of SEQ ID NO:2.

In some embodiments, the disclosure provides an isolated nucleic acid that comprises a nucleic acid sequence that is at least 90% identical to a portion of SEQ ID NO:2, wherein the portion of SEQ ID NO:2 comprises nucleotides 53575 to 53577 of SEQ ID NO:2 and wherein the portion of SEQ ID NO:2 is at least 15 nucleotides in length. In some such embodiments, the portion of SEQ ID NO:2 is at least 20, at least 25, or at least 30 nucleotides in length. In some embodiments, the disclosure provides an isolated nucleic acid that comprises a nucleic acid sequence that is at least 90% identical to a portion of SEQ ID NO:2, wherein the portion of SEQ ID NO:2 comprises nucleotides 53575 to 53577 of SEQ ID NO:2 and wherein the portion of SEQ ID NO:2 is between 15 and 50 nucleotides in length. In some such embodiments, the portion of SEQ ID NO:2 is at least 20, at least 25, or at least 30 nucleotides in length.

In some embodiments, the disclosure provides an isolated nucleic acid that comprises a nucleic acid sequence that is at least 95% identical to a portion of SEQ ID NO:2, wherein the portion of SEQ ID NO:2 comprises nucleotides 53575 to 53577 of SEQ ID NO:2 and wherein the portion of SEQ ID NO:2 is at least 15 nucleotides in length. In some such embodiments, the portion of SEQ ID NO:2 is at least 20, at least 25, or at least 30 nucleotides in length. In some embodiments, the disclosure provides an isolated nucleic acid that comprises a nucleic acid sequence that is at least 95% identical to a portion of SEQ ID NO:2, wherein the portion of SEQ ID NO:2 comprises nucleotides 53575 to 53577 of SEQ ID NO:2 and wherein the portion of SEQ ID NO:2 is between 15 and 50 nucleotides in length. In some such embodiments, the portion of SEQ ID NO:2 is at least 20, at least 25, or at least 30 nucleotides in length.

Such isolated nucleic acid molecules can be used, for example, to express variant B4GALT1 mRNAs and proteins or as exogenous donor sequences. It is understood that gene sequences within a population can vary due to polymorphisms, such as SNPs. The examples provided herein are only exemplary sequences, and other sequences are also possible.

In some embodiments, the isolated nucleic acid molecules comprise a variant B4GALT1 minigene, in which one or more nonessential segments of SEQ ID NO:2 have been deleted with respect to a corresponding wild-type B4GALT1 gene. In some embodiments, the deleted nonessential segments comprise one or more intron sequences. In some embodiments, the B4GALT1 minigenes can comprise, for example, exons corresponding to any one or more of exons 1 to 6, or any combination of such exons, from variant B4GALT1 (SEQ ID NO:2). In some embodiments, the minigene comprises or consists of exon 5 of SEQ ID NO:2. In some embodiments, the B4GALT1 minigene is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:2 comprising any one or more of exons 1 to 6, or any combination of such exons. In some embodiments, the B4GALT1 minigene is at least 70%, at least 75%, at least 80%, at least 85%, at least 90%, at least 95%, at least 96%, at least 97%, at least 98%, at least 99%, or 100% identical to a portion of SEQ ID NO:2 comprising any one or more of exons 1 to 6, or any combination of such exons and comprise nucleotides corresponding to positions 53575 to 53577 of SEQ ID NO:2. In some embodiments, the B4GALT1 minigene is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:2 comprising exon 5.

The present disclosure also provides isolated nucleic acid molecules that hybridize to a variant B4GALT1 genomic sequence or a variant B4GALT1 minigene. In some embodiments, such isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, at least about 12000, at least about 13000, at least about 14000, at least about 15000, at least about 16000, at least about 17000, at least about 18000, at least about 19000, or at least about 20000 nucleotides. In some embodiments, such isolated nucleic acid molecules also hybridize to positions 53575 to 53577 of SEQ ID NO:2. In some embodiments, the isolated nucleic acid molecules hybridize to a portion of variant B4GALT1 genome or minigene at a segment that includes or is within about 1000, within about 500, within about 400, within about 300, within about 200, within about 100, within about 50, within about 45, within about 40, within about 35, within about 30, within about 25, within about 20, within about 15, within about 10, or within about 5 nucleotides of positions 53575 to 53577 of SEQ ID NO:2. In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to variant B4GALT1 genomic DNA or minigene. In some embodiments, such isolated nucleic acid molecules also hybridize to positions 53575 to 53577 of SEQ ID NO:2. In some embodiments, the isolated nucleic acid molecules comprise or consist of from about 15 to about 100 nucleotides, or from about 15 to about 35 nucleotides.

For example, in some embodiments, the disclosure provides an isolated nucleic acid molecule that comprises at least 15 nucleotides, wherein the isolated nucleic acid molecule hybridizes to a nucleic acid comprising the sequence of SEQ ID NO:2, wherein the isolated nucleic acid molecule hybridizes to a portion of SEQ ID NO:2, and wherein the portion of SEQ ID NO:2 comprises nucleotides 53575 to 53577 of SEQ ID NO:2. In some such embodiments, the isolated nucleic acid molecule comprises at least 20, at least 25, or at least 30 nucleotides. In some embodiments, the disclosure provides an isolated nucleic acid molecule that comprises 15 to 50 nucleotides, wherein the isolated nucleic acid molecule hybridizes to a nucleic acid comprising the sequence of SEQ ID NO:2, wherein the isolated nucleic acid molecule hybridizes to a portion of SEQ ID NO:2, and wherein the portion of SEQ ID NO:2 comprises nucleotides 53575 to 53577 of SEQ ID NO:2. In some such embodiments, the isolated nucleic acid molecule comprises at least 20, at least 25, or at least 30 nucleotides.

In some embodiments, the isolated nucleic acid molecules hybridize to at least 15 contiguous nucleotides of a nucleic acid, wherein the contiguous nucleotides are at least 90% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length. In some embodiments, the isolated nucleic acid molecules hybridize to at least 15 contiguous nucleotides of a nucleic acid, wherein the contiguous nucleotides are at least 95% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length. In some embodiments, the isolated nucleic acid molecules hybridize to at least 15 contiguous nucleotides of a nucleic acid, wherein the contiguous nucleotides are at least 100% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length.

In some embodiments, the isolated nucleic acid molecules hybridize to 15 to 50 contiguous nucleotides of a nucleic acid, wherein the contiguous nucleotides are at least 90% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length. In some embodiments, the isolated nucleic acid molecules hybridize to 15 to 50 contiguous nucleotides of a nucleic acid, wherein the contiguous nucleotides are at least 95% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length. In some embodiments, the isolated nucleic acid molecules hybridize to 15 to 50 contiguous nucleotides of a nucleic acid, wherein the contiguous nucleotides are at least 100% identical to a portion of SEQ ID NO:2, wherein the contiguous nucleotides comprise nucleotides 53575 to 53577 of SEQ ID NO:2 at positions that correspond to positions 53757 to 53577 of SEQ ID NO:2. In some such embodiments, the contiguous nucleotides are at least 20, at least 25, or at least 30 nucleotides in length.

Such isolated nucleic acid molecules can be used, for example, as guide RNAs, primers, probes, or exogenous donor sequences.

A representative wild-type B4GALT1 genomic sequence is recited in SEQ ID NO:1. A representative variant B4GALT1 genomic sequence variant is recited in SEQ ID NO:2.

The present disclosure also provides isolated nucleic acid molecules comprising a variant of B4GALT1 mRNA. An exemplary wild-type human B4GALT1 mRNA is assigned NCBI Accession NM_001497 (SEQ ID NO:3), and consists of 4214 nucleotide bases. A variant of human B4GALT1 mRNA is shown in SEQ ID NO:4, and comprises the SNP (A to G at position 1244; referred to herein as a variant B4GALT1), which results in a serine at the position corresponding to position 352 of the encoded B4GALT1 variant polypeptide. The variant human B4GALT1 mRNA comprises, for example, the three bases "agu" encoding a serine at positions corresponding to positions 1243 to 1245 of the wild-type human B4GALT1 mRNA, as opposed to the three bases "aau" at positions 1243 to 1245 of the wild-type human B4GALT1 mRNA (comparing SEQ ID NO:4 to SEQ ID NO:3, respectively). In some embodiments, the isolated nucleic acid molecule comprises SEQ ID NO:4. In some embodiments, the isolated nucleic acid molecule consists of SEQ ID NO:4.

In some embodiments, the isolated nucleic acid molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to SEQ ID NO:4. In some embodiments, such nucleic acid sequences also comprise nucleotides corresponding to positions 1243 to 1245 of SEQ ID NO:4. In some embodiments, the isolated nucleic acid molecules comprise or consist of a nucleotide sequence that is at least about 70%, at least about 75%, at least about 80%, at least about 85%, at least about 90%, at least about 95%, at least about 96%, at least about 97%, at least about 98%, at least about 99%, or 100% identical to a portion of SEQ ID NO:4 comprising exons 1 to 6. In some embodiments, such nucleic acid sequences also comprise nucleotides corresponding to positions 1243 to 1245 of SEQ ID NO:4. In some embodiments, the isolated nucleic acid molecule is a complement of any B4GALT1 mRNA molecule disclosed herein.

In some embodiments, the isolated nucleic acid molecules comprises less than the entire mRNA sequence. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, or at least about 4000 contiguous nucleotides of SEQ ID NO:4. In some embodiments, such isolated nucleic acid molecules also comprise nucleotides corresponding to positions 1243 to 1245 of SEQ ID NO:4. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 contiguous nucleotides of SEQ ID NO:4. In some embodiments, such isolated nucleic acid molecules also comprises nucleotides corresponding to positions 1243 to 1245 of SEQ ID NO:4. In some embodiments, the isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, or at least about 1000 contiguous nucleotides of exons 1 to 6 of SEQ ID NO:4. In some embodiments, such isolated nucleic acid molecules also comprise nucleotides corresponding to positions 1243 to 1245 of SEQ ID NO:4.

In some embodiments, the disclosure provides an isolated nucleic acid molecule that comprises a nucleic acid sequence that is at least 90% identical to a portion of SEQ ID NO:4, wherein the portion of SEQ ID NO:4 comprises nucleotides 1243 to 1245 of SEQ ID NO:4 and wherein the portion of SEQ ID NO:4 comprises at least 15 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is at least 95% identical to a portion of SEQ ID NO:4, wherein the portion of SEQ ID NO:4 comprises nucleotides 1243 to 1245 of SEQ ID NO:4 and wherein the portion of SEQ ID NO:4 comprises at least 15 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is 100% identical to a portion of SEQ ID NO:4, wherein the portion of SEQ ID NO:4 comprises nucleotides 1243 to 1245 of SEQ ID NO:4 and wherein the portion of SEQ ID NO:4 comprises at least 15 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is at least 90% identical to a portion of SEQ ID NO:4, wherein the portion of SEQ ID NO:4 comprises nucleotides 1243 to 1245 of SEQ ID NO:4 and wherein the portion of SEQ ID NO:4 comprises 15 to 50 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is at least 95% identical to a portion of SEQ ID NO:4, wherein the portion of SEQ ID NO:4 comprises nucleotides 1243 to 1245 of SEQ ID NO:4 and wherein the portion of SEQ ID NO:4 comprises 15 to 50 nucleotides of SEQ ID NO:4. In some such embodiments, the portion of SEQ ID NO:4 is at least 20, at least 25 or at least 30 nucleotides of SEQ ID NO:4. In some embodiments, the disclosure provides an isolated nucleic acid molecule that comprises a nucleic acid sequence that is 100% identical to a portion of SEQ ID NO:4, wherein the portion of SEQ ID NO:4 comprises nucleotides 1243 to 1245 of SEQ ID NO:4 and wherein the portion of SEQ ID NO:4 comprises 15 to 50 nucleotides of SEQ ID NO:4. In some such embodiments, the portion of SEQ ID NO:4 is at least 20, at least 25 or at least 30 nucleotides of SEQ ID NO:4.

Such isolated nucleic acid molecules can be used, for example, to express B4GALT1 variant polypeptides or as exogenous donor sequences. It is understood that gene sequences within a population can vary due to polymorphisms such as SNPs. The examples provided herein are only exemplary sequences, and other sequences are also possible.

In some embodiments, the isolated nucleic acid molecules comprise or consist of a nucleic acid sequence encoding a polypeptide at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to the variant Asn352Ser B4GALT1 polypeptide (SEQ ID NO:8), provided that the polypeptide comprises a serine at the position corresponding to position 352. In some embodiments, the isolated nucleic acid molecules comprise or consist of a nucleic acid sequence encoding a polypeptide at least about 90%, identical to SEQ ID NO:8, provided that the polypeptide comprises a serine at the position corresponding to position 352. In some embodiments, the isolated nucleic acid molecules comprise or consist of a nucleic acid sequence encoding a polypeptide at least about 95%, identical to SEQ ID NO:8, provided that the polypeptide comprises a serine at the position corresponding to position 352.

For example, in some embodiments, the isolated nucleic acid molecule comprises a nucleic acid sequence encoding a polypeptide that has an amino acid sequence that is at least 10 amino acids long, wherein the amino acid sequence is 90% identical to a portion of the amino acid sequence of SEQ ID NO:8, wherein the portion comprises a serine at the position corresponding to position 352 of SEQ ID NO:8. In some such embodiments, the nucleic acid sequence encodes a polypeptide that has an amino acid sequence that is at least 15, at least 20 or at least 25 amino acids long. In some embodiments, the isolated nucleic acid molecule comprises a nucleic acid sequence encoding a polypeptide that has an amino acid sequence that is at least 10 amino acids long, wherein the amino acid sequence is 95% identical to a portion of the amino acid sequence of SEQ ID NO:8, wherein the portion comprises a serine at the position corresponding to position 352 of SEQ ID NO:8. In some such embodiments, the nucleic acid sequence encodes a polypeptide that has an amino acid sequence that is at least 15, at least 20 or at least 25 amino acids long. In some embodiments, the isolated nucleic acid molecule comprises a nucleic acid sequence encoding a polypeptide that has an amino acid sequence that is 10 to 50 amino acids long, wherein the amino acid sequence is 90% identical to a portion of the amino acid sequence of SEQ ID NO:8, wherein the portion comprises a serine at the position corresponding to position 352 of SEQ ID NO:8. In some such embodiments, the nucleic acid sequence encodes a polypeptide that has an amino acid sequence that is at least 15, at least 20 or at least 25 amino acids long. In some embodiments, the isolated nucleic acid molecule comprises a nucleic acid sequence encoding a polypeptide that has an amino acid sequence that is 10 to 50 amino acids long, wherein the amino acid sequence is 95% identical to a portion of the amino acid sequence of SEQ ID NO:8, wherein the portion comprises a serine at the position corresponding to position 352 of SEQ ID NO:8. In some such embodiments, the nucleic acid sequence encodes a polypeptide that has an amino acid sequence that is at least 15, at least 20 or at least 25 amino acids long. In some embodiments, the isolated nucleic acid molecules comprise or consist of a nucleic acid sequence encoding a polypeptide identical to SEQ ID NO:8.

The present disclosure also provides isolated nucleic acid molecules that hybridize to a variant B4GALT1 mRNA sequence. In some embodiments, such isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, or at least about 4000 nucleotides. In some embodiments, such isolated nucleic acid molecules also hybridize to positions 1243 to 1245 of SEQ ID NO:4. In some embodiments, the isolated nucleic acid molecules hybridize to a portion of a variant B4GALT1 mRNA at a segment that includes or is within about 1000, within about 500, within about 400, within about 300, within about 200, within about 100, within about 50, within about 45, within about 40, within about 35, within about 30, within about 25, within about 20, within about 15, within about 10, or within about 5 nucleotides of positions 1243 to 1245 of SEQ ID NO:4.

In some embodiments, the isolated nucleic acid molecules comprise or consist of at least 15 nucleotides and hybridize to a portion of a variant B4GALT1 mRNA (for example, SEQ ID NO:4) at a segment that includes or is within 5 nucleotides of positions 1243 to 1245 of SEQ ID NO:4. In some such embodiments, the isolated nucleic acid molecules comprise at least 20, at least 25 or at least 30 nucleotides. In some embodiments, the isolated nucleic acid molecules comprise or consist of at least 15 nucleotides, hybridize to a portion of a variant B4GALT1 mRNA (for example, SEQ ID NO:4) at a segment that includes or is within 5 nucleotides of positions 1243 to 1245 of SEQ ID NO:4 and hybridize to positions 1243 to 1245 of SEQ ID NO:4. In some such embodiments, the isolated nucleic acid molecules comprise at least 20, at least 25 or at least 30 nucleotides. In some embodiments, the isolated nucleic acid molecules comprise 15 to 50 nucleotides and hybridize to a portion of a variant B4GALT1 mRNA (for example, SEQ ID NO:4) at a segment that includes positions 1243 to 1245 of SEQ ID NO:4 and hybridize to positions 1243 to 1245 of SEQ ID NO:4. In some such embodiments, the isolated nucleic acid molecules comprise at least 20, at least 25 or at least 30 nucleotides.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to a variant B4GALT1 mRNA (such as, for example, SEQ ID NO:4). In some embodiments, the isolated nucleic acid molecules also hybridize to positions 1243 to 1245 of SEQ ID NO:4. In some embodiments, the isolated nucleic acid molecules comprise or consist of from about 15 to about 100 nucleotides, or from about 15 to about 35 nucleotides.

In some embodiments, the isolated nucleic acid molecules comprise or consist of at least 15 nucleotides and hybridize to a portion of a variant B4GALT1 mRNA at a segment that includes or is within 5 nucleotides of positions 1243 to 1245 of SEQ ID NO:4, wherein the variant B4GALT1 mRNA is at least 90% identical to a variant B4GALT1 mRNA (such as, for example, SEQ ID NO:4). In some such embodiments, the isolated nucleic acid molecules comprise at least 20, at least 25 or at least 30 nucleotides. In some embodiments, the isolated nucleic acid molecules comprise or consist of at least 15 nucleotides and hybridize to a portion of a variant B4GALT1 mRNA at a segment that includes or is within 5 nucleotides of positions 1243 to 1245 of SEQ ID NO:4, wherein the variant B4GALT1 mRNA is at least 95% identical to a variant B4GALT1 mRNA (such as, for example, SEQ ID NO:4). In some such embodiments, the isolated nucleic acid molecules comprise at least 20, at least 25 or at least 30 nucleotides. In some embodiments, the isolated nucleic acid molecules comprise or consist of at least 15 nucleotides, hybridize to a portion of a variant B4GALT1 mRNA at a segment that includes or is within 5 nucleotides of positions 1243 to 1245 of SEQ ID NO:4 and hybridize to positions 1243 to 1245 of SEQ ID NO:4, wherein the variant B4GALT1 mRNA is at least 90% identical to a variant B4GALT1 mRNA (such as, for example, SEQ ID NO:4). In some such embodiments, the isolated nucleic acid molecules comprise at least 20, at least 25 or at least 30 nucleotides. In some embodiments, the isolated nucleic acid molecules comprise or consist of at least 15 nucleotides, hybridize to a portion of a variant B4GALT1 mRNA at a segment that includes or is within 5 nucleotides of positions 1243 to 1245 of SEQ ID NO:4 and hybridize to positions 1243 to 1245 of SEQ ID NO:4, wherein the variant B4GALT1 mRNA is at least 95% identical to a variant B4GALT1 mRNA (such as, for example, SEQ ID NO:4). In some such embodiments, the isolated nucleic acid molecules comprise at least 20, at least 25 or at least 30 nucleotides. In some embodiments, the isolated nucleic acid molecules comprise or consist of from 15 to 100 nucleotides, or from 15 to 35 nucleotides.

Such isolated nucleic acid molecules can be used, for example, as guide RNAs, primers, probes, or exogenous donor sequences.

A representative wild-type B4GALT1 mRNA sequence is recited in SEQ ID NO:3. A representative variant B4GALT1 mRNA sequence is recited in SEQ ID NO:4.

The present disclosure also provides nucleic acid molecules comprising a variant of B4GALT1 cDNA encoding all or part of a B4GALT1 variant polypeptide. An exemplary wild-type human B4GALT1 cDNA (e.g., coding region of mRNA written as DNA) consists of 1197 nucleotide bases (SEQ ID NO:5). A variant of human B4GALT1 cDNA is shown in SEQ ID NO:6, and comprises the SNP (A to G at position 1055; referred to herein as a variant B4GALT1), which results in a serine at the position corresponding to position 352 of the encoded B4GALT1 variant polypeptide. The variant human B4GALT1 cDNA comprises, for example, "agt" encoding a serine at positions corresponding to positions 1054 to 1056 of the full length/mature wild-type human B4GALT1 cDNA, as opposed to the three bases "aat" of the wild-type human B4GALT1 cDNA at positions 1054 to 1056 (comparing SEQ ID NO:6 to SEQ ID NO:5, respectively). In some embodiments, the nucleic acid molecule comprises SEQ ID NO:6. In some embodiments, the nucleic acid molecule consists of SEQ ID NO:6. In some embodiments, the cDNA molecules are isolated.

In some embodiments, the cDNA molecules comprise or consist of a nucleic acid sequence that is at least about 70%, at least about 75%, at least about 80%, at least about 85%, at least about 90%, at least about 95%, at least about 96%, at least about 97%, at least about 98%, at least about 99%, or 100% identical to SEQ ID NO:6. In some embodiments, the cDNA molecules also comprise nucleotides corresponding to positions 1054 to 1056 of SEQ ID NO:6. In some embodiments, the isolated nucleic acid molecule is a complement of any B4GALT1 cDNA molecule disclosed herein.

In some embodiments, the cDNA molecules comprise less than the entire cDNA sequence. In some embodiments, the cDNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, or at least about 1100 contiguous nucleotides of SEQ ID NO:6. In some embodiments, such cDNA molecules also comprise nucleotides corresponding to positions 1054 to 1056 of SEQ ID NO:6. In some embodiments, the cDNA molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of SEQ ID NO:6. In some embodiments, such cDNA molecules also comprise nucleotides corresponding to positions 1054 to 1056 of SEQ ID NO:6.

For example, in some embodiments, the cDNA molecule comprises at least 15 contiguous nucleotides of SEQ ID NO:6, wherein the contiguous nucleotides include nucleotides 1054 to 1056 of SEQ ID NO:6. In some such embodiments, the isolated nucleic acid molecule comprises at least 20, at least 25 or at least 30 contiguous nucleotides of SEQ ID NO:6. In some embodiments, the cDNA molecule comprises 15 to 50 contiguous nucleotides of SEQ ID NO:6, wherein the contiguous nucleotides include nucleotides 1054 to 1056 of SEQ ID NO:6. In some such embodiments, the isolated nucleic acid molecule comprises at least 20, at least 25 or at least 30 contiguous nucleotides of SEQ ID NO:6. In some embodiments, the disclosure provides a cDNA molecule that comprises a nucleic acid sequence that is at least 90% identical to a portion of SEQ ID NO:6, wherein the portion of SEQ ID NO:6 comprises nucleotides 1054 to 1056 of SEQ ID NO:6 and wherein the portion of SEQ ID NO:6 comprises at least 15 contiguous nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises a nucleic acid sequence that is at least 95% identical to a portion of SEQ ID NO:6, wherein the portion of SEQ ID NO:6 comprises nucleotides 1054 to 1056 of SEQ ID NO:6 and wherein the portion of SEQ ID NO:6 comprises at least 15 contiguous nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises a nucleic acid sequence that is at least 90% identical to a portion of SEQ ID NO:6, wherein the portion of SEQ ID NO:6 comprises nucleotides 1054 to 1056 of SEQ ID NO:6 and wherein the portion of SEQ ID NO:6 comprises 15 to 50 contiguous nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises nucleotides 1054 to 1056 of SEQ ID NO:6 at positions corresponding to nucleotides 1054 to 1056 of SEQ ID NO:6, wherein the cDNA molecule comprises a nucleic acid sequence that is at least 90% identical to a portion of SEQ ID NO:6, wherein the portion of SEQ ID NO:6 comprises nucleotides 1054 to 1056 of SEQ ID NO:6 and wherein the portion of SEQ ID NO:6 comprises at least 15 contiguous nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises nucleotides 1054 to 1056 of SEQ ID NO:6 at positions corresponding to nucleotides 1054 to 1056 of SEQ ID NO:6, wherein the cDNA molecule comprises a nucleic acid sequence that is at least 95% identical to a portion of SEQ ID NO:6, wherein the portion of SEQ ID NO:6 comprises nucleotides 1054 to 1056 of SEQ ID NO:6 and wherein the portion of SEQ ID NO:6 comprises at least 15 contiguous nucleotides nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises nucleotides 1054 to 1056 of SEQ ID NO:6 at positions corresponding to nucleotides 1054 to 1056 of SEQ ID NO:6, wherein the cDNA molecule comprises a nucleic acid sequence that is at least 90% identical to a portion of SEQ ID NO:6, wherein the portion of SEQ ID NO:6 comprises nucleotides 1054 to 1056 of SEQ ID NO:6 and wherein the portion of SEQ ID NO:6 comprises 15 to 50 contiguous nucleotides of SEQ ID NO:6. In some such embodiments, the portion of SEQ ID NO:6 is at least 20, at least 25 or at least 30 contiguous nucleotides of SEQ ID NO:6. In some embodiments, the disclosure provides a cDNA molecule that comprises nucleotides 1054 to 1056 of SEQ ID NO:6 at positions corresponding to nucleotides 1054 to 1056 of SEQ ID NO:6, wherein the cDNA molecule comprises a nucleic acid sequence that is at least 95% identical to a portion of SEQ ID NO:6, wherein the portion of SEQ ID NO:6 comprises nucleotides 1054 to 1056 of SEQ ID NO:6 and wherein the portion of SEQ ID NO:6 comprises 15 to 50 contiguous nucleotides of SEQ ID NO:6. In some such embodiments, the portion of SEQ ID NO:6 is at least 20, at least 25 or at least 30 contiguous nucleotides of SEQ ID NO:6.

Such cDNA molecules can be used, for example, to express B4GALT1 variant proteins or as exogenous donor sequences. It is understood that gene sequences within a population can vary due to polymorphisms such as SNPs. The examples provided herein are only exemplary sequences, and other sequences are also possible.

In some embodiments, the cDNA molecules comprise or consist of a nucleic acid sequence encoding a polypeptide at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to the variant Asn352Ser B4GALT1 polypeptide (SEQ ID NO:8), provided that the polypeptide comprises a serine at the position corresponding to position 352. In some embodiments, the cDNA molecules comprise or consist of a nucleic acid sequence encoding a polypeptide at least about 90%, identical to SEQ ID NO:8, provided that the polypeptide comprises a serine at the position corresponding to position 352. In some embodiments, the cDNA molecules comprise or consist of a nucleic acid sequence encoding a polypeptide at least about 95%, identical to SEQ ID NO:8, provided that the polypeptide comprises a serine at the position corresponding to position 352. In some embodiments, the cDNA molecule comprises or consists of a nucleic acid sequence encoding a polypeptide identical to SEQ ID NO:8.

The present disclosure also provides isolated nucleic acid molecules that hybridize to a variant B4GALT1 cDNA sequence. In some embodiments, such isolated nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, or at least about 1100 nucleotides. In some embodiments, such isolated nucleic acid molecules also hybridize to positions 1054 to 1056 of SEQ ID NO:6. In some embodiments, such isolated nucleic acid molecules hybridize to a portion of a variant B4GALT1 cDNA at a segment that includes or is within about 600, within about 500, within about 400, within about 300, within about 200, within about 100, within about 50, within about 45, within about 40, within about 35, within about 30, within about 25, within about 20, within about 15, within about 10, or within about 5 nucleotides of positions 1054 to 1056 of SEQ ID NO:6. In some embodiments, the isolated nucleic acid molecules hybridize to at least about 15 contiguous nucleotides of a cDNA molecule that is at least about 70%, at least about 75%, at least about 80%, at least about 85%, at least about 90%, at least about 95%, at least about 96%, at least about 97%, at least about 98%, at least about 99%, or 100% identical to a variant B4GALT1 cDNA (such as, for example, SEQ ID NO:6). In some embodiments, the isolated nucleic acid molecules also hybridize to positions 1054 to 1056 of SEQ ID NO:6. In some embodiments, the isolated nucleic acid molecules comprise or consist of from about 15 to about 100 nucleotides, or from about 15 to about 35 nucleotides.

In some embodiments, the isolated nucleic acid molecules comprise or consist of at least 15 nucleotides and hybridize to a portion of a variant B4GALT1 cDNA at a segment that includes or is within 5 nucleotides of positions 1054 to 1056 of SEQ ID NO:6, wherein the variant B4GALT1 cDNA is at least 90% identical to a variant B4GALT1 cDNA (such as, for example, SEQ ID NO:6). In some embodiments, the isolated nucleic acid molecules comprise or consist of at least 15 nucleotides and hybridize to a portion of a variant B4GALT1 cDNA at a segment that includes or is within 5 nucleotides of positions 1054 to 1056 of SEQ ID NO:6, wherein the variant B4GALT1 cDNA is at least 95% identical to a variant B4GALT1 cDNA (such as, for example, SEQ ID NO:6). In some embodiments, the isolated nucleic acid molecules comprise or consist of at least 15 nucleotides and hybridize to a portion of a variant B4GALT1 cDNA at a segment that includes or is within 5 nucleotides of positions 1054 to 1056 of SEQ ID NO:6, wherein the variant B4GALT1 cDNA is 100% identical to a variant B4GALT1 cDNA (such as, for example, SEQ ID NO:6). In some embodiments, the isolated nucleic acid molecules comprise or consist of at least 15 nucleotides, hybridize to a portion of a variant B4GALT1 cDNA at a segment that includes or is within 5 nucleotides of positions 1054 to 1056 of SEQ ID NO:6 and hybridize to positions 1054 to 1056 of SEQ ID NO:6, wherein the variant B4GALT1 cDNA is at least 90% identical to a variant B4GALT1 cDNA (such as, for example, SEQ ID NO:6). In some embodiments, the isolated nucleic acid molecules comprise or consist of at least 15 nucleotides, hybridize to a portion of a variant B4GALT1 cDNA at a segment that includes or is within 5 nucleotides of positions 1054 to 1056 of SEQ ID NO:6 and hybridize to positions 1054 to 1056 of SEQ ID NO:6, wherein the variant B4GALT1 cDNA is at least 95% identical to a variant B4GALT1 cDNA (such as, for example, SEQ ID NO:6). In some embodiments, the isolated nucleic acid molecules comprise or consist of at least 15 nucleotides, hybridize to a portion of a variant B4GALT1 cDNA at a segment that includes or is within 5 nucleotides of positions 1054 to 1056 of SEQ ID NO:6 and hybridize to positions 1054 to 1056 of SEQ ID NO:6, wherein the variant B4GALT1 cDNA is 100% identical to a variant B4GALT1 cDNA (such as, for example, SEQ ID NO:6). In some embodiments, the isolated nucleic acid molecules comprise or consist of from 15 to 100 nucleotides, or from 15 to 35 nucleotides.

Such isolated nucleic acid molecules can be used, for example, as guide RNAs, primers, probes, exogenous donor sequences, antisense RNAs, siRNAs, or shRNAs.

A representative wild-type B4GALT1 cDNA sequence is recited in SEQ ID NO:5. A representative variant B4GALT1 cDNA sequence is recited in SEQ ID NO:6.

The nucleic acid molecules disclosed herein can comprise a nucleic acid sequence of a naturally occurring B4GALT1 gene or mRNA transcript, or can comprise a non-naturally occurring sequence. In some embodiments, the naturally occurring sequence can differ from the non-naturally occurring sequence due to synonymous mutations or mutations that do not affect the encoded B4GALT1 polypeptide. For example, the sequence can be identical with the exception of synonymous mutations or mutations that do not affect the encoded B4GALT1 polypeptide. A synonymous mutation or substitution is the substitution of one nucleotide for another in an exon of a gene coding for a protein such that the produced amino acid sequence is not modified. This is possible because of the degeneracy of the genetic code, with some amino acids being coded for by more than one three-base pair codon. Synonymous substitutions are used, for example, in the process of codon optimization. The nucleic acid molecules disclosed herein can be codon optimized.

Also provided herein are functional polynucleotides that can interact with the disclosed nucleic acid molecules. Functional polynucleotides are nucleic acid molecules that have a specific function, such as binding a target molecule or catalyzing a specific reaction. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

Antisense molecules are designed to interact with a target nucleic acid molecule through either canonical or non-canonical base pairing. The interaction of the antisense molecule and the target molecule is designed to promote the destruction of the target molecule through, for example, RNase-H-mediated RNA-DNA hybrid degradation. Alternately, the antisense molecule is designed to interrupt a processing function that normally would take place on the target molecule, such as transcription or replication. Antisense molecules can be designed based on the sequence of the target molecule. Numerous methods for optimization of antisense efficiency by identifying the most accessible regions of the target molecule exist. Exemplary methods include, but are not limited to, in vitro selection experiments and DNA modification studies using DMS and DEPC. Antisense molecules generally bind the target molecule with a dissociation constant ($k_d$) less than or equal to about $10^{-6}$, less than or equal to about $10^{-8}$, less than or equal to about $10^{-10}$, or less than or equal to about $10^{-12}$. A representative sample of methods and techniques which aid in the design and use of antisense molecules can be found in the following non-limiting list of U.S. Pat. Nos. 5,135,917; 5,294,533; 5,627,158; 5,641,754; 5,691,317; 5,780,607; 5,786,138; 5,849,903; 5,856,103; 5,919,772; 5,955,590; 5,990,088; 5,994,320; 5,998,602; 6,005,095; 6,007,995; 6,013,522; 6,017,898; 6,018,042; 6,025,198; 6,033,910; 6,040,296; 6,046,004; 6,046,319; and 6,057,437. Examples of antisense molecules include, but are not limited to, antisense RNAs, small interfering RNAs (siRNAs), and short hairpin RNAs (shRNAs).

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be in a vector or exogenous donor sequence comprising the isolated nucleic acid molecule and a heterologous nucleic acid sequence. The isolated nucleic acid molecules can also be linked or fused to a heterologous label, such as a fluorescent label. Other examples of labels are disclosed elsewhere herein.

The label can be directly detectable (e.g., fluorophore) or indirectly detectable (e.g., hapten, enzyme, or fluorophore quencher). Such labels can be detectable by spectroscopic, photochemical, biochemical, immunochemical, or chemical means. Such labels include, for example, radiolabels that can be measured with radiation-counting devices; pigments, dyes or other chromogens that can be visually observed or measured with a spectrophotometer; spin labels that can be measured with a spin label analyzer; and fluorescent labels (e.g., fluorophores), where the output signal is generated by the excitation of a suitable molecular adduct and that can be visualized by excitation with light that is absorbed by the dye or can be measured with standard fluorometers or imaging systems. The label can also be, for example, a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term "label" can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a calorimetric substrate (e.g., tetramethylbenzidine (TMB)) or a fluorogenic substrate to detect the presence of HRP. Exemplary labels that can be used as tags to facilitate purification include, but are not limited to, myc, HA, FLAG or 3xFLAG, 6xHis or polyhistidine, glutathione-S-transferase (GST), maltose binding protein, an epitope tag, or the Fc portion of immunoglobulin. Numerous labels are known and include, for example, particles, fluorophores, haptens, enzymes and their calorimetric, fluorogenic and chemiluminescent substrates and other labels.

The disclosed nucleic acid molecules can be made up of, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazadenine. Certain nucleotide analogs such as, for example, 5-substituted pyrimidines, 6-azapyrimidines, and N-2, N-6 and O-6 substituted purines including, but not limited to, 2-aminopropyladenine, 5-propynyluracil, 5-propynylcytosine, and 5-methylcytosine can increase the stability of duplex formation. Often, base modifications can be combined with, for example, a sugar modification, such as 2'-O-methoxyethyl, to achieve unique properties such as increased duplex stability.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m are from 1 to about 10.

Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkyl phosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included.

Nucleotide substitutes include molecules having similar functional properties to nucleotides, but which do not contain a phosphate moiety, such as peptide nucleic acid (PNA). Nucleotide substitutes include molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes also include nucleotides or nucleotide analogs that have had the phosphate moiety or sugar moieties replaced. In some embodiments, nucleotide substitutes may not contain a standard phosphorus atom. Substitutes for the phosphate can be, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

It is also understood in a nucleotide substitute that both the sugar and the phosphate moieties of the nucleotide can be replaced by, for example, an amide type linkage (aminoethylglycine) (PNA).

It is also possible to link other types of molecules (conjugates) to nucleotides or nucleotide analogs to enhance, for example, cellular uptake. Conjugates can be chemically linked to the nucleotide or nucleotide analogs. Such conjugates include, for example, lipid moieties such as a cholesterol moiety, cholic acid, a thioether such as hexyl-S-tritylthiol, a thiocholesterol, an aliphatic chain such as dodecandiol or undecyl residues, a phospholipid such as di-hexadecyl-rac-glycerol or triethylammonium 1,2-di-O-hexadecyl-rac-glycero-3-H-phosphonate, a polyamine or a polyethylene glycol chain, adamantane acetic acid, a palmityl moiety, or an octadecylamine or hexylamino-carbonyl-oxycholesterol moiety.

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (e.g., a circular double-stranded DNA into which additional DNA segments can be ligated). In some embodiments, the vector is a viral vector, wherein additional DNA segments can be ligated into the viral genome. In some embodiments, the vector can autonomously replicate in a host cell into which it is introduced (e.g., bacterial vectors having a bacterial origin of replication and episomal mammalian vectors). In some embodiments, the vector (e.g., non-episomal mammalian vectors) can be integrated into the genome of a host cell upon introduction into the host cell and thereby are replicated along with the host genome. Moreover, particular vectors can direct the expression of genes to which they are operatively linked. Such vectors are referred to herein as "recombinant expression vectors" or "expression vectors." Such vectors can also be targeting vectors (i.e., exogenous donor sequences).

In some embodiments, the proteins encoded by the various genetic variants disclosed herein are expressed by inserting nucleic acid molecules encoding the disclosed genetic variants into expression vectors, such that the genes are operatively linked to expression control sequences, such as transcriptional and translational control sequences. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and the like. In some embodiments, nucleic acid molecules comprising the disclosed genetic variants can be ligated into a vector such that transcriptional and translational control sequences within the vector serve their intended function of regulating the transcription and translation of the genetic variant. The expression vector and expression control sequences are chosen to be compatible with the expression host cell used. Nucleic acid sequences comprising the disclosed genetic variants can be inserted into separate vectors or into the same expression vector as the variant genetic information. A nucleic acid sequence comprising the disclosed genetic variants can be inserted into the expression vector by standard methods (e.g., ligation of complementary restriction sites on the nucleic acid comprising the disclosed genetic variants and vector, or blunt end ligation if no restriction sites are present).

In addition to a nucleic acid sequence comprising the disclosed genetic variants, the recombinant expression vectors can carry regulatory sequences that control the expression of the genetic variant in a host cell. The design of the expression vector, including the selection of regulatory sequences can depend on such factors as the choice of the host cell to be transformed, the level of expression of protein desired, and so forth. Desired regulatory sequences for mammalian host cell expression can include, for example, viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. Methods of expressing polypeptides in bacterial cells or fungal cells (e.g., yeast cells) are also well known.

A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

In addition to a nucleic acid sequence comprising the disclosed genetic variants and regulatory sequences, the recombinant expression vectors can carry additional sequences, such as sequences that regulate replication of the vector in host cells (e.g., origins of replication) and selectable marker genes. A selectable marker gene can facilitate selection of host cells into which the vector has been introduced (see e.g., U.S. Pat. Nos. 4,399,216; 4,634,665; and 5,179,017). For example, a selectable marker gene can confer resistance to drugs, such as G418, hygromycin, or methotrexate, on a host cell into which the vector has been introduced. Exemplary selectable marker genes include, but are not limited to, the dihydrofolate reductase (DHFR) gene (for use in dhfr-host cells with methotrexate selection/amplification), the neo gene (for G418 selection), and the glutamate synthetase (GS) gene.

The present disclosure also provides isolated polypeptides comprising a variant B4GALT1 polypeptide (Asn352Ser). An exemplary wild-type human B4GALT1 polypeptide is assigned UniProt Accession No. P15291 (SEQ ID NO:7), and consists of 398 amino acids. A human variant B4GALT1 polypeptide comprises a serine at the position corresponding to position 352 of the full length/mature B4GALT1 polypeptide (SEQ ID NO:8), as opposed to an asparagine at the same position in the wild-type human B4GALT1 (comparing SEQ ID NO:8 to SEQ ID NO:7, respectively). In some embodiments, the isolated polypeptide comprises SEQ ID NO:8. In some embodiments, the isolated polypeptide consists of SEQ ID NO:8.

In some embodiments, the isolated polypeptides comprise or consist of an amino acid sequence that is at least about 70%, at least about 75%, at least about 80%, at least about 85%, at least about 90%, at least about 95%, at least about 96%, at least about 97%, at least about 98%, at least about 99%, or 100% identical to SEQ ID NO:8. In some embodiments, the isolated polypeptides comprise a serine at the position corresponding to position 352 of SEQ ID NO:8. In some embodiments, the isolated polypeptides comprise or consist of an amino acid sequence that is at least about 90%, at least about 95%, at least about 96%, at least about 97%, at least about 98%, at least about 99%, or 100% identical to SEQ ID NO:8. In some embodiments, the isolated polypeptides comprise a serine at the position corresponding to position 352 of SEQ ID NO:8. In some embodiments, the isolated polypeptides comprise or consist of an amino acid sequence that is at least about 90% identical to SEQ ID NO:8. In some embodiments, the isolated polypeptides comprise or consist of an amino acid sequence that is at least about 90% identical to SEQ ID NO:8 and comprise a serine at the position corresponding to position 352 of SEQ ID NO:8. In some embodiments, the isolated polypeptides comprise or consist of an amino acid sequence that is at least about 90% identical to SEQ ID NO:8, provided that the isolated polypeptides comprise a serine at the position corresponding to position 352 of SEQ ID NO:8.

In some embodiments, the isolated polypeptides comprise a serine at the position corresponding to position 352 of SEQ ID NO:8. In some embodiments, the isolated polypeptides comprise or consist of an amino acid sequence that is at least about 95% identical to SEQ ID NO:8. In some embodiments, the isolated polypeptides comprise or consist of an amino acid sequence that is at least about 95% identical to SEQ ID NO:8 and comprise a serine at the position corresponding to position 352 of SEQ ID NO:8. In some embodiments, the isolated polypeptides comprise or consist of an amino acid sequence that is at least about 95% identical to SEQ ID NO:8, provided that the isolated polypeptides comprise a serine at the position corresponding to position 352 of SEQ ID NO:8. In some embodiments, the isolated polypeptides comprise a serine at the position corresponding to position 352 of SEQ ID NO:8. In some embodiments, the isolated polypeptides comprise or consist of an amino acid sequence that is at least about 98% identical to SEQ ID NO:8. In some embodiments, the isolated polypeptides comprise or consist of an amino acid sequence that is at least about 98% identical to SEQ ID NO:8 and comprise a serine at the position corresponding to position 352 of SEQ ID NO:8. In some embodiments, the isolated polypeptides comprise or consist of an amino acid sequence that is at least about 98% identical to SEQ ID NO:8, provided that the isolated polypeptides comprise a serine at the position corresponding to position 352 of SEQ ID NO:8. In some embodiments, the isolated polypeptides comprise a serine at the position corresponding to position 352 of SEQ ID NO:8. In some embodiments, the isolated polypeptides comprise or consist of an amino acid sequence that is at least about 99% identical to SEQ ID NO:8. In some embodiments, the isolated polypeptides comprise or consist of an amino acid sequence that is at least about 99% identical to SEQ ID NO:8 and comprise a serine at the position corresponding to position 352 of SEQ ID NO:8. In some embodiments, the isolated polypeptides comprise or consist of an amino acid sequence that is at least about 99% identical to SEQ ID NO:8, provided that the isolated polypeptides comprise a serine at the position corresponding to position 352 of SEQ ID NO:8.

In some embodiments, the isolated polypeptides comprise or consist of at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, or at least about 350 contiguous amino acids of SEQ ID NO:8. In some embodiments, the isolated polypeptides also comprise a serine at a position corresponding to position 352 of SEQ ID NO:8. In some embodiments, the isolated polypeptides comprise or consist of an amino acid sequence at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, or at least about 350 contiguous amino acids of SEQ ID NO:8. In some embodiments, the isolated polypeptides also comprise a serine at a position corresponding to position 352 of SEQ ID NO:8. In some embodiments, the isolated polypeptides comprise or consist of an amino acid sequence at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, or at least about 350 contiguous amino acids of SEQ ID NO:8. In some embodiments, the isolated polypeptides also comprise a serine at a position corresponding to position 352 of SEQ ID NO:8.

In some embodiments, the isolated polypeptides comprise or consist of an amino acid sequence at least 90% identical to at least 300 contiguous amino acids of SEQ ID NO:8. In some embodiments, the isolated polypeptides comprise or consist of an amino acid sequence at least 90% identical to at least 300 contiguous amino acids of SEQ ID NO:8 and the isolated polypeptides also comprise a serine at a position corresponding to position 352 of SEQ ID NO:8. In some embodiments, the isolated polypeptides comprise or consist of an amino acid sequence at least 95% identical to at least 300 contiguous amino acids of SEQ ID NO:8. In some embodiments, the isolated polypeptides comprise or consist of an amino acid sequence at least 95% identical to at least 300 contiguous amino acids of SEQ ID NO:8 and the isolated polypeptides also comprise a serine at a position corresponding to position 352 of SEQ ID NO:8. In some embodiments, the isolated polypeptides comprise or consist of an amino acid sequence at least 98% identical to at least 300 contiguous amino acids of SEQ ID NO:8. In some embodiments, the isolated polypeptides comprise or consist of an amino acid sequence at least 98% identical to at least 300 contiguous amino acids of SEQ ID NO:8 and the isolated polypeptides also comprise a serine at a position corresponding to position 352 of SEQ ID NO:8. In some embodiments, the isolated polypeptides comprise or consist of an amino acid sequence at least 99% identical to at least 300 contiguous amino acids of SEQ ID NO:8. In some embodiments, the isolated polypeptides comprise or consist of an amino acid sequence at least 99% identical to at least 300 contiguous amino acids of SEQ ID NO:8 and the isolated polypeptides also comprise a serine at a position corresponding to position 352 of SEQ ID NO:8.

In some embodiments, the isolated polypeptides comprise or consist of at least about 15, at least about 20, at least about 25, at least about 30, at least about 35, at least about 40, at least about 45, at least about 50, at least about 60, at least about 70, at least about 80, at least about 90, or at least about 100 contiguous amino acids of SEQ ID NO:8. In some embodiments, the isolated polypeptides also comprise a serine at a position corresponding to position 352 of SEQ ID NO:8. In some embodiments, the isolated polypeptides comprise or consist of an amino acid sequence at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, or at least about 100 contiguous amino acids of SEQ ID NO:8. In some embodiments, the isolated polypeptides also comprise a serine at a position corresponding to position 352 of SEQ ID NO:8. In some embodiments, the isolated polypeptides comprise or consist of an amino acid sequence at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, or at least about 100 contiguous amino acids of SEQ ID NO:8. In some embodiments, the isolated polypeptides also comprise a serine at a position corresponding to position 352 of SEQ ID NO:8.

A representative wild-type B4GALT1 polypeptide sequence is recited in SEQ ID NO:7. A representative B4GALT1 variant polypeptide sequence is recited in SEQ ID NO:8.

The isolated polypeptides disclosed herein can comprise an amino acid sequence of a naturally occurring B4GALT1 polypeptide, or can comprise a non-naturally occurring sequence. In some embodiments, the naturally occurring sequence can differ from the non-naturally occurring sequence due to conservative amino acid substitutions. For example, the sequence can be identical with the exception of conservative amino acid substitutions.

In some embodiments, the isolated polypeptides disclosed herein are linked or fused to heterologous polypeptides or heterologous molecules or labels, numerous examples of which are disclosed elsewhere herein. For example, the proteins can be fused to a heterologous polypeptide providing increased or decreased stability. The fused domain or heterologous polypeptide can be located at the N-terminus, the C-terminus, or internally within the polypeptide. A fusion partner may, for example, assist in providing T helper epitopes (an immunological fusion partner), or may assist in expressing the protein (an expression enhancer) at higher yields than the native recombinant polypeptide. Certain fusion partners are both immunological and expression enhancing fusion partners. Other fusion partners may be selected to increase the solubility of the polypeptide or to facilitate targeting the polypeptide to desired intracellular compartments. Some fusion partners include affinity tags, which facilitate purification of the polypeptide.

In some embodiments, a fusion protein is directly fused to the heterologous molecule or is linked to the heterologous molecule via a linker, such as a peptide linker. Suitable peptide linker sequences may be chosen, for example, based on the following factors: 1) the ability to adopt a flexible extended conformation; 2) the resistance to adopt a secondary structure that could interact with functional epitopes on the first and second polypeptides; and 3) the lack of hydrophobic or charged residues that might react with the polypeptide functional epitopes. For example, peptide linker sequences may contain Gly, Asn and Ser residues. Other near neutral amino acids, such as Thr and Ala may also be used in the linker sequence. Amino acid sequences which may be usefully employed as linkers include those disclosed in, for example, Maratea et al., *Gene*, 1985, 40, 39-46; Murphy et al., *Proc. Natl. Acad. Sci. USA*, 1986, 83, 8258-8262; and U.S. Pat. Nos. 4,935,233 and 4,751,180. A linker sequence may generally be, for example, from 1 to about 50 amino acids in length. Linker sequences are generally not required when the first and second polypeptides have non-essential N-terminal amino acid regions that can be used to separate the functional domains and prevent steric interference.

In some embodiments, the polypeptides are operably linked to a cell-penetrating domain. For example, the cell-penetrating domain can be derived from the HIV-1 TAT protein, the TLM cell-penetrating motif from human hepatitis B virus, MPG, Pep-1, VP22, a cell-penetrating peptide from Herpes simplex virus, or a polyarginine peptide sequence. See, e.g., WO 2014/089290. The cell-penetrating domain can be located at the N-terminus, the C-terminus, or anywhere within the protein.

In some embodiments, the polypeptides are operably linked to a heterologous polypeptide for ease of tracking or purification, such as a fluorescent protein, a purification tag, or an epitope tag. Examples of fluorescent proteins include, but are not limited to, green fluorescent proteins (e.g., GFP, GFP-2, tagGFP, turboGFP, eGFP, Emerald, Azami Green, Monomeric Azami Green, CopGFP, AceGFP, ZsGreenI), yellow fluorescent proteins (e.g., YFP, eYFP, Citrine, Venus, YPet, PhiYFP, ZsYellowI), blue fluorescent proteins (e.g. eBFP, eBFP2, Azurite, mKalamaI, GFPuv, Sapphire, T-sapphire), cyan fluorescent proteins (e.g. eCFP, Cerulean, CyPet, AmCyanI, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRedI, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include, but are not limited to, glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin. In some embodiments, the heterologous molecule is an immunoglobulin Fc domain, a peptide tag, a transduction domain, poly(ethylene glycol), polysialic acid, or glycolic acid.

In some embodiments, the isolated polypeptides comprise non-natural or modified amino acids or peptide analogs. For example, there are numerous D-amino acids or amino acids which have a different functional substituent than the naturally occurring amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site-specific way.

In some embodiments, the isolated polypeptides are peptide mimetics, which can be produced to resemble peptides, but which are not connected via a natural peptide linkage. For example, linkages for amino acids or amino acid analogs include, but are not limited to, —$CH_2NH$—, —$CH_2S$—, —$CH_2$—, —CH=CH— (cis and trans), —$COCH_2$—, —$CH(OH)CH_2$—, and —$CHH_2SO$—. Peptide analogs can have more than one atom between the bond atoms, such as b-alanine, gaminobutyric acid, and the like. Amino acid analogs and peptide analogs often have enhanced or desirable properties, such as, more economical production, greater chemical stability, enhanced pharmacological properties (half-life, absorption, potency, efficacy, and so forth), altered specificity (e.g., a broad-spectrum of biological activities), reduced antigenicity, and others desirable properties.

In some embodiments, the isolated polypeptides comprise D-amino acids, which can be used to generate more stable peptides because D amino acids are not recognized by peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations (see, e.g., Rizo and Gierasch, *Ann. Rev. Biochem.*, 1992, 61, 387).

The present disclosure also provides nucleic acid molecules encoding any of the polypeptides disclosed herein. This includes all degenerate sequences related to a specific polypeptide sequence (i.e., all nucleic acids having a sequence that encodes one particular polypeptide sequence as well as all nucleic acids, including degenerate nucleic acids, encoding the disclosed variants and derivatives of the protein sequences). Thus, while each particular nucleic acid sequence may not be written out herein, each and every sequence is in fact disclosed and described herein through the disclosed polypeptide sequences.

The present disclosure also provides compositions comprising any one or more of the nucleic acid molecules and/or any one or more of the polypeptides disclosed herein. In some embodiments, the compositions comprise a carrier. In some embodiments, the carrier increases the stability of the nucleic acid molecule and/or polypeptide (e.g., prolonging the period under given conditions of storage (e.g., −20° C., 4° C., or ambient temperature) for which degradation products remain below a threshold, such as below 0.5% by weight of the starting nucleic acid or protein; or increasing the stability in vivo). Examples of carriers include, but are not limited to, poly(lactic acid) (PLA) microspheres, poly (D,L-lactic-coglycolic-acid) (PLGA) microspheres, liposomes, micelles, inverse micelles, lipid cochleates, and lipid microtubules.

The present disclosure also provides methods of producing any of the B4GALT1 polypeptides or fragments thereof disclosed herein. Such B4GALT1 polypeptides or fragments thereof can be produced by any suitable method. For example, B4GALT1 polypeptides or fragments thereof can be produced from host cells comprising nucleic acid molecules (e.g., recombinant expression vectors) encoding such B4GALT1 polypeptides or fragments thereof. Such methods can comprise culturing a host cell comprising a nucleic acid molecule (e.g., recombinant expression vector) encoding an B4GALT1 polypeptide or fragment thereof under conditions sufficient to produce the B4GALT1 polypeptide or fragment thereof, thereby producing the B4GALT1 polypeptide or fragment thereof. The nucleic acid can be operably linked to a promoter active in the host cell, and the culturing can be carried out under conditions whereby the nucleic acid is expressed. Such methods can further comprise recovering the expressed B4GALT1 polypeptide or fragment thereof. The recovering can further comprise purifying the B4GALT1 polypeptide or fragment thereof.

Examples of suitable systems for protein expression include host cells such as, for example: bacterial cell expression systems (e.g., *Escherichia coli, Lactococcus lactis*), yeast cell expression systems (e.g., *Saccharomyces cerevisiae, Pichia pastoris*), insect cell expression systems (e.g., baculovirus-mediated protein expression), and mammalian cell expression systems.

Examples of nucleic acid molecules encoding B4GALT1 polypeptides or fragments thereof are disclosed in more detail elsewhere herein. In some embodiments, the nucleic acid molecules are codon optimized for expression in the host cell. In some embodiments, the nucleic acid molecules are operably linked to a promoter active in the host cell. The promoter can be a heterologous promoter (i.e., a promoter than is not a naturally occurring B4GALT1 promoter). Examples of promoters suitable for *Escherichia coli* include, but are not limited to, arabinose, lac, tac, and T7 promoters. Examples of promoters suitable for *Lactococcus lactis* include, but are not limited to, P170 and nisin promoters. Examples of promoters suitable for *Saccharomyces cerevisiae* include, but are not limited to, constitutive promoters such as alcohol dehydrogenase (ADHI) or enolase (ENO) promoters or inducible promoters such as PHO, CUP1, GAL1, and G10. Examples of promoters suitable for *Pichia pastoris* include, but are not limited to, the alcohol oxidase I (AOX I) promoter, the glyceraldehyde 3 phosphate dehydrogenase (GAP) promoter, and the glutathione dependent formaldehyde dehydrogenase (FLDI) promoter. An example of a promoter suitable for a baculovirus-mediated system is the late viral strong polyhedrin promoter.

In some embodiments, the nucleic acid molecules encode a tag in frame with the B4GALT1 polypeptide or fragment thereof to facilitate protein purification. Examples of tags are disclosed elsewhere herein. Such tags can, for example, bind to a partner ligand (e.g., immobilized on a resin) such that the tagged protein can be isolated from all other proteins (e.g., host cell proteins). Affinity chromatography, high performance liquid chromatography (HPLC), and size exclusion chromatography (SEC) are examples of methods that can be used to improve the purity of the expressed protein.

Other methods can also be used to produce B4GALT1 polypeptides or fragments thereof. For example, two or more peptides or polypeptides can be linked together by protein chemistry techniques. For example, peptides or polypeptides can be chemically synthesized using either Fmoc (9-fluorenylmethyloxycarbonyl) or Boc (tert-butyloxycarbonyl) chemistry. Such peptides or polypeptides can be synthesized by standard chemical reactions. For example, a peptide or polypeptide can be synthesized and not cleaved from its synthesis resin, whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively. Alternately, the peptide or polypeptide can be independently synthesized in vivo as described herein. Once isolated, these independent peptides or polypeptides may be linked to form a peptide or fragment thereof via similar peptide condensation reactions.

In some embodiments, enzymatic ligation of cloned or synthetic peptide segments allow relatively short peptide fragments to be joined to produce larger peptide fragments, polypeptides, or whole protein domains (Abrahmsen et al., *Biochemistry,* 1991, 30, 4151). Alternately, native chemical ligation of synthetic peptides can be utilized to synthetically construct large peptides or polypeptides from shorter peptide fragments. This method can consist of a two-step chemical reaction (see, Dawson et al., *Science,* 1994, 266, 776-779). The first step can be the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate can undergo spontaneous, rapid intramolecular reaction to form a native peptide bond at the ligation site.

In some embodiments, unprotected peptide segments can be chemically linked where the bond formed between the peptide segments as a result of the chemical ligation is an unnatural (non-peptide) bond (see, Schnolzer et al., *Science,* 1992, 256, 221).

The present disclosure also provides cells (e.g., recombinant host cells) comprising any one or more of the nucleic acid molecules and/or any one or more of the polypeptides disclosed herein. The cells can be in vitro, ex vivo, or in vivo. Nucleic acid molecules can be linked to a promoter and other regulatory sequences so they are expressed to produce an encoded protein.

In some embodiments, the cell is a totipotent cell or a pluripotent cell (e.g., an embryonic stem (ES) cell such as a rodent ES cell, a mouse ES cell, or a rat ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

In some embodiments, the cell is a primary somatic cell, or a cell that is not a primary somatic cell. Somatic cells can include any cell that is not a gamete, germ cell, gametocyte, or undifferentiated stem cell. In some embodiments, the cell can also be a primary cell. Primary cells include cells or cultures of cells that have been isolated directly from an organism, organ, or tissue. Primary cells include cells that are neither transformed nor immortal. Primary cells include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

In some embodiments, the cells may normally not proliferate indefinitely but, due to mutation or alteration, have evaded normal cellular senescence and instead can keep undergoing division. Such mutations or alterations can occur naturally or be intentionally induced. Examples of immortalized cells include, but are not limited to, Chinese hamster ovary (CHO) cells, human embryonic kidney cells (e.g., HEK 293 cells), and mouse embryonic fibroblast cells (e.g., 3T3 cells). Numerous types of immortalized cells are well known. Immortalized or primary cells include cells that are typically used for culturing or for expressing recombinant genes or proteins. In some embodiments, the cell is a differentiated cell, such as a liver cell (e.g., a human liver cell).

The cell can be from any source. For example, the cell can be a eukaryotic cell, an animal cell, a plant cell, or a fungal (e.g., yeast) cell. Such cells can be fish cells or bird cells, or such cells can be mammalian cells, such as human cells, non-human mammalian cells, rodent cells, mouse cells or rat cells. Mammals include, but are not limited to, humans, non-human primates, monkeys, apes, cats dogs, horses, bulls, deer, bison, sheep, rodents (e.g., mice, rats, hamsters, guinea pigs), livestock (e.g., bovine species such as cows, steer, etc.; ovine species such as sheep, goats, etc.; and porcine species such as pigs and boars). Birds include, but are not limited to, chickens, turkeys, ostrich, geese, ducks, etc. Domesticated animals and agricultural animals are also included. The term "non-human animal" excludes humans.

The present disclosure also provides methods for detecting the presence of a B4GALT1 variant gene, mRNA, cDNA, and/or polypeptide in a biological sample from a subject human. It is understood that gene sequences within a population and mRNAs and proteins encoded by such genes can vary due to polymorphisms such as single-nucleotide polymorphisms. The sequences provided herein for the B4GALT1 gene, mRNA, cDNA, and polypeptide are only exemplary sequences. Other sequences for the B4GALT1 gene, mRNA, cDNA, and polypeptide are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting a variant B4GALT1 nucleic acid molecule, preliminary processing designed to isolate or enrich the sample for the genomic DNA can be employed. A variety of known techniques may be used for this purpose. When detecting the level of B4GALT1 mRNA, different techniques can be used enrich the biological sample with mRNA. Various methods to detect the presence or level of a mRNA or the presence of a particular variant genomic DNA locus can be used.

In some embodiments, the disclosure provides methods of detecting the presence or absence of a variant B4GALT1 nucleic acid molecule comprising sequencing at least a portion of a nucleic acid in a biological sample to determine whether the nucleic acid comprises nucleotides 53757 to 53577 of SEQ ID NO:2 at positions that correspond to positions 53757 to 53577 of SEQ ID NO:2.

In some embodiments, the disclosure provides methods of detecting the presence or absence of a variant B4GALT1 nucleic acid molecule comprising sequencing at least a portion of a nucleic acid in a biological sample to determine whether the nucleic acid comprises nucleotides 1243 to 1245 of SEQ ID NO:4 at positions that correspond to positions 1243 to 1245 of SEQ ID NO:4.

In some embodiments, the disclosure provides methods of detecting the presence or absence of a variant B4GALT1 nucleic acid molecule comprising sequencing at least a portion of a nucleic acid in a biological sample to determine whether the nucleic acid comprises nucleotides 1054 to 1056 of SEQ ID NO:6 at positions that correspond to positions 1054 to 1056 of SEQ ID NO:6.

In some embodiments, the methods of detecting the presence or absence of a variant B4GALT1 nucleic acid molecule (e.g., gene, mRNA, or cDNA) in a human subject, comprise: performing an assay on a biological sample from the human subject that determines whether a nucleic acid molecule in the biological sample comprises a nucleic acid sequence that encodes a serine at position 352 of SEQ ID NO:8. In some embodiments, the biological sample comprises a cell or cell lysate. Such methods can comprise, for example, obtaining a biological sample from the subject comprising a B4GALT1 gene, mRNA, or cDNA and performing an assay on the biological sample that determines that a position of the B4GALT1 gene, mRNA, or cDNA corresponding to positions 53757 to 53577 of SEQ ID NO:2 (gene), positions 1243 to 1245 of SEQ ID NO:4 (mRNA), or positions 1054 to 1056 of SEQ ID NO:6 (cDNA) encodes a serine instead of an asparagine at a position corresponding to position 352 of the variant B4GALT1 polypeptide. Such assays can comprise, for example determining the identity of these positions of the particular B4GALT1 nucleic acid molecule.

In some embodiments, the assay comprises: sequencing a portion of the B4GALT1 genomic sequence of a nucleic acid molecule in the biological sample from the human subject, wherein the portion sequenced includes positions corresponding to positions 53575 to 53577 of SEQ ID NO:2; sequencing a portion of the B4GALT1 mRNA sequence of a nucleic acid molecule in the biological sample from the human subject, wherein the portion sequenced includes positions corresponding to positions 1243 to 1245 of SEQ ID NO:4; or sequencing a portion of the B4GALT1 cDNA sequence of a nucleic acid molecule in the biological sample from the human subject, wherein the portion sequenced includes positions corresponding to positions 1054 to 1056 of SEQ ID NO:6.

In some embodiments, the assay comprises: a) contacting the biological sample with a primer hybridizing to: i) a portion of the B4GALT1 genomic sequence that is proximate to a position of the B4GALT1 genomic sequence corresponding to positions 53575 to 53577 of SEQ ID NO:2; ii) a portion of the B4GALT1 mRNA sequence that is proximate to a position of the B4GALT1 mRNA corresponding to positions 1243 to 1245 of SEQ ID NO:4; or iii) a portion of the B4GALT1 cDNA sequence that is proximate to a position of the B4GALT1 cDNA corresponding to positions 1054 to 1056 of SEQ ID NO:6; b) extending the primer at least through: i) the position of the B4GALT1 genomic sequence corresponding to positions 53575 to 53577; ii) the position of the B4GALT1 mRNA corresponding to positions 1243 to 1245; or iii) the position of the B4GALT1 cDNA corresponding to positions 1054 to 1056; and c) determining whether the extension product of the primer comprises nucleotides at positions: i) corresponding to positions 53575 to 53577 of the B4GALT1 genomic sequence; ii) corresponding to positions 1243 to 1245 of the B4GALT1 mRNA; or iii) corresponding to positions 1054 to 1056 of the B4GALT1 cDNA; that encode a serine at position 352 of SEQ ID NO:8. In some embodiments, only B4GALT1 genomic DNA is analyzed. In some embodiments, only B4GALT1 mRNA is analyzed. In some embodiments, only B4GALT1 cDNA is analyzed.

In some embodiments, the assay comprises contacting the biological sample with a primer or probe that specifically hybridizes to a variant B4GALT1 genomic sequence, mRNA sequence, or cDNA sequence and not the corresponding wild-type B4GALT1 sequence under stringent conditions, and determining whether hybridization has occurred.

In some embodiments, the assays described above comprise RNA sequencing (RNA-Seq). In some embodiments, the assays also comprise reverse transcription polymerase chain reaction (RT-PCR).

In some embodiments, the methods utilize probes and primers of sufficient nucleotide length to bind to the target nucleic acid sequence and specifically detect and/or identify a polynucleotide comprising a variant B4GALT1 gene, mRNA, or cDNA. The hybridization conditions or reaction conditions can be determined by the operator to achieve this result. This length may be any length that is sufficient to be useful in a detection method of choice. Generally, for example, about 8, about 11, about 14, about 16, about 18, about 20, about 22, about 24, about 26, about 28, about 30, about 40, about 50, about 75, about 100, about 200, about 300, about 400, about 500, about 600, or about 700 nucleotides, or more, or from about 11 to about 20, from about 20 to about 30, from about 30 to about 40, from about 40 to about 50, from about 50 to about 100, from about 100 to about 200, from about 200 to about 300, from about 300 to about 400, from about 400 to about 500, from about 500 to about 600, from about 600 to about 700, or from about 700 to about 800, or more nucleotides in length are used. Such probes and primers can hybridize specifically to a target sequence under high stringency hybridization conditions.

Probes and primers may have complete nucleic acid sequence identity of contiguous nucleotides with the target sequence, although probes differing from the target nucleic acid sequence and that retain the ability to specifically detect and/or identify a target nucleic acid sequence may be designed by conventional methods. Accordingly, probes and primers can share about 80%, about 85%, about 90%, about 91%, about 92%, about 93%, about 94%, about 95%, about 96%, about 97%, about 98%, about 99%, or 100% sequence identity or complementarity to the target nucleic acid molecule.

In some embodiments, specific primers can be used to amplify the variant B4GALT1 locus and/or B4GALT1 variant mRNA or cDNA to produce an amplicon that can be used as a specific probe or can itself be detected for identifying the variant B4GALT1 locus or for determining the level of specific B4GALT1 mRNA or cDNA in a biological sample. The B4GALT1 variant locus can be used to denote a genomic nucleic acid sequence including a position corresponding to positions 53575 to 53577 in SEQ ID NO:2. When the probe is hybridized with a nucleic acid molecule in a biological sample under conditions that allow for the binding of the probe to the nucleic acid molecule, this binding can be detected and allow for an indication of the presence of the variant B4GALT1 locus or the presence or the level of variant B4GALT1 mRNA or cDNA in the biological sample. Such identification of a bound probe has been described. The specific probe may comprise a sequence of at least about 80%, from about 80% to about 85%, from about 85% to about 90%, from about 90% to about 95%, and from about 95% to about 100% identical (or complementary) to a specific region of a variant B4GALT1 gene. The specific probe may comprise a sequence of at least about 80%, from about 80% to about 85%, from about 85% to about 90%, from about 90% to about 95%, and from about 95% to about 100% identical (or complementary) to a specific region of a variant B4GALT1 mRNA. The specific probe may comprise a sequence of at least about 80%, from about 80% to about 85%, from about 85% to about 90%, from about 90% to about 95%, and from about 95% to about 100% identical (or complementary) to a specific region of a variant B4GALT1 cDNA.

In some embodiments, to determine whether the nucleic acid complement of a biological sample comprises the serine encoding nucleotides at positions 53575 to 53577 in the variant B4GALT1 gene locus (SEQ ID NO:2), the biological sample may be subjected to a nucleic acid amplification method using a primer pair that includes a first primer derived from the 5' flanking sequence adjacent to positions 53575 to 53577 and a second primer derived from the 3' flanking sequence adjacent to positions 53575 to 53577 to produce an amplicon that is diagnostic for the presence of the SNP at positions 53575 to 53577 in the variant B4GALT1 gene locus (SEQ ID NO:2). In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions 53575 to 53577 and at least 1, 2, 3, 4, 5, 6, 7, 8, 9, 10, or more nucleotides on each side of positions 53575 to 53577. Similar amplicons can be generated from the mRNA and/or cDNA sequences.

Representative methods for preparing and using probes and primers are described, for example, in *Molecular Cloning: A Laboratory Manual,* 2nd Ed., Vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990). PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

As described in further detail below, any conventional nucleic acid hybridization or amplification or sequencing method can be used to specifically detect the presence of the variant B4GALT1 gene locus and/or the level of variant B4GALT1 mRNA or cDNA. In some embodiments, the nucleic acid molecule can be used either as a primer to amplify a region of the B4GALT1 nucleic acid or the nucleic acid molecule can be used as a probe that hybridizes under stringent conditions to a nucleic acid molecule comprising the variant B4GALT1 gene locus or a nucleic acid molecule comprising a variant B4GALT1 mRNA or cDNA.

A variety of nucleic acid techniques are known, including, for example, nucleic acid sequencing, nucleic acid hybridization, and nucleic acid amplification. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization). In some methods, a target nucleic acid may be amplified prior to or simultaneously with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

Any method can be used for detecting either the non-amplified or amplified polynucleotides including, for example, Hybridization Protection Assay (HPA), quantitative evaluation of the amplification process in real-time, and determining the quantity of target sequence initially present in a sample, but which is not based on a real-time amplification.

Also provided are methods for identifying nucleic acids which do not necessarily require sequence amplification and are based on, for example, the known methods of Southern (DNA:DNA) blot hybridizations, in situ hybridization (ISH), and fluorescence in situ hybridization (FISH) of chromosomal material, using appropriate probes. Southern blotting can be used to detect specific nucleic acid sequences. In such methods, nucleic acid that is extracted from a sample is fragmented, electrophoretically separated on a matrix gel, and transferred to a membrane filter. The filter bound nucleic acid is subject to hybridization with a labeled probe complementary to the sequence of interest. Hybridized probe bound to the filter is detected.

In hybridization techniques, stringent conditions can be employed such that a probe or primer will specifically hybridize to its target. In some embodiments, a polynucleotide primer or probe under stringent conditions will hybridize to its target sequence (e.g., the variant B4GALT1 gene locus, mRNA, or cDNA) to a detectably greater degree than to other sequences (e.g., the corresponding wild-type B4GALT1 locus, mRNA, or cDNA), such as at least 2-fold over background or 10-fold over background. Stringent conditions are sequence-dependent and will be different in different circumstances. By controlling the stringency of the hybridization and/or washing conditions, target sequences that are 100% complementary to the probe can be identified (homologous probing). Alternately, stringency conditions can be adjusted to allow some mismatching in sequences so that lower degrees of identity are detected (heterologous probing). Generally, a probe is less than about 1000 nucleotides in length or less than about 500 nucleotides in length.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 1984, 138, 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1° C., 2° C., 3° C., or 4° C. lower than the thermal melting point ($T_m$); moderately stringent conditions can utilize a hybridization and/or wash at 6° C., 7° C., 8° C., 9° C., or 10° C. lower than the thermal melting point ($T_m$); low stringency conditions can utilize a hybridization and/or wash at 11° C., 12° C., 13° C., 14° C., 15° C., or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used.

Also provided are methods for detecting the presence or levels of variant B4GALT1 polypeptide in a biological sample, including, for example, protein sequencing and immunoassays. In some embodiments, the method of detecting the presence of B4GALT1 Asn352Ser in a human subject, comprises performing an assay on a biological sample from the human subject that determines the presence of B4GALT1 Asn352Ser in the biological sample.

Illustrative non-limiting examples of protein sequencing techniques include, but are not limited to, mass spectrometry and Edman degradation. Illustrative examples of immunoassays include, but are not limited to, immunoprecipitation, Western blot, immunohistochemistry, ELISA, immunocytochemistry, flow cytometry, and immuno-PCR. Polyclonal or monoclonal antibodies detectably labeled using various known techniques (e.g., calorimetric, fluorescent, chemiluminescent, or radioactive) are suitable for use in the immunoassays.

The present disclosure also provides methods for determining a subject's susceptibility to developing a cardiovascular condition or risk of developing a cardiovascular condition. The subject can be any organism, including, for example, a human, a non-human mammal, a rodent, a mouse, or a rat. In some embodiments, the methods comprise detecting the presence of the variant B4GALT1 genomic DNA, mRNA, or cDNA in a biological sample from the subject. It is understood that gene sequences within a population and mRNAs encoded by such genes can vary due to polymorphisms such as SNPs. The sequences provided herein for the B4GALT1 gene, mRNA, cDNA, and polypeptide are only exemplary sequences and other such sequences are also possible.

Non-limiting examples of a cardiovascular condition include an elevated level of one or more serum lipids. The serum lipids comprise one or more of cholesterol, LDL, HDL, triglycerides, HDL-cholesterol, and non-HDL cholesterol, or any subfraction thereof (e.g., HDL2, HDL2a, HDL2b, HDL2c, HDL3, HDL3a, HDL3b, HDL3c, HDL3d, LDL1, LDL2, LDL3, lipoprotein A, Lpa1, Lpa1, Lpa3, Lpa4, or Lpa5). A cardiovascular condition may comprise elevated levels of coronary artery calcification. A cardiovascular condition may comprise Type IId glycosylation (CDG-IId). A cardiovascular condition may comprise elevated levels of pericardial fat. A cardiovascular condition may also comprise coronary artery disease (CAD), myocardial infarction (MI), peripheral artery disease (PAD), stroke, pulmonary embolism, deep vein thrombosis (DVT), and bleeding diatheses and coagulopathies. A cardiovascular condition may comprise an atherothrombotic condition. The atherothrombotic condition may comprise elevated levels of fibrinogen. The atherothrombotic condition may comprises a fibrinogen-mediated blood clot. A cardiovascular condition may comprise elevated levels of fibrinogen. A cardiovascular condition may comprise a fibrinogen-mediated blood clot. A cardiovascular condition may comprise a blood clot formed from the involvement of fibrinogen activity. A fibrinogen-mediated blood clot or blood clot formed from the involvement of fibrinogen activity may be in any vein or artery in the body.

In some embodiments, the methods of determining a human subject's susceptibility to developing a cardiovascular condition, comprise: a) performing an assay on a biological sample from the human subject that determines whether a nucleic acid molecule in the biological sample comprises a nucleic acid sequence that encodes a serine at the position corresponding to position 352 of the full length/mature variant B4GALT1 Asn352Ser polypeptide; and b) classifying the human subject as being at decreased risk for developing the cardiovascular condition if a nucleic acid molecule comprising a nucleic acid sequence that encodes a serine at position 352 of the full length/mature variant B4GALT1 Asn352Ser polypeptide is detected in the biological sample, or classifying the human subject as being at increased risk for developing the cardiovascular condition if a nucleic acid molecule comprising a nucleic acid sequence that encodes a serine at position 352 of the full length/mature variant B4GALT1 Asn352Ser polypeptide is not detected in the biological sample. In some embodiments, the variant B4GALT1 Asn352Ser polypeptide comprises SEQ ID NO:8. In some embodiments, the nucleic acid molecule in the biological sample is genomic DNA, mRNA, or cDNA.

In some embodiments, the disclosure provides methods of determining a human subject's susceptibility to developing a cardiovascular condition, comprising: a) performing an assay on a biological sample from the human subject that determines whether a nucleic acid molecule in the biological sample comprises nucleotides 53757 to 53577 of SEQ ID NO:2 at positions that correspond to positions 53757 to 53577 of SEQ ID NO:2; and b) classifying the human subject as being at decreased risk for developing the cardiovascular condition if a nucleic acid molecule comprising nucleotides 53757 to 53577 of SEQ ID NO:2 at positions that correspond to positions 53757 to 53577 of SEQ ID NO:2 is detected in the biological sample, or classifying the human subject as being at increased risk for developing the cardiovascular condition if a nucleic acid molecule comprising nucleotides 53757 to 53577 of SEQ ID NO:2 at positions that correspond to positions 53757 to 53577 of SEQ ID NO:2 is not detected in the biological sample.

In some embodiments, the disclosure provides methods of determining a human subject's susceptibility to developing a cardiovascular condition, comprising: a) performing an assay on a biological sample from the human subject that determines whether a nucleic acid molecule in the biological sample comprises nucleotides 1243 to 1245 of SEQ ID NO:4 at positions that correspond to positions 1243 to 1245 of SEQ ID NO:4; and b) classifying the human subject as being at decreased risk for developing the cardiovascular condition if a nucleic acid molecule comprising nucleotides 1243 to 1245 of SEQ ID NO:4 at positions that correspond to positions 1243 to 1245 of SEQ ID NO:4 is detected in the biological sample, or classifying the human subject as being at increased risk for developing the cardiovascular condition if a nucleic acid molecule comprising nucleotides 1243 to 1245 of SEQ ID NO:4 at positions that correspond to positions 1243 to 1245 of SEQ ID NO:4 is not detected in the biological sample.

In some embodiments, the disclosure provides methods of determining a human subject's susceptibility to developing a cardiovascular condition, comprising: a) performing an assay on a biological sample from the human subject that determines whether a nucleic acid molecule in the biological sample comprises nucleotides 1054 to 1056 of SEQ ID NO:6 at positions that correspond to positions 1054 to 1056 of SEQ ID NO:6; and b) classifying the human subject as being at decreased risk for developing the cardiovascular condition if a nucleic acid molecule comprising nucleotides 1054 to 1056 of SEQ ID NO:6 at positions that correspond to positions 1054 to 1056 of SEQ ID NO:6 is detected in the biological sample, or classifying the human subject as being at increased risk for developing the cardiovascular condition if a nucleic acid molecule comprising nucleotides 1054 to 1056 of SEQ ID NO:6 at positions that correspond to positions 1054 to 1056 of SEQ ID NO:6 is not detected in the biological sample.

In some embodiments, the methods comprise detecting the presence of a variant B4GALT1 genomic DNA in a biological sample. In some embodiments, such methods comprise determining a subject's susceptibility to developing a cardiovascular condition or risk of developing a cardiovascular condition, comprising: a) obtaining a biological sample from the subject that comprises genomic DNA; b) performing an assay on the genomic DNA that determines the identity of the nucleotides in the DNA occupying positions corresponding to positions 53575 to 53577 of the variant B4GALT1 gene (see, for example, SEQ ID NO:2); and c) classifying the subject as being at decreased risk for developing the cardiovascular condition if the positions in the genomic DNA corresponding to positions 53575 to 53577 of the variant B4GALT1 gene encodes a serine rather than an asparagine. Alternately, the subject can be classified as being at increased risk for developing the cardiovascular condition if the positions in the genomic DNA corresponding to positions 53575 to 53577 of the variant B4GALT1 gene do not encode a serine rather than an asparagine.

In some embodiments, such methods comprise diagnosing a subject with cardiovascular condition, comprising: a) obtaining a biological sample from the subject that comprises genomic DNA; b) performing an assay on the genomic DNA that determines the identity of the nucleotides in the DNA occupying positions corresponding to positions 53575 to 53577 of the variant B4GALT1 gene (see, for example, SEQ ID NO:2); and c) classifying the subject as having a cardiovascular condition if the positions in the genomic DNA corresponding to positions 53575 to 53577 of the variant B4GALT1 gene encodes a serine rather than an asparagine. Alternately, the subject can be classified as not having a cardiovascular condition if the positions in the genomic DNA corresponding to positions 53575 to 53577 of the variant B4GALT1 gene do not encode a serine rather than an asparagine.

In some embodiments, the methods comprise detecting the presence of a variant B4GALT1 mRNA in a biological sample. In some embodiments, such methods comprise determining a subject's susceptibility to developing a cardiovascular condition or risk of developing a cardiovascular condition, comprising: a) obtaining a biological sample from the subject that comprises mRNA; b) performing an assay on the mRNA that determines the identity of the nucleotides in the mRNA occupying positions corresponding to positions 1243 to 1245 of the variant B4GALT1 mRNA (see, for example, SEQ ID NO:4); and c) classifying the subject as being at decreased risk for developing the cardiovascular condition if the positions in the mRNA corresponding to positions 1243 to 1245 of the variant B4GALT1 mRNA encodes a serine rather than an asparagine. Alternately, the subject can be classified as being at increased risk for developing the cardiovascular condition if the positions in the mRNA corresponding to positions 1243 to 1245 of the variant B4GALT1 mRNA do not encode a serine rather than an asparagine.

In some embodiments, such methods comprise diagnosing a subject with cardiovascular condition, comprising: a) obtaining a biological sample from the subject that comprises mRNA; b) performing an assay on the mRNA that determines the identity of the nucleotides in the mRNA occupying positions corresponding to positions 1243 to 1245 of the variant B4GALT1 mRNA (see, for example, SEQ ID NO:4); and c) classifying the subject as having a cardiovascular condition if the positions in the mRNA corresponding to positions 1243 to 1245 of the variant B4GALT1 mRNA encodes a serine rather than an asparagine. Alternately, the subject can be classified as not having a cardiovascular condition if the positions in the mRNA corresponding to positions 1243 to 1245 of the variant B4GALT1 mRNA do not encode a serine rather than an asparagine.

In some embodiments, the methods comprise detecting the presence of a variant B4GALT1 cDNA in a biological sample. In some embodiments, such methods comprise determining a subject's susceptibility to developing a cardiovascular condition or risk of developing a cardiovascular condition, comprising: a) obtaining a biological sample from the subject that comprises cDNA; b) performing an assay on the cDNA that determines the identity of the nucleotides in the cDNA occupying positions corresponding to positions 1054 to 1056 of the variant B4GALT1 cDNA (see, for example, SEQ ID NO:6); and c) classifying the subject as being at decreased risk for developing the cardiovascular condition if the positions in the cDNA corresponding to positions 1054 to 1056 of the variant B4GALT1 cDNA encodes a serine rather than an asparagine. Alternately, the subject can be classified as being at increased risk for developing the cardiovascular condition if the positions in the cDNA corresponding to positions 1054 to 1056 of the variant B4GALT1 cDNA do not encode a serine rather than an asparagine.

In some embodiments, such methods comprise diagnosing a subject with cardiovascular condition, comprising: a) obtaining a biological sample from the subject that comprises cDNA; b) performing an assay on the cDNA that determines the identity of the nucleotides in the cDNA occupying positions corresponding to positions 1054 to 1056 of the variant B4GALT1 cDNA (see, for example, SEQ ID NO:6); and c) classifying the subject as having a cardiovascular condition if the positions in the cDNA corresponding to positions 1054 to 1056 of the variant B4GALT1 cDNA encodes a serine rather than an asparagine. Alternately, the subject can be classified as not having a cardiovascular condition if the positions in the cDNA corresponding to positions 1054 to 1056 of the variant B4GALT1 cDNA do not encode a serine rather than an asparagine.

In some embodiments, the assay comprises: sequencing a portion of the B4GALT1 genomic sequence of a nucleic acid molecule in the biological sample from the human subject, wherein the portion sequenced includes positions corresponding to positions 53575 to 53577 of SEQ ID NO:2; sequencing a portion of the B4GALT1 mRNA sequence of a nucleic acid molecule in the biological sample from the human subject, wherein the portion sequenced includes positions corresponding to positions 1243 to 1245 of SEQ ID NO:4; or sequencing a portion of the B4GALT1 cDNA sequence of a nucleic acid molecule in the biological sample from the human subject, wherein the portion sequenced includes positions corresponding to positions 1054 to 1056 of SEQ ID NO:6.

In some embodiments, the assay comprises: a) contacting the biological sample with a primer hybridizing to: i) a portion of the B4GALT1 genomic sequence that is proximate to a position of the B4GALT1 genomic sequence corresponding to positions 53575 to 53577 of SEQ ID NO:2; ii) a portion of the B4GALT1 mRNA sequence that is proximate to a position of the B4GALT1 mRNA corresponding to positions 1243 to 1245 of SEQ ID NO:4; or iii) a portion of the B4GALT1 cDNA sequence that is proximate to a position of the B4GALT1 cDNA corresponding to positions 1054 to 1056 of SEQ ID NO:6; b) extending the primer at least through: i) the position of the B4GALT1 genomic sequence corresponding to positions 53575 to 53577; ii) the position of the B4GALT1 mRNA corresponding to positions 1243 to 1245; or iii) the position of the B4GALT1 cDNA corresponding to positions 1054 to 1056; and c) determining the whether the extension product of the primer comprises nucleotides at positions: i) corresponding to positions 53575 to 53577 of the B4GALT1 genomic sequence; ii) corresponding to positions 1243 to 1245 of the B4GALT1 mRNA; or iii) corresponding to positions 1054 to 1056 of the B4GALT1 cDNA; that encode a serine at position 352 of SEQ ID NO:8.

In some embodiments, the assay comprises contacting the biological sample with a primer or probe that specifically hybridizes to the variant B4GALT1 genomic sequence, mRNA sequence, or cDNA sequence and not the corresponding wild-type B4GALT1 sequence under stringent conditions, and determining whether hybridization has occurred. In some embodiments, the primer or probe specifically hybridizes to positions within the genomic DNA in the biological sample that corresponds to positions 53575 to 53577 of SEQ ID NO:2. In some embodiments, the primer or probe specifically hybridizes to positions within the mRNA in the biological sample that corresponds to positions 1243 to 1245 of SEQ ID NO:4. In some embodiments, the primer or probe specifically hybridizes to positions within the cDNA in the biological sample that corresponds to positions 1054 to 1056 of SEQ ID NO:6.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by determination of the presence and quantity of variant mRNA or cDNA in the biological sample.

The present disclosure also provides methods of determining a human subject's susceptibility to developing a cardiovascular condition or diagnosing a subject with cardiovascular condition, comprising: a) performing an assay on a biological sample from the human subject that determines whether a B4GALT1 polypeptide in the biological sample comprises a serine at a position corresponding to position 352 of SEQ ID NO:8; and b) classifying the human subject as being at decreased risk for developing the cardiovascular condition if a B4GALT1 polypeptide comprising a serine at a position corresponding to position 352 of SEQ ID NO:8 is detected in the biological sample, or classifying the human subject as being at increased risk for developing the cardiovascular condition if a B4GALT1 polypeptide comprising a serine at a position corresponding to position 352 of SEQ ID NO:8 is not detected in the biological sample. In some embodiments, the methods further comprise obtaining a biological sample from the subject.

In some embodiments, where a subject has been diagnosed with a cardiovascular condition or as having an increased risk for developing a cardiovascular condition, a therapeutic or prophylactic agent that treats or prevents the cardiovascular condition is administered to the subject. Alternately, the method can further comprise administering a therapeutic agent tailored to prevent or alleviate one or more symptoms associated with progression to more clinically advanced stages of cardiovascular condition, particularly in patients with increased LDL levels and/or those patients who have had or are at increased risk of thrombotic events.

The present disclosure also provides methods for modifying a cell through use of any combination of nuclease agents, exogenous donor sequences, transcriptional activators, transcriptional repressors, antisense molecules such as antisense RNA, siRNA, and shRNA, B4GALT1 polypeptides or fragments thereof, and expression vectors for expressing a recombinant B4GALT1 gene or a nucleic acid encoding an B4GALT1 polypeptide. The methods can occur in vitro, ex vivo, or in vivo. The nuclease agents, exogenous donor sequences, transcriptional activators, transcriptional repressors, antisense molecules such as antisense RNA, siRNA, and shRNA, B4GALT1 polypeptides or fragments thereof, and expression vectors can be introduced into the cell in any form and by any means as described elsewhere herein, and all or some can be introduced simultaneously or sequentially in any combination. Some methods involve only altering an endogenous B4GALT1 gene in a cell. Some methods involve only altering expression of an endogenous B4GALT1 gene through use of transcriptional activators or repressors or through use of antisense molecules such as antisense RNA, siRNA, and shRNA. Some methods involve only introducing a recombinant B4GALT1 gene or nucleic acid encoding a B4GALT1 polypeptide or fragment thereof into a cell. Some methods involve only introducing a B4GALT1 polypeptide or fragment thereof into a cell (e.g., any one of or any combination of the B4GALT1 polypeptides or fragments thereof disclosed herein). Other methods involve both altering an endogenous B4GALT1 gene in a cell and introducing a B4GALT1 polypeptide or fragment thereof or recombinant B4GALT1 gene or nucleic acid encoding a B4GALT1 polypeptide or fragment thereof into the cell. Other methods involve both altering expression of an endogenous B4GALT1 gene in a cell and introducing a B4GALT1 polypeptide or fragment thereof or recombinant B4GALT1 gene or nucleic acid encoding a B4GALT1 polypeptide or fragment thereof into the cell.

The present disclosure provides methods for modifying an endogenous B4GALT1 gene in a genome within a cell (e.g., a pluripotent cell or a differentiated cell) through use of nuclease agents and/or exogenous donor sequences. The methods can occur in vitro, ex vivo, or in vivo. The nuclease agent can be used alone or in combination with an exogenous donor sequence. Alternately, the exogenous donor sequence can be used alone or in combination with a nuclease agent.

Repair in response to double-strand breaks (DSBs) occurs principally through two conserved DNA repair pathways: non-homologous end joining (NHEJ) and homologous recombination (HR) (see, Kasparek & Humphrey, *Seminars in Cell & Dev. Biol.*, 2011, 22, 886-897). Repair of a target nucleic acid (e.g., an endogenous B4GALT1 gene) mediated by an exogenous donor sequence can include any process of exchange of genetic information between the two polynucleotides. For example, NHEJ can also result in the targeted integration of an exogenous donor sequence through direct ligation of the break ends with the ends of the exogenous donor sequence (i.e., NHEJ-based capture). Repair can also occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target.

Targeted genetic modifications to an endogenous B4GALT1 gene in a genome can be generated by contacting a cell with an exogenous donor sequence comprising a 5' homology arm that hybridizes to a 5' target sequence at a target genomic locus within the endogenous B4GALT1 gene and a 3' homology arm that hybridizes to a 3' target sequence at the target genomic locus within the endogenous B4GALT1 gene. The exogenous donor sequence can recombine with the target genomic locus to generate the targeted genetic modification to the endogenous B4GALT1 gene. As one example, the 5' homology arm can hybridize to a target sequence 5' of the position corresponding to positions 53575 to 53577 of SEQ ID NO:1, and the 3' homology arm can hybridize to a target sequence 3' of the position corresponding to positions 53575 to 53577 of SEQ ID NO:1. Such methods can result, for example, in a B4GALT1 gene which contains a nucleotide sequence that encodes a serine at the position corresponding to position 352 of the full length/mature polypeptide produced therefrom. Examples of exogenous donor sequences are disclosed elsewhere herein.

For example, targeted genetic modifications to an endogenous B4GALT1 gene in a genome can be generated by contacting a cell or the genome of a cell with a Cas protein and one or more guide RNAs that hybridize to one or more guide RNA recognition sequences within a target genomic locus in the endogenous B4GALT1 gene. For example, such methods can comprise contacting a cell with a Cas protein and a guide RNA that hybridizes to a guide RNA recognition sequence within the endogenous B4GALT1 gene. In some embodiments, the guide RNA recognition sequence is located within a region corresponding to exon 5 of SEQ ID NO:1. In some embodiments, the guide RNA recognition sequence can include or is proximate to a position corresponding to positions 53575 to 53577 of SEQ ID NO:1. For example, the guide RNA recognition sequence can be within about 1000, within about 500, within about 400, within about 300, within about 200, within about 100, within about 50, within about 45, within about 40, within about 35, within about 30, within about 25, within about 20, within about 15, within about 10, or within about 5 nucleotides of the position corresponding to positions 53575 to 53577 of SEQ ID NO:1. As yet another example, the guide RNA recognition sequence can include or be proximate to the start codon of an endogenous B4GALT1 gene or the stop codon of an endogenous B4GALT1 gene. For example, the guide RNA recognition sequence can be within about 10, within about 20, within about 30, within about 40, within about 50, within about 100, within about 200, within about 300, within about 400, within about 500, or within about 1,000 nucleotides of the start codon or the stop codon. The Cas protein and the guide RNA form a complex, and the Cas protein cleaves the guide RNA recognition sequence. Cleavage by the Cas protein can create a double-strand break or a single-strand break (e.g., if the Cas protein is a nickase). Such methods can result, for example, in an endogenous B4GALT1 gene in which the region corresponding to exon 5 of SEQ ID NO:1 is disrupted, the start codon is disrupted, the stop codon is disrupted, or the coding sequence is deleted. Examples and variations of Cas (e.g., Cas9) proteins and guide RNAs that can be used in the methods are described elsewhere herein.

In some embodiments, two or more nuclease agents can be used. For example, two nuclease agents can be used, each targeting a nuclease recognition sequence within a region corresponding to exon 5 of SEQ ID NO:1, or including or proximate to a position corresponding to positions 53575 to 53577 of SEQ ID NO:1 (e.g., within about 1000, within about 500, within about 400, within about 300, within about 200, within about 100, within about 50, within about 45, within about 40, within about 35, within about 30, within about 25, within about 20, within about 15, within about 10, or within about 5 nucleotides of the positions corresponding to positions 53575 to 53577 of SEQ ID NO:1). As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. As yet another example, three or more nuclease agents can be used, with one or more (e.g., two) targeting nuclease recognition sequences including or proximate to the start codon, and one or more (e.g., two) targeting nuclease recognition sequences including or proximate to the stop codon, wherein cleavage by the nuclease agents can result in deletion of the coding region between the nuclease recognition sequences including or proximate to the start codon and the nuclease recognition sequence including or proximate to the stop codon.

In some embodiments, the cell can be further contacted with one or more additional guide RNAs that hybridize to additional guide RNA recognition sequences within the target genomic locus in the endogenous B4GALT1 gene. By contacting the cell with one or more additional guide RNAs (e.g., a second guide RNA that hybridizes to a second guide RNA recognition sequence), cleavage by the Cas protein can create two or more double-strand breaks or two or more single-strand breaks (e.g., if the Cas protein is a nickase).

In some embodiments, the cell can additionally be contacted with one or more exogenous donor sequences which recombine with the target genomic locus in the endogenous B4GALT1 gene to generate a targeted genetic modification. Examples and variations of exogenous donor sequences that can be used in the methods are disclosed elsewhere herein.

The Cas protein, guide RNA(s), and exogenous donor sequence(s) can be introduced into the cell in any form and by any means as described elsewhere herein, and all or some of the Cas protein, guide RNA(s), and exogenous donor sequence(s) can be introduced simultaneously or sequentially in any combination.

In some embodiments, the repair of the target nucleic acid (e.g., the endogenous B4GALT1 gene) by the exogenous donor sequence occurs via homology-directed repair (HDR). Homology-directed repair can occur when the Cas protein cleaves both strands of DNA in the endogenous B4GALT1 gene to create a double-strand break, when the Cas protein is a nickase that cleaves one strand of DNA in the target nucleic acid to create a single-strand break, or when Cas nickases are used to create a double-strand break formed by two offset nicks. In such methods, the exogenous donor sequence comprises 5' and 3' homology arms corresponding to 5' and 3' target sequences. The guide RNA recognition sequence(s) or cleavage site(s) can be adjacent to the 5' target sequence, adjacent to the 3' target sequence, adjacent to both the 5' target sequence and the 3' target sequence, or adjacent to neither the 5' target sequence nor the 3' target sequence. In some embodiments, the exogenous donor sequence can further comprise a nucleic acid insert flanked by the 5' and 3' homology arms, and the nucleic acid insert is inserted between the 5' and 3' target sequences. If no nucleic acid insert is present, the exogenous donor sequence can function to delete the genomic sequence between the 5' and 3' target sequences. Examples of exogenous donor sequences are disclosed elsewhere herein.

Alternately, the repair of the endogenous B4GALT1 gene mediated by the exogenous donor sequence can occur via non-homologous end joining (NHEJ)-mediated ligation. In such methods, at least one end of the exogenous donor sequence comprises a short single-stranded region that is complementary to at least one overhang created by Cas-mediated cleavage in the endogenous B4GALT1 gene. The complementary end in the exogenous donor sequence can flank a nucleic acid insert. For example, each end of the exogenous donor sequence can comprise a short single-stranded region that is complementary to an overhang created by Cas-mediated cleavage in the endogenous B4GALT1 gene, and these complementary regions in the exogenous donor sequence can flank a nucleic acid insert.

Overhangs (i.e., staggered ends) can be created by resection of the blunt ends of a double-strand break created by Cas-mediated cleavage. Such resection can generate the regions of microhomology needed for fragment joining, but this can create unwanted or uncontrollable alterations in the B4GALT1 gene. Alternately, such overhangs can be created by using paired Cas nickases. For example, the cell can be contacted with first and second nickases that cleave opposite strands of DNA, whereby the genome is modified through double nicking. This can be accomplished by contacting a cell with a first Cas protein nickase, a first guide RNA that hybridizes to a first guide RNA recognition sequence within the target genomic locus in the endogenous B4GALT1 gene, a second Cas protein nickase, and a second guide RNA that hybridizes to a second guide RNA recognition sequence within target genomic locus in the endogenous B4GALT1 gene. The first Cas protein and the first guide RNA form a first complex, and the second Cas protein and the second guide RNA form a second complex. The first Cas protein nickase cleaves a first strand of genomic DNA within the first guide RNA recognition sequence, the second Cas protein nickase cleaves a second strand of genomic DNA within the second guide RNA recognition sequence, and optionally the exogenous donor sequence recombines with the target genomic locus in the endogenous B4GALT1 gene to generate the targeted genetic modification.

The first nickase can cleave a first strand of genomic DNA (i.e., the complementary strand), and the second nickase can cleave a second strand of genomic DNA (i.e., the non-complementary strand). The first and second nickases can be created, for example, by mutating a catalytic residue in the RuvC domain (e.g., the D10A mutation described elsewhere herein) of Cas9 or mutating a catalytic residue in the HNH domain (e.g., the H840A mutation described elsewhere herein) of Cas9. In such methods, the double nicking can be employed to create a double-strand break having staggered ends (i.e., overhangs). The first and second guide RNA recognition sequences can be positioned to create a cleavage site such that the nicks created by the first and second nickases on the first and second strands of DNA create a double-strand break. Overhangs are created when the nicks within the first and second CRISPR RNA recognition sequences are offset. The offset window can be, for example, at least about 5 bp, at least about 10 bp, at least about 20 bp, at least about 30 bp, at least about 40 bp, at least about 50 bp, at least about 60 bp, at least about 70 bp, at least about 80 bp, at least about 90 bp, at least about 100 bp, or more. See, e.g., Ran et al., *Cell*, 2013, 154, 1380-1389; Mali et al., *Nat. Biotech.*, 213, 31, 833-838; and Shen et al., *Nat. Methods*, 2014, 11, 399-404.

Various types of targeted genetic modifications can be introduced using the methods described herein. Such targeted modifications can include, for example, additions of one or more nucleotides, deletions of one or more nucleotides, substitutions of one or more nucleotides, a point mutation, or a combination thereof. For example, at least 1, at least 2, at least 3, at least 4, at least 5, at least 7, at least 8, at least 9, or at least 10, or more nucleotides can be changed (e.g., deleted, inserted, or substituted) to form the targeted genomic modification.

Such targeted genetic modifications can result in disruption of a target genomic locus. Disruption can include alteration of a regulatory element (e.g., promoter or enhancer), a missense mutation, a nonsense mutation, a frame-shift mutation, a truncation mutation, a null mutation, or an insertion or deletion of small number of nucleotides (e.g., causing a frameshift mutation), and it can result in inactivation (i.e., loss of function) or loss of an allele. For example, a targeted modification can comprise disruption of the start codon of an endogenous B4GALT1 gene such that the start codon is no longer functional.

In some embodiments, a targeted modification can comprise a deletion between the first and second guide RNA recognition sequences or Cas cleavage sites. If an exogenous donor sequence (e.g., repair template or targeting vector) is used, the modification can comprise a deletion between the first and second guide RNA recognition sequences or Cas cleavage sites as well as an insertion of a nucleic acid insert between the 5' and 3' target sequences.

In some embodiments, if an exogenous donor sequence is used, alone or in combination with a nuclease agent, the modification can comprise a deletion between the 5' and 3' target sequences as well as an insertion of a nucleic acid insert between the 5' and 3' target sequences in the pair of first and second homologous chromosomes, thereby resulting in a homozygous modified genome. Alternately, if the exogenous donor sequence comprises 5' and 3' homology arms with no nucleic acid insert, the modification can comprise a deletion between the 5' and 3' target sequences.

The deletion between the first and second guide RNA recognition sequences or the deletion between the 5' and 3' target sequences can be a precise deletion wherein the deleted nucleic acid consists of only the nucleic acid sequence between the first and second nuclease cleavage sites or only the nucleic acid sequence between the 5' and 3' target sequences such that there are no additional deletions or insertions at the modified genomic target locus. The deletion between the first and second guide RNA recognition sequences can also be an imprecise deletion extending beyond the first and second nuclease cleavage sites, consistent with imprecise repair by non-homologous end joining (NHEJ), resulting in additional deletions and/or insertions at the modified genomic locus. For example, the deletion can extend about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more beyond the first and second Cas protein cleavage sites. Likewise, the modified genomic locus can comprise additional insertions consistent with imprecise repair by NHEJ, such as insertions of about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more.

The targeted genetic modification can be, for example, a biallelic modification or a monoallelic modification. Biallelic modifications include events in which the same modification is made to the same locus on corresponding homologous chromosomes (e.g., in a diploid cell), or in which different modifications are made to the same locus on corresponding homologous chromosomes. In some embodiments, the targeted genetic modification is a monoallelic modification. A monoallelic modification includes events in which a modification is made to only one allele (i.e., a modification to the endogenous B4GALT1 gene in only one of the two homologous chromosomes). Homologous chromosomes include chromosomes that have the same genes at the same loci but possibly different alleles (e.g., chromosomes that are paired during meiosis).

A monoallelic mutation can result in a cell that is heterozygous for the targeted B4GALT1 modification. Heterozygosity includes situation in which only one allele of the B4GALT1 gene (i.e., corresponding alleles on both homologous chromosomes) have the targeted modification.

A biallelic modification can result in homozygosity for a targeted modification. Homozygosity includes situations in which both alleles of the B4GALT1 gene (i.e., corresponding alleles on both homologous chromosomes) have the targeted modification. Alternately, a biallelic modification can result in compound heterozygosity (e.g., hemizygosity) for the targeted modification. Compound heterozygosity includes situations in which both alleles of the target locus (i.e., the alleles on both homologous chromosomes) have been modified, but they have been modified in different ways (e.g., a targeted modification in one allele and inactivation or disruption of the other allele).

The methods disclosed herein can further comprise identifying a cell having a modified B4GALT1 gene. Various methods can be used to identify cells having a targeted genetic modification, such as a deletion or an insertion. Such methods can comprise identifying one cell having the targeted genetic modification in the B4GALT1 gene. Screening can be performed to identify such cells with modified genomic loci. The screening step can comprise a quantitative assay for assessing modification of allele (MOA) (e.g., loss-of-allele (LOA) and/or gain-of-allele (GOA) assays) of a parental chromosome.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology. Conventional assays for screening for targeted modifications, such as long-range PCR, Southern blotting, or Sanger sequencing, can also be used. Such assays typically are used to obtain evidence for a linkage between the inserted targeting vector and the targeted genomic locus. For example, for a long-range PCR assay, one primer can recognize a sequence within the inserted DNA while the other recognizes a target genomic locus sequence beyond the ends of the targeting vector's homology arms.

Next generation sequencing (NGS) can also be used for screening. Next-generation sequencing can also be referred to as "NGS" or "massively parallel sequencing" or "high throughput sequencing." In some embodiments, it is not necessary to screen for targeted cells using selection markers. For example, the MOA and NGS assays described herein can be relied on without using selection cassettes.

The present disclosure also provides methods for altering expression of nucleic acids encoding B4GALT1 polypeptides. In some embodiments, expression is altered through cleavage with a nuclease agent to cause disruption of the nucleic acid encoding the endogenous B4GALT1 polypeptide, as described in further detail elsewhere herein. In some embodiments, expression is altered through use of a DNA-binding protein fused or linked to a transcription activation domain or a transcription repression domain. In some embodiments, expression is altered through use of RNA interference compositions, such as antisense RNA, shRNA, or siRNA.

In some embodiments, expression of an endogenous B4GALT1 gene or a nucleic acid encoding a B4GALT1 polypeptide can be modified by contacting a cell or the genome within a cell with a nuclease agent that induces one or more nicks or double-strand breaks at a recognition sequence at a target genomic locus within the endogenous B4GALT1 gene or nucleic acid encoding a B4GALT1 polypeptide. Such cleavage can result in disruption of expression of the endogenous B4GALT1 gene or nucleic acid encoding a B4GALT1 polypeptide. For example, the nuclease recognition sequence can include or be proximate to the start codon of the endogenous B4GALT1 gene. For example, the recognition sequence can be within about 10, within about 20, within about 30, within about 40, within about 50, within about 100, within about 200, within about 300, within about 400, within about 500, or within about 1,000 nucleotides of the start codon, and cleavage by the nuclease agent can disrupt the start codon. In some embodiments, two or more nuclease agents can be used, each targeting a nuclease recognition sequence including or proximate to the start codon. In some embodiments, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. In some embodiments, three or more nuclease agents can be used, with one or more (e.g., two) targeting nuclease recognition sequences including or proximate to the start codon, and one or more (e.g., two) targeting nuclease recognition sequences including or proximate to the stop codon, wherein cleavage by the nuclease agents can result in deletion of the coding region between the nuclease recognition sequences including or proximate to the start codon and the nuclease recognition sequence including or proximate to the stop codon. Other examples of modifying an endogenous B4GALT1 gene or a nucleic acid encoding a B4GALT1 polypeptide are disclosed elsewhere herein.

In some embodiments, expression of an endogenous B4GALT1 gene or a nucleic acid encoding a B4GALT1 polypeptide can be modified by contacting a cell or the genome within a cell with a DNA-binding protein that binds to a target genomic locus within the endogenous B4GALT1 gene. The DNA-binding protein can be, for example, a nuclease-inactive Cas protein fused to a transcriptional activator domain or a transcriptional repressor domain. Other examples of DNA-binding proteins include zinc finger proteins fused to a transcriptional activator domain or a transcriptional repressor domain, or Transcription Activator-Like Effector (TALE) proteins fused to a transcriptional activator domain or a transcriptional repressor domain. Examples of such proteins are disclosed elsewhere herein.

The recognition sequence (e.g., guide RNA recognition sequence) for the DNA-binding protein can be anywhere within the endogenous B4GALT1 gene or a nucleic acid encoding a B4GALT1 polypeptide suitable for altering expression. In some embodiments, the recognition sequence can be within a regulatory element, such as an enhancer or promoter, or can be in proximity to a regulatory element. For example, the recognition sequence can include or be proximate to the start codon of an endogenous B4GALT1 gene. In some embodiments, the recognition sequence can be within about 10, within about 20, within about 30, within about 40, within about 50, within about 100, within about 200, within about 300, within about 400, within about 500, or within about 1,000 nucleotides of the start codon.

In some embodiments, antisense molecules can be used to alter expression of an endogenous B4GALT1 gene or a nucleic acid encoding a B4GALT1 polypeptide. Examples of antisense molecules include, but are not limited to, antisense RNAs, siRNAs, and shRNAs. Such antisense RNAs, siRNAs, or shRNAs can be designed to target any region of an mRNA. For example, the antisense RNAs, siRNAs, or shRNAs can be designed to target a region unique of the B4GALT1 mRNA.

The nucleic acids and proteins disclosed herein can be introduced into a cell by any means. In some embodiments, the introducing can be accomplished by any means, and one or more of the components (e.g., two of the components, or all of the components) can be introduced into the cell simultaneously or sequentially in any combination. For example, an exogenous donor sequence can be introduced prior to the introduction of a nuclease agent, or it can be introduced following introduction of nuclease agent (e.g., the exogenous donor sequence can be administered about 1, about 2, about 3, about 4, about 8, about 12, about 24, about 36, about 48, or about 72 hours before or after introduction of the nuclease agent). Contacting the genome of a cell with a nuclease agent or exogenous donor sequence can comprise introducing one or more nuclease agents or nucleic acids encoding nuclease agents (e.g., one or more Cas proteins or nucleic acids encoding one or more Cas proteins, and one or more guide RNAs or nucleic acids encoding one or more guide RNAs (i.e., one or more CRISPR RNAs and one or more tracrRNAs)) and/or one or more exogenous donor sequences into the cell. Contacting the genome of cell (i.e., contacting a cell) can comprise introducing only one of the above components, one or more of the components, or all of the components into the cell.

A nuclease agent can be introduced into the cell in the form of a protein or in the form of a nucleic acid encoding the nuclease agent, such as an RNA (e.g., messenger RNA (mRNA)) or DNA. When introduced in the form of a DNA, the DNA can be operably linked to a promoter active in the cell. Such DNAs can be in one or more expression constructs.

In some embodiments, a Cas protein can be introduced into the cell in the form of a protein, such as a Cas protein complexed with a gRNA, or in the form of a nucleic acid encoding the Cas protein, such as an RNA (e.g., messenger RNA (mRNA)) or DNA. A guide RNA can be introduced into the cell in the form of an RNA or in the form of a DNA encoding the guide RNA. When introduced in the form of a DNA, the DNA encoding the Cas protein and/or the guide RNA can be operably linked to a promoter active in the cell. Such DNAs can be in one or more expression constructs. For example, such expression constructs can be components of a single nucleic acid molecule. Alternately, they can be separated in any combination among two or more nucleic acid molecules (i.e., DNAs encoding one or more CRISPR RNAs, DNAs encoding one or more tracrRNAs, and DNA encoding a Cas protein can be components of separate nucleic acid molecules).

In some embodiments, DNA encoding a nuclease agent (e.g., a Cas protein and a guide RNA) and/or DNA encoding an exogenous donor sequence can be introduced into a cell via DNA minicircles. DNA minicircles are supercoiled DNA molecules that can be used for non-viral gene transfer that have neither an origin of replication nor an antibiotic selection marker. Thus, DNA minicircles are typically smaller in size than plasmid vector. These DNAs are devoid of bacterial DNA, and thus lack the unmethylated CpG motifs found in bacterial DNA.

The methods described herein do not depend on a particular method for introducing a nucleic acid or protein into the cell, only that the nucleic acid or protein gains access to the interior of a least one cell. Methods for introducing nucleic acids and proteins into various cell types are known and include, but are not limited to, stable transfection methods, transient transfection methods, and virus-mediated methods.

Transfection protocols as well as protocols for introducing nucleic acids or proteins into cells may vary. Non-limiting transfection methods include chemical-based transfection methods using liposomes, nanoparticles, calcium, dendrimers, and cationic polymers such as DEAE-dextran or polyethylenimine. Non-chemical methods include electroporation, sono-poration, and optical transfection. Particle-based transfection includes the use of a gene gun, or magnet-assisted transfection. Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In some embodiments, nucleofection is performed using the LONZA® NUCLEOFECTOR™ system.

Introduction of nucleic acids or proteins into a cell can also be accomplished by microinjection. Microinjection of an mRNA is usually into the cytoplasm (e.g., to deliver mRNA directly to the translation machinery), while microinjection of a protein or a DNA encoding a DNA encoding a Cas protein is usually into the nucleus. Alternately, microinjection can be carried out by injection into both the nucleus and the cytoplasm: a needle can first be introduced into the nucleus and a first amount can be injected, and while removing the needle from the cell a second amount can be injected into the cytoplasm. If a nuclease agent protein is injected into the cytoplasm, the protein may comprise a nuclear localization signal to ensure delivery to the nucleus/pronucleus.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. Methods of administering nucleic acids or proteins to a subject to modify cells in vivo are disclosed elsewhere herein. Introduction of nucleic acids and proteins into cells can also be accomplished by hydrodynamic delivery (HDD).

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. In some embodiments, a nucleic acid or protein can be introduced into a cell in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule.

The introduction of nucleic acids or proteins into the cell can be performed one time or multiple times over a period of time. In some embodiments, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

In some embodiments, the cells employed in the methods and compositions have a DNA construct stably incorporated into their genome. In such cases, the contacting can comprise providing a cell with the construct already stably incorporated into its genome. In some embodiments, a cell employed in the methods disclosed herein may have a preexisting Cas-encoding gene stably incorporated into its genome (i.e., a Cas-ready cell). In some embodiments, the polynucleotide integrates into the genome of the cell and is capable of being inherited by progeny thereof. Any protocol may be used for the stable incorporation of the DNA constructs or the various components of the targeted genomic integration system.

Any nuclease agent that induces a nick or double-strand break into a desired recognition sequence or any DNA-binding protein that binds to a desired recognition sequence can be used in the methods and compositions disclosed herein. A naturally occurring or native nuclease agent can be employed so long as the nuclease agent induces a nick or double-strand break in a desired recognition sequence. Likewise, a naturally occurring or native DNA-binding protein can be employed so long as the DNA-binding protein binds to the desired recognition sequence. Alternately, a modified or engineered nuclease agent or DNA-binding protein can be employed. An engineered nuclease agent or DNA-binding protein can be derived from a native, naturally occurring nuclease agent or DNA-binding protein or it can be artificially created or synthesized. The engineered nuclease agent or DNA-binding protein can recognize a recognition sequence, for example, wherein the recognition sequence is not a sequence that would have been recognized by a native (non-engineered or non-modified) nuclease agent or DNA-binding protein. The modification of the nuclease agent or DNA-binding protein can be as few as one amino acid in a protein cleavage agent or one nucleotide in a nucleic acid cleavage agent.

Recognition sequences for a nuclease agent includes a DNA sequence at which a nick or double-strand break is induced by a nuclease agent. Likewise, recognition sequences for a DNA-binding protein include a DNA sequence to which a DNA-binding protein will bind. The recognition sequence can be endogenous (or native) to the cell or the recognition sequence can be exogenous to the cell. The recognition sequence can also exogenous to the polynucleotides of interest that one desires to be positioned at the target locus. In some embodiments, the recognition sequence is present only once in the genome of the host cell.

Active variants and fragments of the exemplified recognition sequences are also provided. Such active variants can comprise at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, or 100% sequence identity to the given recognition sequence, wherein the active variants retain biological activity and are capable of being recognized and cleaved by a nuclease agent in a sequence-specific manner. Assays to measure the double-strand break of a recognition sequence by a nuclease agent are known (e.g., TAQMAN® qPCR assay, Frendewey et al., *Methods in Enzymology,* 2010, 476, 295-307).

The length of the recognition sequence can vary, and includes, for example, recognition sequences that are from about 30 to about 36 bp for a zinc finger protein or zinc finger nuclease (ZFN) pair (i.e., from about 15 to about 18 bp for each ZFN), about 36 bp for a TALE protein or Transcription Activator-Like Effector Nuclease (TALEN), or about 20 bp for a CRISPR/Cas9 guide RNA.

The recognition sequence of the DNA-binding protein or nuclease agent can be positioned anywhere in or near the target genomic locus. The recognition sequence can be located within a coding region of a gene (e.g., the B4GALT1 gene), or within regulatory regions that influence the expression of the gene. A recognition sequence of the DNA-binding protein or nuclease agent can be located in an intron, an exon, a promoter, an enhancer, a regulatory region, or any non-protein coding region.

One type of DNA-binding protein that can be employed in the various methods and compositions disclosed herein is a TALE. A TALE can be fused or linked to, for example, an epigenetic modification domain, a transcriptional activation domain, or a transcriptional repressor domain. Examples of such domains are described with respect to Cas proteins, below, and can also be found, for example, in PCT Publication WO 2011/145121. Correspondingly, one type of nuclease agent that can be employed in the various methods and compositions disclosed herein is a TALEN. Transcription activator-like (TAL) effector nucleases are a class of sequence-specific nucleases that can be used to make double-strand breaks at specific target sequences in the genome of a prokaryotic or eukaryotic organism. TAL effector nucleases are created by fusing a native or engineered TAL effector, or functional part thereof, to the catalytic domain of an endonuclease such as FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. Examples of suitable TAL nucleases, and methods for preparing suitable TAL nucleases, are disclosed, for example, in U.S. Patent Application Publications 2011/0239315; 2011/0269234; 2011/0145940; 2003/0232410; 2005/0208489; 2005/0026157; 2005/0064474; 2006/0188987; and 2006/0063231.

In some TALENs, each monomer of the TALEN comprises from about 33 to about 35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (from about 12 to about 20 bp), and wherein the FokI nuclease subunits dimerize to create an active nuclease that makes a double strand break at a target sequence.

Another example of a DNA-binding protein is a zinc finger protein. Such zinc finger proteins can be linked or fused to, for example, an epigenetic modification domain, a transcriptional activation domain, or a transcriptional repressor domain. Examples of such domains are described with respect to Cas proteins, below, and can also be found, for example, in PCT Publication WO 2011/145121. Correspondingly, another example of a nuclease agent that can be employed in the various methods and compositions disclosed herein is a ZFN. In some ZFNs, each monomer of the ZFN comprises three or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5 to about 7 bp spacer, and wherein the FokI nuclease subunits dimerize to create an active nuclease that makes a double strand break.

Other suitable DNA-binding proteins and nuclease agents for use in the methods and compositions described herein include CRISPR-Cas systems, which are described elsewhere herein.

The DNA-binding protein or nuclease agent may be introduced into the cell by any known means. A polypeptide encoding the DNA-binding protein or nuclease agent may be directly introduced into the cell. Alternately, a polynucleotide encoding the DNA-binding protein or nuclease agent can be introduced into the cell. When a polynucleotide encoding the DNA-binding protein or nuclease agent is introduced into the cell, the DNA-binding protein or nuclease agent can be transiently, conditionally, or constitutively expressed within the cell. For example, the polynucleotide encoding the DNA-binding protein or nuclease agent can be contained in an expression cassette and be operably linked to a conditional promoter, an inducible promoter, a constitutive promoter, or a tissue-specific promoter. Such promoters are discussed in further detail elsewhere herein. In some embodiments, the DNA-binding protein or nuclease agent can be introduced into the cell as an mRNA encoding a DNA-binding protein or a nuclease agent.

A polynucleotide encoding a DNA-binding protein or nuclease agent can be stably integrated in the genome of the cell and operably linked to a promoter active in the cell. Alternately, a polynucleotide encoding a DNA-binding protein or nuclease agent can be in a targeting vector or in a vector or a plasmid that is separate from the targeting vector comprising the insert polynucleotide.

When the DNA-binding protein or nuclease agent is provided to the cell through the introduction of a polynucleotide encoding the DNA-binding protein or nuclease agent, such a polynucleotide encoding a DNA-binding protein or nuclease agent can be modified to substitute codons having a higher frequency of usage in the cell of interest, as compared to the naturally occurring polynucleotide sequence encoding the DNA-binding protein or nuclease agent. In some embodiments, the polynucleotide encoding the DNA-binding protein or nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

The methods disclosed herein can utilize Clustered Regularly Interspersed Short Palindromic Repeats (CRISPR)/ CRISPR-associated (Cas) systems or components of such systems to modify a genome within a cell. CRISPR-Cas systems include transcripts and other elements involved in the expression of, or directing the activity of, Cas genes. A CRISPR-Cas system can be a type I, a type II, or a type III system. Alternately a CRISPR/Cas system can be, for example, a type V system (e.g., subtype V-A or subtype V-B). The methods and compositions disclosed herein can employ CRISPR-Cas systems by utilizing CRISPR complexes (comprising a guide RNA (gRNA) complexed with a Cas protein) for site-directed cleavage of nucleic acids.

The CRISPR-Cas systems used in the methods disclosed herein are non-naturally occurring. For example, some CRISPR-Cas systems employ non-naturally occurring CRISPR complexes comprising a gRNA and a Cas protein that do not naturally occur together.

Cas proteins generally comprise at least one RNA recognition or binding domain that can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. A wild-type Cas9 protein will typically create a blunt cleavage product. Alternately, a wild-type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break in the endogenous B4GALT1 gene (e.g., a double-strand break with blunt ends), or it can be a nickase that creates a single-strand break in the endogenous B4GALT1 gene.

Examples of Cas proteins include, but are not limited to, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

In some embodiments, the Cas protein is a Cas9 protein or is derived from a Cas9 protein from a type II CRISPR-Cas system. Cas9 proteins are from a type II CRISPR-Cas system and typically share four key motifs with a conserved architecture. Motifs 1, 2, and 4 are RuvC-like motifs, and motif 3 is an HNH motif. Exemplary Cas9 proteins include, but are not limited to, those are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Badcillus pseudomycoides, Bacillus selenitireducens, Exiguobacterium sibiricum, Lactobacillus delbrueckii, Lactobadllus salivarius, Microscilla marina, Burkholderiales bacterium, Polaromonas naphthaleniv-*

*orans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium diffidle, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. Additional examples of the Cas9 family members are described in PCT Publication WO 2014/131833. Cas9 from *S. pyogenes* (assigned SwissProt accession number Q99ZW2) is an exemplary enzyme. Cas9 from *S. aureus* (assigned UniProt accession number J7RUA5) is another exemplary enzyme.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. Exemplary Cpf1 proteins include, but are not limited to, those from *Francisella tularensis* 1, *Francisella tularensis* subsp. *novicida, Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acdaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary enzyme.

Cas proteins can be wild-type proteins (i.e., those that occur in nature), modified Cas proteins (i.e., Cas protein variants), or fragments of wild-type or modified Cas proteins. Cas proteins can also be active variants or fragments of wild-type or modified Cas proteins. Active variants or fragments can comprise at least 80%, at least 85%, at least 90%, at least 91%, at least 92%, at least 93%, at least 94%, at least 95%, at least 96%, at least 97%, at least 98%, or at least 99%, or 100% sequence identity to the wild-type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can comprise at least one nuclease domain, such as a DNase domain. For example, a wild-type Cpf1 protein generally comprises a RuvC-like domain that cleaves both strands of target DNA, perhaps in a dimeric configuration. Cas proteins can comprise at least two nuclease domains, such as DNase domains. For example, a wild-type Cas9 protein generally comprises a RuvC-like nuclease domain and an HNH-like nuclease domain. The RuvC and HNH domains can each cut a different strand of double-stranded DNA to make a double-stranded break in the DNA.

Cas proteins (e.g., nuclease-active Cas proteins or nuclease-inactive Cas proteins) can also be operably linked to heterologous polypeptides as fusion proteins. For example, a Cas protein can be fused to a cleavage domain, an epigenetic modification domain, a transcriptional activation domain, or a transcriptional repressor domain. Examples of transcriptional activation domains include a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, and an NFAT (nuclear factor of activated T-cells) activation domain. Other examples include, but are not limited to, activation domains from Oct1, Oct-2A, SP1, AP-2, CTF1, P300, CBP, PCAF, SRC1, PvALF, ERF-2, OsGAI, HALF-1, C1, AP1, ARF-5, ARF-6, ARF-7, ARF-8, CPRF1, CPRF4, MYC-RP/GP, TRAB1PC4, and HSF1. See, e.g., U.S. Patent Application Publication 2016/0237456, European Patent EP3045537, and PCT Publication WO 2011/145121.

In some embodiments, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al., *Nature*, 2015, 517, 583-588. Examples of transcriptional repressor domains include inducible cAMP early repressor (ICER) domains, Kruppel-associated box A (KRAB-A) repressor domains, YY1 glycine rich repressor domains, Sp1-like repressors, E(spl) repressors, IκB repressor, and MeCP2. Other examples include, but are not limited to, transcriptional repressor domains from A/B, KOX, TGF-beta-inducible early gene (TIEG), v-erbA, SID, SID4X, MBD2, MBD3, DNMT1, DNMG3A, DNMT3B, Rb, ROM2, See, e.g., European Patent EP3045537 and PCT Publication WO 2011/145121. Cas proteins can also be fused to a heterologous polypeptide providing increased or decreased stability. The fused domain or heterologous polypeptide can be located at the N-terminus, the C-terminus, or internally within the Cas protein.

An example of a Cas fusion protein is a Cas protein fused to a heterologous polypeptide that provides for subcellular localization. Such heterologous polypeptides can include, for example, one or more nuclear localization signals (NLS) such as the SV40 NLS for targeting to the nucleus, a mitochondrial localization signal for targeting to the mitochondria, an ER retention signal, and the like. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be operably linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenI), yellow fluorescent proteins (e.g., YFP, eYFP, Citrine, Venus, YPet, PhiYFP, ZsYellowI), blue fluorescent proteins (e.g. eBFP, eBFP2, Azurite, mKalamaI, GFPuv, Sapphire, T-sapphire), cyan fluorescent proteins (e.g. eCFP, Cerulean, CyPet, AmCyanI, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRedI, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas9 proteins can also be tethered to exogenous donor sequences or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous donor sequence or labeled nucleic acid can be tethered to the C-terminus, the N-terminus, or to an internal region within the Cas9 protein. In some embodiments, the exogenous donor sequence or labeled nucleic acid is tethered to the C-terminus or the N-terminus of the Cas9 protein. Likewise, the Cas9 protein can be tethered to the 5' end, the 3' end, or to an internal region within the exogenous donor sequence or labeled nucleic acid. In some embodiments, the Cas9 protein is tethered to the 5' end or the 3' end of the exogenous donor sequence or labeled nucleic acid.

Cas proteins can be provided in any form. For example, a Cas protein can be provided in the form of a protein, such as a Cas protein complexed with a gRNA. Alternately, a Cas protein can be provided in the form of a nucleic acid encoding the Cas protein, such as an RNA (e.g., messenger RNA (mRNA)) or DNA. In some embodiments, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternately, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternately, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. In some embodiments, the promoter can be a bidirectional promoter driving expression of both a Cas protein in one direction and a guide RNA in the other direction. Such bidirectional promoters can consist of: 1) a complete, conventional, unidirectional Pol III promoter that contains 3 external control elements: a distal sequence element (DSE), a proximal sequence element (PSE), and a TATA box; and 2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. Use of a bidirectional promoter to express genes encoding a Cas protein and a guide RNA simultaneously allow for the generation of compact expression cassettes to facilitate delivery.

The present disclosure also provides guide RNA (gRNA) that binds to a Cas protein (e.g., Cas9 protein) and targets the Cas protein to a specific location within a target DNA (e.g., the B4GALT1 gene). In some embodiments, the guide RNA is effective to direct a Cas enzyme to bind to or cleave an endogenous B4GALT1 gene, wherein the guide RNA comprises a DNA-targeting a segment that hybridizes to a guide RNA recognition sequence within the endogenous B4GALT1 gene that includes or is proximate to, for example, positions 53575 to 53577 of SEQ ID NO:1. For example, the guide RNA recognition sequence can be within about 5, within about 10, within about 15, within about 20, within about 25, within about 30, within about 35, within about 40, within about 45, within about 50, within about 100, within about 200, within about 300, within about 400, within about 500, or within about 1,000 nucleotides of positions 53575 to 53577 of SEQ ID NO:1. Other exemplary guide RNAs comprise a DNA-targeting segment that hybridizes to a guide RNA recognition sequence within the endogenous B4GALT1 gene that is within a region corresponding to exon 5 of SEQ ID NO:1. Other exemplary guide RNAs comprise a DNA-targeting segment that hybridizes to a guide RNA recognition sequence within the endogenous B4GALT1 gene that includes or is proximate to the start codon of the endogenous B4GALT1 gene or includes or is proximate to the stop codon of the endogenous B4GALT1 gene. For example, the guide RNA recognition sequence can be within about 5, within about 10, within about 15, within about 20, within about 25, within about 30, within about 35, within about 40, within about 45, within about 50, within about 100, within about 200, within about 300, within about 400, within about 500, or within about 1,000 nucleotides of the start codon or within about 5, within about 10, within about 15, within about 20, within about 25, within about 30, within about 35, within about 40, within about 45, within about 50, within about 100, within about 200, within about 300, within about 400, within about 500, or within about 1,000 nucleotides of the stop codon. The endogenous B4GALT1 gene can be a B4GALT1 gene from any organism. For example, the B4GALT1 gene can be a human B4GALT1 gene or an ortholog from another organism, such as a non-human mammal, a rodent, a mouse, or a rat.

In some embodiments, guide RNA recognition sequences are present at the 5' end of the human B4GALT1 gene. In some embodiments, guide RNA recognition sequences are adjacent to the transcription start site (TSS) of the human B4GALT1 gene. In some embodiments, guide RNA recognition sequences are present at the 3' end of the human B4GALT1 gene. In some embodiments, guide RNA recognition sequences are proximate to positions 53575 to 53577 of SEQ ID NO:1. Exemplary guide RNA recognition sequences proximate to positions 53575 to 53577 of SEQ ID NO:1 include, but are not limited to, ATTAGTTTTTAGAGGCATGT (SEQ ID NO:9) and GGCTCTCAGGCCAAGTGTAT (SEQ ID NO:10) (both 5' to positions 53575 to 53577 of SEQ ID NO:1) and TACTCCTTCCCCCTTTAGGA (SEQ ID NO:11) and GTCCGAGGCTCTGGGCCTAG (SEQ ID NO:12) (both 3' to positions 53575 to 53577 of SEQ ID NO:1).

Guide RNAs can comprise two segments: a DNA-targeting segment and a protein-binding segment. Some gRNAs comprise two separate RNA molecules: an activator-RNA (e.g., tracrRNA) and a targeter-RNA (e.g., CRISPR RNA or crRNA). Other gRNAs are a single RNA molecule (single RNA polynucleotide; single-molecule gRNA, single-guide RNA, or sgRNA). For Cas9, for example, a single-guide RNA can comprise a crRNA fused to a tracrRNA (e.g., via a linker). For Cpf1, for example, only a crRNA is needed to achieve cleavage. gRNAs include both double-molecule (i.e., modular) gRNAs and single-molecule gRNAs.

The DNA-targeting segment (crRNA) of a given gRNA comprises a nucleotide sequence that is complementary to a sequence (i.e., the guide RNA recognition sequence) in a target DNA. The DNA-targeting segment of a gRNA interacts with a target DNA (e.g., the B4GALT1 gene) in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR-Cas system and organism but often contain a targeting segment from about 21 to about 72 nucleotides length, flanked by two direct repeats (DR) of a length from about 21 to about 46 nucleotides. In the case of S. pyogenes, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., U.S. Application Publication 2016/0024523. For Cas9 from S. pyogenes, a typical DNA-targeting segment is from about 16 to about 20 nucleotides in length or from about 17 to about 20 nucleotides in length. For Cas9 from S. aureus, a typical DNA-targeting segment is from about 21 to about 23 nucleotides in length. For Cpf1, a typical DNA-targeting segment is at least about 16 nucleotides in length or at least about 18 nucleotides in length.

The percent complementarity between the DNA-targeting sequence and the guide RNA recognition sequence within the target DNA can be at least about 60%, at least about 65%, at least about 70%, at least about 75%, at least about 80%, at least about 85%, at least about 90%, at least about 95%, at least about 97%, at least about 98%, at least about 99%, or 100%). The percent complementarity between the DNA-targeting sequence and the guide RNA recognition sequence within the target DNA can be at least about 60% over about 20 contiguous nucleotides. As an example, the percent complementarity between the DNA-targeting sequence and the guide RNA recognition sequence within the target DNA is about 100% over about 14 contiguous nucleotides at the 5' end of the guide RNA recognition sequence within the complementary strand of the target DNA and as low as about 0% over the remainder. In such a case, the DNA-targeting sequence can be considered to be about 14 nucleotides in length. As another example, the percent complementarity between the DNA-targeting sequence and the guide RNA recognition sequence within the target DNA is about 100% over the seven contiguous nucleotides at the 5' end of the guide RNA recognition sequence within the complementary strand of the target DNA and as low as about 0% over the remainder. In such a case, the DNA-targeting sequence can be considered to be about 7 nucleotides in length. In some guide RNAs, at least about 17 nucleotides within the DNA-target sequence are complementary to the target DNA. For example, the DNA-targeting sequence can be about 20 nucleotides in length and can comprise 1, 2, or 3 mismatches with the target DNA (the guide RNA recognition sequence). In some embodiments, the mismatches are not adjacent to a protospacer adjacent motif (PAM) sequence (e.g., the mismatches are in the 5' end of the DNA-targeting sequence, or the mismatches are at least 2, at least 3, at least 4, at least 5, at least 6, at least 7, at least 8, at least 9, at least 10, at least 11, at least 12, at least 13, at least 14, at least 15, at least 16, at least 17, at least 18, or at least 19 base pairs away from the PAM sequence).

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. For example, gRNAs can be prepared by in vitro transcription using, for example, T7 RNA polymerase. Guide RNAs can also be prepared by chemical synthesis.

The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively. When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternately, DNAs encoding gRNAs can be operably linked to a promoter in an expression construct. For example, the DNA encoding the gRNA can be in a vector comprising a heterologous nucleic acid. The vector can further comprise an exogenous donor sequence and/or the vector can further comprise a nucleic acid encoding a Cas protein. Alternately, the DNA encoding the gRNA can be in a vector or a plasmid that is separate from the vector comprising an exogenous donor sequence and/or the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem cell, or a zygote. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

The present disclosure also provides compositions comprising one or more guide RNAs (e.g., 1, 2, 3, 4, or more guide RNAs) disclosed herein and a carrier increasing the stability of the isolated nucleic acid or protein (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Examples of such carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein. Such compositions can further comprise one or more (e.g., 1, 2, 3, 4, or more) exogenous donor sequences and/or one or more (e.g., 1, 2, 3, 4, or more) targeting vectors and/or one or more (e.g., 1, 2, 3, 4, or more) expression vectors as disclosed elsewhere herein.

Guide RNA recognition sequences include nucleic acid sequences present in a target DNA (e.g., the B4GALT1 gene) to which a DNA-targeting segment of a gRNA will bind, provided sufficient conditions for binding exist. For example, guide RNA recognition sequences include sequences to which a guide RNA is designed to have complementarity, where hybridization between a guide RNA recognition sequence and a DNA targeting sequence promotes the formation of a CRISPR complex. Full complementarity is not necessarily required, provided that there is sufficient complementarity to cause hybridization and promote formation of a CRISPR complex. Guide RNA recognition sequences also include cleavage sites for Cas proteins, described in more detail below. A guide RNA recognition sequence can comprise any polynucleotide, which can be located, for example, in the nucleus or cytoplasm of a cell or within an organelle of a cell, such as a mitochondrion or chloroplast.

The guide RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions are known.

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a guide RNA recognition sequence and complexed with a Cas protein) can result in cleavage of one or both strands in or near (e.g., within 1, within 2, within 3, within 4, within 5, within 6, within 7, within 8, within 9, within 10, within 20, or within 50, or more base pairs from) the nucleic acid sequence present in a target DNA to which a DNA-targeting segment of a gRNA will bind. The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). In some embodiments, the guide RNA recognition sequence of the nickase on the first strand is separated from the guide RNA recognition sequence of the nickase on the second strand by at least 2, at least 3, at least 4, at least 5, at least 6, at least 7, at least 8, at least 9, at least 10, at least 15, at least 20, at least 25, at least 30, at least 40, at least 50, at least 75, at least 100, at least 250, at least 500, or at least 1,000 base pairs.

Site-specific cleavage of target DNA by Cas proteins can occur at locations determined by both i) base-pairing complementarity between the gRNA and the target DNA and ii) a short motif, called the protospacer adjacent motif (PAM), in the target DNA. The PAM can flank the guide RNA recognition sequence. In some embodiments, the guide RNA recognition sequence can be flanked on the 3' end by the PAM. Alternately, the guide RNA recognition sequence can be flanked on the 5' end by the PAM. For example, the cleavage site of Cas proteins can be about 1 to about 10, or about 2 to about 5 base pairs (e.g., 3 base pairs) upstream or downstream of the PAM sequence. In some cases (e.g., when Cas9 from S. pyogenes or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA. As such, the PAM sequence of the complementary strand would be 5'-$CCN_2$-3', where $N_2$ is any DNA nucleotide and is immediately 5' of the guide RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from S. aureus, the PAM can be NNGRRT (SEQ ID NO:13) or NNGRR (SEQ ID NO:14) where N can A, G, C, or T, and R can be G or A. In some cases (e.g., for FnCpf1), the PAM sequence can be upstream of the 5' end and have the sequence 5'-TTN-3'.

Examples of guide RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas9 protein, such as $GN_{19}$NGG (SEQ ID NO:15) or $N_{20}$NGG (SEQ ID NO:16) (see, e.g., PCT Publication WO 2014/165825). The guanine at the 5' end can facilitate transcription by RNA polymerase in cells. Other examples of guide RNA recognition sequences can include two guanine nucleotides at the 5' end (e.g., $GGN_{20}$NGG; SEQ ID NO:17) to facilitate efficient transcription by T7 polymerase in vitro. See, e.g., PCT Publication WO 2014/065596. Other guide RNA recognition sequences can have from about 4 to about 22 nucleotides in length, including the 5' G or GG and the 3' GG or NGG. In some embodiments, the guide RNA recognition sequences can have from about 14 to about 20 nucleotides in length.

The guide RNA recognition sequence can be any nucleic acid sequence endogenous or exogenous to a cell. The guide RNA recognition sequence can be a sequence coding a gene product (e.g., a protein) or a non-coding sequence (e.g., a regulatory sequence) or can include both.

In some embodiments, the guide RNA recognition sequence can be within a region corresponding to exon 5 of SEQ ID NO:1. In some embodiments, the guide RNA recognition sequence can includes or is proximate to positions 53575 to 53577 of SEQ ID NO:1. For example, the guide RNA recognition sequence can be within about 1000, within about 500, within about 400, within about 300, within about 200, within about 100, within about 50, within about 45, within about 40, within about 35, within about 30, within about 25, within about 20, within about 15, within about 10, or within about 5 nucleotides of the position corresponding to positions 53575 to 53577 of SEQ ID NO:1. In some embodiments, the guide RNA recognition sequence can include or be proximate to the start codon of an endogenous B4GALT1 gene or the stop codon of an endogenous B4GALT1 gene. For example, the guide RNA recognition sequence can be within about 10, within about 20, within about 30, within about 40, within about 50, within about 100, within about 200, within about 300, within about 400, within about 500, or within about 1,000 nucleotides of the start codon or the stop codon.

The methods and compositions disclosed herein can utilize exogenous donor sequences (e.g., targeting vectors or repair templates) to modify an endogenous B4GALT1 gene, either without cleavage of the endogenous B4GALT1 gene or following cleavage of the endogenous B4GALT1 gene with a nuclease agent. An exogenous donor sequence refers to any nucleic acid or vector that includes the elements that are required to enable site-specific recombination with a target sequence. Using exogenous donor sequences in combination with nuclease agents may result in more precise modifications within the endogenous B4GALT1 gene by promoting homology-directed repair.

In such methods, the nuclease agent cleaves the endogenous B4GALT1 gene to create a single-strand break (nick) or double-strand break, and the exogenous donor sequence recombines with the endogenous B4GALT1 gene via non-homologous end joining (NHEJ)-mediated ligation or through a homology-directed repair event. Repair with the exogenous donor sequence may remove or disrupt the nuclease cleavage site so that alleles that have been targeted cannot be re-targeted by the nuclease agent.

Exogenous donor sequences can comprise deoxyribonucleic acid (DNA) or ribonucleic acid (RNA), they can be single-stranded or double-stranded, and they can be in linear or circular form. For example, an exogenous donor sequence can be a single-stranded oligodeoxynucleotide (ssODN). An exemplary exogenous donor sequence is from about 50 nucleotides to about 5 kb in length, from about 50 nucleotides to about 3 kb in length, or from about 50 to about 1,000 nucleotides in length. Other exemplary exogenous donor sequences are from about 40 to about 200 nucleotides in length. For example, an exogenous donor sequence can be from about 50 to about 60, from about 60 to about 70, from about 70 to about 80, from about 80 to about 90, from about 90 to about 100, from about 100 to about 110, from about 110 to about 120, from about 120 to about 130, from about 130 to about 140, from about 140 to about 150, from about 150 to about 160, from about 160 to about 170, from about 170 to about 180, from about 180 to about 190, or from about 190 to about 200 nucleotides in length. Alternately, an exogenous donor sequence can be from about 50 to about 100, from about 100 to about 200, from about 200 to about 300, from about 300 to about 400, from about 400 to about 500, from about 500 to about 600, from about 600 to about 700, from about 700 to about 800, from about 800 to about 900, or from about 900 to about 1,000 nucleotides in length. Alternately, an exogenous donor sequence can be from about 1 kb to about 1.5 kb, from about 1.5 kb to about 2 kb, from about 2 kb to about 2.5 kb, from about 2.5 kb to about 3 kb, from about 3 kb to about 3.5 kb, from about 3.5 kb to about 4 kb, from about 4 kb to about 4.5 kb, or from about 4.5 kb to about 5 kb in length. Alternately, an exogenous donor sequence can be, for example, no more than about 5 kb, no more than about 4.5 kb, no more than about 4 kb, no more than about 3.5 kb, no more than about 3 kb, no more than about 2.5 kb, no more than about 2 kb, no more than about 1.5 kb, no more than about 1 kb, no more than about 900 nucleotides, no more than about 800 nucleotides, no more than about 700 nucleotides, no more than about 600 nucleotides, no more than about 500 nucleotides, no more than about 400 nucleotides, no more than about 300 nucleotides, no more than about 200 nucleotides, no more than about 100 nucleotides, or no more than about 50 nucleotides in length.

In some embodiments, an exogenous donor sequence is a ssODN that is from about 80 nucleotides to about 200 nucleotides in length (e.g., about 120 nucleotides in length). In another example, an exogenous donor sequences is a ssODN that is from about 80 nucleotides to about 3 kb in length. Such an ssODN can have homology arms, for example, that are each from about 40 nucleotides to about 60 nucleotides in length. Such a ssODN can also have homology arms, for example, that are each from about 30 nucleotides to 100 nucleotides in length. The homology arms can be symmetrical (e.g., each about 40 nucleotides or each about 60 nucleotides in length), or they can be asymmetrical (e.g., one homology arm that is about 36 nucleotides in length, and one homology arm that is about 91 nucleotides in length).

Exogenous donor sequences can include modifications or sequences that provide for additional desirable features (e.g., modified or regulated stability; tracking or detecting with a fluorescent label; a binding site for a protein or protein complex; and so forth). Exogenous donor sequences can comprise one or more fluorescent labels, purification tags, epitope tags, or a combination thereof. For example, an exogenous donor sequence can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and -6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor sequence that has been directly integrated into a cleaved endogenous B4GALT1 gene having protruding ends compatible with the ends of the exogenous donor sequence. The label or tag can be at the 5' end, the 3' end, or internally within the exogenous donor sequence. For example, an exogenous donor sequence can be conjugated at 5' end with the IR700 fluorophore from Integrated DNA Technologies (5'IRDYE® 700).

Exogenous donor sequences can also comprise nucleic acid inserts including segments of DNA to be integrated into the endogenous B4GALT1 gene. Integration of a nucleic acid insert in the endogenous B4GALT1 gene can result in addition of a nucleic acid sequence of interest in the endogenous B4GALT1 gene, deletion of a nucleic acid sequence of interest in the endogenous B4GALT1 gene, or replacement of a nucleic acid sequence of interest in the endogenous B4GALT1 gene (i.e., deletion and insertion). Some exogenous donor sequences are designed for insertion of a nucleic acid insert in the endogenous B4GALT1 gene without any corresponding deletion in the endogenous B4GALT1 gene. Other exogenous donor sequences are designed to delete a nucleic acid sequence of interest in the endogenous B4GALT1 gene without any corresponding insertion of a nucleic acid insert. Other exogenous donor sequences are designed to delete a nucleic acid sequence of interest in the endogenous B4GALT1 gene and replace it with a nucleic acid insert.

The nucleic acid insert and the corresponding nucleic acid in the endogenous B4GALT1 gene being deleted and/or replaced can be various lengths. An exemplary nucleic acid insert or corresponding nucleic acid in the endogenous B4GALT1 gene being deleted and/or replaced is from about 1 nucleotide to about 5 kb in length or is from about 1 nucleotide to about 1,000 nucleotides in length. For example, a nucleic acid insert or a corresponding nucleic acid in the endogenous B4GALT1 gene being deleted and/or replaced can be from about 1 to about 10, from about 10 to about 20, from about 20 to about 30, from about 30 to about 40, from about 40 to about 50, from about 50 to about 60, from about 60 to about 70, from about 70 to about 80, from about 80 to about 90, from about 90 to about 100, from about 100 to about 110, from about 110 to about 120, from about 120 to about 130, from about 130 to about 140, from about 140 to about 150, from about 150 to about 160, from about 160 to about 170, from about 170 to about 180, from about 180 to about 190, or from about 190 to about 200 nucleotides in length. Likewise, a nucleic acid insert or a corresponding nucleic acid in the endogenous B4GALT1 gene being deleted and/or replaced can be from about 1 to about 100, from about 100 to about 200, from about 200 to about 300, from about 300 to about 400, from about 400 to about 500, from about 500 to about 600, from about 600 to about 700, from about 700 to about 800, from about 800 to about 900, or from about 900 to about 1,000 nucleotides in length. Likewise, a nucleic acid insert or a corresponding nucleic acid in the endogenous B4GALT1 gene being deleted and/or replaced can be from about 1 kb to about 1.5 kb, from about 1.5 kb to about 2 kb, from about 2 kb to about 2.5 kb, from about 2.5 kb to about 3 kb, from about 3 kb to about 3.5 kb, from about 3.5 kb to about 4 kb, from about 4 kb to about 4.5 kb, or from about 4.5 kb to about 5 kb in length.

The nucleic acid insert can comprise genomic DNA or any other type of DNA. For example, the nucleic acid insert can comprise cDNA.

The nucleic acid insert can comprise a sequence that is homologous to all or part of the endogenous B4GALT1 gene (e.g., a portion of the gene encoding a particular motif or region of a B4GALT1 polypeptide). For example, the nucleic acid insert can comprise a sequence that comprises one or more point mutations (e.g., 1, 2, 3, 4, 5, or more) or one or more nucleotide insertions or deletions compared with a sequence targeted for replacement in the endogenous B4GALT1 gene.

The nucleic acid insert or the corresponding nucleic acid in the endogenous B4GALT1 gene being deleted and/or replaced can be a coding region such as an exon; a non-coding region such as an intron, an untranslated region, or a regulatory region (e.g., a promoter, an enhancer, or a transcriptional repressor-binding element); or any combination thereof.

Nucleic acid inserts can also comprise a polynucleotide encoding a selection marker. Alternately, the nucleic acid inserts can lack a polynucleotide encoding a selection marker. The selection marker can be contained in a selection cassette. In some embodiments, the selection cassette can be a self-deleting cassette. As an example, the self-deleting cassette can comprise a Cre gene (comprises two exons encoding a Cre recombinase, which are separated by an intron) operably linked to a mouse Prm1 promoter and a neomycin resistance gene operably linked to a human ubiquitin promoter. Exemplary selection markers include neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted. Examples of promoters are described elsewhere herein.

The nucleic acid insert can also comprise a reporter gene. Exemplary reporter genes include those encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. Such reporter genes can be operably linked to a promoter active in a cell being targeted. Examples of promoters are described elsewhere herein.

The nucleic acid insert can also comprise one or more expression cassettes or deletion cassettes. A particular cassette can comprise one or more of a nucleotide sequence of interest, a polynucleotide encoding a selection marker, and a reporter gene, along with various regulatory components that influence expression. Examples of selectable markers and reporter genes that can be included are discussed in detail elsewhere herein.

The nucleic acid insert can comprise a nucleic acid flanked with site-specific recombination target sequences. Alternately, the nucleic acid insert can comprise one or more site-specific recombination target sequences. Although the entire nucleic acid insert can be flanked by such site-specific recombination target sequences, any region or individual polynucleotide of interest within the nucleic acid insert can also be flanked by such sites. Site-specific recombination target sequences, which can flank the nucleic acid insert or any polynucleotide of interest in the nucleic acid insert can include, for example, loxP, lox511, lox2272, lox66, lox71, loxM2, lox5171, FRT, FRT11, FRT71, attp, att, FRT, rox, or a combination thereof. In some embodiments, the site-specific recombination sites flank a polynucleotide encoding a selection marker and/or a reporter gene contained within the nucleic acid insert. Following integration of the nucleic acid insert into the endogenous B4GALT1 gene, the sequences between the site-specific recombination sites can be removed. In some embodiments, two exogenous donor sequences can be used, each with a nucleic acid insert comprising a site-specific recombination site. The exogenous donor sequences can be targeted to 5' and 3' regions flanking a nucleic acid of interest. Following integration of the two nucleic acid inserts into the target genomic locus, the nucleic acid of interest between the two inserted site-specific recombination sites can be removed.

Nucleic acid inserts can also comprise one or more restriction sites for restriction endonucleases (i.e., restriction enzymes), which include Type I, Type II, Type III, and Type IV endonucleases. Type I and Type III restriction endonucleases recognize specific recognition sequences, but typically cleave at a variable position from the nuclease binding site, which can be hundreds of base pairs away from the cleavage site (recognition sequence). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sequences and cleave outside of the recognition sequence, Type IIb enzymes cut sequences twice with both sites outside of the recognition sequence, and Type IIs enzymes recognize an asymmetric recognition sequence and cleave on one side and at a defined distance of about 1 to about 20 nucleotides from the recognition sequence. Type IV restriction enzymes target methylated DNA.

In some embodiments, the exogenous donor sequences have short single-stranded regions at the 5' end and/or the 3' end that are complementary to one or more overhangs created by nuclease-mediated or Cas-protein-mediated cleavage at the target genomic locus (e.g., in the B4GALT1 gene). These overhangs can also be referred to as 5' and 3' homology arms. For example, some exogenous donor sequences have short single-stranded regions at the 5' end and/or the 3' end that are complementary to one or more overhangs created by Cas-protein-mediated cleavage at 5' and/or 3' target sequences at the target genomic locus. In some embodiments, such exogenous donor sequences have a complementary region only at the 5' end or only at the 3' end. For example, some such exogenous donor sequences have a complementary region only at the 5' end complementary to an overhang created at a 5' target sequence at the target genomic locus or only at the 3' end complementary to an overhang created at a 3' target sequence at the target genomic locus. Other such exogenous donor sequences have complementary regions at both the 5' and 3' ends. For example, other such exogenous donor sequences have complementary regions at both the 5' and 3' ends e.g., complementary to first and second overhangs, respectively, generated by Cas-mediated cleavage at the target genomic locus. For example, if the exogenous donor sequence is double-stranded, the single-stranded complementary regions can extend from the 5' end of the top strand of the donor sequence and the 5' end of the bottom strand of the donor sequence, creating 5' overhangs on each end. Alternately, the single-stranded complementary region can extend from the 3' end of the top strand of the donor sequence and from the 3' end of the bottom strand of the template, creating 3' overhangs.

The complementary regions can be of any length sufficient to promote ligation between the exogenous donor sequence and the endogenous B4GALT1 gene. Exemplary complementary regions are from about 1 to about 5 nucleotides in length, from about 1 to about 25 nucleotides in length, or from about 5 to about 150 nucleotides in length. For example, a complementary region can be at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides in length. Alternately, the complementary region can be about 5 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA recognition sequences corresponding with first, second, third, and fourth guide RNAs. The first and second guide RNA recognition sequences can be positioned to create a first cleavage site such that the nicks created by the first and second nickases on the first and second strands of DNA create a double-strand break (i.e., the first cleavage site comprises the nicks within the first and second guide RNA recognition sequences). Likewise, the third and fourth guide RNA recognition sequences can be positioned to create a second cleavage site such that the nicks created by the third and fourth nickases on the first and second strands of DNA create a double-strand break (i.e., the second cleavage site comprises the nicks within the third and fourth guide RNA recognition sequences). In some embodiments, the nicks within the first and second guide RNA recognition sequences and/or the third and fourth guide RNA recognition sequences can be off-set nicks that create overhangs. The offset window can be, for example, at least about 5 bp, at least about 10 bp, at least about 20 bp, at least about 30 bp, at least about 40 bp, at least about 50 bp, at least about 60 bp, at least about 70 bp, at least about 80 bp, at least about 90 bp, or at least about 100 bp or more. In such embodiments, a double-stranded exogenous donor sequence can be designed with single-stranded complementary regions that are complementary to the overhangs created by the nicks within the first and second guide RNA recognition sequences and by the nicks within the third and fourth guide RNA recognition sequences. Such an exogenous donor sequence can then be inserted by non-homologous-end-joining-mediated ligation.

In some embodiments, the exogenous donor sequences (i.e., targeting vectors) comprise homology arms. If the exogenous donor sequence also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor sequence.

A homology arm and a target sequence correspond to one another when the two regions share a sufficient level of sequence identity to one another to act as substrates for a homologous recombination reaction. The sequence identity between a particular target sequence and the corresponding homology arm found in the exogenous donor sequence can be any degree of sequence identity that allows for homologous recombination to occur. For example, the amount of sequence identity shared by the homology arm of the exogenous donor sequence (or a fragment thereof) and the target sequence (or a fragment thereof) can be at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity, such that the sequences undergo homologous recombination. Moreover, a corresponding region of homology between the homology arm and the corresponding target sequence can be of any length that is sufficient to promote homologous recombination. Exemplary homology arms are from about 25 nucleotides to about 2.5 kb in length, from about 25 nucleotides to about 1.5 kb in length, or from about 25 to about 500 nucleotides in length. For example, a given homology arm (or each of the homology arms) and/or corresponding target sequence can comprise corresponding regions of homology that are from about 25 to about 30, from about 30 to about 40, from about 40 to about 50, from about 50 to about 60, from about 60 to about 70, from about 70 to about 80, from about 80 to about 90, from about 90 to about 100, from about 100 to about 150, from about 150 to about 200, from about 200 to about 250, from about 250 to about 300, from about 300 to about 350, from about 350 to about 400, from about 400 to about 450, or from about 450 to about 500 nucleotides in length, such that the homology arms have sufficient homology to undergo homologous recombination with the corresponding target sequences within the endogenous B4GALT1 gene. Alternately, a particular homology arm (or each homology arm) and/or corresponding target sequence can comprise corresponding regions of homology that are from about 0.5 kb to about 1 kb, from about 1 kb to about 1.5 kb, from about 1.5 kb to about 2 kb, or from about 2 kb to about 2.5 kb in length. For example, the homology arms can each be about 750 nucleotides in length. The homology arms can be symmetrical (each about the same size in length), or they can be asymmetrical (one longer than the other).

The homology arms can correspond to a locus that is native to a cell (e.g., the targeted locus). Alternately, they can correspond to a region of a heterologous or exogenous segment of DNA that was integrated into the genome of the cell, including, for example, transgenes, expression cassettes, or heterologous or exogenous regions of DNA. In some embodiments, the homology arms of the targeting vector can correspond to a region of a yeast artificial chromosome (YAC), a bacterial artificial chromosome (BAC), a human artificial chromosome, or any other engineered region contained in an appropriate host cell. In some embodiments, the homology arms of the targeting vector can correspond to or be derived from a region of a BAC library, a cosmid library, or a P1 phage library, or can be derived from synthetic DNA.

When a nuclease agent is used in combination with an exogenous donor sequence, the 5' and 3' target sequences are generally located in sufficient proximity to the nuclease cleavage site so as to promote the occurrence of a homologous recombination event between the target sequences and the homology arms upon a single-strand break (nick) or double-strand break at the nuclease cleavage site. Nuclease cleavage sites include a DNA sequence at which a nick or double-strand break is created by a nuclease agent (e.g., a Cas9 protein complexed with a guide RNA). The target sequences within the endogenous B4GALT1 gene that correspond to the 5' and 3' homology arms of the exogenous donor sequence are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous donor sequence can be, for example, within at least 1 nucleotide of a given nuclease cleavage site or within at least 10 nucleotides to about 1,000 nucleotides of a particular nuclease cleavage site. In some embodiments, the nuclease cleavage site can be immediately adjacent to at least one or both of the target sequences.

The spatial relationship of the target sequences that correspond to the homology arms of the exogenous donor sequence and the nuclease cleavage site can vary. In some embodiments, the target sequences can be located 5' to the nuclease cleavage site, target sequences can be located 3' to the nuclease cleavage site, or the target sequences can flank the nuclease cleavage site.

The present disclosure also provides therapeutic methods and methods of treatment or prophylaxis of a cardiovascular condition in a subject having or at risk of having the disease using the methods disclosed herein for modifying or altering expression of an endogenous B4GALT1 gene. The present disclosure also provides therapeutic methods and methods of treatment or prophylaxis of a cardiovascular condition in a subject having or at risk for the disease using methods for decreasing expression of endogenous B4GALT1 mRNA or using methods for providing recombinant nucleic acids encoding B4GALT1 polypeptides, providing mRNAs encoding B4GALT1 polypeptides, or providing B4GALT1 polypeptides to the subject. The methods can comprise introducing one or more nucleic acid molecules or proteins into the subject, into an organ of the subject, or into a cell of the subject (e.g., in vivo or ex vivo).

In some embodiments, the disclosure provides mRNAs encoding B4GALT1 polypeptides (e.g. polynucleotides as discussed herein, for example an mRNA that comprises the sequence of SEQ ID NO:4) for use in therapy. In some such embodiments, the therapy is treating or preventing a cardiovascular condition.

In some embodiments, the disclosure provides B4GALT1 polypeptides (e.g. polypeptides as discussed herein, for example polypeptides that comprise the sequence of SEQ ID NO:8) for use in therapy. In some such embodiments the therapy is treating or preventing a cardiovascular condition.

Subjects include human and other mammalian subjects (e.g., feline, canine, rodent, mouse, or rat) or non-mammalian subjects (e.g., poultry) that receive either prophylactic or therapeutic treatment. Such subjects can be, for example, a subject (e.g., a human) who is not a carrier of the variant B4GALT1 (or is only a heterozygous carrier of the variant B4GALT1) and has or is susceptible to developing a cardiovascular condition.

Non-limiting examples of a cardiovascular condition include an elevated level of one or more serum lipids. The serum lipids comprise one or more of cholesterol, LDL, HDL, triglycerides, HDL-cholesterol, and non-HDL cholesterol, or any subfraction thereof (e.g., HDL2, HDL2a, HDL2b, HDL2c, HDL3, HDL3a, HDL3b, HDL3c, HDL3d, LDL1, LDL2, LDL3, lipoprotein A, Lpa1, Lpa1, Lpa3, Lpa4, or Lpa5). A cardiovascular condition may comprise elevated levels of coronary artery calcification. A cardiovascular condition may comprise Type IId glycosylation (CDG-IId). A cardiovascular condition may comprise elevated levels of pericardial fat. A cardiovascular condition may comprise an atherothrombotic condition. The atherothrombotic condition may comprise elevated levels of fibrinogen. The atherothrombotic condition may comprises a fibrinogen-mediated blood clot. A cardiovascular condition may comprise elevated levels of fibrinogen. A cardiovascular condition may comprise a fibrinogen-mediated blood clot. A cardiovascular condition may comprise a blood clot formed from the involvement of fibrinogen activity. A fibrinogen-mediated blood clot or blood clot formed from the involvement of fibrinogen activity may be in any vein or artery in the body.

Such methods can comprise genome editing or gene therapy. For example, an endogenous B4GALT1 gene that is not the variant B4GALT1 can be modified to comprise the variation associated with the variant B4GALT1 (i.e., replacement of asparagine with a serine at the position corresponding to position 352 of the full length/mature B4GALT1 polypeptide). As another example, an endogenous B4GALT1 gene that is not the variant B4GALT1 can be knocked out or inactivated. Likewise, an endogenous B4GALT1 gene that is not the variant B4GALT1 can be knocked out or inactivated, and an B4GALT1 gene comprising the modification associated with the variant B4GALT1 (e.g., the complete variant B4GALT1 or a minigene comprising the modification) can be introduced and expressed. Similarly, an endogenous B4GALT1 gene that is not the variant B4GALT1 can be knocked out or inactivated, and a recombinant DNA encoding the B4GALT1 variant polypeptide can be introduced and expressed, an mRNA encoding the B4GALT1 variant polypeptide can be introduced and expressed (e.g., intracellular protein replacement therapy), and/or a variant B4GALT1 polypeptide can be introduced (e.g., protein replacement therapy).

In some embodiments, the methods comprise introducing and expressing a recombinant B4GALT1 gene comprising the modification associated with the B4GALT1 rs551564683 variant (e.g., the complete variant B4GALT1 or a minigene comprising the modification), introducing and expressing recombinant nucleic acids (e.g., DNA) encoding the variant B4GALT1 polypeptide or fragments thereof, introducing and expressing one or more mRNAs encoding the variant B4GALT1 polypeptide or fragments thereof (e.g., intracellular protein replacement therapy), or introducing the variant B4GALT1 polypeptide or fragments thereof (e.g., protein replacement therapy) without knocking out or inactivating an endogenous B4GALT1 gene that is not the variant B4GALT1. In some embodiments, such methods can also be carried out in combination with methods in which endogenous B4GALT1 mRNA that is not the variant B4GALT1 is targeted for reduced expression, such as through use of antisense RNA, siRNA, or shRNA.

A B4GALT1 gene or minigene or a DNA encoding the variant B4GALT1 polypeptide or fragments thereof can be introduced and expressed in the form of an expression vector that does not modify the genome, it can be introduced in the form of a targeting vector such that it genomically integrates into an endogenous B4GALT1 locus, or it can be introduced such that it genomically integrates into a locus other than the endogenous B4GALT1 locus, such as a safe harbor locus. The genomically integrated B4GALT1 gene can be operably linked to a B4GALT1 promoter or to another promoter, such as an endogenous promoter at the site of integration. Safe harbor loci are chromosomal sites where transgenes can be stably and reliably expressed in all tissues of interest without adversely affecting gene structure or expression. Safe harbor loci can have, for example, one or more or all of the following characteristics: 1) a distance of greater than about 50 kb from the 5' end of any gene; a distance of greater than about 300 kb from any cancer-related gene; a distance of greater than about 300 kb from any microRNA; outside a gene transcription unit, and outside of ultra-conserved regions. Examples of suitable safe harbor loci include, but are not limited to, adeno-associated virus site 1 (AAVS1), the chemokine (CC motif) receptor 5 (CCR5) gene locus, and the human orthologue of mouse ROSA26 locus.

In some embodiments, the methods comprise a method of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject: a) a nuclease agent (or nucleic acid encoding) that binds to a nuclease recognition sequence within an endogenous B4GALT1 gene, wherein the nuclease recognition sequence includes or is proximate to positions 53575 to 53577 of SEQ ID NO:1; and b) an exogenous donor sequence comprising a 5' homology arm that hybridizes to a target sequence 5' of positions 53575 to 53577 of SEQ ID NO:1, and a nucleic acid insert comprising a nucleic acid sequence encoding a serine flanked by the 5' homology arm and the 3' homology arm. The nuclease agent can cleave the endogenous B4GALT1 gene in a cell in the subject, and the exogenous donor sequence can recombine with the endogenous B4GALT1 gene in the cell, wherein upon recombination of the exogenous donor sequence with the endogenous B4GALT1 gene, the nucleic acid sequence encoding a serine is inserted at nucleotides corresponding to positions 53575 to 53577 of SEQ ID NO:1. Examples of nuclease agents (e.g., a Cas9 protein and a guide RNA) that can be used in such methods are disclosed elsewhere herein.

In some embodiments, the methods comprise a method of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject an exogenous donor sequence comprising a 5' homology arm that hybridizes to a target sequence 5' of the position corresponding to positions 53575 to 53577 of SEQ ID NO:1, a 3' homology arm that hybridizes to a target sequence 3' of positions 53575 to 53577 of SEQ ID NO:1, and a nucleic acid insert comprising a nucleotide sequence encoding a serine flanked by the 5' homology arm and the 3' homology arm. The exogenous donor sequence can recombine with the endogenous B4GALT1 gene in the cell, wherein upon recombination of the exogenous donor sequence with the endogenous B4GALT1 gene, the nucleotide sequence encoding a serine is inserted at nucleotides corresponding to positions 53575 to 53577 of SEQ ID NO:1.

Some such methods comprise a method of treating a subject who is not a carrier of the variant B4GALT1 ant (or is only a heterozygous carrier of the variant B4GALT1) and has or is susceptible to developing a cardiovascular condition, comprising introducing into the subject or introducing into a cell in the subject: a) a nuclease agent (or nucleic acid encoding) that binds to a nuclease recognition sequence within an endogenous B4GALT1 gene, wherein the nuclease recognition sequence comprises the start codon for the endogenous B4GALT1 gene or is within about 10, about 20, about 30, about 40, about 50, about 100, about 200, about 300, about 400, about 500, or about 1,000 nucleotides of the start codon or is selected from SEQ ID NOS:9-12. The nuclease agent can cleave and disrupt expression of the endogenous B4GALT1 gene in a cell in the subject.

In some embodiments, the methods comprise a method of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject: a) a nuclease agent (or nucleic acid encoding) that binds to a nuclease recognition sequence within an endogenous B4GALT1 gene, wherein the nuclease recognition sequence comprises the start codon for the endogenous B4GALT1 gene or is within about 10, within about 20, within about 30, within about 40, within about 50, within about 100, within about 200, within about 300, within about 400, within about 500, or within about 1,000 nucleotides of the start codon or is selected from SEQ ID NOS:9-12; and b) an expression vector comprising a recombinant B4GALT1 gene comprising a nucleotide sequence at positions 53575 to 53577 encoding a serine at the position corresponding to position 352 of the full length/mature B4GALT1 polypeptide. The expression vector can be one that does not genomically integrate. Alternately, a targeting vector (i.e., exogenous donor sequence) can be introduced comprising a recombinant B4GALT1 gene comprising a nucleotide sequence at positions 53575 to 53577 encoding a serine at the position corresponding to position 352 of the full length/mature B4GALT1 polypeptide. The nuclease agent can cleave and disrupt expression of the within B4GALT1 gene in a cell in the subject, and the expression vector can express the recombinant B4GALT1 gene in the cell in the subject.

Alternately, the genomically integrated, recombinant B4GALT1 gene can be expressed in the cell in the subject. Examples of nuclease agents (e.g., a nuclease-active Cas9 protein and guide RNA) that can be used in such methods are disclosed elsewhere herein. Examples of suitable guide RNAs and guide RNA recognition sequences are also disclosed elsewhere herein. Step b) can alternately comprise introducing an expression vector or targeting vector comprising a nucleic acid (e.g., DNA) encoding a B4GALT1 polypeptide that is at least 90%, at least 95%, at least 96%, at least 97%, at least 98%, at least 99%, or 100% identical to the variant B4GALT1 Asn352Ser polypeptide or a fragment thereof and/or comprising a sequence that is at least 90%, at least 95%, at least 96%, at least 97%, at least 98%, at least 99%, or 100% identical to the variant B4GALT1 mRNA or a fragment thereof. Likewise, step b) can also comprise introducing an mRNA encoding a B4GALT1 Asn352Ser polypeptide that is at least 90%, at least 95%, at least 96%, at least 97%, at least 98%, at least 99%, or 100% identical to the variant B4GALT1 Asn352Ser polypeptide or a fragment thereof and/or having a complementary DNA (or a portion thereof) that is at least 90%, at least 95%, at least 96%, at least 97%, at least 98%, at least 99%, or 100% identical to the variant B4GALT1 mRNA or a fragment thereof. Likewise, step b) can also comprise introducing a protein comprising an amino acid sequence that is at least 90%, at least 95%, at least 96%, at least 97%, at least 98%, at least 99%, or 100% identical to the variant B4GALT1 Asn352Ser polypeptide or a fragment thereof.

In some embodiments, a second nuclease agent is also introduced into the subject or into the cell in the subject, wherein the second nuclease agent binds to a second nuclease recognition sequence within the endogenous B4GALT1 gene, wherein the second nuclease recognition sequence comprises the stop codon for the endogenous B4GALT1 gene or is within about 10, within about 20, within about 30, within about 40, within about 50, within about 100, within about 200, within about 300, within about 400, within about 500, or within about 1,000 nucleotides of the stop codon or is selected from SEQ ID NOS:9-12, wherein the nuclease agent cleaves the endogenous B4GALT1 gene in the cell within both the first nuclease recognition sequence and the second nuclease recognition sequence, wherein the cell is modified to comprise a deletion between the first nuclease recognition sequence and the second nuclease recognition sequence. In some embodiments, the second nuclease agent can be a Cas9 protein and a guide RNA. Suitable guide RNAs and guide RNA recognition sequences in proximity to the stop codon are disclosed elsewhere herein.

In some embodiments, the methods can also comprise a method of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject: an antisense RNA, an siRNA, or an shRNA that hybridizes to a sequence within a region of within endogenous B4GALT1 mRNA. For example, the antisense RNA, siRNA, or shRNA can hybridize to sequence within a region in exon 5 of SEQ ID NO:3 (B4GALT1 mRNA) and decrease expression of B4GALT1 mRNA in a cell in the subject. In some embodiments, such methods can further comprise introducing into the subject an expression vector comprising a recombinant B4GALT1 gene comprising a nucleotide sequence encoding a serine inserted at positions 53575 to 53577 of SEQ ID NO:2. The expression vector can be one that does not genomically integrate. Alternately, a targeting vector (i.e., exogenous donor sequence) can be introduced comprising a recombinant B4GALT1 gene comprising nucleic acid sequence encoding a serine at positions corresponding to positions 53575 to 53577 of SEQ ID NO:2. In methods in which an expression vector is used, the expression vector can express the recombinant B4GALT1 gene in the cell in the subject. Alternately, in methods in which a recombinant B4GALT1 gene is genomically integrated, the recombinant B4GALT1 gene can express in the cell in the subject.

In some embodiments, such methods can alternately comprise introducing an expression vector or targeting vector comprising a nucleic acid (e.g., DNA) encoding a B4GALT1 polypeptide that is at least 90%, at least 95%, at least 96%, at least 97%, at least 98%, at least 99%, or 100% identical to the variant B4GALT1 Asn352Ser polypeptide or a fragment thereof and/or comprising a sequence that is at least 90%, at least 95%, at least 96%, at least 97%, at least 98%, at least 99%, or 100% identical to variant B4GALT1 mRNA or a fragment thereof. Likewise, such methods can alternately comprise introducing an mRNA encoding a polypeptide that is at least 90%, at least 95%, at least 96%, at least 97%, at least 98%, at least 99%, or 100% identical to the variant B4GALT1 Asn352Ser polypeptide or a fragment thereof and/or having a complementary DNA (or a portion thereof) that is at least 90%, at least 95%, at least 96%, at least 97%, at least 98%, at least 99%, or 100% identical to the variant B4GALT1 mRNA or a fragment thereof. Likewise, such methods can alternately comprise introducing a polypeptide comprising a sequence that is at least 90%, at least 95%, at least 96%, at least 97%, at least 98%, at least 99%, or 100% identical to the variant B4GALT1 Asn352Ser polypeptide or a fragment thereof.

In some embodiments, such methods can comprise methods of treating a subject who is not a carrier of the variant B4GALT1 (or is only a heterozygous carrier of the variant B4GALT1) and has or is susceptible to developing a cardiovascular condition, comprising introducing into the subject or introducing into a cell in the subject an expression vector, wherein the expression vector comprises a recombinant B4GALT1 gene comprising a nucleotide sequence at positions 53575 to 53577 that encode a serine at the position corresponding to position 352 of the full length/mature B4GALT1 polypeptide, wherein the expression vector expresses the recombinant B4GALT1 gene in a cell in the subject. The expression vector can be one that does not genomically integrate. Alternately, a targeting vector (i.e., exogenous donor sequence) can be introduced comprising a recombinant B4GALT1 gene comprising a nucleotide sequence at positions 53575 to 53577 of SEQ ID NO:2 that encode a serine at the position corresponding to position 352 of the full length/mature B4GALT1 polypeptide. In methods in which an expression vector is used, the expression vector can express the recombinant B4GALT1 gene in the cell in the subject. Alternately, in methods in which a recombinant B4GALT1 gene is genomically integrated, the recombinant B4GALT1 gene can express in the cell in the subject.

Such methods can alternately comprise introducing an expression vector or targeting vector comprising a nucleic acid (e.g., DNA) encoding a B4GALT1 polypeptide that is at least 90%, at least 95%, at least 96%, at least 97%, at least 98%, at least 99%, or 100% identical to the variant B4GALT1 Asn352Ser polypeptide or a fragment thereof and/or comprising a sequence that is at least 90%, at least 95%, at least 96%, at least 97%, at least 98%, at least 99%, or 100% identical to the variant B4GALT1 mRNA or a fragment thereof. Likewise, such methods can alternately comprise introducing an mRNA encoding a polypeptide that is at least 90%, at least 95%, at least 96%, at least 97%, at least 98%, at least 99%, or 100% identical to the variant B4GALT1 polypeptide or a fragment thereof and/or having a complementary DNA (or a portion thereof) that is at least 90%, at least 95%, at least 96%, at least 97%, at least 98%, at least 99%, or 100% identical to the variant B4GALT1 mRNA or a fragment thereof. Likewise, such methods can alternately comprise introducing a protein comprising a sequence that is at least 90%, at least 95%, at least 96%, at least 97%, at least 98%, at least 99%, or 100% identical to the variant B4GALT1 Asn352Ser polypeptide or a fragment thereof.

Suitable expression vectors and recombinant B4GALT1 genes for use in any of the above methods are disclosed elsewhere herein. For example, the recombinant B4GALT1 gene can be the complete B4GALT1 variant gene or can be a B4GALT1 minigene in which one or more nonessential segments of the gene have been deleted with respect to a corresponding wild-type B4GALT1 gene. As an example, the deleted segments can comprise one or more intronic sequences, and the minigene can comprise exons 1 through 6. An example of a complete B4GALT1 variant gene is one that is at least 90%, at least 95%, at least 96%, at least 97%, at least 98%, at least 99%, or 100% identical to SEQ ID NO:2.

In some embodiments, such methods comprise a method of modifying a cell in a subject having or susceptible to developing a cardiovascular condition. In such methods, the nuclease agents and/or exogenous donor sequences and/or recombinant expression vectors can be introduced into the cell via administration in an effective regime meaning a dosage, route of administration and frequency of administration that delays the onset, reduces the severity, inhibits further deterioration, and/or ameliorates at least one sign or symptom of a cardiovascular condition being treated. The term "symptom" refers to a subjective evidence of a disease as perceived by the subject, and a "sign" refers to objective evidence of a disease as observed by a physician. If a subject is already suffering from a disease, the regime can be referred to as a therapeutically effective regime. If the subject is at elevated risk of the disease relative to the general population but is not yet experiencing symptoms, the regime can be referred to as a prophylactically effective regime. In some instances, therapeutic or prophylactic efficacy can be observed in an individual patient relative to historical controls or past experience in the same subject. In other instances, therapeutic or prophylactic efficacy can be demonstrated in a preclinical or clinical trial in a population of treated subjects relative to a control population of untreated subjects.

Delivery can be any suitable method, as disclosed elsewhere herein. For example, the nuclease agents or exogenous donor sequences or recombinant expression vectors can be delivered by, for example, vector delivery, viral delivery, particle-mediated delivery, nanoparticle-mediated delivery, liposome-mediated delivery, exosome-mediated delivery, lipid-mediated delivery, lipid-nanoparticle-mediated delivery, cell-penetrating-peptide-mediated delivery, or implantable-device-mediated delivery. Specific examples include hydrodynamic delivery, virus-mediated delivery, and lipid-nanoparticle-mediated delivery.

Administration can be by any suitable route including, but not limited to, parenteral, intravenous, oral, subcutaneous, intra-arterial, intracranial, intrathecal, intraperitoneal, topical, intranasal, or intramuscular. A specific example which is often used, for example, for protein replacement therapies is intravenous infusion. The frequency of administration and the number of dosages can depend on the half-life of the nuclease agents or exogenous donor sequences or recombinant expression vectors, the condition of the subject, and the route of administration among other factors. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

Other such methods comprise an ex vivo method in a cell from a subject having or susceptible to developing a cardiovascular condition. The cell with the targeted genetic modification can then be transplanted back into the subject.

The present disclosure provides methods of decreasing LDL in a subject in need thereof, by reducing expression of endogenous wild-type B4GALT1 or increasing expression of B4GALT1 Asn352Ser, by any of the methods described herein. The present disclosure provides methods of decreasing total cholesterol in a subject in need thereof, by reducing expression of endogenous wild-type B4GALT1 or increasing expression of B4GALT1 Asn352Ser, by any of the methods described herein. The present disclosure provides methods of decreasing fibrinogen in a subject in need thereof, by reducing expression of endogenous wild-type B4GALT1 or increasing expression of B4GALT1 Asn352Ser, by any of the methods described herein. The present disclosure provides methods of decreasing eGFR in a subject in need thereof, by reducing expression of endogenous wild-type B4GALT1 or increasing expression of B4GALT1 Asn352Ser, by any of the methods described herein. The present disclosure provides methods of increasing AST, but not ALT, in a subject in need thereof, by reducing expression of endogenous wild-type B4GALT1 or increasing expression of B4GALT1 Asn352Ser, by any of the methods described herein. The present disclosure provides methods of increasing creatinine in a subject in need thereof, by reducing expression of endogenous wild-type B4GALT1 or increasing expression of B4GALT1 Asn352Ser, by any of the methods described herein.

The present disclosure also provides methods of diagnosing the risk of developing a cardiovascular condition, or diagnosing the risk of developing a cardiovascular condition and treating the same in a subject in need thereof, comprising: requesting a test providing the results of an analysis of a sample from the subject for the presence or absence of variant B4GALT1 gene, mRNA, cDNA, or polypeptide, as described herein; and, in those subjects not having the variant B4GALT1 gene, mRNA, cDNA, or polypeptide, administering a therapeutic agent, such as described herein, to the subject. Any of the tests described herein whereby the presence or absence of variant B4GALT1 gene, mRNA, cDNA, or polypeptide is determined can be used.

The present disclosure also provides uses of any of the variant B4GALT1 genes, mRNAs, cDNAs, polypeptides, and hybridizing nucleic acid molecules disclosed herein in the manufacture of a medicament for decreasing LDL, decreasing total cholesterol, decreasing fibrinogen, decreasing eGFR, increasing AST (but not ALT), and increasing creatinine in a subject in need thereof. The present disclosure also provides uses of any of the variant B4GALT1 genes, mRNAs, cDNAs, polypeptides, and hybridizing nucleic acid molecules in the manufacture of a medicament for treating coronary artery disease, coronary artery calcification, and related disorders.

The present disclosure also provides uses of any of the variant B4GALT1 genes, mRNAs, cDNAs, polypeptides, and hybridizing nucleic acid molecules disclosed herein for decreasing LDL, decreasing total cholesterol, decreasing fibrinogen, decreasing eGFR, increasing AST (but not ALT), and increasing creatinine in a subject in need thereof.

The present disclosure also provides uses of any of the variant B4GALT1 genes, mRNAs, cDNAs, polypeptides, and hybridizing nucleic acid molecules for treating coronary artery disease, coronary artery calcification, Type IId glycosylation (CDG-IId), and related disorders.

The present disclosure also provides uses of any of the variant B4GALT1 genes, mRNAs, cDNAs, polypeptides, and hybridizing nucleic acid molecules disclosed herein for modifying a B4GALT1 gene in a cell in a subject in need thereof.

The present disclosure also provides uses of any of the variant B4GALT1 genes, mRNAs, cDNAs, polypeptides, and hybridizing nucleic acid molecules disclosed herein for altering expression of a B4GALT1 gene in a cell in a subject in need thereof.

The present disclosure also provides uses of any of the variant B4GALT1 genes, mRNAs, cDNAs, polypeptides, and hybridizing nucleic acid molecules disclosed herein for diagnosing the risk of developing any of the cardiovascular conditions disclosed herein.

The present disclosure also provides uses of any of the variant B4GALT1 genes, mRNAs, cDNAs, polypeptides, and hybridizing nucleic acid molecules disclosed herein for diagnosing a subject of having any of the cardiovascular conditions disclosed herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The nucleotide and amino acid sequences recited herein are shown using standard letter abbreviations for nucleotide bases, and one-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

The following examples are provided to describe the embodiments in greater detail. They are intended to illustrate, not to limit, the claimed embodiments.

EXAMPLES

Example 1: Determination of a Novel Locus on Chromosome 9p.21 Associated with Serum Lipid Traits at Genome-Wide Statistical Significance Materials and Methods:

Chip Genotyping and QC:

Genomic DNA was extracted from whole blood from individuals of the OOA, and quantitated using picogreen. Genome-wide genotyping was performed with Affymetrix 500K and 6.0 chips at the University of Maryland Biopolymer Core Facility. The BRLMM algorithm was used for genotype calling. Samples with call rate <0.93, high level of Mendelian error, or gender mismatch were excluded. SNPs with call rate <0.95, HWEpval<1.0E-6, or MAF<0.01 were excluded. SNPs on chromosomes X and Y, and the mitochondrial genome were also excluded.

WGS and QC:

Library preparation and whole genome sequencing was performed by the Broad Institute of MIT and Harvard. The NHLBI Informatics Resource Core at the University of Michigan performed alignment, base calling, and sequence quality scoring of all TOPMed samples and delivered bcf files for all variants passing all quality filters with read depth at least 10, which was used for the analysis. Further QC applied to this files including removing all sites in LCR, or X chromosomes. Variants with >5% missing rates, HWE p-value <1.0E-09 and MAF<0.1% were also removed. Sample QC was performed to remove samples with >5% missing rates, high level of Mendelian error (in some instances), or identical (MZ) twins (one of each pair).

WES and QC:

Exome capturing and sequencing was performed at the Regeneron Genetics Center (RGC) as described below in more detail. Briefly, the captured libraries were sequenced on the Illumina HiSeq 2500 platform with v4 chemistry using paired-end 75 bp reads. Paired-end sequencing of the captured bases was performed so that >85% of the bases were covered at 20× or greater, which is sufficient for calling heterozygous variants across most of the targeted bases. Read alignment and variant calling were performed using BWA-MEM and GATK as implemented in the RGC DNAseq analysis pipeline. Samples with call rate <0.90, high level of Mendelian errors, identical (MZ) twins (one of each pair), or gender mismatch were excluded. SNPs with call rate <0.90, and monomorphic SNPs were also excluded. SNPs in chromosomes X and Y, and the mitochondrial genome were also excluded.

Association Analysis:

Fasting blood samples were collected and used for lipid analysis. LDL was calculated using the Friedewald formula, and in some analyses with subjects on lipid lowering medication adjusted by dividing their LDL levels by 0.7. The genetic association analysis was performed using linear mixed models to account for familial correlation using the pedigree based kinship matrix and/or familial correction that estimates kinship from WES. The analysis was also adjusted for age, age squared, sex, cohort, and APOB R3527Q genotype. APOB R3527Q is enriched in the Amish and was previously identified to have a strong effect on LDL levels (58 mg/dl) (Shen et al., Arch Intern. Med., 2010, 170, 1850-1855), and, therefore, the effect of this variant in the LDL analysis was taken into consideration. Genome-wide corrected p-value of 5.0E-08 was used as the significance threshold.

Identifying the Association Between Chromosome 9p Region and LDL Using Genome Wide Association Study (GWAS):

To identify causative variants in novel genes associated with cardiovascular risk factors, a genome-wide association analysis was performed using 1852 Old Order Amish subjects genotyped with Affymetrix 500K and 6.0 chips. The basic characteristics of these participants are shown in Table 1.

TABLE 1

Basic characteristics of the study populations

| | GWAS Discovery | WGS Fine mapping | WES Confirmation |
|---|---|---|---|
| N | 1852 | 1083 | 4565 |
| Male (%) | 48 | 50 | 43 |
| Age (years) | 51.1 ± 16.3 | 50.4 ± 16.8 | 41.7 ± 15.2 |
| BMI (kg/m$^2$) | 27.4 ± 5.0 | 26.9 ± 4.5 | 26.6 ± 4.9 |
| SBP (mmHg) | 121.1 ± 16.0 | 120.9 ± 15.6 | 115.1 ± 16.1 |
| DBP (mmHg) | 73.6 ± 9.4 | 74.4 ± 9.6 | 71.6 ± 9.6 |
| Cholesterol (mg/dl) | 210.6 ± 46.3 | 211.8 ± 46.9 | 208.2 ± 49.2 |
| HDL (mg/dl) | 56.1 ± 14.8 | 55.9 ± 15.6 | 60.9 ± 16.4 |
| LDL (mg/dl) | 138.2 ± 42.1 | 140.4 ± 43.2 | 132.7 ± 44.9 |
| Triglycerides (mg/dl) | 80.4 ± 53.0 | 77.7 ± 48.8 | 72.1 ± 45.6 |
| Cholesterol lowering med. (%) | 2.4 | 3.2 | 1.9 |
| Diabetes (%) | 2.6 | 2.4 | 2.2 |

Almost all of WGS fine mapping samples (96%) were included in GWAS discovery samples.

Only 30% of WES samples were included in GWAS or WGS samples.

As shown in FIG. 1, a strong novel association signal between LDL and a locus on chromosome 9p was discovered. The lead associated SNP was rs855453 (p=2.2E-08) and had a frequency of 15% in the Amish and 25% in the general population. The minor 'T' allele was associated with a 10 mg/dl lower LDL level. Thus, this GWAS SNP is common in both Amish and non-Amish and has large effect size, but has never been identified in any of the large GWAS meta analyses. These characteristics match those of previous studies (APOC3 and LIPE), and based on that it was concluded that this GWAS SNP was not the causal/functional variant in this region but rather in linkage disequilibrium (LD) with another variant that is rare in the general population but common in the Amish population. Furthermore, multiple studies based on 5 independent crosses of multiple strains also found the syntenic region of the rat genome, located on rat chromosome 5, harbors a QTL for serum cholesterol and triglyceride level (The Rat Genome Database (RGD). ScI12.26. 35. 44, 54 and StI 28).

Confirmation Using Whole Exome Sequencing (WES):

High quality QC'd WES for 4,565 Amish individuals, the basic characteristics of which are shown in Table 1, were subsequently used. The results of a mixed model exome wide analysis of LDL identified the B4GALT1 rs551564683 missense variant as the most significant association with a p-value of 3.3E-18 and effect size of 14.7 mg/dl lower LDL. The rs551564683 variant had a MAF of 6% in the Amish while extremely rare in the general population. The variant is in dbSNP without frequency or population information, does not exist in the ExAC database (60,000 samples), and only one copy was found in the WGS from 15,387 non-Amish in the NHLBI Trans-Omics for Precision Medicine (TOPMed) dataset. Moreover, in a collective data set of other population cohorts available to the investigators—totaling 125,401 individuals—only 79 heterozygotes and 5 homozygotes of this variant were found (showing over one thousand-fold enrichment in the Amish population). This missense variant is 500 Kb away from the GWAS variant with an r2 estimate of LD of 0.5. There are no perfectly correlated variants with rs551564683; in fact, the next most significant SNP is rs149557496 with p-value E-14. Thus, not only does the strength of the rs551564683 association confirm that the chromosome 9 GWAS locus is real, but rs551564683 has all the characteristics expected of the casual variant.

Fine-Mapping the Chromosome 9p Region Using Whole Genome Sequencing (WGS):

WGS available on a smaller sample was used to fill in the gaps in the exome sequencing to provide further evidence that rs551564683 is causal. WGS data for 1083 OOA was generated as part of the TOPMed program. Basic characteristics of the WGS samples are shown in Table 1. WGS captures all the SNPs and Indels (insertion/deletion)—both coding and non-coding—that might be correlated with the top variants in the region of interest. Since the top variants are ~6% frequency, it is very unlikely there would be insufficient sequence reads to cause the variant caller to miss a variant. However, there may be variants excluded during the QC procedure. By investigating the variants that did not pass QC, 2 additional variants were added in the analysis. The association analysis identified the missense SNP (N352S) rs551564683 in the B4GALT1 gene as the most significantly associated variant with LDL in this region with p-value of 2.9E-06 and effect size of −16.4 mg/dl (see, Table 2).

TABLE 2

Mean (n) LDL levels (mg/dl) by rs551564683-containing genotype in the OOA

| Cohort | TT | TC | CC | p-value |
|---|---|---|---|---|
| WES Confirmation (n = 4,565) | 135 (n = 4025) | 118 (n = 529) | 103 (n = 12) | $3.3 \times 10^{-18}$ |
| WGS Fine mapping (n = 1,083) | 144 (n = 952) | 128 (n = 130) | 87 (n = 1) | $2.9 \times 10^{-6}$ |

Figure 2:
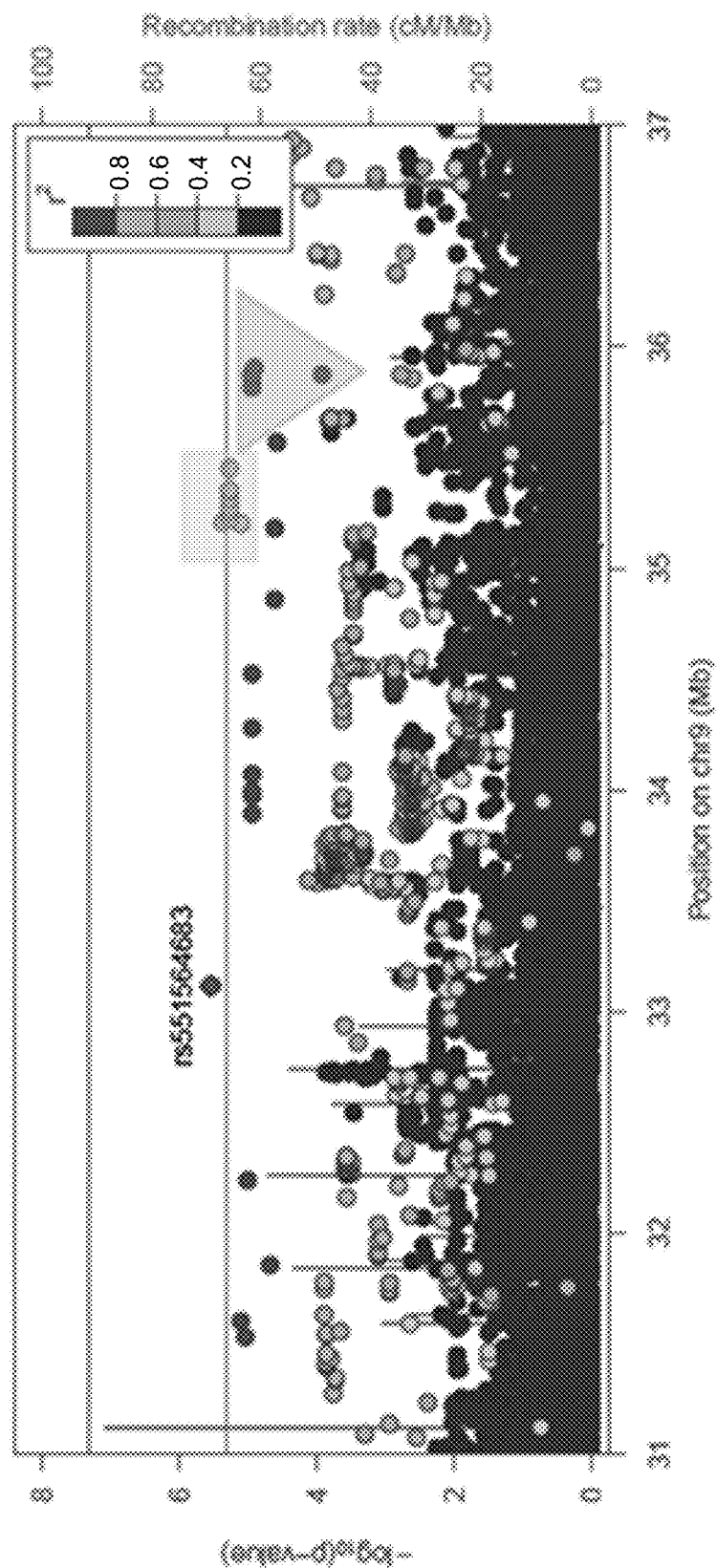
FIG. 2 shows the results of a representative TOPMed WGS association of variant B4GALT1 with LDL.

The TOPMed WGS data set provided 20 variants associated with LDL with p-values from 2.9E-06 to 2.5E-05, and highly, but not perfectly, correlated with the top hit rs551564683 (r2=0.83-0.94) (see, red in FIG. 2). Conditional analysis adjusting for rs551564683 completely abolished the association signal of the 20 variants and did not reveal any other signal in this region, strongly implicating a single causal variant.

By carefully investigating these 20 variants (see, red in FIG. 2) the variants were split into 2 groups: 7 red variants inside the shaded triangle and 13 unshaded red variants. The 7 red variants in the shaded triangle were almost fully correlated with each other and had r2 of 0.83 with the top hit rs551564683. These 7 variants were safely excluded as causal/functional based on three reasons: 1) they are relatively common outside the OOA (maf>1%), 2) they did not show any association with LDL in 3877 samples from Framingham Heart Study (FHS) within TOPMed, and 3) one of these 7 variants had an LDL association p-value of 6.3E-14 vs 3.3E-18 for the top hit rs551564683 in the WES data of 4,565 OOA subjects.

Another group of variants in the shaded rectangle in FIG. 2 also had association p-values only of about 10E-6 and were fully correlated with each other and had r2 of 0.68 with the top hit rs551564683. This group was also excluded as causal/functional because they are common outside the OOA (maf~4%), and did not show any association with LDL in 3877 samples from FHS within TOPMed.

The top hit rs551564683 and 13 unshaded red variants in FIG. 2, which extend over 4 Mb on the short arm of chromosome 9 from 31.5 Mb to 35.5 Mb, remained. As described above, these 13 variants were almost fully correlated with each other and had r2 of 0.91-0.94 with the top hit rs551564683. Among these variants, the top hit rs551564683 was the only coding variant, and it was classified as damaging or deleterious by 5 out of 9 algorithms that predict the effect of a variant on protein function. The top hit rs551564683 and these 13 variants had maf of 6% in the OOA while being almost not existent in the general population.

Haplotype Analysis:

Imperfect r2 between distinct loci is a result of recombination events. A detailed analysis of the primary 14-SNP haplotypes was undertaken. FIG. 3 shows 3 main haplotypes in this 4 Mb region. There are 115 subjects (1 homozygote, and 114 heterozygotes) with Haplotype A, which had identical genotypes at the 14 SNPs, provided no information as to which SNP might be causal. Six subjects had haplotype B, which contained heterozygote genotypes at rs551564683 plus 4 upstream SNPs, and 7 subjects had haplotype C, which contained heterozygote genotypes at rs551564683 plus 9 downstream SNPs. The recombinant haplotypes B and C clustered in related subjects, providing evidence they are not artifacts of genotyping error. Table 3 shows the p-values of rs551564683 after adding individuals with haplotypes B and C into a single group compared to individuals with haplotype A.

TABLE 3

Haplotype analysis results

| | A | B | C | B + C |
|---|---|---|---|---|
| Carriers | 115 | 7 | 6 | 13 |
| Total N | 1063 | 1070 | 1069 | 1076 |
| rs551564683 | 3.43E−05 | 1.40E−05 | 1.18E−05 | 4.82E−06 |

Adding each of haplotypes B and C individually improved the p-value and adding both of them improved the p-value even more. The improved p-values indicated that both haplotypes B and C carry the causal allele. The only SNP in common between B and C was rs551564683, which was considered to be the causal variant.

B4GALT1 Congenital Disorder of Glycosylation Supports rs551564683 Functional Role:

A phenotype-wide association study (PheWAS) was performed to test the association of rs551564683 with all traits in the Amish database. The strongest association after LDL (p=3.3E-18) and total cholesterol (p=3.0E-18) was found with aspartate transaminase (AST) (p=3.0E-8) where the minor allele homozygotes had a two-fold increase in AST levels over wild-type homozygotes. Higher AST was previously reported in a Congenital Disorder of Glycosylation (CGD) case caused by a frame shift insertion in the B4GALT1 that resulted in a truncated dysfunctional protein. Moreover, a strong association was observed with fibrinogen levels (p=5.0E-4) where the minor homozygote level was about 20% lower than the wild-type, consistent with a blood clotting defect in the same CDG patient. Moreover, in a small experiment, a 50% increase (p=0.02) in creatine kinase serum levels was found in 13 minor allele homozygotes compared to 13 wild-type homozygotes. This consistency in the phenotype associated with the missense SNP and those caused by a truncating insertion in B4GALT1 further strengthen the evidence that B4GALT1 rs551564683 SNP is the causal/functional gene and variant in this region.

The association between lipid subfractions and rs551564683 was examined in a subset of 759 Amish individuals, and an association with lower levels of almost all subfractions with significant or non significant p-values was found, as shown in Table 4.

Coronary calcification score, aortic calcification score, and pericardial fat showed trend of association with lower levels, but with no significant p-values.

PheWAS also found rs551564683 to be associated with higher creatinine and lower eGFR, as well as higher hematocrit and lower basophils.

TABLE 4

Association between rs551564683 and lipid subfractions in 759 OOA individuals

| TRAIT | effect size | p-value |
|---|---|---|
| Chol | −1.66E+01 | 3.79E−04 |
| HDL | −4.16E+00 | 8.72E−03 |
| HDL2 | −1.51E+00 | 4.53E−02 |
| HDL2a | −9.26E−01 | 9.93E−02 |
| HDL2b | −1.94E−01 | 2.96E−01 |
| HDL2c | −2.64E−01 | 2.14E−01 |
| HDL3 | −2.64E+00 | 3.98E−03 |
| HDL3a | −1.51E+00 | 2.00E−02 |
| HDL3b | −1.68E−01 | 4.16E−01 |
| HDL3c | −5.93E−01 | 1.47E−02 |
| HDL3d | −4.44E−01 | 2.48E−02 |
| IDL | −7.31E−01 | 4.92E−01 |
| IDL1 | −1.19E−02 | 9.73E−01 |
| IDL2 | −7.65E−01 | 3.37E−01 |
| LDL | −1.23E+01 | 2.37E−03 |
| LDL1 | −2.22E+00 | 7.20E−02 |
| LDL2 | −5.64E+00 | 3.99E−02 |
| LDL3 | −3.81E+00 | 1.32E−01 |
| LDL4 | −3.96E−02 | 9.65E−01 |
| LDLReal | −1.12E+01 | 9.53E−04 |
| Lpa | −2.15E−01 | 6.34E−01 |
| Lpa1 | −2.91E−01 | 3.00E−01 |
| Lpa2 | 4.67E−02 | 8.27E−01 |
| Lpa3 | 2.31E−01 | 5.04E−01 |
| Lpa4 | −2.91E−02 | 9.19E−01 |
| Lpa5 | −2.48E−01 | 3.11E−01 |
| RemnantLipoprotien | −7.23E−01 | 5.97E−01 |
| TCHDLRatio | −3.29E−02 | 7.68E−01 |
| TotalNonHDL | −1.24E+01 | 3.97E−03 |
| TotalVLDL | −1.03E−01 | 8.70E−01 |
| Triglyceride | 2.19E+00 | 6.46E−01 |
| VLDL1Plus2 | −4.10E−02 | 8.86E−01 |
| VLDL3 | 6.15E−03 | 9.86E−01 |
| VLDL3a | 2.28E−02 | 8.97E−01 |
| VLDL3b | −6.57E−02 | 7.30E−01 |

Example 2: Sample Preparation and Sequencing

Genomic DNA sample concentrations were obtained from the Amish subjects, and then transferred to an in-house facility and stored at −80° C. (LiCONiC TubeStore) until sequence analysis. Sample quantity was determined by fluorescence (Life Technologies) and quality was assessed by running 100 ng of sample on a 2% pre-cast agarose gel (Life Technologies).

DNA samples were normalized and a sample of each was sheared to an average fragment length of 150 base pairs using focused acoustic energy (Covaris LE220). The sheared genomic DNA was prepared for exome capture with a custom reagent kit from Kapa Biosystems using a fully-automated approach developed in house. A unique 6 base pair barcode was added to each DNA fragment during library preparation to facilitate multiplexed exome capture and sequencing. Equal amounts of sample were pooled prior to exome capture on the xGen design available from IDT with some modifications. The multiplexed samples were sequenced using 75 bp paired-end sequencing on an Illumina v4 HiSeq 2500.

Raw sequence data generated on the Illumina Hiseq 2500 platform was uploaded to the high-performance computing resource in DNAnexus (DNAnexus Inc., Mountain View, Calif.), and automated workflows processed the raw .bcl files into annotated variant calls. Raw reads were assigned to appropriate samples for analysis based on sample specific barcodes using CASAVA software (Illumina Inc., San Diego, Calif.).

The sample specific reads were then aligned to the reference sequence using BWA-mem (Li and Durbin, Bioinformatics, 2009, 25, 1754-1760). This produced a binary alignment file (BAM) for each sample with all of a particular sample's reads and the genomic coordinates to which each read mapped. Once aligned, a sample's reads were evaluated to identify and flag duplicate reads with the Picard MarkDuplicates tool (picard.sourceforge.net), producing an alignment file with each duplicate read marked (duplicatesMarked.BAM).

The Genome Analysis Toolkit (GATK) (Van der Auwera, Cur. Protocols in Bioinformatics, 2013, 11, 11-33; McKenna, Genome Res., 2010, 20, 1297-1303) was then used to conduct local realignment of the aligned and duplicate-marked reads of each sample. The GATK Haplotype Caller was then used to process the realigned, duplicate-marked reads and to identify all exonic positions at which the sample varies from the genome reference, including single nucleotide variations and INDELs, and the zygosity of the variant within a sample at any position where that particular sample differs from the reference.

Associated metrics, including read counts assigned to both reference and alternate allele, genotype quality representing the confidence of the genotype call, and the overall quality of the variant call at that position were output at every variant site. Variant Quality Score Recalibration (VQSR) from GATK was then employed to evaluate the overall quality score of a sample's variants using training datasets to assess and recalculate this score to increase specificity. Metric statistics were captured for each sample to evaluate capture performance, alignment performance, and variant calling. Following completion of cohort sequencing, a project-level VCF was generated by joint-genotyping using GATK to produce genotype and the associated metric information for all samples at any site where any sample in the cohort carries a variant from the reference genome. It was this project-level VCF that was used for down-stream statistical analyses. In addition to VQSR, variants were annotated with the Quality By Depth (QD) metric using GATK, and bi-allelic variants with QD>2.0, missingness rates <1%, and with Hardy-Weinberg equilibrium p-values >$1.0 \times 10^{-6}$ were retained for further analysis.

Prior to downstream sequence data analysis, samples with reported gender that was discordant with genetically determined gender, samples with high rates of heterozygosity, low sequence coverage (defined as 20× coverage of less than 75% of targeted bases), or unusually high degree of cryptic relatedness, and genetically identified sample duplicates were excluded.

Sequence variants were annotated using an annotation pipeline that uses ANNOVAR (Wang et al., Nuc. Acids Res., 2010, 38, e164) and other customized algorithms for annotation and analysis. Variants were classified according to their potential functional effects, and subsequently filtered by their observed frequencies in publicly available population control databases, and databases in order to filter out common polymorphisms and high frequency, likely benign variants. Algorithms for bioinformatic prediction of functional effects of variants along with conservation scores based on multiple species alignments were incorporated as part of the annotation process of variants and used to inform on the potential deleteriousness of identified candidate variants.

Example 3: B4GALT1 rs551564683 N352S Frequency is Enriched in the Amish

Figure 4:
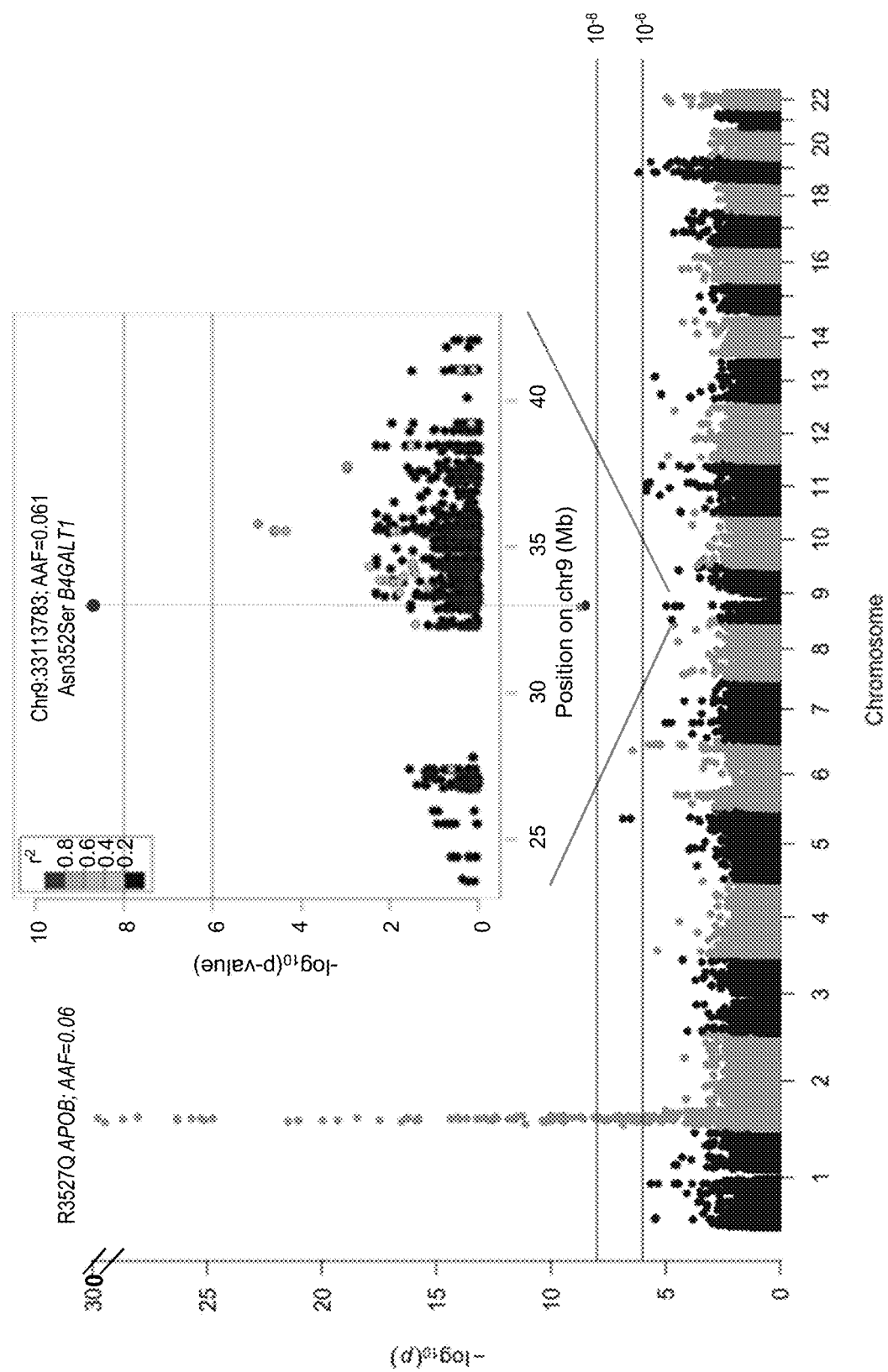
FIG. 4 shows the association of the variant B4GALT1 gene with LDL in the Amish identified by exome sequencing.

Through exome sequencing and association analysis in 4700 Amish subjects, rs551564683 on chromosome 9 was found to be highly associated with total cholesterol levels (p=1.3E-10)(see, FIG. 4). RS551564683 encodes a missense variant in which serine is changed to asparagine at position 352 in the B4GALT1 protein. The next most highly LDL-associated variant in the region was rs149557496 with a p-value of only $10^{-5}$ suggesting the N352S variant as being the most likely causative variant. Referring specifically to FIG. 4, in exome sequence data, the variant in highest LD with Asn352Ser B4GALT1 was rs149557496 in HRCT1, 2.8 Mb distant, $R^2$ 0.78, P-value with LDL in Amish of $10^{-5}$. Whole genome sequence data in the Amish (TOPMED) failed to identify a variant more highly associated with LDL-C in this region.

Figure 5A:
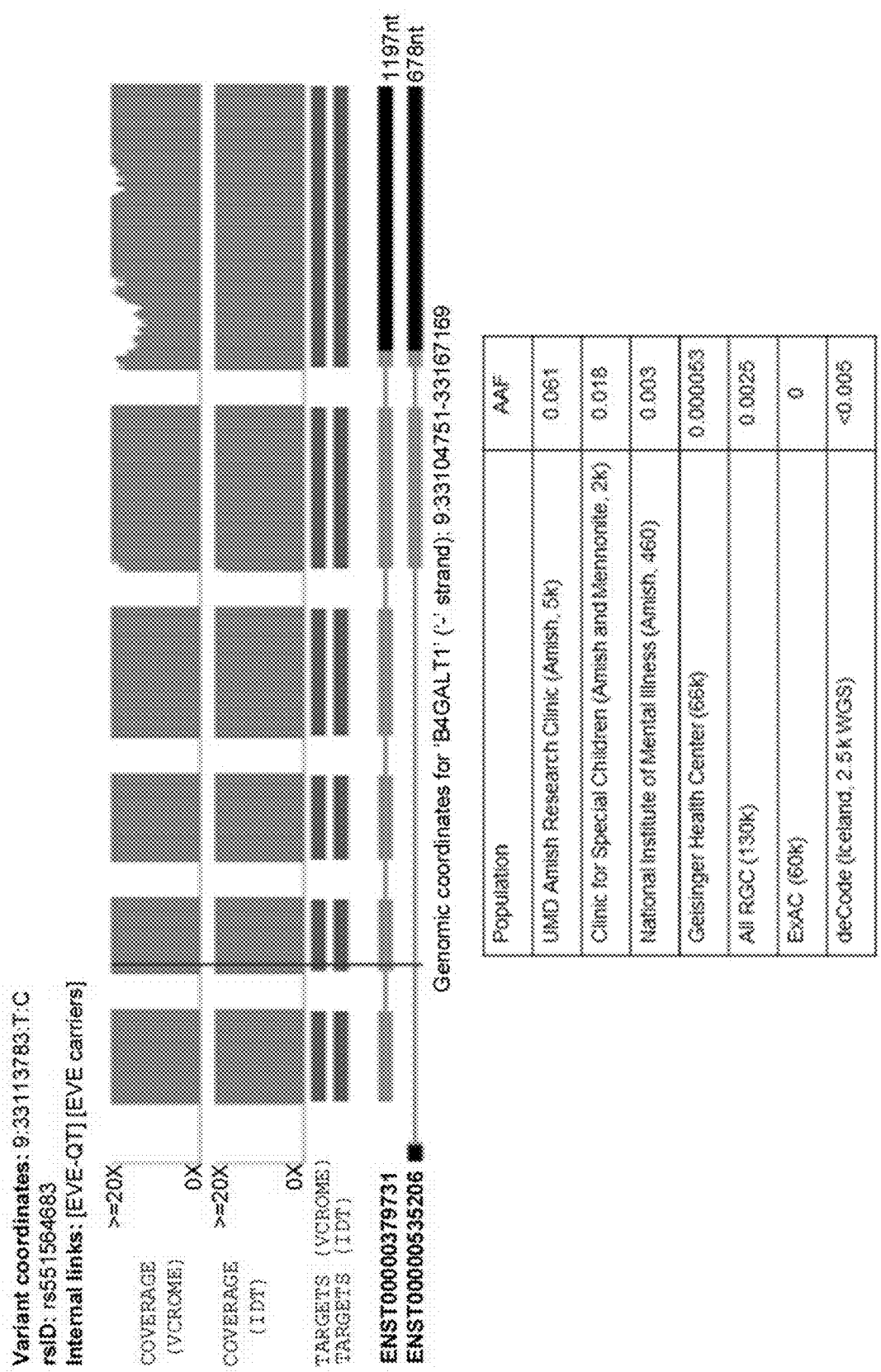

Further analysis revealed that the B4GALT1 N352S variant frequency was over one thousand-fold enriched in the Amish population (see, FIG. 5). The data showed that in the cohort of 4725 Amish, 548 heterozygous carriers for the rs551564683-containing allele were identified, and 13 carriers were homozygous for the allele (see, FIG. 5). In comparison, a collective data set of other population cohorts available to the investigators—totaling 125,401 individuals—was analyzed, and only 79 heterozygotes and 5 homozygotes were identified in this collective data set. The allele frequency in the Amish cohort was estimated to be about 0.06, compared to about 0.0025 in the collective date set (see, FIG. 5). It is believed that genetic drift may account for the higher frequency of this allele in the Amish.

Example 4: B4GALT1 N352S Associates with Decreased Serum Lipids and Increased AST Association of the B4GALT1 N352S variation with various phenotypes, including serum lipids, coronary artery disease (CAD), and liver traits was assessed. The associations were carried out based on the Amish cohort, with individuals who were homozygous for the reference allele, who were heterozygous for the alternate allele, and who were homozygous for the alternate allele. The genotypic means for the lipid and liver traits and risk of CAD were determined, with the effect measures adjusted by removing the effects of subject age and age squared, subject sex, and study (since the phenotype data were collected from several studies over a period of years). In the case of pericardial fat, the genotypic means were further adjusted for BMI. The effect sizes of the variation on the measured phenotypes were measured at the 95% confidence interval. The traits and the results are presented in FIG. 6, FIG. 7, and FIG. 8.

Figures 7A, 7B:
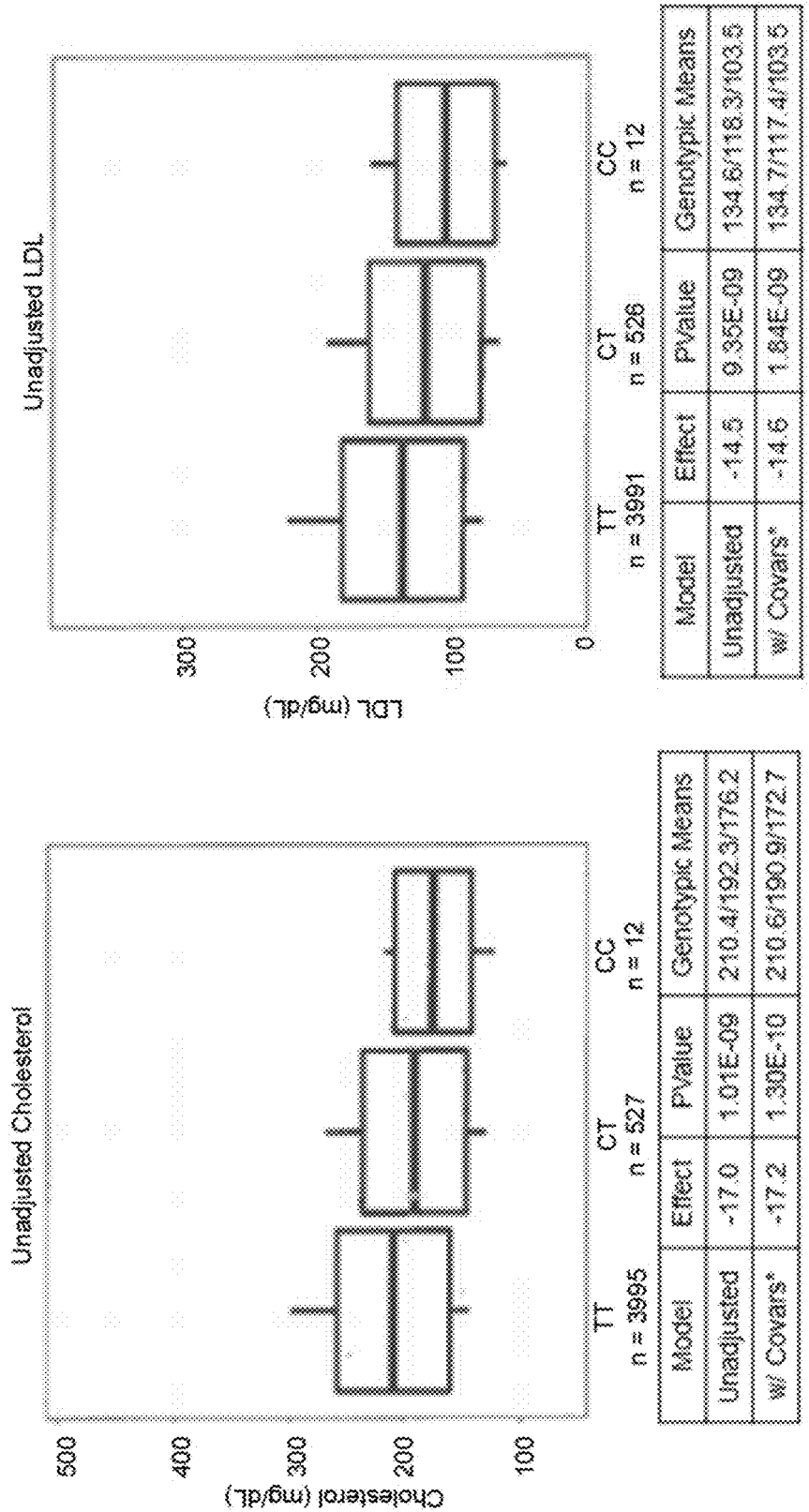
FIGS. 7A, 7B, and 7C show the high degree of association of B4GALT1 Asn352Ser with decreased serum lipids and increased AST.
Figure 7C:
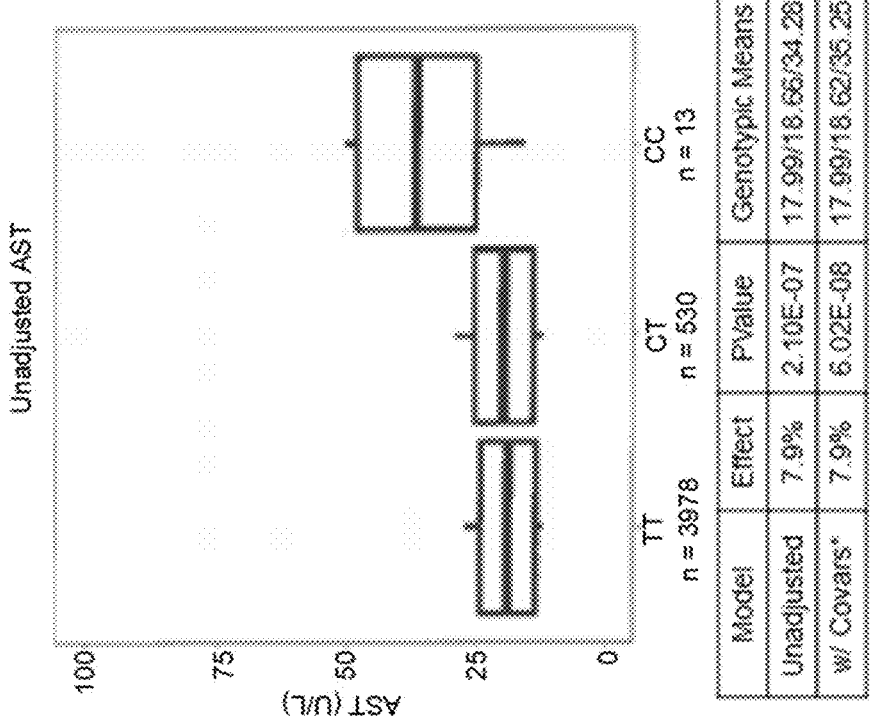

As shown in FIG. 6, the presence of the N352S variation generally correlated with decreased serum lipids, particularly for total cholesterol (p-value $1.3 \times 10^{-10}$) and LDL (p-value $1.8 \times 10^{-9}$) levels, which achieved strong statistical significance. Individuals heterozygous and homozygous for this alteration showed 17.3 mg/dL and 31.2 mg/dL reduction, respectively, for LDL levels. There was a trend between the variant and decreased coronary artery calcification. In addition, the presence of this variation correlated with increased aspartate aminotransferase (AST) levels (p-value $6.0 \times 10^{-8}$). The recessive model p-value for the AST levels was determined to be $9 \times 10^{-23}$. The variation did not appear to correlate with increased alanine aminotransferase (ALT) levels, alkaline phosphatase levels, or liver fat levels. The cholesterol, LDL, and AST levels are shown graphically in FIG. 7. In FIG. 7, the levels of cholesterol, LDL, and AST are shown for subjects who were homozygous (TT) for the reference allele, heterozygous (CT) for the alternate allele, and homozygous (CC) for the alternate allele. Values shown are unadjusted. The values were recalculated based on adjustments for subject age and age squared, sex, and study (tabulated in the bottom of the FIG. 7).

The effect of the N352S alteration on lipid subfractions was also assessed. These results are shown in FIG. 8. The associations were carried out based on the Amish cohort, with individuals who were homozygous for the reference allele, who were heterozygous for the alternate allele, and who were homozygous for the alternate allele. The results in FIG. 8 show that the B4GALT1 N352S alteration associates with decreases in all lipid subfractions tested.

Example 5: B4GALT1 N352S Associates with Decreased Fibrinogen Levels

Association of the B4GALT1 N352S variation with fibrinogen levels was also assessed in a subset of samples. As for the serum lipids, CAD, and liver traits assessed in Example 4, the association with fibrinogen levels was carried out based on the Amish cohort, with individuals who were homozygous for the alternate allele, who were heterozygous for the reference allele, and who were homozygous for the alternate allele. The genotypic means for fibrinogen levels were determined in two subgroups of individuals—individuals not on a clopidogrel regimen (drug naïve) and individuals on a clopidogrel regimen (on-clopidogrel) and, as part of the analysis, the mean levels in each group were adjusted by removing the effects of subject age and age squared, subject sex, and study. The effect sizes of the variation on fibrinogen levels was measured at the 95% confidence interval. As shown in FIG. 9, the presence of the N352S variation was associated with decreased fibrinogen levels in each of the drug naïve (p-value $1.15 \times 10^{-3}$) and on-clopidogrel (p-value $2.74 \times 10^{-5}$) groups. The drug naïve subgroup showed a decrease of approximately 24 mg/dL of fibrinogen (see, FIG. 9). The on-clopidogrel subgroup showed a decrease of approximately 32.5 mg/dL of fibrinogen (see, FIG. 9).

Example 6: Additional B4GALT1 N352S Associations

Within the Amish cohort, assessment of associations between the B4GALT1 N352S variation and other traits, including creatinine levels, estimated glomerular filtration rate (eGFR), basophil levels, and hematocrit percentage was also carried out. As shown in FIG. 9, the variant weakly associated with a small increase in creatinine levels, but did not significantly associate with eGFR, basophil levels, or the hematocrit percentage.

Example 7: b4galt1 Ortholog Knockdown in Zebrafish

In parallel to the evidence in cell-based assays, a zebrafish model was pursued to investigate the effect of B4GALT1 p.Asn352Ser on LDL.

Zebrafish Husbandry, Morpholino Injection and Validation

Wild-type (Tubingen) zebrafish stocks were used to generate embryos for morpholino injection. Adult fish were maintained and bred at 27-29° C. and embryos were raised at 28.5° C. All animals were housed and maintained in accordance with protocols approved by the University of Maryland Institutional Animal Care and Use Committee. Morpholino antisense oligonucleotides (MOs) were obtained (Gene Tools, Inc.) based on previously published MOs targeted against b4galt1 (Machingo et al., Dev. Biol., 2006, 297, 471-482). MOs were injected at the 1-2 cell stage and validated by qRT-PCR quantification of wild type b4galt1 transcript. Off-target toxicity was assessed by qRT-PCR quantification of the delta113 isoform of p53 (Robu et al., PLoS Genet., 2007, 3, e78). For mRNA rescue experiments, human B4GALT1 mRNA was transcribed from a pCS2+ plasmid vector containing the open reading frame (ORF) of the wild-type or N352S variant of the gene. mRNA was mixed with MO at varying concentrations and co-injected into 1-2 cell stage embryos. For each injection experiment, a total of 200-400 embryos were injected and each experiment was repeated a minimum of three times.

LDL Quantification in Zebrafish

One hundred 5 days post fertilization (dpf) larvae were homogenized per experiment in 400 µl of ice-cold 10 µM butylated hydroxytoluene. The homogenate was filtered through a 0.45 µm Dura PVDF membrane filter (Millipore) in preparation for lipid extraction. Using the HDL and LDL/VLDL Cholesterol Assay Kit (Cell Biolabs, Inc.), the homogenate was processed as per manufacturer's protocol. After precipitation and dilution, samples were analyzed by fluorimetric analysis using a SpectraMax Gemini EM plate reader and SoftMax Pro microplate data acquisition and analysis software (Molecular Devices).

Figure 10:
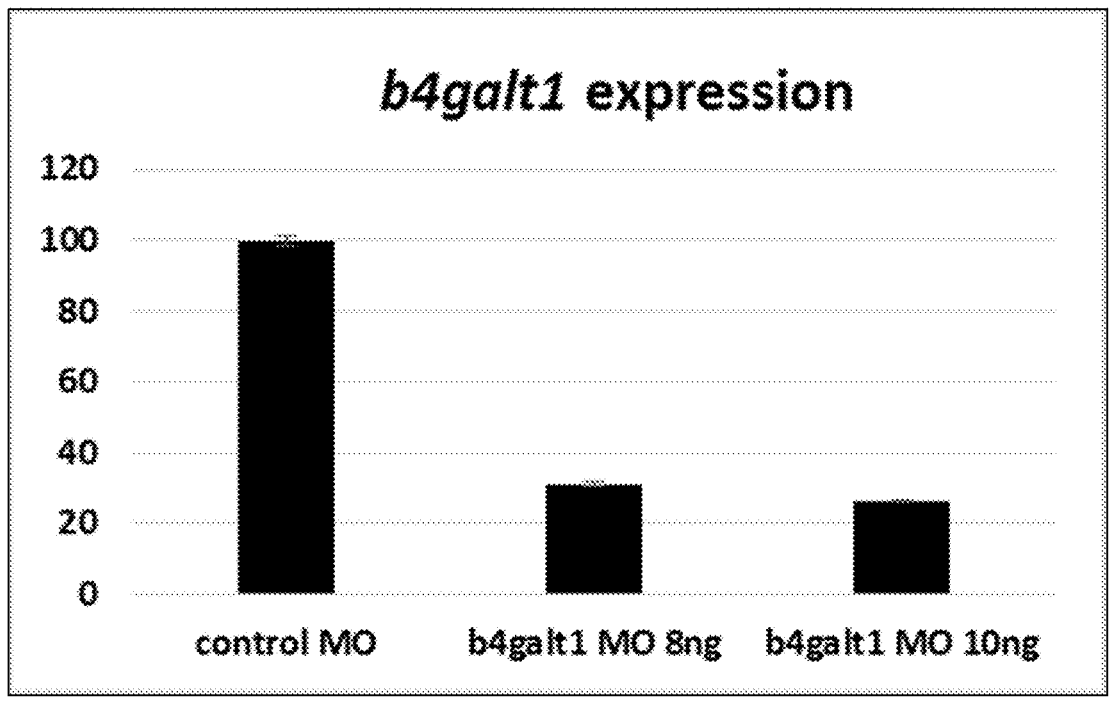
FIG. 10 shows reduced b4galt1 transcript in 5 days post fertilization of zebrafish larvae injected with antisense morpholino oligonucleotide at the indicated concentrations.
Figure 11:
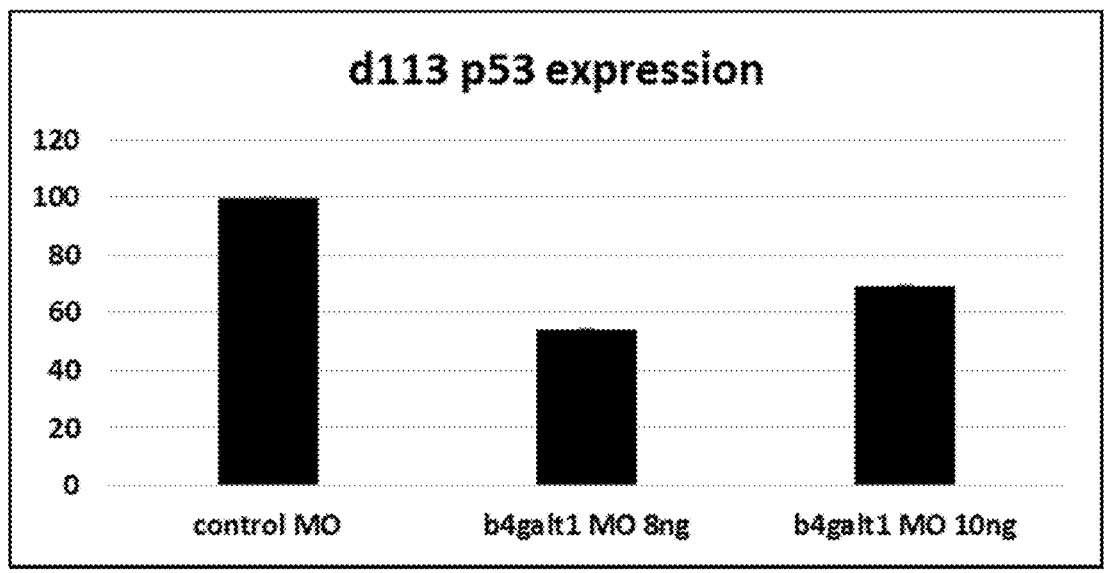
FIG. 11 shows diagnostic marker of antisense morpholino oligonucleotide off-target effects in 5 days post fertilization zebrafish larvae injected with antisense morpholino oligonucleotide at the indicated concentrations.
Figure 12:
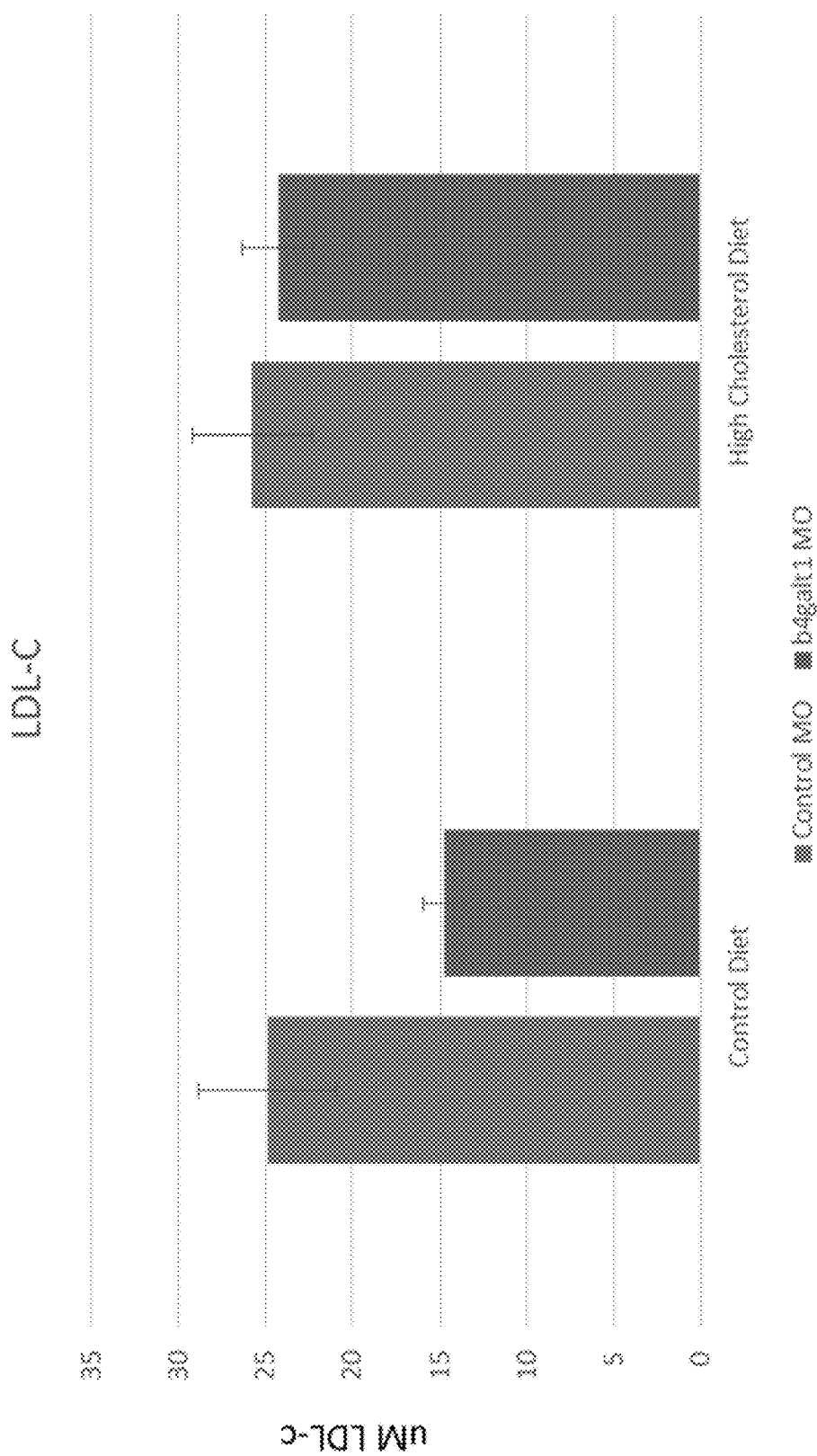
FIG. 12 shows average LDL concentration in homogenates of 100 5 days post fertilization zebrafish larvae per experiment.
Figure 13:
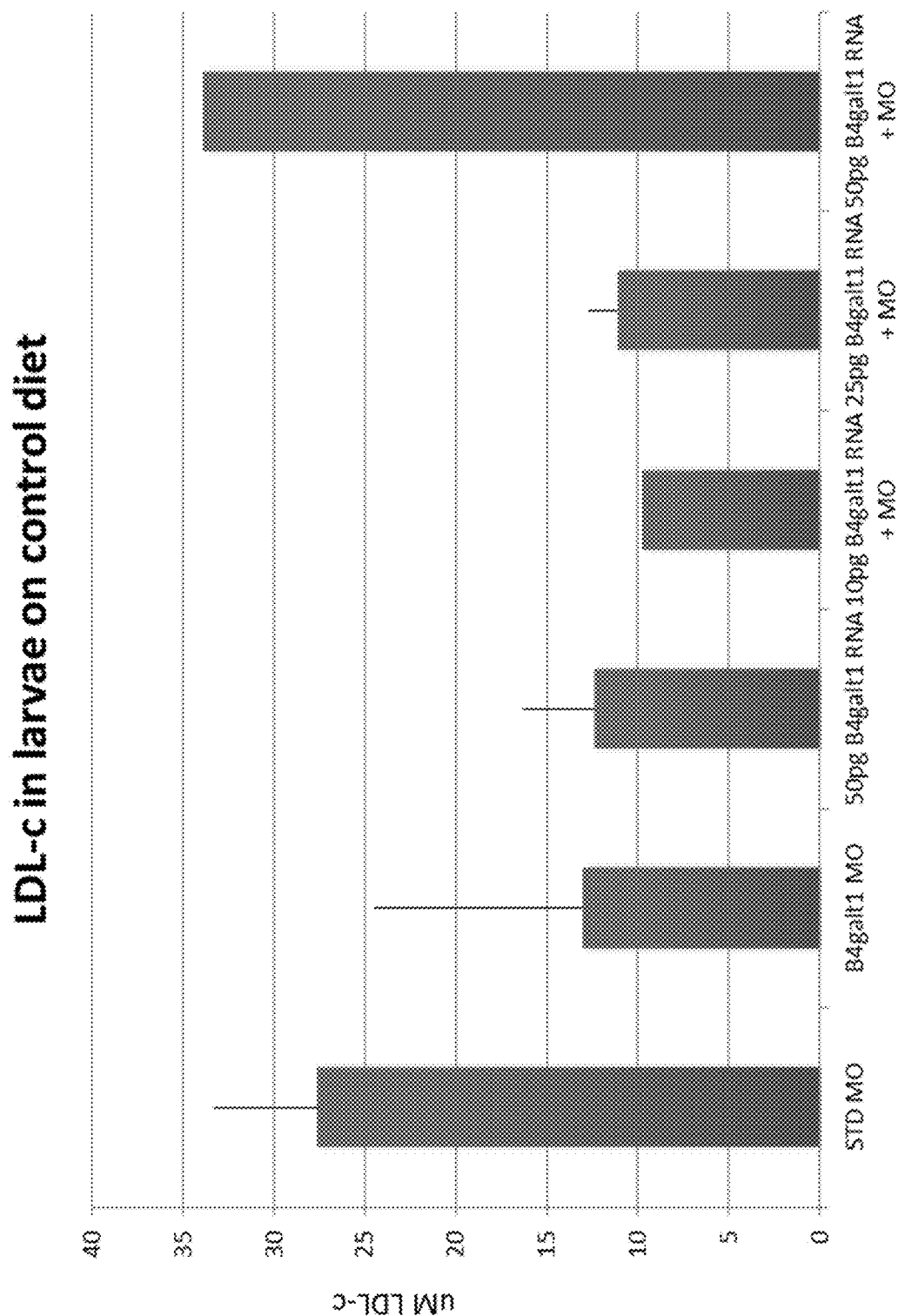
FIG. 13 shows a rescue of LDL-c phenotype by co-expression of 50 pg human B4GALT1 mRNA in the zebrafish.

A genomic knockout of the zebrafish ortholog (b4galt1) was generated using CRISPR/Cas9-mediated targeting of exon 2. Consistent with mouse reports of embryonic lethality in knockout animals, injected F0 animals were not viable to adulthood and consistently died at juvenile stages. To circumvent the lack of viability, a knockdown approach using a previously reported splice-blocking antisense morpholino oligonucleotide (MO) injected into embryos (Machingo et al., Dev. Biol., 2006, 297, 471-482) was employed. The efficacy of the MO was validated at two different concentrations by qRT-PCR (see, FIG. 10) and ruled out the possibility of off-target toxicity (see, FIG. 11). To quantify changes in LDL levels, 8 ng of MO was injected and injected embryos were cultured until 5 days post fertilization (dpf), at which stage larvae were assayed for total LDL as per previously published protocols (O'Hare et al., J. Lipid Res., 2014, 55, 2242-2253). A significant decrease in LDL in MO-injected larvae was observed compared to control larvae consistent with a role for b4galt1 in LDL homeostasis (see, FIG. 12). This result was confirmed using a second splice-blocking MO targeting exon 2 which produced a reduction in LDL concentration upon injection of 2 ng of MO (data not shown). To validate the specificity of these observations and to test the functionality of human B4GALT1 in zebrafish, full length capped mRNA encoding the human gene was generated by in vitro transcription from a pCS2' plasmid carrying the open reading frame (ORF) of the human gene. To assess the capacity of the wild type human mRNA to rescue the knockdown phenotype, it was co-injected with b4galt1 MO into embryos and LDL in unfed larvae was assessed. Three concentrations of mRNA (10 pg, 25 pg, and 50 pg) were co-injected with 8 ng of MO. Co-injection of 50 pg of B4GALT1 mRNA resulted in LDL levels that were statistically indistinguishable from those in larvae injected only with a control MO (p-value=0.14), suggesting that the human mRNA could rescue the effects of knockdown of the zebrafish gene (see, FIG. 12; larvae were treated with MO against b4galt1, MO co-injected with WT human B4GALT1 mRNA (WT rescue), or MO co-injected with B4GALT1 mRNA encoding the Asn352Ser mutation (N352S rescue)).

These data support the use of this system for functional interpretation of variants in human B4GALT1, and suggest that human wild type B4GALT1 mRNA is functional in zebrafish with respect to regulation of systemic LDL levels. The impact of p.Asn352Ser on B4GALT1 function was further investigated. Using site-directed mutagenesis (O'Hare et al., Hepatology, 2017, 65, 1526-1542), a T to C change was introduced in the coding sequence of the human B4GALT1 ORF construct to generate full length mRNA. Co-injection of the B4GALT1 p.352Ser mRNA with MO resulted in a reduced capacity for rescue of the LDL phenotype. The resulting LDL concentration was 15% lower than that resulting from co-injection of wild type mRNA with MO, a statistically significant effect (39.9 µM compared to 46.6 µM, p-value=0.02). This level of LDL was also statistically greater, however, than b4galt1 MO alone (p-value=0.01) (see, FIG. 12), suggesting a partial defect in function introduced by the missense variant.

Example 8: Targeted Genotyping

Figure 14:
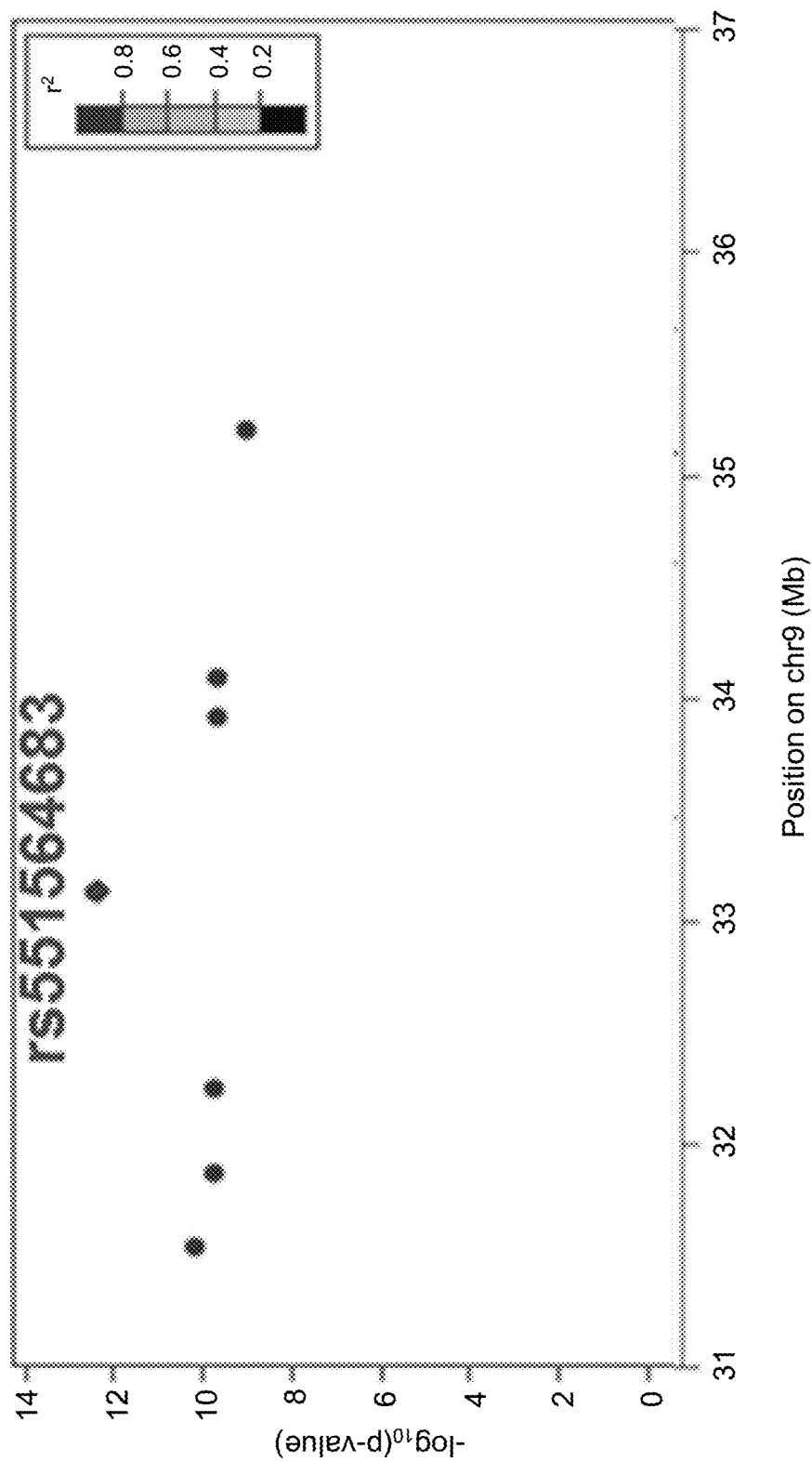
FIG. 14 shows the genetic association results between B4GALT1 N352S and LDL using targeted genotyping.

Targeted SNP genotyping using the QuantStudio system (Thermo Fisher Scientific) was performed for 3,236 OOA subjects. Based on the LD structure of the 14 SNPs, seven SNPs were selected for genotyping, and the association evidence for rs551564683 was 4.1E-13, while it was about E-10 for the other SNPs (FIG. 14), confirming that rs551564683 is the causal variant in this region.

Figure 15:
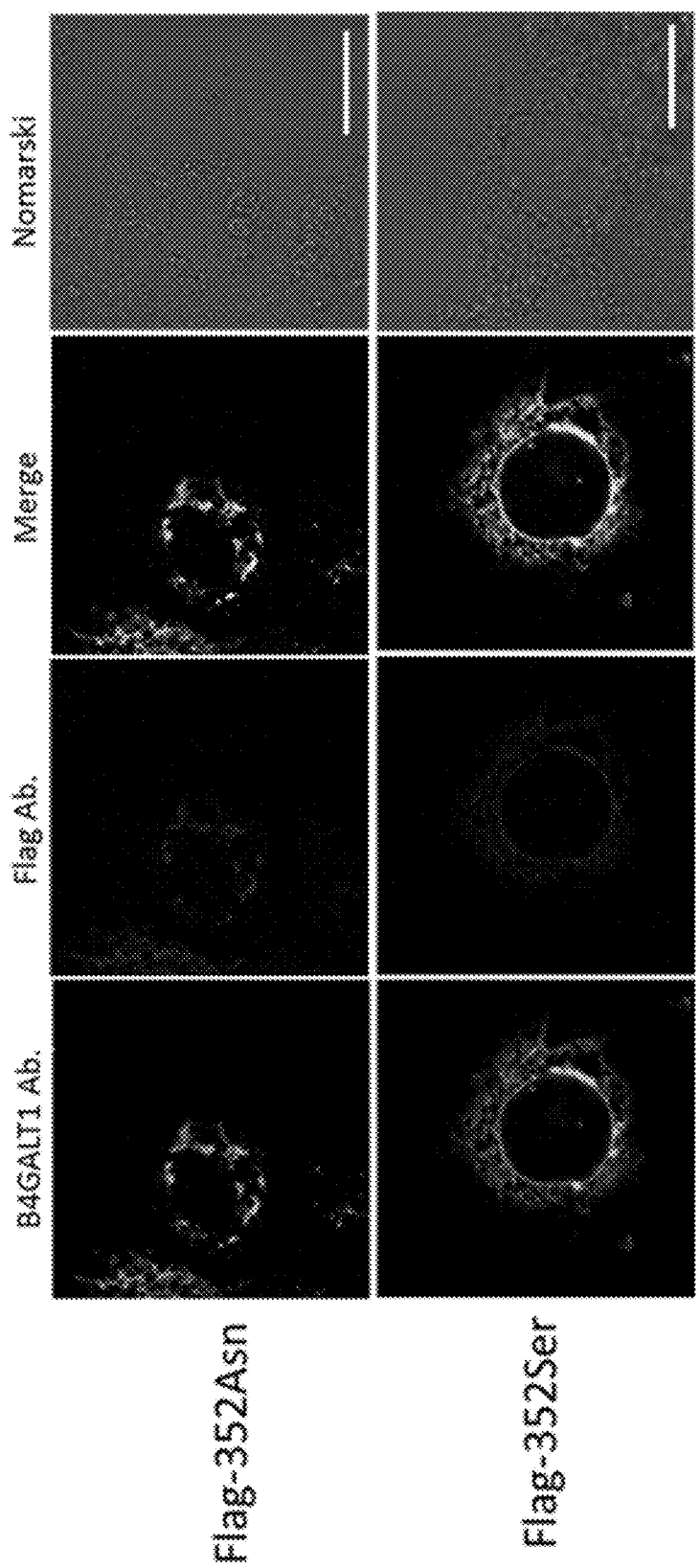
FIG. 15 shows confocal microscopy images of Flag-352Asn or Flag-352Ser subcellular localization.
Figure 16:
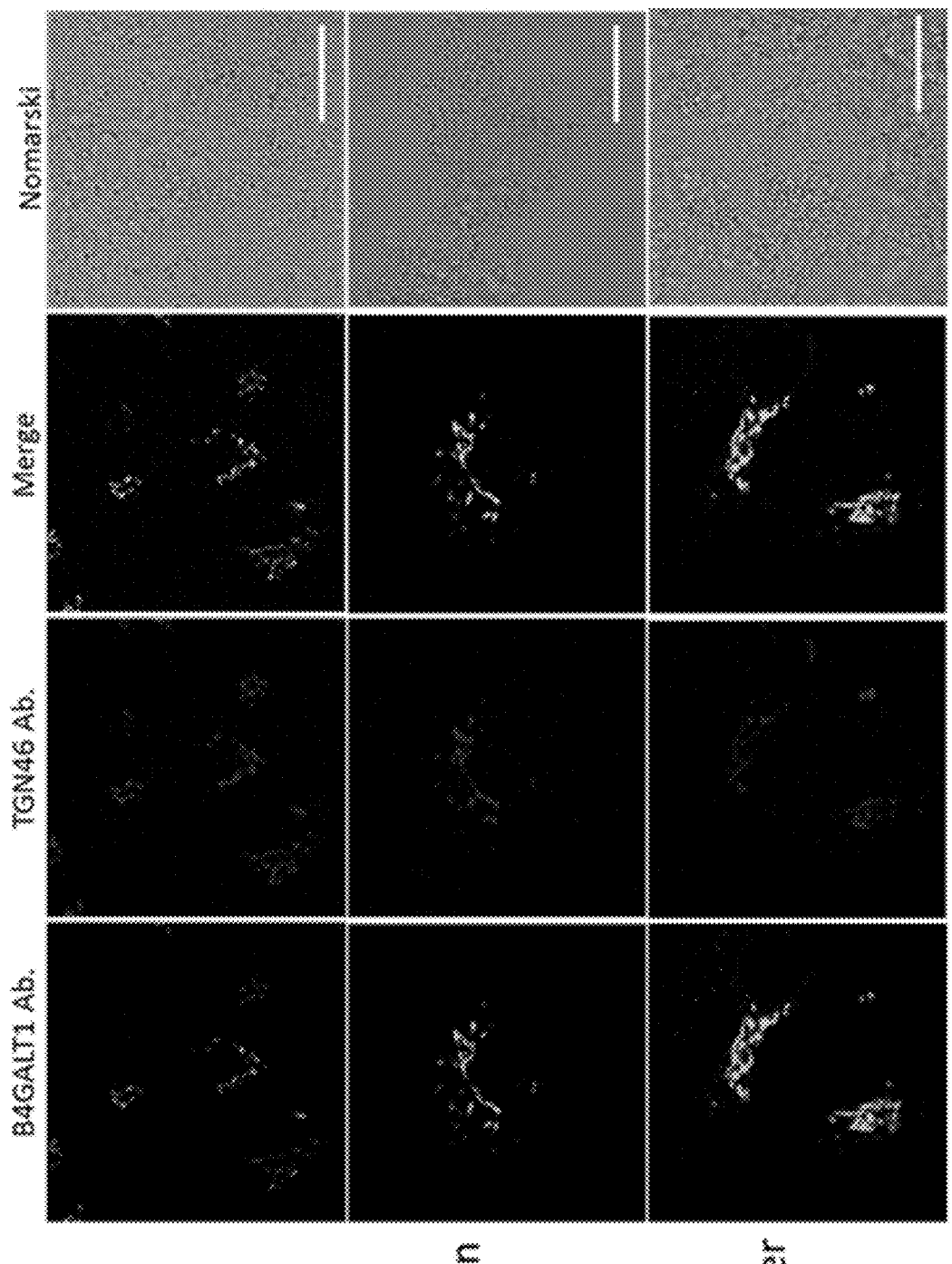
FIG. 16 shows confocal microscopy images of endogenous B4GALT1, Flag-352Asn, and Flag-352Se sub-cellular localization in relation with the trans Golgi Network marker TGN46.

Example 9: B4GALT1 N352S Causes Reduced Enzymatic Activity in Absence of Change in Protein Stability or Cellular Localization Investigations of the properties of B4GALT1 were carried out in COS-7 and Huh7 cells overexpressing human epitope-tagged Flag-B4GALT1352Asn or epitope-tagged Flag-B4GALT1 352Ser (FIGS. 15 and 16). Referring to FIG. 15, confocal microscopy images of Flag-352Asn or Flag-352Ser using B4GALT1 or Flag antibodies indicate an identical pattern of staining (scale bars=10 µm). Referring to FIG. 16, subcellular localization by indirect immunofluorescence of Huh7 cells showed a co-localization of endogenously expressed B4GALT1 and TGN56, a Golgi apparatus marker. A similar co-localization pattern was observed whether human epitope-tagged Flag-B4GALT1 352Asn or epitope-tagged Flag-B4GALT1 352Ser were over expressed (FIG.

16). Referring to FIG. 16, endogenous B4GALT1, Flag-352Asn, and Flag-352ser overexpressed in human hepatoma Huh7 cells co-localized with the Trans Golgi Network marker TGN46. Shown are confocal microscopy images of endogenous B4GALT1, Flag-352Asn, and Flag-352Se subcellular localization in relation with the trans Golgi Network marker TGN46, with scale bars=10 μm.

Figure 17:
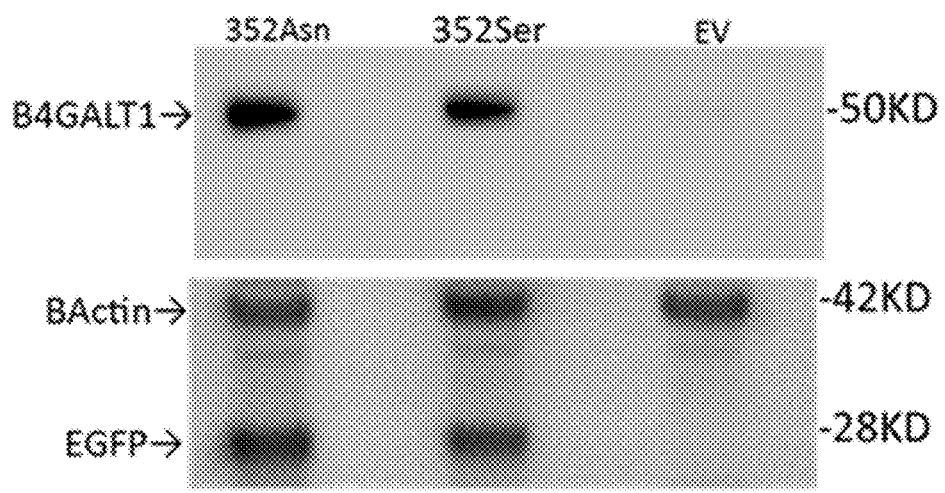
FIG. 17 (Panels A and B) shows the effect of 352Ser on steady-state levels of B4GALT1 protein; (Panel A) COS7 cells expressing either 352Asn or 352Ser Flag tag proteins fusion with free EGFP; and (Panel B) mRNA expression levels for B4GALT1 gene determined by RT-qPCR analysis.
Figure 17:
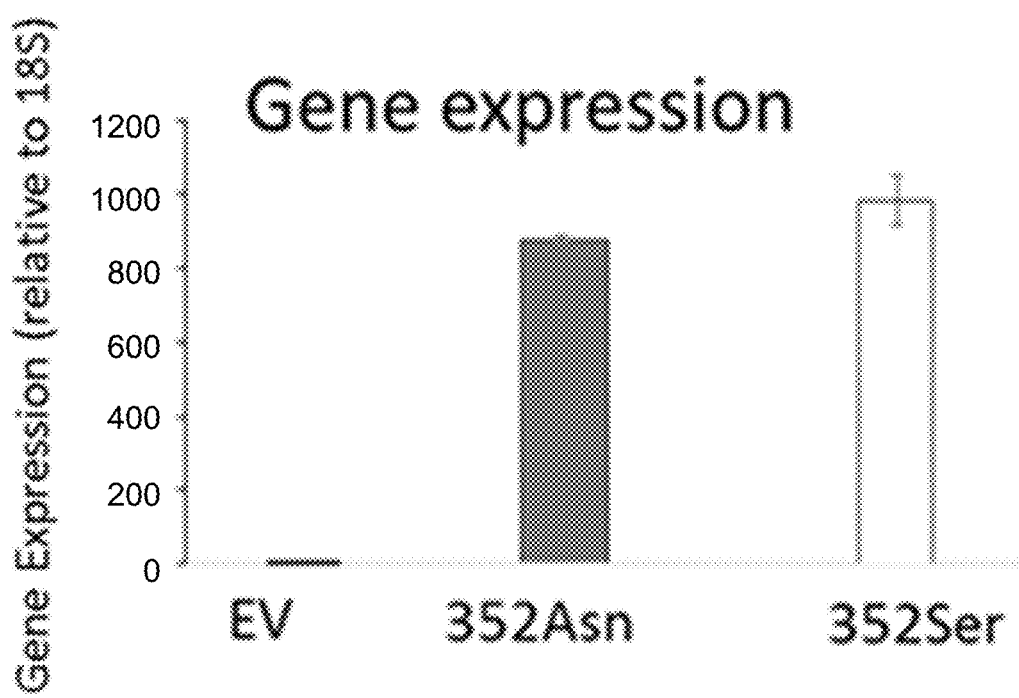

COS-7 cells were observed to have a low content of endogenous B4GALT1 (FIG. 17, Panel B), so this cell line was used to assess the effect of the missense mutation on protein stability and/or steady-state levels, and galactosyltransferase activity. The results showed that the missense mutation does not affect protein stability and/or steady-state levels (by Western blot) (FIG. 17). Referring to FIG. 17, the effect of 352Ser on protein stability and/or steady-state levels is shown. Panel A shows COS7 cells expressing either 352Asn or 352Ser Flag tag proteins fusion with free EGFP were expressed in COS7 cells. Cell lysates were analyzed by Western blot for B4GALT1, Bactin, and EGFP using commercial antibodies. One of four similar experiments is shown. Panel B shows mRNA expression levels for B4GALT1 gene determined by RT-qPCR analysis. Data represent means±S.E. of 4 experiments.

To determine the catalytic activity of 352Ser, lysates of nontransfected COS-7 cells and COS-7 cells transfected with the expression vector alone or containing the cDNA insert of wild-type or mutant B4GALT1 were analyzed for galactosyltransferase activity. When normalized relative to the expression of FLAG-tagged protein (immunoblotting experiment in FIG. 18, Panels A and B), the enzymatic activity of the 352Ser was approximately 50% decreased in comparison to 352Asn (FIG. 18, Panel C). Referring to FIG. 18, the effect of 352Ser mutation on activity is shown. Panels A and B show COS7 cells expressing either 352Asn or 352Ser Flag tag proteins fusion expressed in COS7 cells. Cell lysates were incubated with rabbit anti-Flag IgG or rabbit pre-immune control IgG. Immunoprecipitates were analyzed by Western blot for B4GALT1 or Flag using commercial antibodies. One of four similar experiments is shown. Panel C shows B4GALT1 activity in the immunoprecipitates measured with a commercial kit (R&D). Each data point represents the average of the calculated ratio of B4GALT1 specific activity with the amount of 352Asn or 352Ser protein recovered in the immunoprecipitates. Signals from Western blots ECL were quantified by densitometry using ImageJ software. Data represent means±S.E. of 4 experiments (*, p<0.05, 352Asn vs 352Ser).

These experiments show that this missense mutation has no effect on the level of protein expression and its localization, but it leads to lower enzymatic activity.

Example 10: Carbohydrate Deficient Transferrin for Congenital Disorders of Glycosylation (CDG) Test The CDG test was performed using 0.1 ml serum samples from 24 subjects from the 3 genotype groups (8 minor homozygotes, 8 heterozygotes and 8 major homozygotes). Each minor homozygote was matched with a heterozygote and a major homozygote that are either sibs or closely related same sex individual based on the kinship coefficient. The age, and the carrier status were also matched for major lipid-altering gene alleles in APOB$^{R3527Q}$.

Water diluted samples were double washed using an immunoaffinity column. Glycosylation profiling of eluted proteins was performed using a mass spectrometer operated with 2 scan ranges specific for APOCIII and transferrin. Glycoform ratios of each protein were used to determine glycosylation deficiency. The CDG test was performed at the Mayo medical laboratory of the Mayo Clinic.

Figure 19:
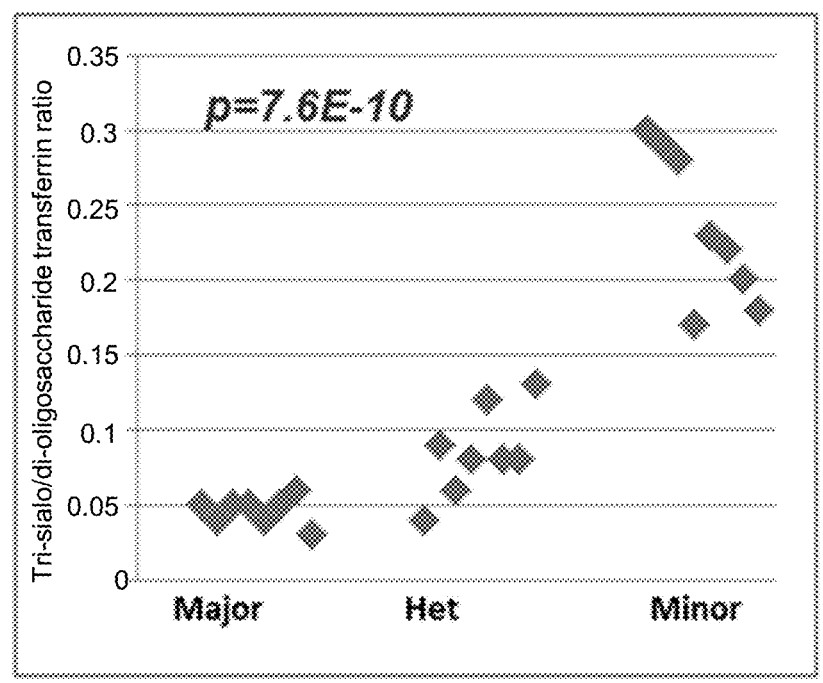
FIG. 19 shows the tri-sialo/di-oligo ratio by B4GALT1 N352S genotype group.

The results showed that all 24 samples had normal levels of the mono-oligosaccharide/di-oligosaccharide transferrin ratio, the a-oligosaccharide/di-oligosaccharide transferrin ratio, the ApoCIII-1/ApoCIII-2 ratio, and the ApoCIII-0/ApoCIII-2 ratio. However, while all wild type samples had normal levels of the tri-sialo/di-oligosaccharide transferrin ratio, the level in all heterozygotes were in the intermediate range and the level in all minor homozygotes was abnormal and significantly higher than matched wild type and heterozygotes (p=7.6 E-10) (FIG. 19). These results show that this missense mutation is associated with defective glycosylation as a result of the decreased enzymatic activity of B4GALT1.

Example 11: Global N-Linked Glycan Analysis of Plasma Glycoproteins

Figure 20A:
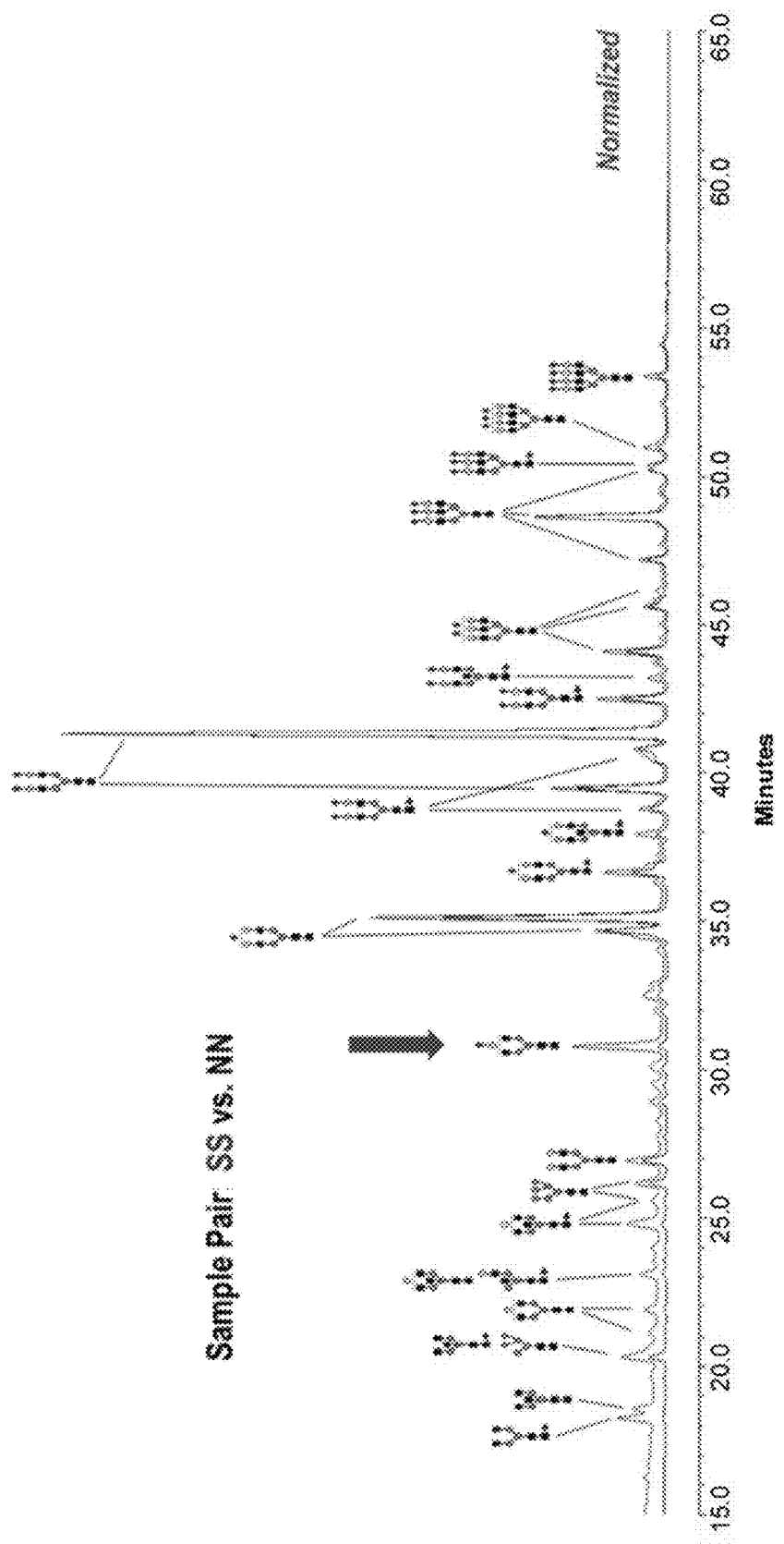
FIGS. 20A and 20B show a representative HILIC-FLR-MS spectrum of N-Glycan analysis of Glycoprotein from a matched pair of minor (SS) and major (NN) homozygotes of B4GALT1 N352S.
Figure 20B:
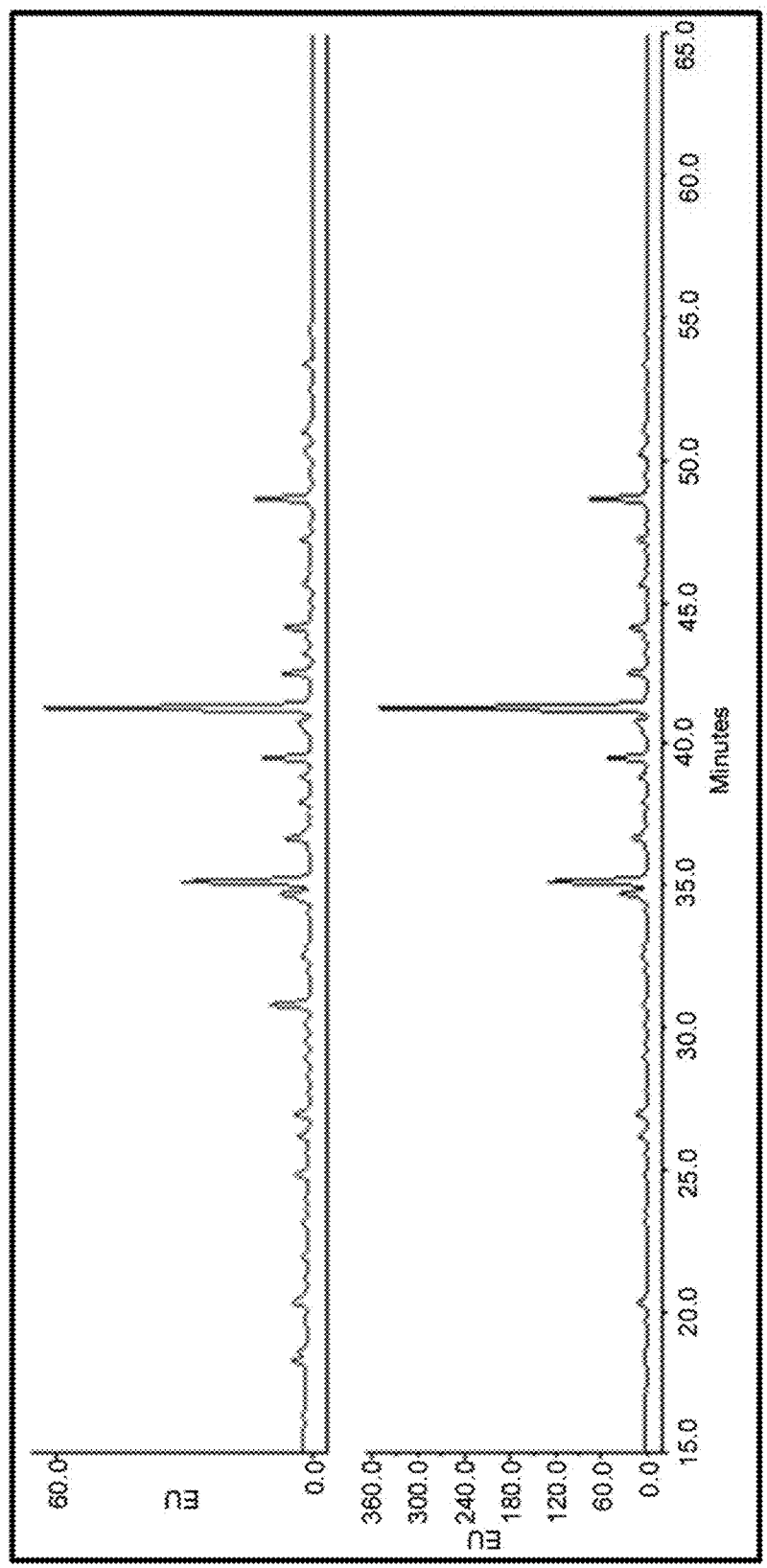

To determine if the desialylation and hypogalactsylation are affecting only transferrin or extending to other glycoproteins, global N-Glycan analysis was performed by the analytical chemistry group at Regneron. Lectin enriched glycoproteins were extracted from serum of 5 pairs of major and minor homozygotes in duplicate, and Global N-linked glycan separation was performed for labeled glycans using hydrophilic interaction chromatography and detected by fluorescence and analyzed by mass spectrometry (HILIC-FLR-MS) (FIG. 20 and Table 5). Referring to FIG. 20, a representative HILIC-FLR-MS spectrum of N-Glycan analysis of Glycoprotein from a matched pair of minor (SS) and major (NN) homozygotes of B4GALT1 N352S is shown. The results showed that the minor homozygotes have significantly higher levels of hypogalactosylated and less sialylated glycans including biantennary glycans with only one galactose and one sialic acid (p=3.1 E-5), asialylated biantennary glycans with one galactose (p=0.001), and truncated biantennary glycans missing both galactoses and sialic acids (p=0.005). On the other hand, the minor homozygotes have significantly lower levels (p=0.001) of biantennary glycans with two galactose and two sialic acid (Table 5). There was a significantly lower overall galactosylation (p=9.2 E-5) and sialylation (p=0.001) among minor homozygotes, while there was no difference in fucosylation level (p=0.5). Both CDT and global N-glycan analysis of serum show significantly increased levels of carbohydrate-deficient glycoproteins in minor homozygotes, indicating that B4GALT1N352S is leading to defective protein glycosylation.

TABLE 5

Mean (±sd) of % peak area of significantly different glycans between minor and major homozygotes

| Glycan | Major Homozygote | Minor Homozygote | P value |
| --- | --- | --- | --- |
| G0F | 0.58 ± 0.34 | 1.84 ± 0.48 | 0.005 |
| G1 | 0.19 ± 0.12 | 0.91 ± 0.16 | 0.001 |
| G1S1 | 0.63 ± 0.16 | 4.7 ± 0.38 | 3.1E-5 |
| G2S2 | 39.3 ± 0.79 | 31.5 ± 1.8 | 0.001 |

The disclosure is not limited to the embodiments described and exemplified above, but is capable of variation and modification within the scope of the appended claims. The disclosure is also not to be limited in any manner by the use of any headers recited herein.

What is claimed is:

1. A cDNA molecule comprising a nucleotide sequence encoding a human Beta-1,4-galactosyltransferase 1 (B4GALT1) polypeptide, wherein the nucleotide sequence comprises SEQ ID NO:6.

2. A vector, comprising the nucleic acid molecule of claim 1.

3. The vector of claim 2, further comprising an exogenous donor sequence.

4. The vector of claim 2, wherein the vector comprises a plasmid.

5. The vector of claim 2, wherein the vector comprises a virus.

6. A composition, comprising the nucleic acid molecule of claim 1 and a carrier.

7. A composition comprising the vector of claim 2 and a carrier.

8. A host cell comprising the nucleic acid molecule of claim 1.

9. A host cell comprising the vector of claim 2.

10. The host cell of claim 8, wherein the nucleic acid molecule is operably linked to a promoter active in the host cell.

11. The host cell of claim 10, wherein the promoter is an inducible promoter.

12. The host cell of claim 8, wherein the host cell is a bacterial cell, a yeast cell, or an insect cell.

13. The host cell of claim 8, wherein the host cell is a mammalian cell.

* * * * *